(12) United States Patent
Nakai et al.

(10) Patent No.: US 11,389,539 B2
(45) Date of Patent: Jul. 19, 2022

(54) HYALURONIC ACID DERIVATIVES INTO WHICH CATIONIC AND HYDROPHOBIC GROUPS ARE INTRODUCED

(71) Applicant: CHUGAI SEIYAKU KABUSHIKI KAISHA, Tokyo (JP)

(72) Inventors: Takashi Nakai, Gotemba (JP); Teruo Nakamura, Gotemba (JP); Sayan Chuanoi, Gotemba (JP); Hideyuki Togawa, Gotemba (JP); Tsuyoshi Shimoboji, Gotemba (JP); Kazuo Hattori, Gotemba (JP); Takashi Emura, Gotemba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/099,770

(22) PCT Filed: May 11, 2017

(86) PCT No.: PCT/JP2017/017954
§ 371 (c)(1),
(2) Date: Nov. 8, 2018

(87) PCT Pub. No.: WO2017/195880
PCT Pub. Date: Nov. 16, 2017

(65) Prior Publication Data
US 2019/0142959 A1   May 16, 2019

(30) Foreign Application Priority Data
May 11, 2016   (JP) .............................. JP2016-095533

(51) Int. Cl.
| *A01N 37/44* | (2006.01) |
| *A61K 31/575* | (2006.01) |
| *A61K 39/00* | (2006.01) |
| *A61K 47/36* | (2006.01) |
| *A61K 47/61* | (2017.01) |
| *A61K 9/00* | (2006.01) |
| *C08L 5/08* | (2006.01) |

(52) U.S. Cl.
CPC .............. *A61K 47/61* (2017.08); *A61K 9/006* (2013.01); *A61K 31/575* (2013.01); *A61K 47/36* (2013.01); *C08L 5/08* (2013.01); *A61K 9/0043* (2013.01); *C08L 2201/06* (2013.01); *C08L 2203/02* (2013.01)

(58) Field of Classification Search
CPC ...... A61K 47/61; A61K 9/006; A61K 31/575; A61K 47/36; C08L 5/08
See application file for complete search history.

(56) References Cited

U.S. PATENT DOCUMENTS

| 6,958,325 | B2 | 10/2005 | Domb |
| 2009/0281056 | A1 | 11/2009 | Mori et al. |
| 2010/0197904 | A1 | 8/2010 | Asaoka et al. |
| 2010/0204102 | A1* | 8/2010 | Akiyoshi |
| 2011/0177017 | A1 | 7/2011 | Coffindaffer |
| 2011/0212901 | A1 | 9/2011 | Akiyoshi et al. |
| 2015/0231268 | A1 | 8/2015 | Nakai et al. |

FOREIGN PATENT DOCUMENTS

| CN | 103143027 | | 6/2013 |
| CN | 104945538 | A | 9/2015 |
| JP | 2013-516498 | | 5/2013 |
| KR | 2010-0037494 | | 4/2010 |
| WO | 2007/063725 | A1 | 6/2007 |
| WO | 2008/133267 | A1 | 11/2008 |
| WO | 2010/053140 | A1 | 5/2010 |
| WO | 2011/148116 | A2 | 12/2011 |
| WO | 2014/038641 | A1 | 3/2014 |

OTHER PUBLICATIONS

Hirofumi Takeuchi et al., "Mucoadhesive nanoparticulate systems for peptide drug delivery", Advanced Drug Delivery Reviews, vol. 47, p. 39-54, 2001.
Mitsutaka Maruta et al., "Real-time in vivo imaging of surface-modified liposomes to evaluate their behavior after pulmonary administration", European Journal of Pharmaceutics and Biopharmaceutics, vol. 86, p. 115-119 (2014).
Kohei Hironaka et al., "Design and evaluation of a liposomal delivery system targeting the posterior segment of the eye", Journal of Controlled Release, vol. 136, p. 247-253, 2009.
Lisa R. Schopf et al., "Topical Ocular Drug Delivery to the Back of the Eye by Mucus-Penetrating Particles", Trans Vis Sci Tech, 2015, vol. 4, No. 3, Article 11, pp. 1-12.
Jingguo Li et al., "Positively charged micelles based on a triblock copolymer demonstrate enhanced corneal penetration", Int J Nanomedcine, 2015, vol. 10, No. 1, pp. 6027-6037.
Laura Garcia-Posadas et al., "Hyaluronan receptors in the human ocular surface: a descriptive and comparative study of RHAMM and CD44 in tissues, cell lines and freshly collected samples", Histochemistry and Cell Biology, vol. 137, p. 165-176, 2012.
M de la Fuente et al., "Bioadhesive hyaluronan-chitosan nanoparticles can transport genes across the ocular mucosa and transfect ocular tissue", Gene Therapy, 2008, vol. 15, pp. 668-676.

(Continued)

*Primary Examiner* — Alma Pipic
(74) *Attorney, Agent, or Firm* — Browdy and Neimark, PLLC

(57) ABSTRACT

The present invention provides hyaluronic acid derivatives into which a certain cationic group and a certain hydrophobic group are introduced, the hyaluronic acid derivatives including one or more repeating units represented by the formula (Ia) and one or more repeating units represented by the formula (Ib).

13 Claims, 18 Drawing Sheets
Specification includes a Sequence Listing.

(56) References Cited

OTHER PUBLICATIONS

Jae Hyung Park et al., "Targeted delivery of low molecular drugs using chitosan and its derivatives", Advanced Drug Delivery Reviews, vol. 62, p. 28-41, 2010.
Heebeom Koo et al., "The movement of self-assembled amphiphilic polymeric nanoparticles in the vitreous and retina after intravitreal injection", Biomaterials, vol. 33, p. 3485-3493, 2012.
Hirohito Ayame et al.., "Self-Assembled Cationic Nanogels for Intracellular Protein Delivery", Bioconjugate Chemistry, vol. 19, p. 882-890, 2008.
Carole E. Schante et al., "Improvement of hyaluronic acid enzymatic stability by the grafting of amino-acids", Carbohydrate Polymers, vol. 87, p. 2211-2216, 2012.
Ki Young Choi, "Self-assembled hyaluronic acid nanoparticles as a potential drug carrier for cancer therapy: synthesis, characterization, and in vivo biodistribution", Journal of Materials Chemistry, vol. 19, p. 4102-4107, 2009.
Yan Shen et al., "Synthesis and characterization of low molecular weight hyaluronic acid-based cationic micelles for efficient siRNA deliveryl", Carbohydrate Polymers, vol. 77 (No. 1), p. 95-104, 2009.
Li, Jing et al., "Redox-sensitive micelles self-assembled from amphiphilic hyaluronic aciddeoxycholic acid conjugates for targeted intracellular delivery of paclitaxel", Biomaterials, 2012, vol. 33, pp. 2310-2320, ISSN 0142-9612.
Miao, Wenjun et al., "Cholesteryl hyaluronic acid-coated, reduced graphene oxide nanosheets for anti-cancer drug delivery", Biomaterials, 2013, vol. 34, pp. 9638-9647, ISSN 0142-9612.
Dong, Xuemeng et al., "Preparation and Characterization of Self-Assembled Nanopartides of Hyaluronic Acid-Deoxycholic Acid Conjugates", Journal of Nanomaterials, 2010, pp. 1-9, Article ID906936, ISSN 1687-4129.
Changyong Choi et al., "Preparation and Characterization of Deoxycholic Acid-Grafted Hyaluronic Acid as a Durg Carrier", Polymer(Korea), 2011, vol. 35, No. 2, pp. 119-123, ISSN 0379-153X.
International Search Report of PCT/JP2017/017954 dated Aug. 8, 2017.

\* cited by examiner

99k HA-Chol-17%/ArgNH₂-31%
0.02N DCl/(DMSO-d₆/D₂O)

99k HA-Chol-17%/EDA-37%
0.02N DCl/(DMSO-d₆/D₂O)

10k HA-Chol-15%/DET-69%
0.02N DCl/(DMSO-d$_6$/D$_2$O)

10k HA-Chol-15%/DET-69%
D$_2$O

99k HA-Chol-16%/LysNH$_2$-36%
0.02N DCl/(DMSO-d$_6$/D$_2$O)

10k HA-Chol-38%/ArgNH$_2$-22%/Me-17%
0.02N DCl/(DMSO-d$_6$/D$_2$O)

10k HA-Chol-33%/EDA-30%/Me-10%
0.02N DCl/(DMSO-$d_6$/$D_2O$)

10k HA-Chol-17%/DET-29%/Me-43%
0.02N DCl/(DMSO-$d_6$/$D_2O$)

10k HA-Chol-17%/DET-29%/Me-43%
D₂O

10k HA-Chol-37%/LysNH₂-22%/Me-11%
0.02N DCl/(DMSO-d₆/D₂O)

99k HA-Chol-27%/SPR-37%/Me-16%
0.02N DCl/(DMSO-$d_6$/$D_2O$)

10k HA-Chol-29%/PTMA-29%/Me-31%
0.02N DCl/(DMSO-$d_6$/$D_2O$)

10k HA-Chol-31%/PrOH-19%
0.02N DCl/ (DMSO-d$_6$/D$_2$O)

10k HA-Chol-31%/ArgNH$_2$-11%/PrOH-19%
0.02N DCl/ (DMSO-d$_6$/D$_2$O)

10k HA-Chol-16%/ArgNH₂-16%/EtOH-69%
DMSO-d₆

10k HA-Chol-17%/EDOBEA-52%
0.02N DCl/(DMSO-d₆/D₂O)

10k HA-Chol-17%/DEG-51%
0.02N DCl/(DMSO-d$_6$/D$_2$O)

10k HA-Chol-17%/AGMT-68%
0.02N DCl/(DMSO-d$_6$/D$_2$O)

10k HA-Chol-16%/IMD-67%
0.02N DCl/(DMSO-$d_6$/$D_2O$)

10k HA-Chol-15%/DPT-60%
0.02N DCl/(DMSO-$d_6$/$D_2O$)

10k HA-Chol-17%/BAEA-63%
0.02N DCl/(DMSO-d₆/D₂O)

10k HA-Chol-17%/DMA-76%
0.02N DCl/(DMSO-d₆/D₂O)

10k HA-Chol-12%/MPD-51%
0.02N DCl/(DMSO-$d_6$/$D_2O$)

10k HA-LysNH$_2$-91%/CA-23%
0.02N DCl/(DMSO-$d_6$/$D_2O$)

HA-C$_3$H$_6$-OCOO-Chol-20%/LysNH$_2$-29%
0.02N DCl/(DMSO-d$_6$/D$_2$O)

HA-CH$_2$-COO-Chol-13%/LysNH$_2$-70%
0.02N DCl/(DMSO-d$_6$/D$_2$O)

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial sequence
<220> FEATURE:
<223> OTHER INFORMATION: Apo B sense

<400> SEQUENCE: 1
gucaucacac ugaauaccaa u                                          21

<210> SEQ ID NO 2
<211> LENGTH: 23
<212> TYPE: RNA
<213> ORGANISM: Artificial sequence
<220> FEATURE:
<223> OTHER INFORMATION: Apo B antisense

<400> SEQUENCE: 2
auugguauuc agugugauga cac                                        23
```

HYALURONIC ACID DERIVATIVES INTO WHICH CATIONIC AND HYDROPHOBIC GROUPS ARE INTRODUCED

TECHNICAL FIELD

The present invention relates to hyaluronic acid derivatives modified by a cationic group and having a hydrophobic group introduced therein, complexes of the hyaluronic acid derivative and a drug, pharmaceutical compositions containing the hyaluronic acid derivative and a drug, and pharmaceutical compositions containing the hyaluronic acid derivative as an active ingredient.

BACKGROUND ART

In the human body, mucous membranes such as the gastrointestinal, throat, oral cavity, nasal cavity, aural cavity, corneal, conjunctival, lung, vaginal, and anal mucosae are present at various sites exposed to the external environment and internal organs. Mucous membranes are viscoelastic gels that function as barriers for protecting bodies from physicochemical stimuli such as drying and warming and pathogens such as viruses and disease germs.

Transmucosal drug administration is employed for systemic or topical applications; the former is beneficial from the viewpoint of QOL because it is noninvasive, and the latter is beneficial because it allows high-dose exposure to the target tissue with reduced systemic toxicity. In many cases, however, the mucoadhesion and permeability of the administered drug are low, and its effects are inadequate. In particular, when administered as eye drops, permeability of the drug is known to be very low due to tear excretion (NPL 1).

Liposomes (NPL 2 to 4), surface-modified nanosuspensions (NPL 5) and polymer micelles (NPL 6) have been reported as transmucosal drug delivery agents. These agents, however, are suitable for low-molecular-weight drugs, and they are unsuitable for protein and peptide drugs because of low enclosing efficiency, degeneration, and others. It cannot be acknowledged that they are widely used for small molecules, peptides, and proteins.

Additionally, for safety reasons, matrices for pharmaceutical agent must be non-antigenic, non-mutagenic, non-toxic, and biodegradable.

Polysaccharides were recently reported to be used as matrices for pharmaceutical carriers. One of these, hyaluronic acid (HA) is a biomaterial (polysaccharide) that was isolated from the vitreous body of a bull's eye by K. Meyer in 1934, and it has long been known as a main component of the extracellular matrix. HA is a type of glycosaminoglycan, which is consisted of disaccharide units having D-glucuronic acid and N-acetylglucosamine connected by a β(1→3)glycosidic linkage. The structure of HA does not differ chemically and physically between species and humans also have a metabolic pathway for HA. Therefore, it is one of the safest biomaterials for medical use, also with respect to the immunity and toxicity.

Besides its safety as a material, the properties of hyaluronic acid as a physiologically active material for inducing cell adhesion, proliferation, and migration have recently attracted interest. Furthermore, with respect to production, the mass production of high-molecular-weight hyaluronic acid has been made possible by employing microorganisms. For these reasons, several studies on drug delivery systems (DDS) with hyaluronic acid used as a matrix have been conducted. Successful conjugation of drugs with hyaluronic acid has been reported in drug targeting of cancerous tissue (PTL 4), liver targeting (PTL 5), and reduction of antigenicity (PTL 6). HA receptors, including CD44, RHAMM (Receptor for Hyaluronic Acid-Mediated Motility), LYVE-1 (LymphaticVessel Endothelial HA Receptor-1), and HARE (Hyaluronic acid Receptor for Endocytosis) have been reported to be present in the living body (NPL 16 and NPL 17). In particular, CD44 and RHAMM are overexpressed in many cancer cells. Therefore, attempts were made to use HA as a matrix for cancer targeting carrier. Examples include paclitaxel-HA conjugates (NPLs 18-20 and PTL 11), camptothecin-HA conjugates (PTL 12), doxorubicin-HPMA [N-(2-hydroxypropyl)methacrylamide]-HA conjugates (NPL 21), butyric acid-HA conjugates (NPL 22), doxorubicin enclosing HA-PEG-PLGA nanoparticles (NPL 23), siRNA-containing HA gels (NPL 24), and doxorubicin-containing HA-coated liposomes (NPL 25). Furthermore, HA derivatives conjugated with cholic acid via an ethylenediamine linker introduced by an amide linkage have been reported (NPL 26). These carriers containing HA as a matrix have been reported to be efficiently taken up in vitro by cells with high expression of CD44 (see, for example, NPL 18). Furthermore, it has been reported that CD44 and RHAMM are also expressed in the human cornea and conjunctiva (NPL 7), and that nucleic acid uptake is enhanced by hyaluronic acid (NPL 8). On the other hand, to prolong the retention in blood, hyaluronic acid derivatives with a highly modified carboxy in their glucuronic acid moieties have been developed and shown to be useful (PTL 7).

As further examples of drug carriers derived from polysaccharides, pullulan derivatives into which a cholesteryl group was introduced has been reported to form nano-sized fine particles in aqueous solution and serve as host molecules that form complexes with hydrophobic low-molecular-weight molecules, peptides, and proteins (NPL 13). Thermodynamic analyses of the pullulan derivatives after protein uptake indicated that the incorporated protein was stabilized by hydrogen bonding with the hydroxy in pullulan (NPL 14).

Further, carboxymethylcellulose (CMC; PTL 19) and chitosan modified with linoleic acid (NPL 15) have been reported to be used as materials for forming complexes with protein. Additionally, PTL 10 discloses a composition containing a hyaluronic acid derivative with a crosslinking group and a hydrophilic polysaccharide derivative with a hydrophobic group, in which the hyaluronic acid derivative with the crosslinking group was prepared by a crosslinking reaction of hyaluronic acid or its derivative having a group capable of crosslinking in the presence of the hydrophilic polysaccharide derivative. PTL 13 discloses that a hyaluronic acid derivative into which a cholesteryl group is introduced as a hydrophobic group, forms fine particles by association in water and forms complexes with drugs. In PTL 1, it has been reported that hyaluronic acid derivatives into which an amino acid and a group having a hydrophobic group are introduced form fine particles by association in water, form a complex with a drug, and exhibit high retention in blood.

There are reports describing introducing a hydrophobic group into a cationic polysaccharide chitosan and using it as a drug-enclosing carrier (NPL 9 and 10) and describing cationizing hydrophobized pullulan (NPL 11). For the cationized hyaluronic acids, there are reports describing that arginine was introduced (NPL 12, PTL 8) or quaternary amines were introduced (PTL 2 and 3).

It is known that hyaluronic acid derivatives in which the carboxy of the hyaluronic acid and that of a succinic acid monotocopherol ester are bound via $H_2N-(CH_2)_6-NH_2$, $H_2N-(CH_2)_2-S-S-(CH_2)_2-NH_2$, or $H_2N-(CH_2)_3-COOH$ can form micelles in aqueous solutions, which can be used as carriers to deliver water insoluble drugs (PTL 14).

Furthermore, it is known that the transfection efficiency of plasmid DNA was increased by introducing spermine or its ammonium salt into dextran and, into part of it, further introducing a cholesteryl group or a long-chain alkyl amine (PTL 15); compounds in which a hydrophobic long-chain amine and spermine as a cationic element are introduced into the carboxy of low-molecular-weight hyaluronic acid are useful for forming a complex with siRNA (NPL 27); cationized cellulose: polyoctanium 10 as a commercial product (PTL 16); compounds in which the carboxy of hyaluronic acid and cholic acid are bound via ethylenediamine are useful as drug carriers (PTL 17); and compounds in which the carboxy of hyaluronic acid and the hydroxy of a fat-soluble compound tocopherol are bonded via a diamine or hydroxyalkylamine can be used as drug carriers (PTL 18).

CITATION LIST

Patent Literature

PTL 1: International publication No. 2014/038641
PTL 2: International publication No. 2008/133267
PTL 3: International publication No. 2007/63725
PTL 4: International publication No. 92/06714
PTL 5: Japanese Unexamined Patent Application Publication No. 2001-81103
PTL 6: Japanese Unexamined Patent Application Publication No. Hei 2-273176
PTL 7: International publication No. 2006/028110
PTL 8: International publication No. 2011/148116
PTL 9: International publication No. 2002/022154
PTL 10: International publication No. 2008/136536
PTL 11: International publication No. 2004/035629
PTL 12: International publication No. 2009/074678
PTL 13: International publication No. 2010/053140
PTL 14: Chinese patent publication No. 104945538
PTL 15: U.S. Pat. No. 6,958,325
PTL 16: Japanese translation of PCT International publication No. 2013-516498
PTL 17: Chinese patent publication No. 103143027
PTL 18: Chinese patent publication No. 104945538

Non Patent Literature

NPL 1: Advanced Drug Delivery Reviews, Vol. 61, p. 158-171, 2009
NPL 2: Advanced Drug Delivery Reviews, Vol. 47, p. 39-54, 2001
NPL 3: European Journal of Pharmaceutics and Biopharmaceutics, Vol. 86, p. 115-119, 2014
NPL 4: Journal of Controlled Release, Vol. 136, p. 247-253, 2009
NPL 5: Translational Vision Science and Technology, Vol. 4, No. 3, Article 11, p. 1-12, 2015
NPL 6: International Journal of Nanomedicine, Vol. 10, p. 6027-6037, 2015
NPL 7: Histochemistry and Cell Biology, Vol. 137, p. 165-176, 2012
NPL 8: Gene Therapy, Vol. 15, p. 668-676, 2008
NPL 9: Advanced Drug Delivery Reviews, Vol. 62, p. 28-41, 2010
NPL 10: Biomaterials, Vol. 33, p. 3485-3493, 2012
NPL 11: Bioconjugate Chemistry, Vol. 19, p. 882-890, 2008
NPL 12: CARBOHYDRATE Polymers, Vol. 87, p. 2211-2216, 2012
NPL 13: Macromolecules, Vol. 26, p. 3062-3068, 1993
NPL 14: Colloids and Surfaces, Vol. 112, p. 91-95, 1996
NPL 15: Carbohydrate Polymers, Vol. 62, p. 293-298, 2005
NPL 16: MOLECULAR PHARMACEUTICS, Vol. 5, p. 474-486, 2008
NPL 17: Journal of Drug Targeting, Vol. 16, p. 91-107, 2008
NPL 18: Bioconjugate Chemistry, Vol. 10, p. 755-763, 1999
NPL 19: Clinical Cancer Research, Vol. 14, p. 3598-3606, 2008
NPL 20: Bioconjugate Chemistry, Vol. 19, p. 1319-1325, 2008
NPL 21: Pharmaceutical Research, Vol. 19, p. 396-402, 2002
NPL 22: Clinical Cancer Research, Vol. 10, p. 4822-4830, 2004
NPL 23: Nanomedicine: Nanotechnology, Biology, and Medicine, Vol. 3, p. 246-257, 2007
NPL 24: Journal of Controlled Release, Vol. 119, p. 245-252, 2007
NPL 25: Neoplasia, Vol. 6, p. 343-353, 2004
NPL 26: Journal of Materials Chemistry, Vol. 19, p. 4102-4107, 2009
NPL 27: Carbohydrate Polymers, Vol. 77 (No. 1), p. 95-104, 2009

SUMMARY OF INVENTION

Technical Problem

An object of the invention is to provide hyaluronic acid derivatives having properties of both safety and mucoadhesive property/mucosal permeability. Another object of the invention is to provide pharmaceutical compositions comprising the hyaluronic acid derivative, in particular, complexes of the hyaluronic acid derivative and a drug.

Solution to Problem

In the study to solve the problems, the present inventors found that hyaluronic acid derivatives into which a certain cationic group and a certain hydrophobic group are introduced have safety and mucoadhesive property/mucosal permeability, and that complexes of the hyaluronic acid derivative and a drug have good properties as pharmaceutical compositions, thereby completing the present invention.

The present invention relates to hyaluronic acid derivatives having both mucoadhesive property and mucosal permeability, and to complexes containing the hyaluronic acid derivative and a compound having a pharmacological activity. Furthermore, the present invention relates to methods for producing the hyaluronic acid derivatives and to pharmaceutical compositions suitable for transmucosal administration containing a drug and the hyaluronic acid derivative and methods for producing the compositions.

In an aspect of the present invention, hyaluronic acid derivatives according to the following (1) to (15) are provided.

(1) A hyaluronic acid derivative comprising:
one or more repeating units, the repeating unit being represented by the formula (Ia):

[Chem. 1]

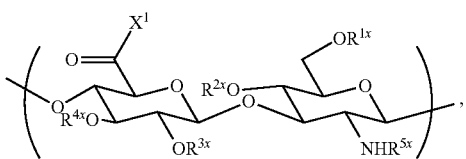
(Ia)

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl) carbonyl;
$R^{5x}$ is selected from a hydrogen atom, formyl, and ($C_{1-6}$ alkyl)carbonyl;
$X^1$ represents -$NR^7$—$CHR^8$—$(CH_2)_{n1}$-$A^1$-$B^1$;
$R^7$ represents a hydrogen atom or $C_{1-6}$ alkyl;
$R^8$ is selected from a hydrogen atom, —$CONR^9R^{10}$, and —$CO_2R^{11}$;
$A^1$ is selected from a single bond, —$(Y^1$—$CH_2$—$CH_2)_{n2}$—, and —$(Y^2$—$CH_2$—$CH_2$—$(CH_2)_{na})_{n3}$—;
$B^1$ is selected from —$NR^{12}R^{13}$, —$N^+R^{12}R^{13}R^{14}Q^-$, —$N(-A^2$-$NR^{12}R^{13})_2$, 5- to 10-membered heteroaryl having 1 to 4 nitrogen atoms, —$NHC(=NH)NH_2$, and a group:

[Chem. 2]

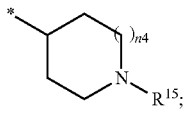

$Y^1$ and $Y^2$ independently represent an oxygen atom or —$NR^{16}$—;
n1 represents an integer of 1 to 6, n2 and n3 independently represent an integer of 1 to 10, na is an integer of 1 or 2, and n4 is an integer of 0 to 3;
$A^2$ represents $C_{2-10}$ alkylene;
$R^9$, $R^{10}$, $R^{11}$, $R^{12}$, $R^{13}$, $R^{14}$, $R^{15}$, $R^{16}$, and $R^{16a}$ independently represent a hydrogen atom or $C_{1-6}$ alkyl; and
$Q^-$ represents a counter anion;
with the proviso that when $R^8$ is a hydrogen atom and $B^1$ is —$NR^{12}R^{13}$, i) n1 is an integer of 1 to 3 and $A^1$ is a single bond, or ii) n1 is 1, $A^1$ is —$(Y^1$—$CH_2$—$CH_2)_{n2}$—, and n2 is an integer of 1 to 3; and
one or more repeating units, the repeating unit being represented by the formula (Ib):

[Chem. 3]

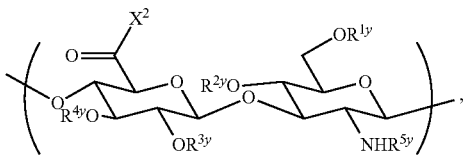
(Ib)

wherein
$R^{1y}$, $R^{2y}$, $R^{3y}$, and $R^{4y}$ are each independently selected from a hydrogen atom, $C_{1-6}$ alkyl, formyl, and ($C_{1-6}$ alkyl) carbonyl;
$R^{5y}$ is selected from a hydrogen atom, formyl, and ($C_{1-6}$ alkyl)carbonyl;
$X^2$ is selected from —O—$Z^3$, —O—$Z^1$—$Z^2$, —O—$Z^0$—$Z^1$—$Z^2$, —O—$Z^0$—$Z^2$, —$NR^b$—$Z^3$, —$NR^6$—$Z^1$—$Z^2$, and —$NR^{31}$—$CHR^{32}$—$(CH_2)_{n11}$-$A^3$-$B^2$;
$R^6$ represents a hydrogen atom or $C_{1-6}$ alkyl;
$Z^0$ is selected from the following groups:

[Chem. 4]

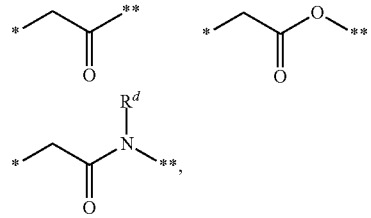

wherein "*" represents the position attached to an oxygen atom and "**" represents the position attached to $Z^1$ or $Z^2$;
$Z^1$ is $C_{1-30}$ alkylene or —$(CH_2CH_2O)_m$—$CH_2CH_2$—, wherein one to five groups independently selected from —O—, —$NR^g$—, and —S—S— are optionally inserted into the alkylene, and m is an integer selected from 1 to 100;
$Z^2$ is selected from the following groups:
-$NR^b$—$Z^3$,
-$NR^b$—COO—$Z^3$,
-$NR^b$—CO—$Z^3$,
-$NR^b$—CO—$NR^c$—$Z^3$,
—COO—$Z^3$,
—CO—$NR^c$—$Z^3$,
—O—$Z^3$,
—O—CO—$NR^c$—$Z^3$,
—O—COO—$Z^3$,
—S—$Z^3$,
—CO—$Z^a$—S—$Z^3$,
—O—CO—$Z^b$—S—$Z^3$,
-$NR^b$—CO—$Z^b$—S—$Z^3$, and
—S—S—$Z^3$;
$R^b$ and $R^c$ are independently selected from a hydrogen atom, $C_{1-20}$ alkyl, amino $C_{2-20}$ alkyl, and hydroxy $C_{2-20}$ alkyl, wherein one to three groups independently selected from —O— and —$NR^f$— are optionally inserted into the alkyl moiety of the group;
$R^d$ independently represents a hydrogen atom or $C_{1-6}$ alkyl;
$R^f$ is independently selected from a hydrogen atom, $C_{1-12}$ alkyl, amino $C_{2-12}$ alkyl, and hydroxy $C_{2-12}$ alkyl, wherein one or two groups selected from —O— and —NH— are optionally inserted into the alkyl moiety of the group;
$R^g$ is independently selected from a hydrogen atom, $C_{1-20}$ alkyl, amino $C_{2-20}$ alkyl, and hydroxy $C_{2-20}$ alkyl, wherein one to three groups independently selected from —O— and —NH— are optionally inserted into the alkyl moiety of the group;
$Z^3$ is a steryl group;
$Z^a$ is $C_{1-5}$ alkylene;
$Z^b$ is $C_{2-8}$ alkylene or $C_{2-8}$ alkenylene;
$R^{31}$ represents a hydrogen atom or $C_{1-6}$ alkyl;
$R^{32}$ is selected from a hydrogen atom, —$CONR^{33}R^{34}$, and —$CO_2R^{35}$;

A³ is selected from a single bond, —(Y³—CH₂—CH₂)$_{n12}$—, and —(Y⁴—CH₂—CH₂—(CH₂)$_{n14}$)$_{n13}$—;

B² is selected from —NR³⁶—X⁴, —N(—X⁴)₂, —N(-A⁴-NR³⁶R³⁷)(-A⁴-NR³⁶—X⁴), —N(-A⁴-NR³⁶—X⁴)₂, and —NHC(=NH)NH—X⁴;

Y³ and Y⁴ independently represent an oxygen atom or —NR$^{16a}$—;

n11 represents an integer of 1 to 6, n12 and n13 independently represent an integer of 1 to 10, and n14 represents an integer of 1 or 2;

A⁴ represents C$_{2-10}$ alkylene;

R³³, R³⁴, R³⁵, R³⁶, and R³⁷ independently represent a hydrogen atom or C$_{1-6}$ alkyl;

X⁴ is —CO₂—Z³, —CO₂—Z¹—Z², —CO₂—Z⁰—Z¹—Z², —CO₂—Z⁰—Z², —CO—Z¹—Z², —CO—Z⁰—Z¹—Z², —CO—Z⁰—Z², —COR$^a$, —Z³, —O—Z³, —Z¹—Z², —Z⁰—Z¹—Z¹—Z² or —Z⁰—Z²; and R$^a$ is selected from C$_{8-50}$ alkyl, C$_{8-50}$ alkenyl, and C$_{8-50}$ alkynyl.

(2) The hyaluronic acid derivative according to (1), further comprising one or more repeating units, the repeating unit being represented by the formula (II):

[Chem. 5]

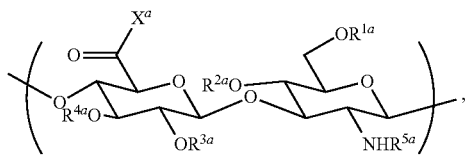

(II)

wherein

R$^{1a}$, R$^{2a}$, R$^{3a}$, and R$^{4a}$ are each independently selected from a hydrogen atom, C$_{1-6}$ alkyl, formyl, and (C$_{1-6}$ alkyl)carbonyl;

R$^{5a}$ is selected from a hydrogen atom, formyl, and (C$_{1-6}$ alkyl)carbonyl; and X$^a$ is selected from hydroxy and —O⁻Q⁺, wherein Q⁺ represents a counter cation.

(3) The hyaluronic acid derivative according to (1) or (2), further comprising one or more repeating units, the repeating unit being represented by the formula (III):

[Chem. 6]

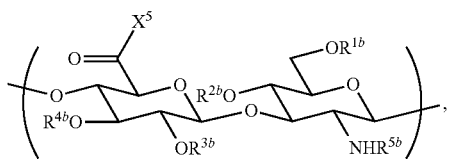

(III)

wherein

R$^{1b}$, R$^{2b}$, R$^{3b}$, and R$^{4b}$ are each independently selected from a hydrogen atom, C$_{1-6}$ alkyl, formyl, and (C$_{1-6}$ alkyl)carbonyl;

R$^{5b}$ is selected from a hydrogen atom, formyl, and (C$_{1-6}$ alkyl)carbonyl;

X⁵ represents -NR¹⁷—R¹⁸;

R¹⁷ represents a hydrogen atom or C$_{1-6}$ alkyl; and

R¹⁸ represents C$_{1-10}$ alkyl optionally substituted with one or more hydroxy.

(4) The hyaluronic acid derivative according to any of (1) to (3), wherein X¹ is independently selected from the following formulas:

[Chem. 7]

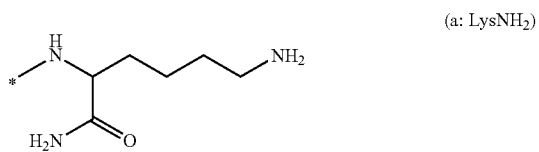
(a: LysNH₂)

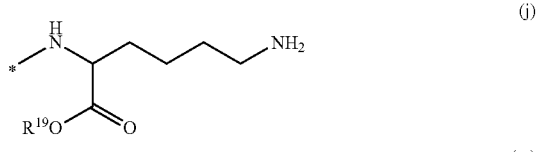
(j)

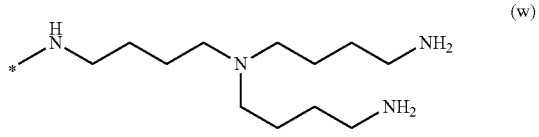
(w)

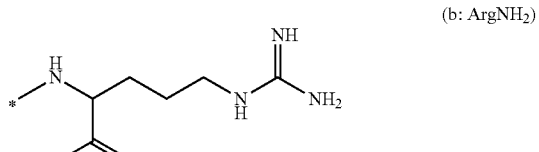
(b: ArgNH₂)

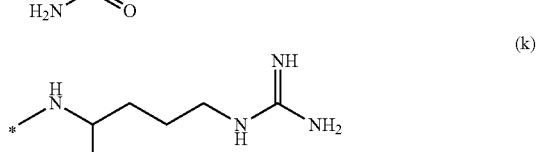
(k)

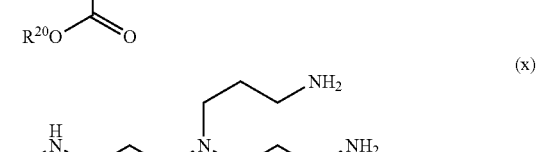
(x)

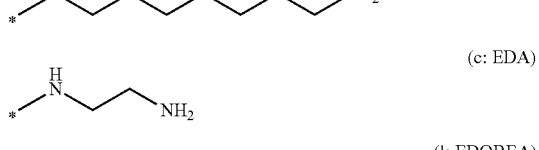
(c: EDA)

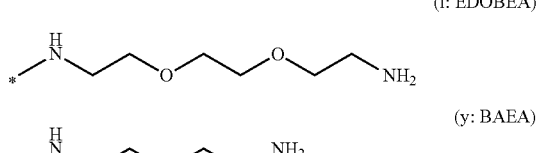
(l: EDOBEA)

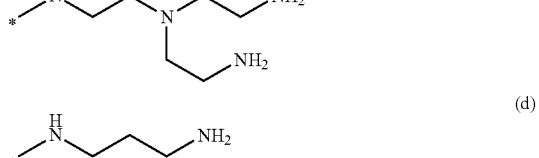
(y: BAEA)

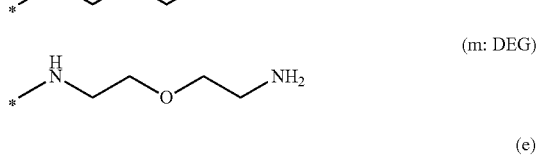
(d)

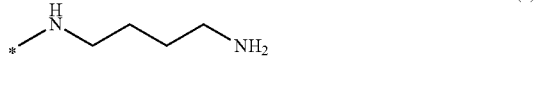
(m: DEG)

(e)

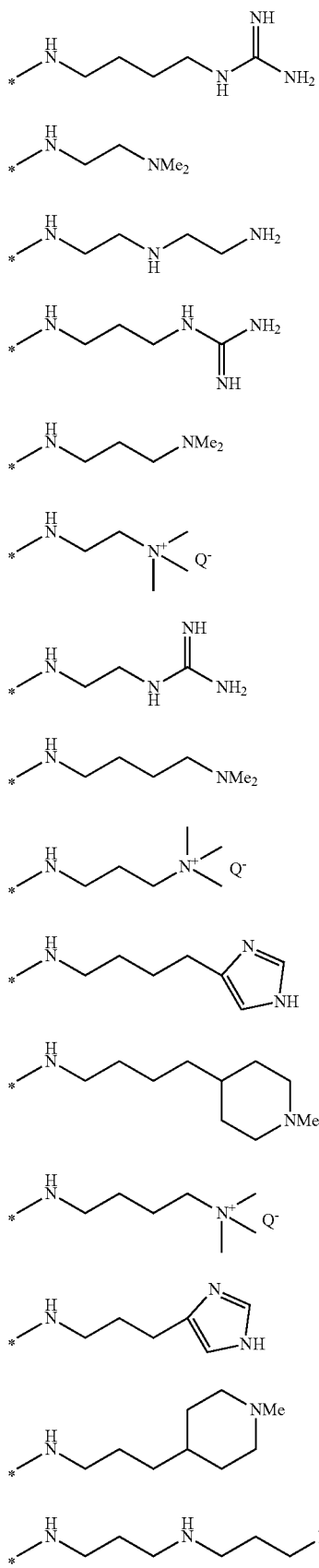
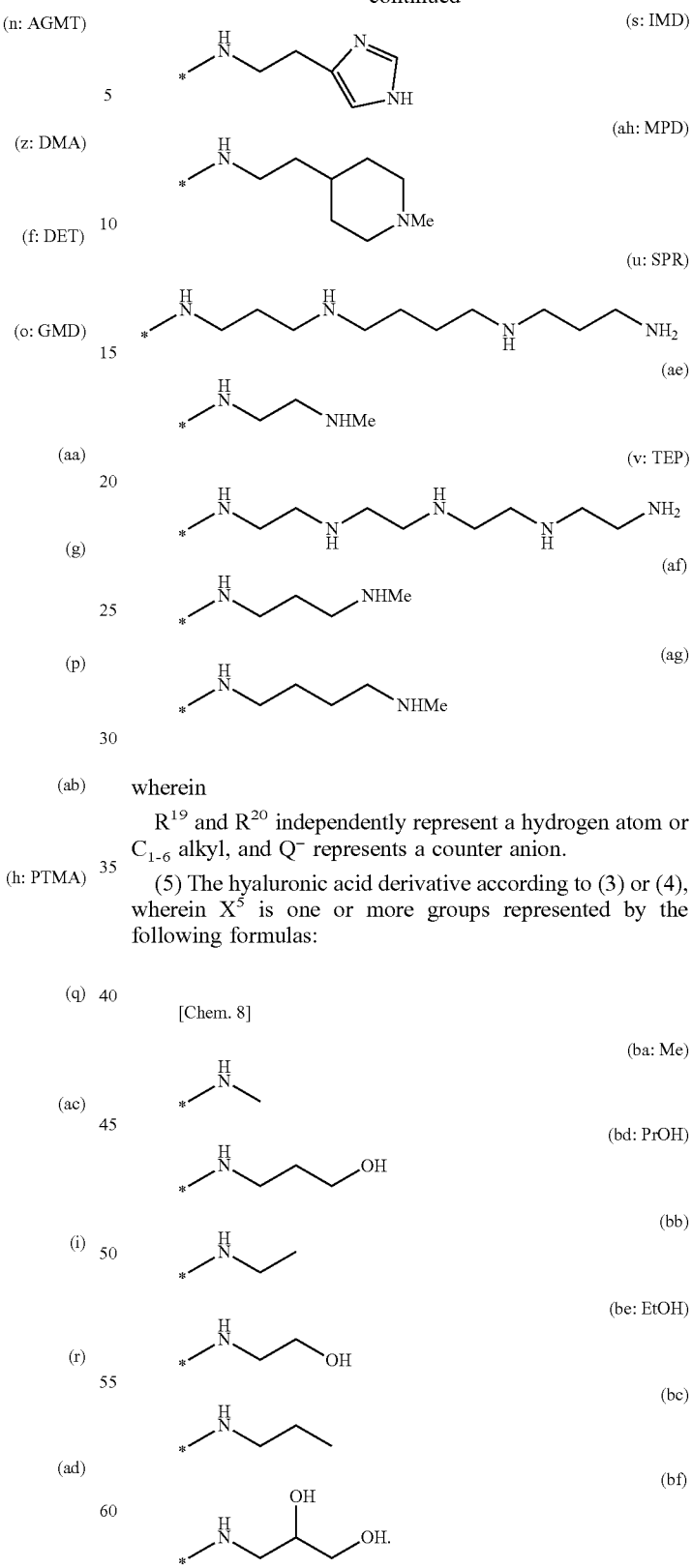
wherein
R[19] and R[20] independently represent a hydrogen atom or $C_{1-6}$ alkyl, and $Q^-$ represents a counter anion.
(5) The hyaluronic acid derivative according to (3) or (4), wherein $X^5$ is one or more groups represented by the following formulas:
(6) The hyaluronic acid derivative according to any of (1) to (5), wherein the steryl group is represented by any one of the following formulas:

[Chem. 9]

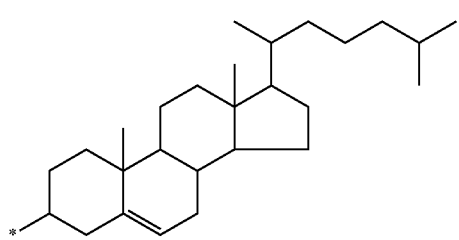
(ck)

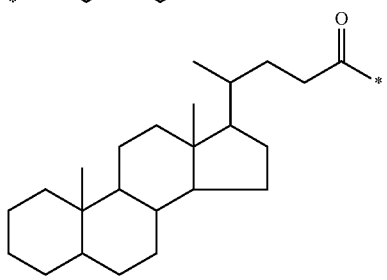
(cl: CA)

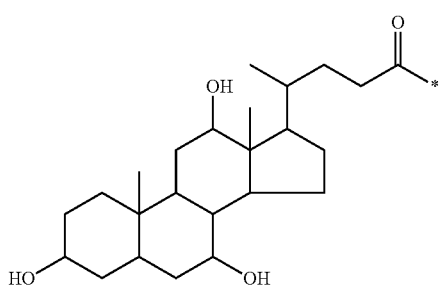
(cm)

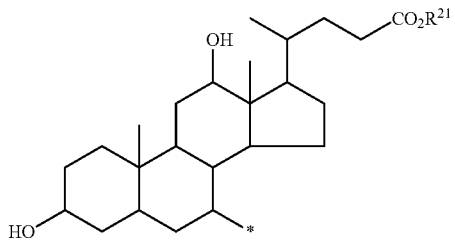
(cn)

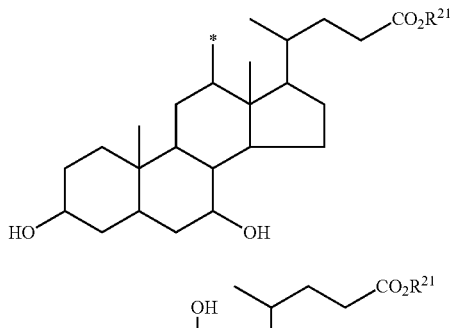
(co)

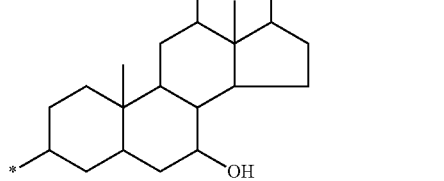
(cp)

wherein
$R^{21}$ independently represents a hydrogen atom or $C_{1-6}$ alkyl.

(7) The hyaluronic acid derivative according to any of (1) to (6), wherein $X^2$ is —$NR^6$—$Z^1$—$Z^2$, —O—$Z^1$—$Z^2$ or —O—$Z^0$—$Z^2$; or $X^2$ is —$NR^{31}$—$CHR^{32}$—$(CH_2)_{n11}$-$A^3$-$B^2$ and $X^4$ is —CO—$Z^1$—$Z^2$ or —$Z^3$.

(8) The hyaluronic acid derivative according to any of (1) to (7), wherein a proportion of the repeating units represented by the formula (Ib) wherein $X^2$ is —O—$Z^3$, —O—$Z^1$—$Z^2$, —O—$Z^0$—$Z^2$, —$NR^6$—$Z^1$—$Z^2$ or —$NR^{31}$—$CHR^{32}$—$(CH_2)_{n11}$-$A^3$-$B^2$ in repeating units of disaccharide present in the hyaluronic acid derivative is 3 to 55%.

(9) The hyaluronic acid derivative according to any of (1) to (8), wherein a proportion of the repeating units represented by the formula (Ia) in repeating units of disaccharide present in the hyaluronic acid derivative is 1 to 75%.

(10) The hyaluronic acid derivative according to any of (1) to (7), wherein a sum of a proportion of the repeating units represented by the formula (Ia) and a proportion of the repeating units represented by the formula (Ib) wherein $X^2$ is —$NR^{31}$—$CHR^{32}$—$(CH_2)_{n11}$-$A^3$-$B^2$ in repeating units of disaccharide present in the hyaluronic acid derivative is 30 to 100%.

(11) The hyaluronic acid derivative according to any of (1) to (10), wherein
$R^8$ is selected from —$CONR^9R^{10}$ and —$CO_2R^{11}$; or
$B^1$ is selected from —$N^+R^{12}R^{13}R^{14}Q^-$, 5- to 10-membered heteroaryl having 1 to 4 nitrogen atoms, —NHC(=NH)NH$_2$, and a group:

[Chem. 10]

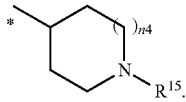

(12) A pharmaceutical composition comprising the hyaluronic acid derivative according to any of (1) to (11).

(13) A method of producing a pharmaceutical composition with an increased mucosal permeability, the method comprising the step of complexing a drug and a hyaluronic acid derivative, the hyaluronic acid derivative comprising:
one or more repeating units, the repeating unit being represented by the formula (Ia):

[Chem. 11]

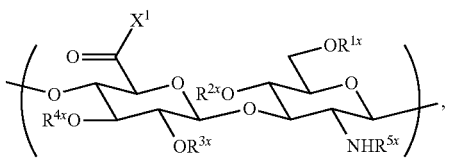
(Ia)

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;
$R^{5x}$ is selected from a hydrogen atom, formyl, and ($C_{1-6}$ alkyl)carbonyl;
$X^1$ represents -$NR^7$—$CHR^8$—$(CH_2)_{n1}$-$A^1$-$B^1$;
$R^7$ represents a hydrogen atom or $C_{1-6}$ alkyl;

$R^8$ is selected from a hydrogen atom, —$CONR^9R^{10}$, and —$CO_2R^{11}$;

$A^1$ is selected from a single bond, —$(Y^1-CH_2-CH_2)_{n2}$—, and —$(Y^2-CH_2-CH_2-(CH_2)_{na})_{n3}$—;

$B^1$ is selected from —$NR^{12}R^{13}$, —$N^+R^{12}R^{13}R^{14}Q^-$, —$N(-A^2-NR^{12}R^{13})_2$, 5- to 10-membered heteroaryl having 1 to 4 nitrogen atoms, —$NHC(=NH)NH_2$, and a group:

[Chem. 12]

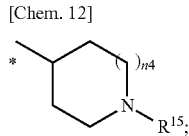

$Y^1$ and $Y^2$ independently represent an oxygen atom or —$NR^{16}$—;

n1 represents an integer of 1 to 6, n2 and n3 independently represent an integer of 1 to 10, na represents an integer of 1 or 2, and n4 represents an integer of 0 to 3;

$A^2$ represents $C_{2-10}$ alkylene;

$R^9$, $R^{10}$, $R^{11}$, $R^{12}$, $R^{13}$, $R^{14}$, $R^{15}$, $R^{16}$, and $R^{16a}$ independently represent a hydrogen atom or $C_{1-6}$ alkyl; and $Q^-$ represents a counter anion; and one or more repeating units, the repeating unit being represented by the formula (Ib):

[Chem. 13]

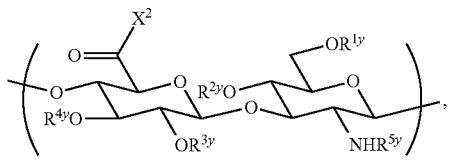

(Ib)

wherein $R^{1y}$, $R^{2y}$, $R^{3y}$, and $R^{4y}$ are each independently selected from a hydrogen atom, $C_{1-6}$ alkyl, formyl, and ($C_{1-6}$ alkyl)carbonyl;

$R^{5y}$ is selected from a hydrogen atom, formyl, and ($C_{1-6}$ alkyl)carbonyl;

$X^2$ is selected from —$O-Z^3$, —$OR^a$, —$NR^aR^{5z}$, —$O-Z^1-Z^2$, —$O-Z^0-Z^1-Z^2$, —$O-Z^0-Z^2$, —$NR^b-Z^3$, —$NR^6-Z^1-Z^2$, and —$NR^{31}-CHR^{32}-(CH_2)_{n11}-A^3-B^2$;

$R^{5z}$ and $R^6$ represent a hydrogen atom or $C_{1-6}$ alkyl;

$R^a$ is selected from $C_{8-50}$ alkyl, $C_{8-50}$ alkenyl, and $C_{8-50}$ alkynyl;

$Z^0$ is selected from the following groups:

[Chem. 14]

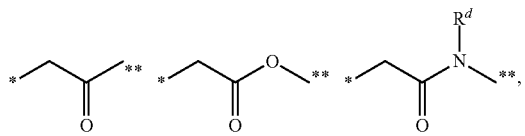

wherein "*" represents the position attached to an oxygen atom and "**" represents the position attached to $Z^1$ or $Z^2$;

$Z^1$ is $C_{1-30}$ alkylene or —$(CH_2CH_2O)_m-CH_2CH_2$—, wherein one to five groups independently selected from —O—, —$NR^g$—, and —S—S— are optionally inserted into the alkylene, and m is an integer selected from 1 to 100;

$Z^2$ is selected from the following groups:
-$NR^b-Z^3$,
-$NR^b-COO-Z^3$,
-$NR^b-CO-Z^3$,
-$NR^b-CO-NR^c-Z^3$,
—$COO-Z^3$,
—$CO-NR^c-Z^3$,
—$O-Z^3$,
—$O-CO-NR^c-Z^3$,
—$O-COO-Z^3$,
—$S-Z^3$,
—$CO-Z^a-S-Z^3$,
—$O-CO-Z^b-S-Z^3$,
-$NR^b-CO-Z^b-S-Z^3$, and
—$S-S-Z^3$;

$R^b$ and $R^c$ are independently selected from a hydrogen atom, $C_{1-20}$ alkyl, amino $C_{2-20}$ alkyl, and hydroxy $C_{2-20}$ alkyl, wherein one to three groups independently selected from —O— and —$NR^f$— are optionally inserted into the alkyl moiety of the group;

$R^d$ independently represents a hydrogen atom or $C_{1-6}$ alkyl;

$R^f$ is independently selected from a hydrogen atom, $C_{1-12}$ alkyl, amino $C_{2-12}$ alkyl, and hydroxy $C_{2-12}$ alkyl, wherein one or two groups selected from —O— and —NH— are optionally inserted into the alkyl moiety of the group;

$R^g$ is independently selected from a hydrogen atom, $C_{1-20}$ alkyl, amino $C_{2-20}$ alkyl, and hydroxy $C_{2-20}$ alkyl, wherein one to three groups independently selected from —O— and —NH— are optionally inserted into the alkyl moiety of the group;

$Z^3$ is a steryl group;

$Z^a$ is $C_{1-5}$ alkylene;

$Z^b$ is $C_{2-8}$ alkylene or $C_{2-8}$ alkenylene;

$R^{31}$ represents a hydrogen atom or $C_{1-6}$ alkyl;

$R^{32}$ is selected from a hydrogen atom, —$CONR^{33}R^{34}$, and —$CO_2R^{35}$;

$A^3$ is selected from a single bond, —$(Y^3-CH_2-CH_2)_{n12}$—, and —$(Y^4-CH_2-CH_2-(CH_2)_{n14})_{n13}$—;

$B^2$ is selected from —$NR^{36}-X^4$, —$N(-X^4)_2$, —$N(-A^4-NR^{36}R^{37})(-A^4-NR^{36}-X^4)$, —$N(-A^4-NR^{36}-X^4)_2$, and —$NHC(=NH)NH-X^4$;

n11 represents an integer of 1 to 6, n12 and n13 independently represent an integer of 1 to 10, and n14 represents an integer of 1 or 2;

$A^4$ represents $C_{2-10}$ alkylene;

$R^{33}$, $R^{34}$, $R^{35}$, $R^{36}$, and $R^{37}$ independently represent a hydrogen atom or $C_{1-6}$ alkyl; and $X^4$ represents —$CO_2-Z^3$, —$CO_2-Z^1-Z^2$, —$CO_2-Z^0-Z^1-Z^2$, —$CO_2-Z^0-Z^2$, —$CO-Z^1-Z^2$, —$CO-Z^0-Z^1-Z^2$, —$CO-Z^0-Z^2$, —$COR^a$, —$Z^3$, —$O-Z^3$, —$Z^1-Z^2$, —$Z^0-Z^1-Z^2$ or —$Z^0-Z^2$.

(14) The method of producing according to (13), wherein the hyaluronic acid derivative is a hyaluronic acid derivative according to any of (1) to (11).

(15) A pharmaceutical composition for transmucosal administration comprising:
a drug; and
the hyaluronic acid derivative according to (13).

As the hyaluronic acid derivative according to (13), the hyaluronic acid derivatives according to (1) to (11) are preferable. Further, the pharmaceutical compositions for transmucosal administration are preferably used for preventing or treating ophthalmic diseases such as dry eye syndrome, uveitis, conjunctivitis, age-related macular degeneration, glaucoma, optic nerve protection, and retinitis pigmentosa, respiratory diseases, gastrointestinal diseases, ear, nose and throat diseases, reproductive organ diseases, and stomatitis. When the pharmaceutical compositions for transmucosal administration are used for preventing or treating stomatitis, they may include the hyaluronic acid derivative according to (13) without the drug.

In another aspect of the present invention, hyaluronic acid derivatives according to the following (2-1) to (2-15) are provided.

(2-1) A hyaluronic acid derivative comprising:

one or more repeating units, the repeating unit being represented by the formula (Ia):

[Chem. 15]

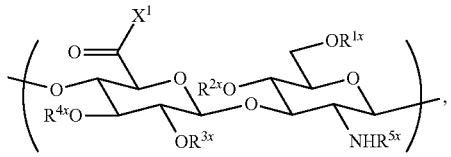

(Ia)

wherein $R^{1x}$, $R^{2x}$, $R^{3x}$, and $R^{4x}$ are each independently selected from a hydrogen atom, $C_{1-6}$ alkyl, formyl, and ($C_{1-6}$ alkyl) carbonyl;

$R^{5x}$ is selected from a hydrogen atom, formyl, and ($C_{1-6}$ alkyl)carbonyl;

$X^1$ represents $-NR^7-CHR^8-(CH_2)_{n1}-A^1-B^1$;

$R^7$ represents a hydrogen atom or $C_{1-6}$ alkyl;

$R^8$ is selected from a hydrogen atom, $-CONR^9R^{10}$, and $-CO_2R^{11}$;

$A^1$ is selected from a single bond, $-(Y^1-CH_2-CH_2)_{n2}-$, and $-(Y^2-CH_2-CH_2-(CH_2)_{na})_{n3}-$;

$B^1$ is selected from $-NR^{12}R^{13}$, $-N^+R^{12}R^{13}R^{14}Q^-$, $-N(-A^2-NR^{12}R^{13})_2$, 4- to 10-membered heteroaryl having 1 to 4 nitrogen atoms, $-NHC(=NH)NH_2$, and a group:

[Chem. 16]

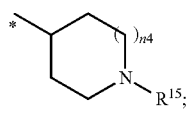

$Y^1$ and $Y^2$ independently represent an oxygen atom or $-NR^{16}-$;

n1 represents an integer of 1 to 6, n2 and n3 independently represent an integer of 1 to 10, na represents an integer of 1 or 2, and n4 represents an integer of 0 to 3;

$A^2$ represents $C_{2-10}$ alkylene;

$R^9$, $R^{10}$, $R^{11}$, $R^{12}$, $R^{13}$, $R^{14}$, $R^{15}$, and $R^{16}$ independently represent a hydrogen atom or $C_{1-6}$ alkyl;

$Q^-$ represents a counter anion;

with the proviso that when $R^8$ is a hydrogen atom and $B^1$ is $-NR^{12}R^{13}$, i) n1 is an integer of 1 to 3 and $A^1$ is a single bond, or ii) n1 is 1, $A^1$ is $-(Y^1-CH_2-CH_2)_{n2}-$, and n2 is an integer of 1 to 3; and one or more repeating units, the repeating unit being represented by the formula (Ib):

[Chem. 17]

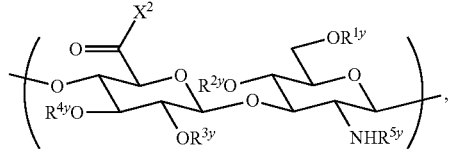

(Ib)

wherein $R^{1y}$, $R^{2y}$, $R^{3y}$, and $R^{4y}$ are each independently selected from a hydrogen atom, $C_{1-6}$ alkyl, formyl, and ($C_{1-6}$ alkyl) carbonyl;

$R^{5y}$ is selected from a hydrogen atom, formyl, and ($C_{1-6}$ alkyl)carbonyl;

$X^2$ is selected from $-O-Z^3$, $-O-Z^1-Z^2$, $-NR^6-Z^1-Z^2$, and $-NR^{31}-CHR^{32}-(CH_2)_{n11}-A^3-B^2$;

$R^6$ represents a hydrogen atom or $C_{1-6}$ alkyl;

$Z^1$ is $C_{2-30}$ alkylene or $-(CH_2CH_2O)_m-CH_2CH_2-$, wherein one to five groups independently selected from $-O-$, $-NR^g-$, and $-S-S-$ are optionally inserted into the alkylene, and m is an integer selected from 1 to 100;

$Z^2$ is selected from the following groups:
-$NR^b-Z^3$,
-$NR^b-COO-Z^3$,
-$NR^b-CO-Z^3$,
-$NR^b-CO-NR^c-Z^3$,
$-COO-Z^3$,
$-CO-NR^c-Z^3$,
$-O-CO-NR^c-Z^3$,
$-O-COO-Z^3$,
$-S-Z^3$,
$-CO-Z^a-S-Z^3$,
$-O-CO-Z^b-S-Z^3$,
-$NR^b-CO-Z^b-S-Z^3$, and
$-S-S-Z^3$;

$R^b$ and $R^c$ are independently selected from a hydrogen atom, $C_{1-20}$ alkyl, amino $C_{2-20}$ alkyl, and hydroxy $C_{2-20}$ alkyl, wherein one to three groups independently selected from $-O-$ and $-NR^f-$ are optionally inserted into the alkyl moiety of the group;

$R^f$ is independently selected from a hydrogen atom, $C_{1-12}$ alkyl, amino $C_{2-12}$ alkyl, and hydroxy $C_{2-12}$ alkyl, wherein one or two groups selected from $-O-$ and $-NH-$ are optionally inserted into the alkyl moiety of the group;

$R^g$ is independently selected from a hydrogen atom, $C_{1-20}$ alkyl, amino $C_{2-20}$ alkyl, and hydroxy $C_{2-20}$ alkyl, wherein one to three groups independently selected from $-O-$ and $-NH-$ are optionally inserted into the alkyl moiety of the group;

$Z^3$ is a steryl group;

$Z^a$ is $C_{1-5}$ alkylene;

$Z^b$ is $C_{2-8}$ alkylene or $C_{2-8}$ alkenylene;

$R^{31}$ represents a hydrogen atom or $C_{1-6}$ alkyl;

$R^{32}$ is selected from a hydrogen atom, $-CONR^{33}R^{34}$, and $-CO_2R^{35}$;

$A^3$ is selected from a single bond, $-(Y^3-CH_2-CH_2)_{n12}-$, and $-(Y^4-CH_2-CH_2-(CH_2)_{n14})_{n13}-$;

$B^2$ is selected from $-NR^{36}-X^4$, $-N(-A^4-NR^{36}R^{37})(-A^4-NR^{36}-X^4)$, $-N(-A^4-NR^{36}-X^4)_2$, and $-NHC(=NH)NH-X^4$;

n11 represents an integer of 1 to 6, n12 and n13 independently represent an integer of 1 to 10, and n14 represents an integer of 1 or 2;

$Y^3$ and $Y^4$ independently represent an oxygen atom or $-NR^{16}-$;

$A^4$ represents $C_{2-10}$ alkylene;

$R^{33}$, $R^{34}$, $R^{35}$, $R^{36}$, and $R^{37}$ independently represent a hydrogen atom or $C_{1-6}$ alkyl;

$X^4$ is $-CO_2-Z^3$, $-CO-Z^1-Z^2$, $-COR^a$ or $Z^3$; and $R^a$ is selected from $C_{8-50}$ alkyl, $C_{8-50}$ alkenyl, and $C_{8-50}$ alkynyl.

(2-2) The hyaluronic acid derivative according to (2-1), further comprising one or more repeating units, the repeating unit being represented by the formula (II):

[Chem. 18]

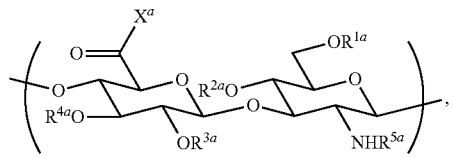

(II)

wherein $R^{1a}$, $R^{2a}$, $R^{3a}$, and $R^{4a}$ are each independently selected from a hydrogen atom, $C_{1-6}$ alkyl, formyl, and ($C_{1-6}$ alkyl)carbonyl;

$R^{5a}$ is selected from a hydrogen atom, formyl, and ($C_{1-6}$ alkyl)carbonyl; and $X^a$ is selected from hydroxy and $-O^-Q^+$, wherein $Q^+$ represents a counter cation.

(2-3) The hyaluronic acid derivative according to (2-1) or (2-2), further comprising one or more repeating units, the repeating unit being represented by the formula (III):

[Chem. 19]

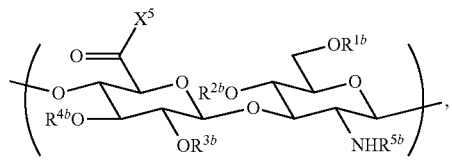

(III)

wherein $R^{1b}$, $R^{2b}$, $R^{3b}$, and $R^{4b}$ are each independently selected from a hydrogen atom, $C_{1-6}$ alkyl, formyl, and ($C_{1-6}$ alkyl)carbonyl;

$R^{5b}$ is selected from a hydrogen atom, formyl, and ($C_{1-6}$ alkyl)carbonyl;

$X^5$ represents $-NR^{17}-R^{18}$;

$R^{17}$ represents a hydrogen atom or $C_{1-6}$ alkyl; and $R^{18}$ represents $C_{1-10}$ alkyl optionally substituted with one or more hydroxy.

(2-4) The hyaluronic acid derivative according to any of (2-1) to (2-3), wherein $X^1$ is independently selected from the following formulas:

[Chem. 20]

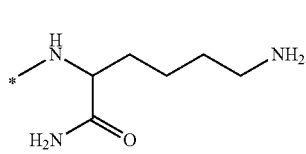

(a: LysNH$_2$)

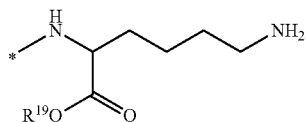

(j)

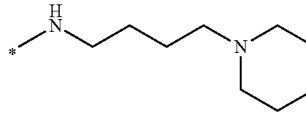

(w)

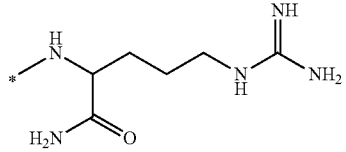

(b: ArgNH$_2$)

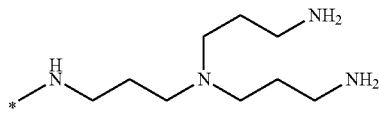

(k)

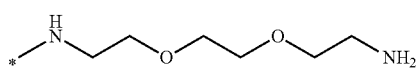

(x)

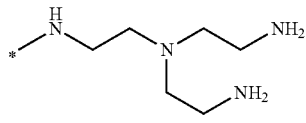

(c: EDA)

(l: EDOBEA)

(y: BAEA)

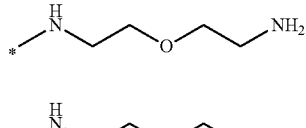

(d)

(m: DEG)

(e)

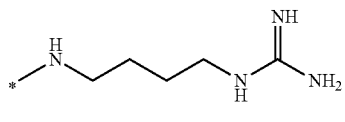

(n)

-continued

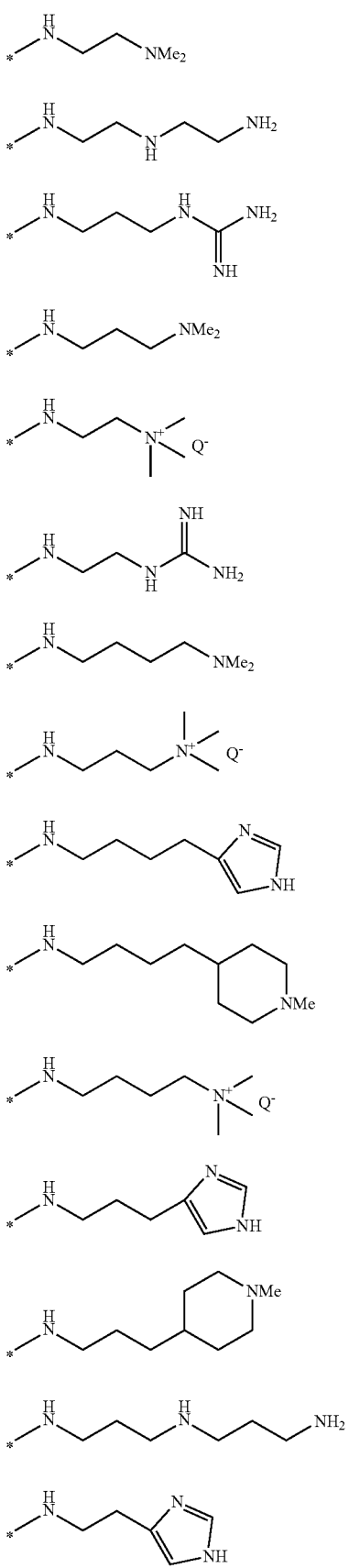
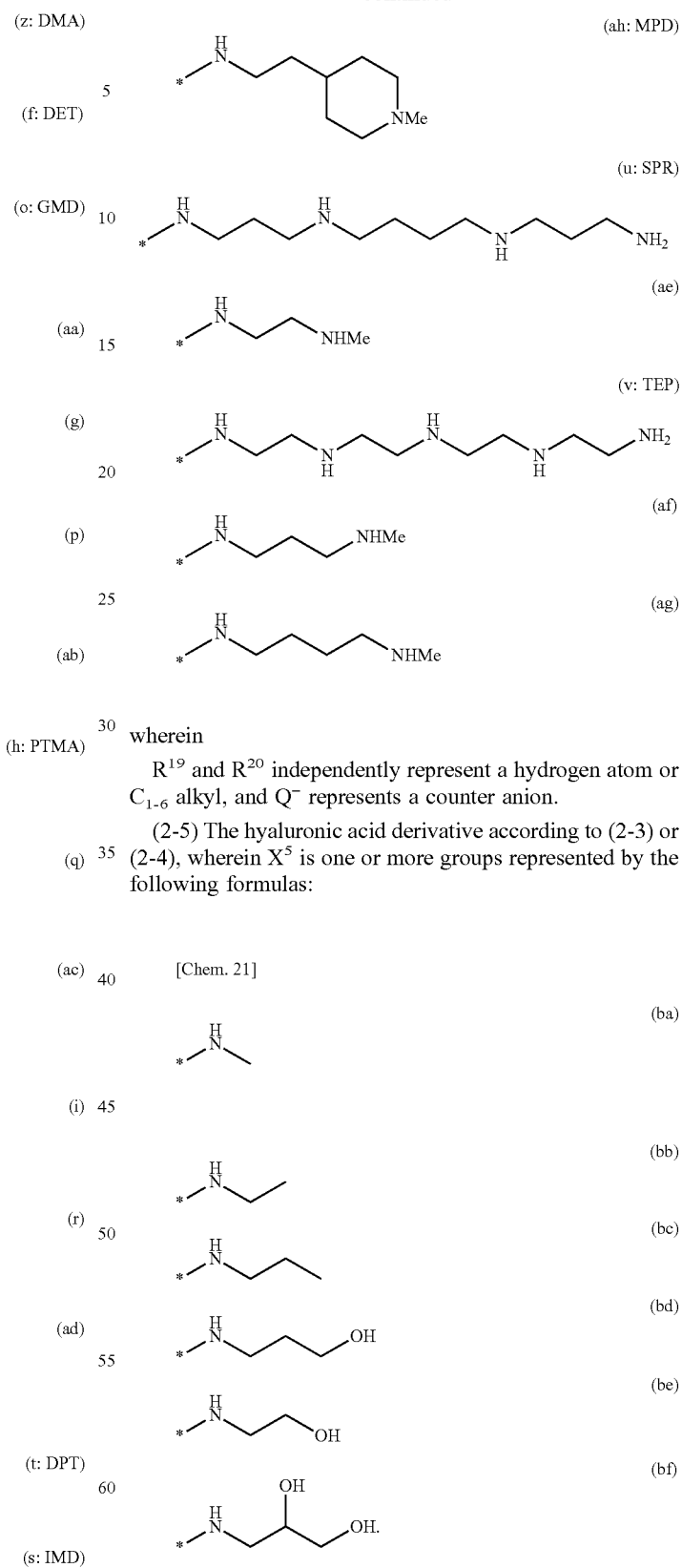

wherein $R^{19}$ and $R^{20}$ independently represent a hydrogen atom or $C_{1-6}$ alkyl, and $Q^-$ represents a counter anion.

(2-5) The hyaluronic acid derivative according to (2-3) or (2-4), wherein $X^5$ is one or more groups represented by the following formulas:

[Chem. 21]

(2-6) The hyaluronic acid derivative according to any of (2-1) to (2-5), wherein the steryl group is represented by any one of the following formulas:

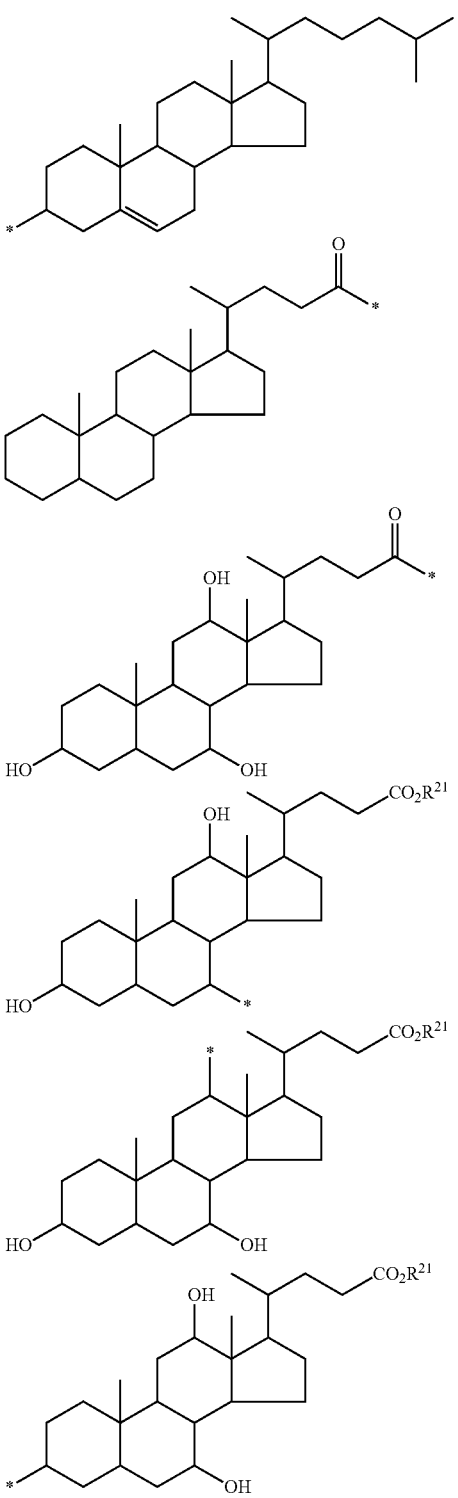

wherein

R$^{21}$ independently represents a hydrogen atom or C$_{1-6}$ alkyl.

(2-7) The hyaluronic acid derivative according to any of (2-1) to (2-6), wherein X$^2$ is —NR$^6$—Z$^1$—Z$^2$ or —NR$^{31}$—CHR$^{32}$—(CH$_2$)$_{n11}$-A$^3$-B$^2$, and X$^4$ is —CO—Z$^1$—Z$^2$.

(2-8) The hyaluronic acid derivative according to any of (2-1) to (2-7), wherein a proportion of the repeating units represented by the formula (Ib) wherein X$^2$ is —O—Z$^3$, —O—Z$^1$—Z$^2$, or —NR$^6$—Z$^1$—Z$^2$ in repeating units of disaccharide present in the hyaluronic acid derivative is 3 to 55%.

(2-9) The hyaluronic acid derivative according to any of (2-1) to (2-8), wherein a proportion of the repeating units represented by the formula (Ia) in repeating units of disaccharide present in the hyaluronic acid derivative is 1 to 75%.

(2-10) The hyaluronic acid derivative according to any of (2-1) to (2-7), wherein a sum of a proportion of the repeating units represented by the formula (Ia) and a proportion of the repeating units represented by the formula (Ib) wherein X$^2$ is —NR$^{31}$—CHR$^{32}$—(CH$_2$)$_{n11}$-A$^3$-B$^2$ in repeating units of disaccharide present in the hyaluronic acid derivative is 30 to 100%.

(2-11) The hyaluronic acid derivative according to any of (2-1) to (2-10), wherein R$^8$ is selected from —CONR$^9$R$^{10}$ and —CO$_2$R$^{11}$; or B$^1$ is selected from —N$^+$R$^{12}$R$^{13}$R$^{14}$Q$^-$, 4- to 10-membered heteroaryl having 1 to 4 nitrogen atoms, —NHC(=NH)NH$_2$, and a group:

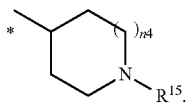

(2-12) A method of producing a pharmaceutical composition with an increased mucosal permeability, the method comprising the step of complexing a drug and a hyaluronic acid derivative, the hyaluronic acid derivative comprising:

one or more repeating units, the repeating unit being represented by the formula (Ia):

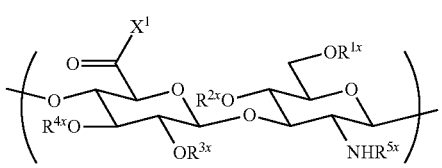

R$^{1x}$, R$^{2x}$, R$^{3x}$, and R$^{4x}$ are each independently selected from a hydrogen atom, C$_{1-6}$ alkyl, formyl, and (C$_{1-6}$ alkyl) carbonyl;

R$^{5x}$ is selected from a hydrogen atom, formyl, and (C$_{1-6}$ alkyl)carbonyl;

X$^1$ represents -NR$^7$—CHR$^8$—(CH$_2$)$_{n1}$-A$^1$-B$^1$;

R$^7$ represents a hydrogen atom or C$_{1-6}$ alkyl;

R$^8$ is selected from a hydrogen atom, —CONR$^9$R$^{10}$, and —CO$_2$R$^{11}$;

A is selected from a single bond, —(Y$^1$—CH$_2$—CH$_2$)$_{n2}$—, and —(Y$^2$—CH$_2$—CH$_2$—(CH$_2$)$_{na}$)$_{n3}$—;

B$^1$ is selected from —NR$^{12}$R$^{13}$, —N$^+$R$^{12}$R$^{13}$R$^{14}$Q$^-$, —N(-A$^2$-NR$^{12}$R$^{13}$)$_2$, 4- to 10-membered heteroaryl having 1 to 4 nitrogen atoms, —NHC(=NH)NH$_2$, and a group:

[Chem. 25]

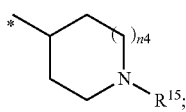

Y¹ and Y² independently represent an oxygen atom or —NR$^{16}$—;

n1 represents an integer of 1 to 6, n2 and n3 independently represent an integer of 1 to 10, na represents an integer of 1 or 2, and n4 represents an integer of 0 to 3;

A² represents $C_{2-10}$ alkylene;

R⁹, R¹⁰, R¹¹, R¹², R¹³, R¹⁴, R¹⁵, and R¹⁶ independently represent a hydrogen atom or $C_{1-6}$ alkyl;

Q⁻ represents a counter anion; and one or more repeating units, the repeating unit being represented by the formula (Ib):

[Chem. 26]

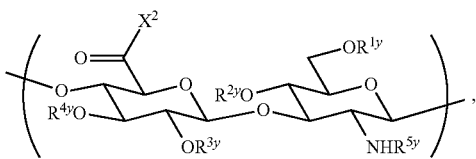

(Ib)

wherein

R$^{1y}$, R$^{2y}$, R$^{3y}$, and R$^{4y}$ are each independently selected from a hydrogen atom, $C_{1-6}$ alkyl, formyl, and ($C_{1-6}$ alkyl) carbonyl;

R$^{5y}$ is selected from a hydrogen atom, formyl, and ($C_{1-6}$ alkyl)carbonyl;

X² is selected from —O—Z³, —OR$^a$, —NR$^a$R$^{5z}$, —O—Z¹—Z², —NR⁶—Z¹—Z², and —NR$^{31}$—CHR$^{32}$—(CH$_2$)$_{n11}$-A³-B²;

R$^{5z}$ and R⁶ represent a hydrogen atom or $C_{1-6}$ alkyl;

R$^a$ is selected from $C_{8-50}$ alkyl, $C_{8-50}$ alkenyl, and $C_{8-50}$ alkynyl;

Z¹ is $C_{2-30}$ alkylene or —(CH$_2$CH$_2$O)$_m$—CH$_2$CH$_2$—, wherein one to five groups independently selected from —O—, —NR$^g$—, and —S—S— are optionally inserted into the alkylene, and m is an integer selected from 1 to 100;

Z² is selected from the following groups:
-NR$^b$—Z³,
-NR$^b$—COO—Z³,
-NR$^b$—CO—Z³,
-NR$^b$—CO—NR$^c$—Z³,
—COO—Z³,
—CO—NR$^c$—Z³,
—O—CO—NR$^c$—Z³,
—O—COO—Z³,
—S—Z³,
—CO—Z$^a$—S—Z³,
—O—CO—Z$^b$—S—Z³,
-NR$^b$—CO—Z$^b$—S—Z³, and
—S—S—Z³;

R$^b$ and R$^c$ are independently selected from a hydrogen atom, $C_{1-20}$ alkyl, amino $C_{2-20}$ alkyl, and hydroxy $C_{2-20}$ alkyl, wherein one to three groups independently selected from —O— and —NR$^f$— are optionally inserted into the alkyl moiety of the group;

R$^f$ is independently selected from a hydrogen atom, $C_{1-12}$ alkyl, amino $C_{2-12}$ alkyl, and hydroxy $C_{2-12}$ alkyl, wherein one or two groups selected from —O— and —NH— are optionally inserted into the alkyl moiety of the group;

R$^g$ is independently selected from a hydrogen atom, $C_{1-20}$ alkyl, amino $C_{2-20}$ alkyl, and hydroxy $C_{2-20}$ alkyl, wherein one to three groups independently selected from —O— and —NH— are optionally inserted into the alkyl moiety of the group;

Z³ is a steryl group;

Z$^a$ is $C_{1-5}$ alkylene;

Z$^b$ is $C_{2-8}$ alkylene or $C_{2-8}$ alkenylene;

R$^{31}$ represents a hydrogen atom or $C_{1-6}$ alkyl;

R$^{32}$ is selected from a hydrogen atom, —CONR$^{33}$R$^{34}$, and —CO$_2$R$^{35}$;

A³ is selected from a single bond, —(Y³—CH$_2$—CH$_2$)$_{n12}$—, and —(Y⁴—CH$_2$—CH$_2$—(CH$_2$)$_{n14}$)$_{n13}$—;

B² is selected from —NR$^{36}$—X⁴, —N(-A⁴-NR$^{36}$R$^{37}$)(-A⁴-NR$^{36}$—X⁴), —N(-A⁴-NR$^{36}$—X⁴)$_2$, and —NHC(=NH)NH—X⁴;

Y³ and Y⁴ independently represent an oxygen atom or —NR$^{16}$—;

n11 represents an integer of 1 to 6, n12 and n13 independently represent an integer of 1 to 10, and n14 represents an integer of 1 or 2;

A⁴ represents $C_{2-10}$ alkylene;

R$^{33}$, R$^{34}$, R$^{35}$, R$^{36}$, and R$^{37}$ independently represent a hydrogen atom or $C_{1-6}$ alkyl; and X⁴ represents —CO$_2$—Z³, —CO—Z¹—Z², —COR$^a$ or Z³.

(2-13) The method according to (2-12), wherein the hyaluronic acid derivative is a hyaluronic acid derivative according to any of (2-1) to (2-11).

(2-14) A pharmaceutical composition for transmucosal administration comprising:

a drug; and the hyaluronic acid derivative according to (2-12).

(2-15) The pharmaceutical composition according to (2-14), wherein the hyaluronic acid derivative is a hyaluronic acid derivative according to any of (2-1) to (2-11).

When R⁸ is a hydrogen atom, B¹ is —NR$^{12}$R$^{13}$, and A¹ is a single bond, n1 is preferably 1 to 2.

When R$^{18}$ is substituted with one or more hydroxy, R$^{18}$ is preferably $C_{2-10}$ alkyl.

Note that na's whose number is n3 and n14's whose number is n13 may be the same or different.

When X⁴ is Z³, Z³ is preferably a cholanoyl group.

n4 is preferably 0, 1 or 2, more preferably 0 or 1, and even more preferably 1.

Pharmaceutical compositions obtained by forming a complex of the hyaluronic acid derivative of the present invention and a drug make it possible to increase the mucosal permeability of the drug. Further, pharmaceutical compositions with better properties such as those with better mucoadhesive property of the drug, a higher absorptivity of the drug, a higher bioavailability of the drug, a lower toxicity or less adverse effect of the drug, a longer retention time of the drug in mucous membranes, better tissue migration including intraocular migration of the drug, a longer retention time of the drug in tissues, a higher chemical stability of the drug, a higher physical stability of the drug, and a higher efficacy of the drug can be produced by forming complexes of the hyaluronic acid derivatives of the present invention and a drug. These pharmaceutical compositions are suitable for transmucosal administration. Further, the hyaluronic acid derivatives of the present invention themselves have a great safety because hyaluronic acid which is a safe biomaterial for medical use is used as a starting material.

In pharmaceutical compositions for transmucosal administration including a drug and the hyaluronic acid derivative according to (12), complexes of the hyaluronic acid derivative according to (12) and an effective drug such as a low-molecular-weight compound, a protein or a peptide can be formed preferably by a) mixing nanosized particles (nanogel) having a size of the nanometer order (1 to 1000 nm) formed by self-association of the hyaluronic acid derivative according to (12) and a drug in aqueous solution to enclose the drug in the nanogel or adhere it onto the surface of the nanogel, b) coating particles obtained by pulverizing the drug with the hyaluronic acid derivative according to (12), c) mixing or blending the drug with the hyaluronic acid derivative according to (12) in a dry form. Complexes of a drug and the hyaluronic acid derivative can also be formed by coating crystalline or amorphous fine particles of the drug or a complex of the drug and another substrate such as a lactic acid/glycolic acid copolymer (PLGA) with the hyaluronic acid derivative of the present invention. Alternatively, complexes can be formed by mixing dry drug and the hyaluronic acid derivative of the present invention in a dry form. By such formations of complexes, it is possible to produce pharmaceutical compositions having an increased mucosal permeability and pharmaceutical compositions for transmucosal administration.

Advantageous Effects of Invention

By using the hyaluronic acid derivatives of the present invention, a preparation for transmucosal administration enclosing, in a large amount while maintaining its bioactivities, a drug, in particular, a low-molecular-weight compound, a nucleic acid or a protein or a peptide having an efficacy can be provided. In addition, hyaluronic acid derivatives of the present invention are excellent with respect to the safety compared with polyethylene imine having a similar cationic property and have especially excellent properties as a carrier for pharmaceutical compositions with respect to both mucoadhesive property/mucosal permeability and cytotoxicity of the drug. Further, hyaluronic acid derivatives of the present invention can be buccally administered as an active ingredient to prevent or treat diseases such as stomatitis.

BRIEF DESCRIPTION OF DRAWINGS

FIG. 3-1 represents an example of $^1$H-NMR spectrum of HA-Chol/DET prepared in Example 2-3 in a DC1/DMSO/D$_2$O mixed solution (the percent incorporation of cholesteryl: 15% and the percent incorporation of DET: 69%).

FIG. 3-2 represents an example of $^1$H-NMR spectrum of HA-Chol/DET prepared in Example 2-3 in D$_2$O (the percent incorporation of cholesteryl: 15% and the percent incorporation of DET: 69%).

FIG. 7-1 represents an example of $^1$H-NMR spectrum of HA-Chol/DET/Me prepared in Example 2-7 in a DC1/DMSO/D$_2$O mixed solution (the percent incorporation of cholesteryl: 17%, the percent incorporation of DET: 29%, and the percent incorporation of Me: 43%).

FIG. 7-2 represents an example of $^1$H-NMR spectrum of HA-Chol/DET/Me prepared in Example 2-7 in D$_2$O (the percent incorporation of cholesteryl: 17%, the percent incorporation of DET: 29%, the percent incorporation of Me: 43%).

FIG. 11-1 represents an example of $^1$H-NMR spectrum of HA-Chol/PrOH prepared in Example 2-14 in a DC1/DMSO/D$_2$O mixed solution (the percent incorporation of cholesteryl: 31% and the percent incorporation of PrOH: 19%).

FIG. 11-2 represents an example of $^1$H-NMR spectrum of HA-Chol/ArgNH$_2$/PrOH prepared in Example 2-14 in a DC1/DMSO/D$_2$O mixed solution (the percent incorporation of cholesteryl: 31%, the percent incorporation of ArgNH$_2$: 11%, and the percent incorporation of PrOH: 19%).

FIG. 13-1 represents an example of $^1$H-NMR spectrum of HA-Chol/EDOBEA prepared in Example 4-1-1 in a DC1/DMSO/D$_2$O mixed solution (the percent incorporation of cholesteryl: 17% and the percent incorporation of EDOBEA: 52%).

FIG. 13-2 represents an example of $^1$H-NMR spectrum of HA-Chol/DEG prepared in Example 4-1-2 in a DC1/DMSO/D$_2$O mixed solution (the percent incorporation of cholesteryl: 17% and the percent incorporation of DEG: 51%).

FIG. 13-3 represents an example of $^1$H-NMR spectrum of HA-Chol/AGMT prepared in Example 4-1-3 in a DC1/

DMSO/D₂O mixed solution (the percent incorporation of cholesteryl: 17% and the percent incorporation of AGMT: 68%).

Figure 4:
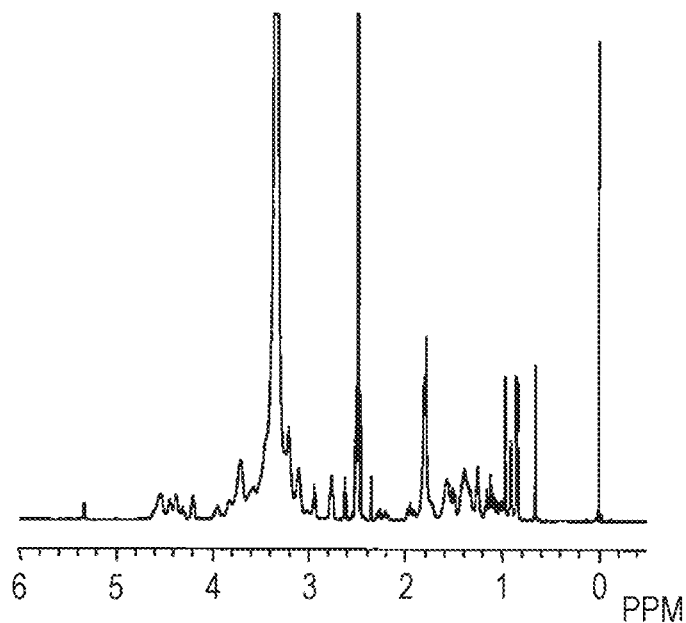
FIG. 4 represents an example of $^1$H-NMR spectrum of HA-Chol/LysNH$_2$ prepared in Example 2-4 in a DC1/DMSO/D$_2$O mixed solution (the percent incorporation of cholesteryl: 16% and the percent incorporation of LysNH$_2$: 36%).
Figures 1, 13:
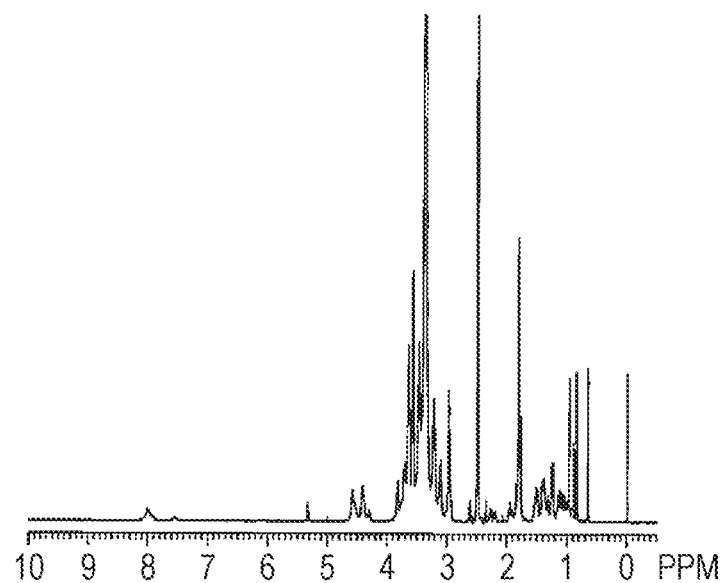
Figures 2, 13:
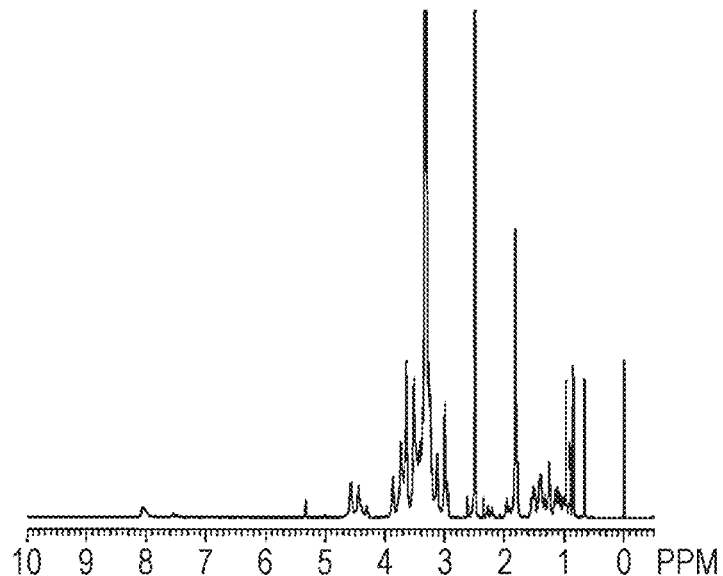
Figures 3, 13:
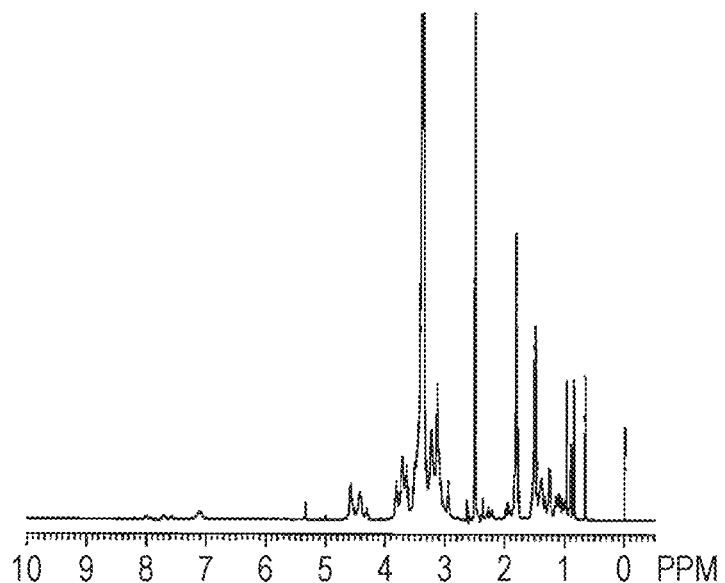
Figures 4, 13:
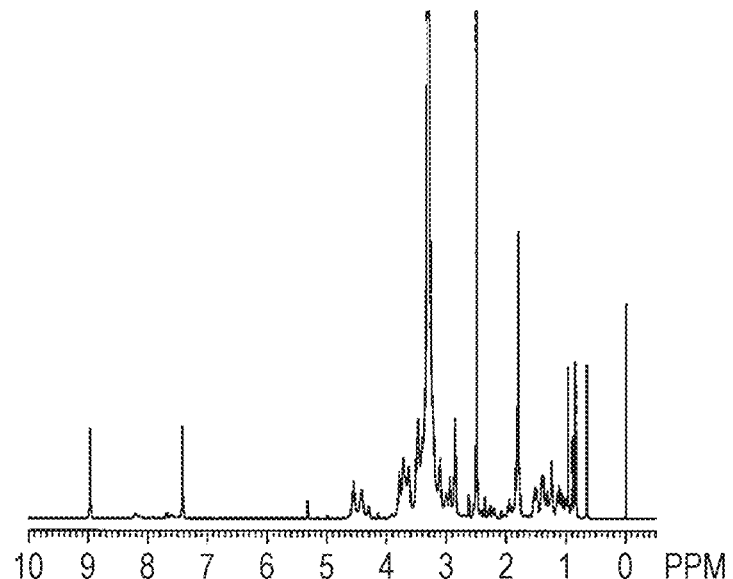
Figures 5, 13:
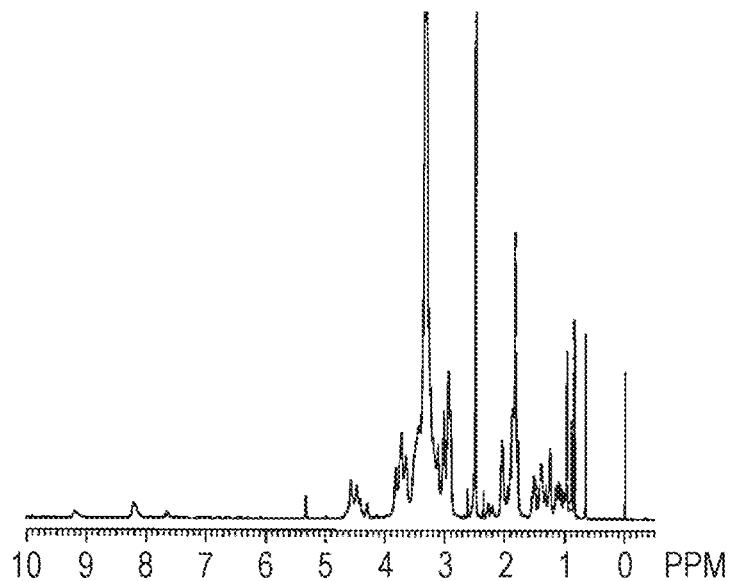
Figures 6, 13:
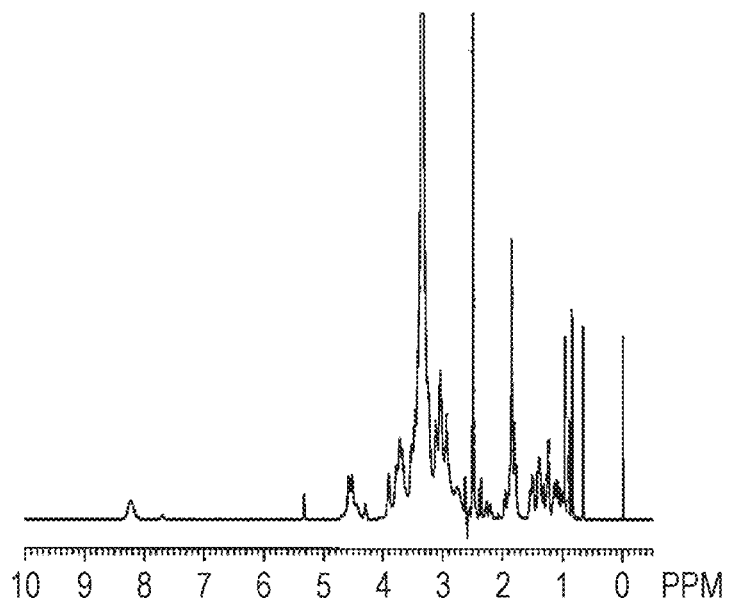
Figures 7, 13:
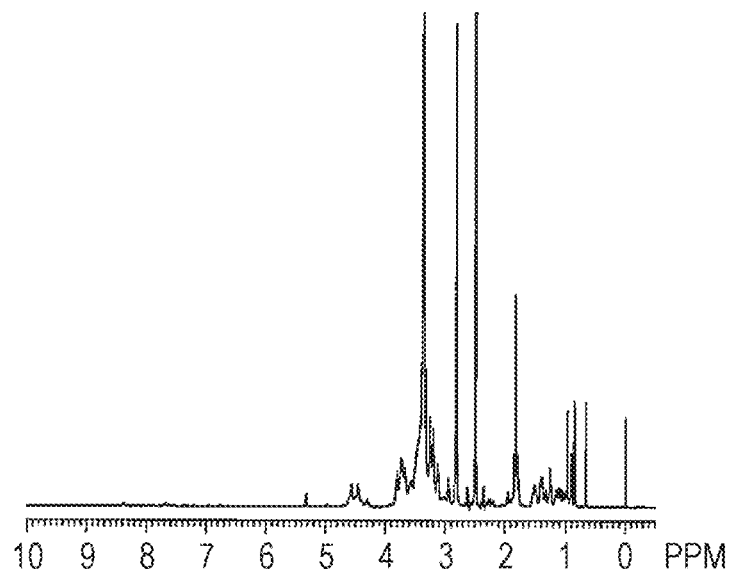
Figures 8, 13:
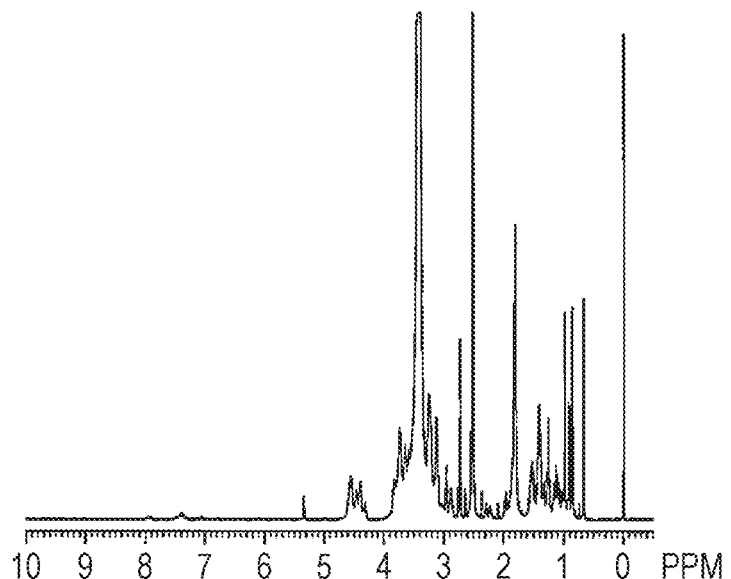
Figures 9, 13:
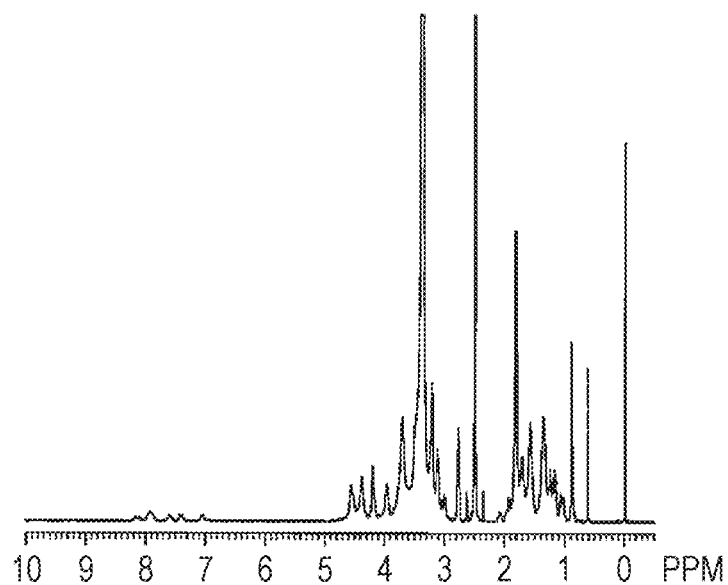

FIG. 13-4 represents an example of $^1$H-NMR spectrum of HA-Chol/IMD prepared in Example 4-1-4 in a DC1/DMSO/D₂O mixed solution (the percent incorporation of cholesteryl: 16% and the percent incorporation of IMD: 67%).

Figure 5:
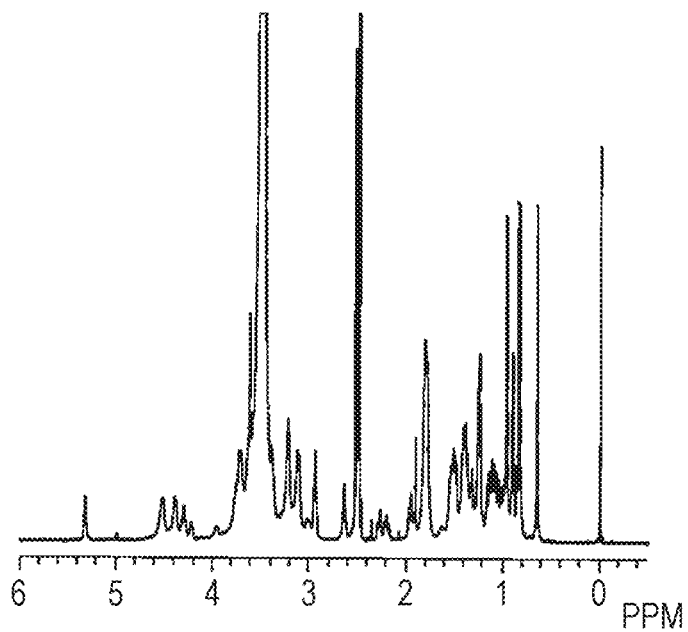
FIG. 5 represents an example of $^1$H-NMR spectrum of HA-Chol/ArgNH$_2$/Me prepared in Example 2-5 in a DC1/DMSO/D$_2$O mixed solution (the percent incorporation of cholesteryl: 38%, the percent incorporation of ArgNH$_2$: 22%, and the percent incorporation of Me: 17%).

FIG. 13-5 represents an example of $^1$H-NMR spectrum of HA-Chol/DPT prepared in Example 4-1-5 in a DC1/DMSO/D₂O mixed solution (the percent incorporation of cholesteryl: 15% and the percent incorporation of DPT: 60%).

Figure 6:
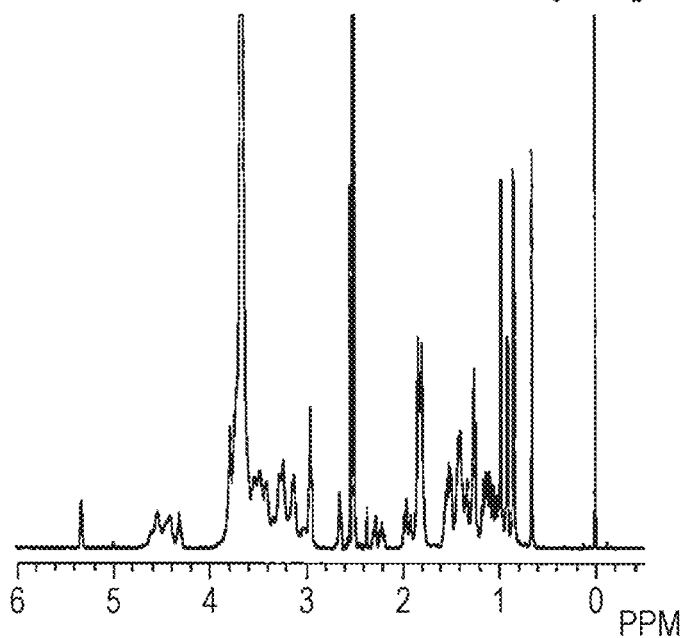
FIG. 6 represents an example of $^1$H-NMR spectrum of HA-Chol/EDA/Me prepared in Example 2-6 in a DC1/DMSO/D$_2$O mixed solution (the percent incorporation of cholesteryl: 33%, the percent incorporation of EDA: 30%, and the percent incorporation of Me: 10%).

FIG. 13-6 represents an example of $^1$H-NMR spectrum of HA-Chol/BAEA prepared in Example 4-1-6 in a DC1/DMSO/D₂O mixed solution (the percent incorporation of cholesteryl: 17% and the percent incorporation of BAEA: 63%).

Figures 1, 7:
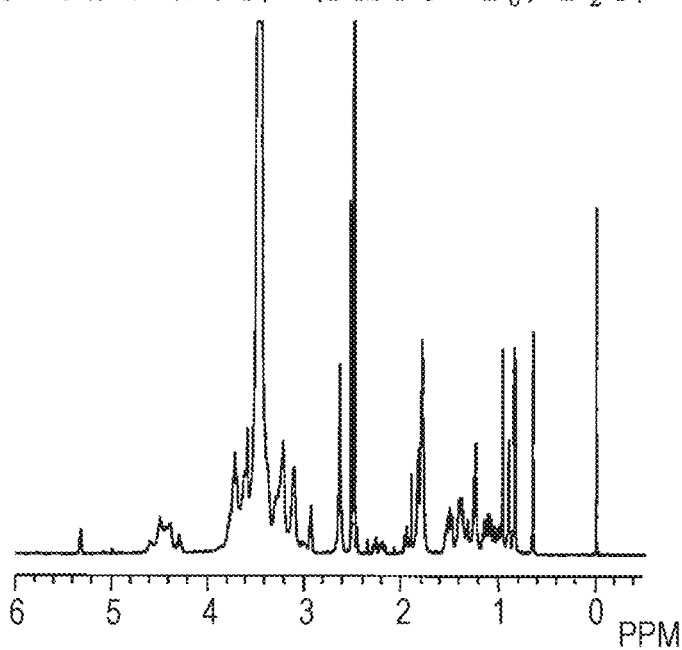
Figures 2, 7:
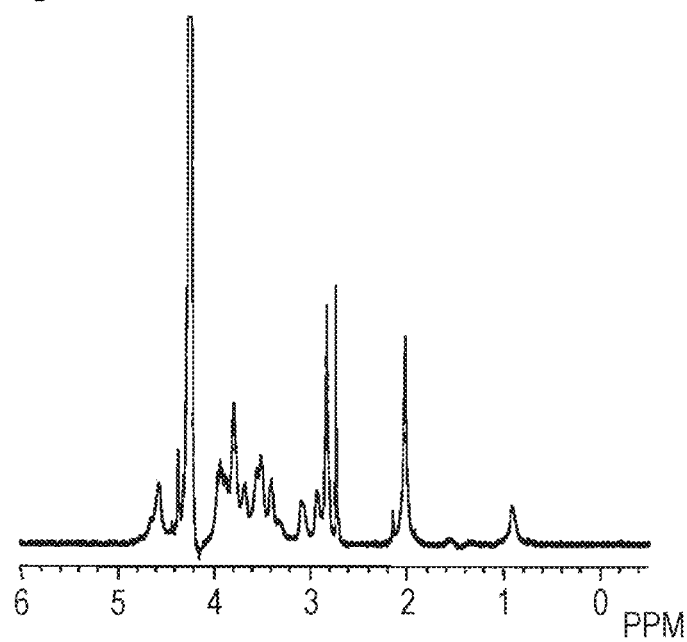

FIG. 13-7 represents an example of $^1$H-NMR spectrum of HA-Chol/DMA prepared in Example 4-1-7 in a DC1/DMSO/D₂O mixed solution (the percent incorporation of cholesteryl: 17% and the percent incorporation of DMA: 76%).

Figure 8:
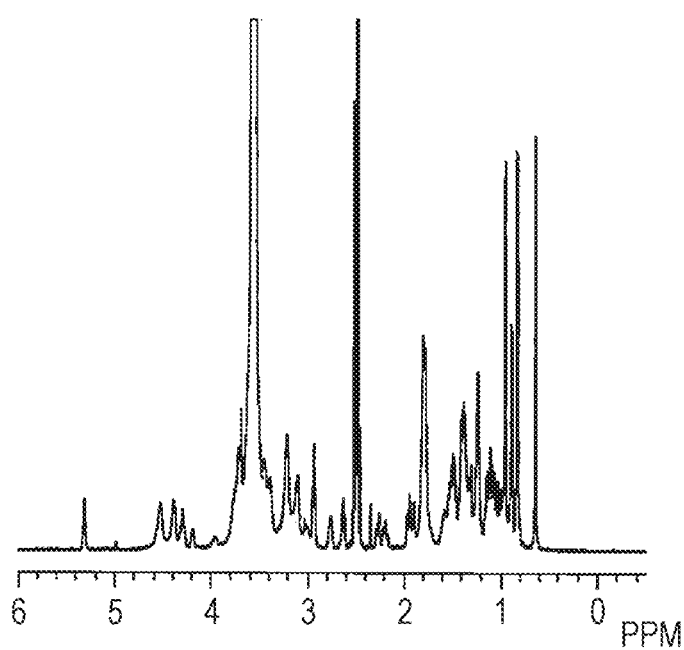
FIG. 8 represents an example of $^1$H-NMR spectrum of HA-Chol/LysNH$_2$/Me prepared in Example 2-8 in a DC1/DMSO/D$_2$O mixed solution (the percent incorporation of cholesteryl: 37%, the percent incorporation of LysNH$_2$: 22%, and the percent incorporation of Me: 11%).

FIG. 13-8 represents an example of $^1$H-NMR spectrum of HA-Chol/MPD prepared in Example 4-1-8 in a DC1/DMSO/D₂O mixed solution (the percent incorporation of cholesteryl: 12% and the percent incorporation of MPD: 51%).

Figure 9:
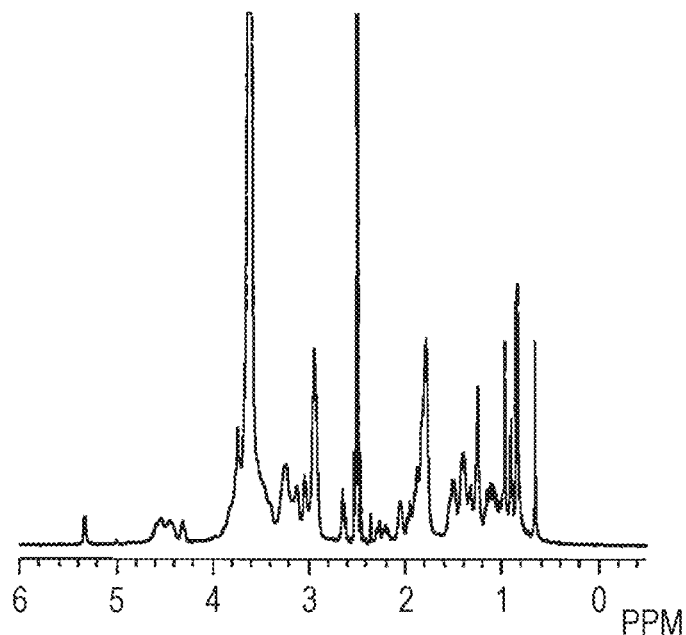
FIG. 9 represents an example of $^1$H-NMR spectrum of HA-Chol/SPR/Me prepared in Example 2-10 in a DC1/DMSO/D$_2$O mixed solution (the percent incorporation of cholesteryl: 27%, the percent incorporation of SPR: 37%, and the percent incorporation of Me: 16%).

FIG. 13-9 represents an example of $^1$H-NMR spectrum of HA-LysNH₂/CA prepared in Example 4-2 in a DC1/DMSO/D₂O mixed solution (the percent incorporation of LysNH₂: 91% and the percent incorporation of CA: 23%).

Figure 1:
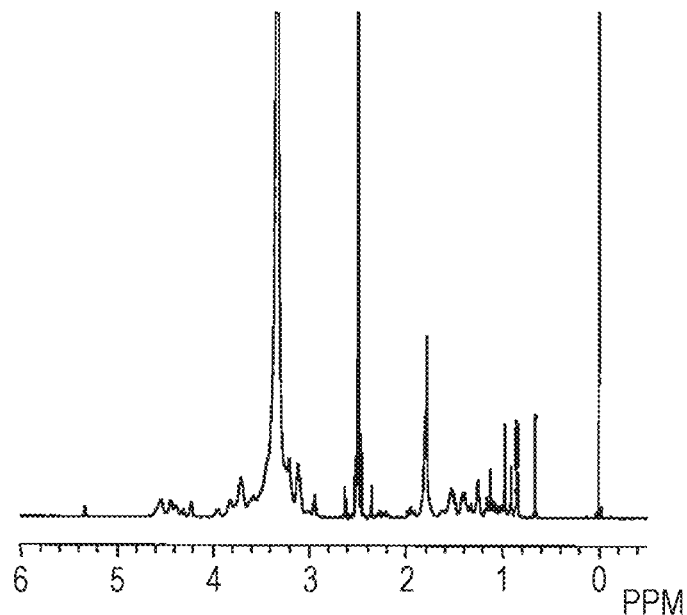
FIG. 1 represents an example of $^1$H-NMR spectrum of HA-Chol/ArgNH$_2$ prepared in Example 2-1 in a DC1/DMSO/D$_2$O mixed solution (the percent incorporation of cholesteryl: 17% and the percent incorporation of ArgNH$_2$: 31%).
Figures 1, 14:
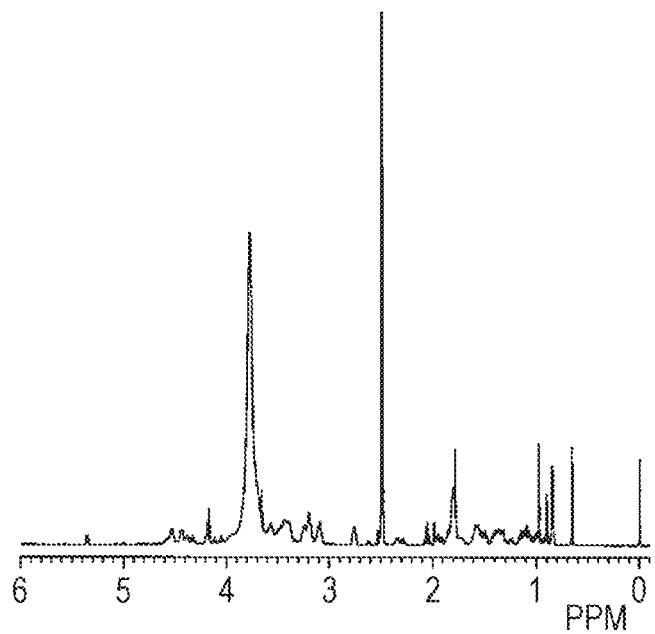
Figures 2, 14:
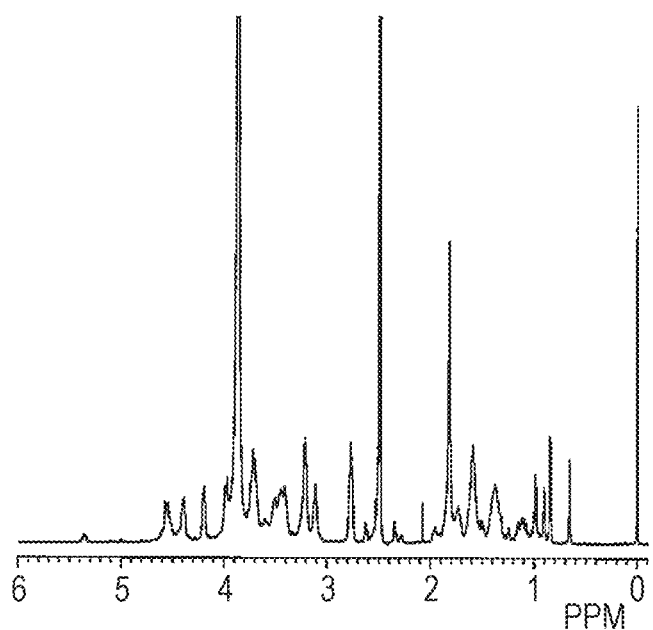

FIG. 14-1 represents an example of $^1$H-NMR spectrum of HA-C₃H₆—OCOO-Chol/LysNH₂ prepared in Example 5-2 in a DC1/DMSO/D₂O mixed solution (the percent incorporation of cholesteryl: 20% and the percent incorporation of LysNH₂: 29%).

Figure 2:
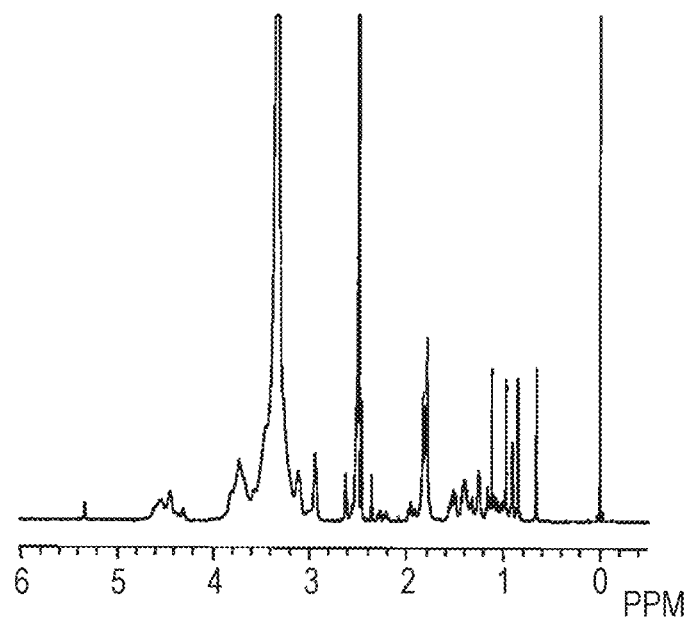
FIG. 2 represents an example of $^1$H-NMR spectrum of HA-Chol/EDA prepared in Example 2-2 in a DC1/DMSO/D$_2$O mixed solution (the percent incorporation of cholesteryl: 17% and the percent incorporation of EDA: 37%).

FIG. 14-2 represents an example of $^1$H-NMR spectrum of HA-CH₂—COO-Chol/LysNH₂ prepared in Example 5-4 in a DC1/DMSO/D₂O mixed solution (the percent incorporation of cholesteryl: 13% and the percent incorporation of LysNH₂: 70%).

Figures 1, 15:
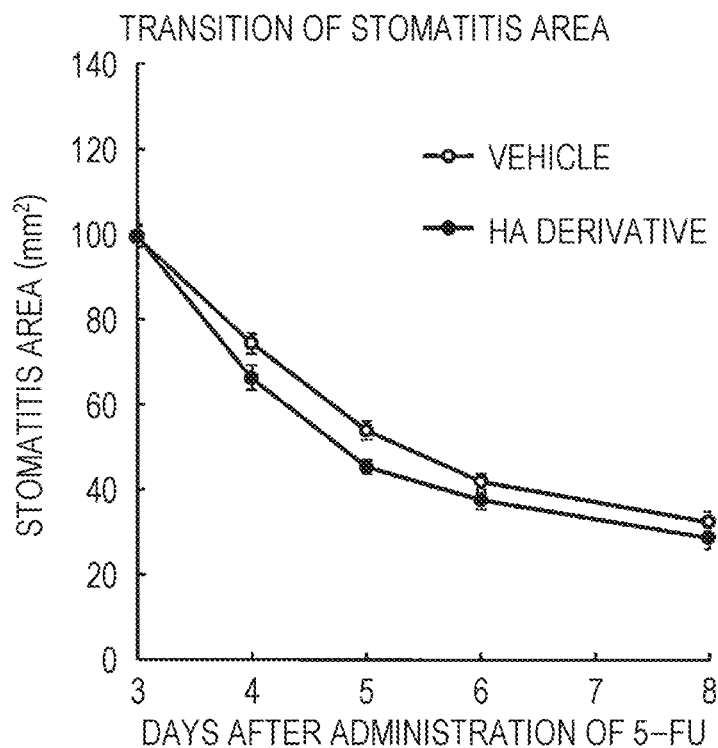
Figures 2, 15:
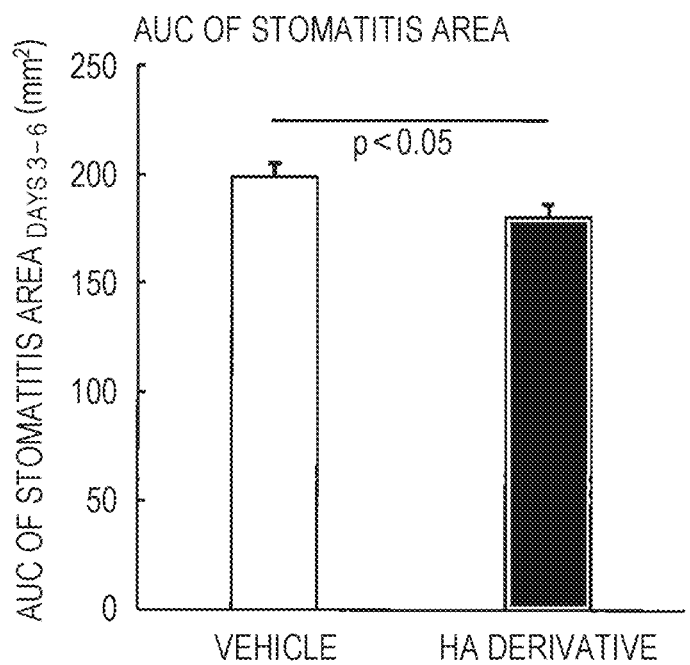

FIG. 15-1 is a graph illustrating transition in stomatitis area by topical administration of a HA derivative in hamster models with 5-FU-induced stomatitis (Mean±SE, n=10).

FIG. 15-2 is a graph illustrating AUC of stomatitis area by topical administration of a HA derivative in hamster models with 5-FU-induced stomatitis (Mean+SE, n=10, p: t-test).

Figures 1, 16:
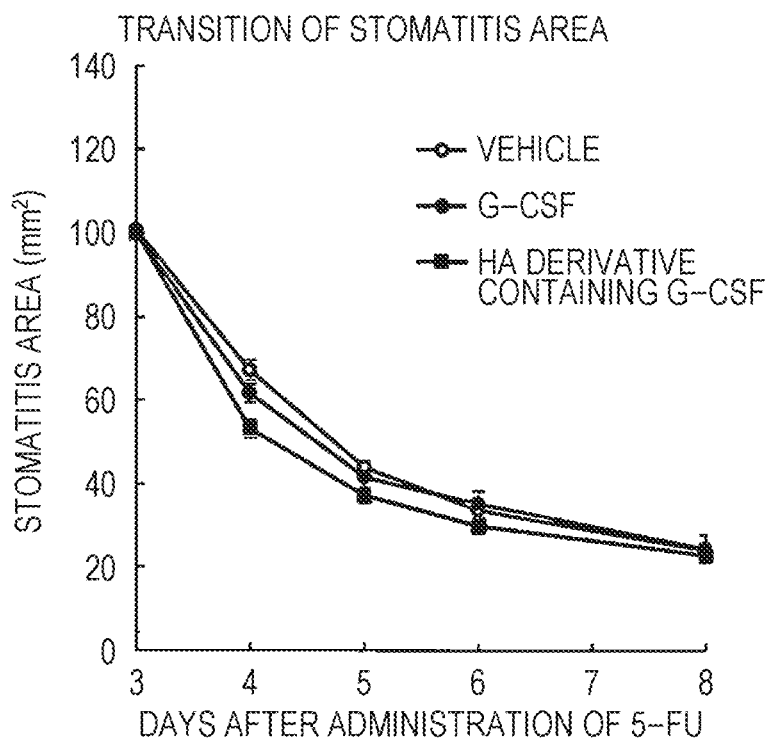
Figures 2, 16:
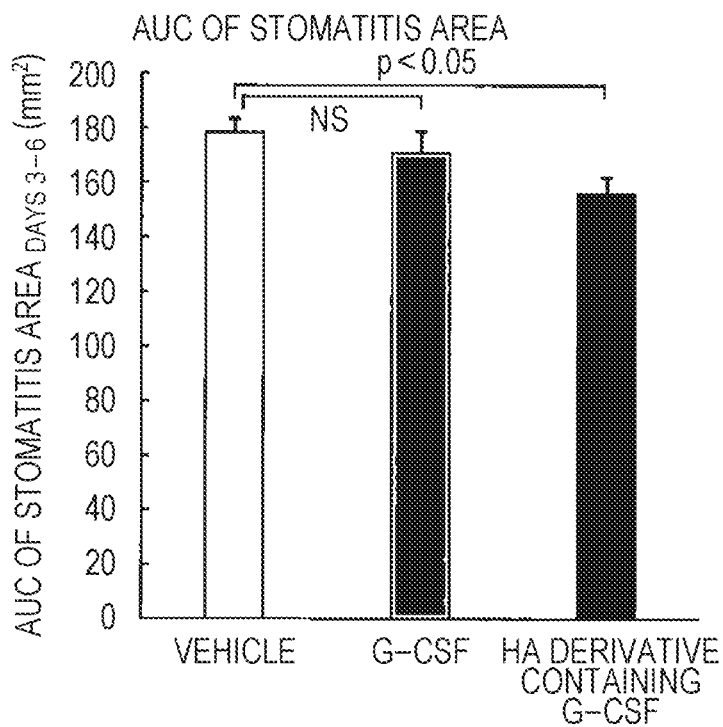

FIG. 16-1 is a graph illustrating transition in stomatitis area by topical administration of a HA derivative containing G-CSF in hamster models with 5-FU-induced stomatitis (Mean±SE, n=6).

FIG. 16-2 is a graph illustrating AUC of stomatitis area by topical administration of a HA derivative containing G-CSF in hamster models with 5-FU-induced stomatitis (Mean+SE, n=6, p: Dunnett-test).

Figures 1, 17:
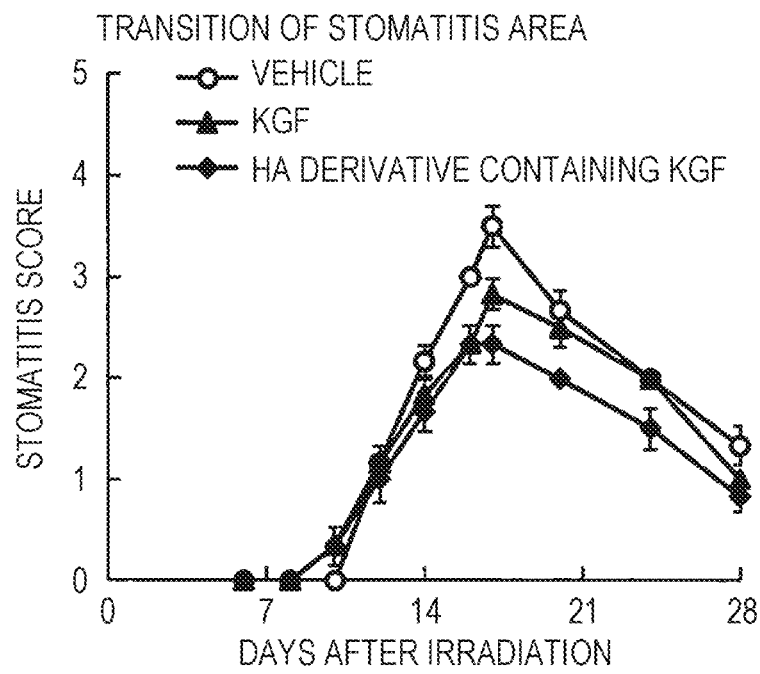
Figures 2, 17:
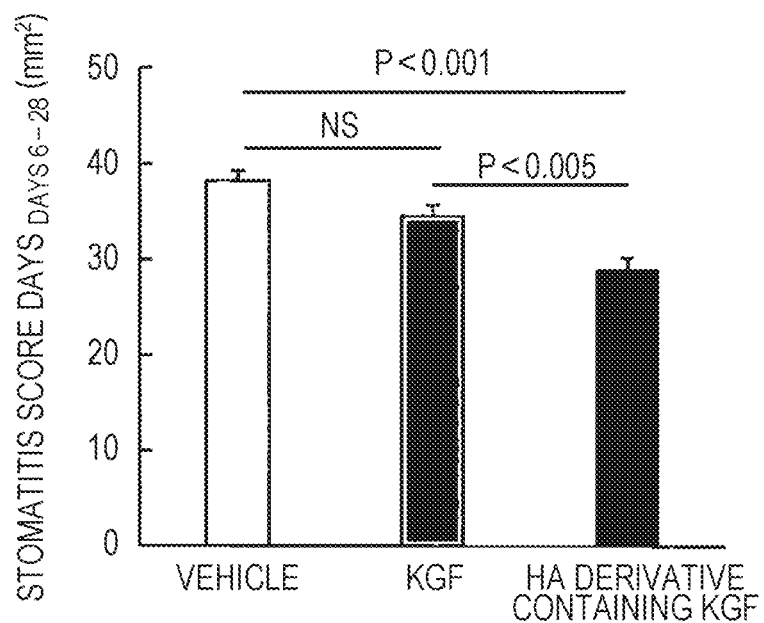
Figures 3, 17:
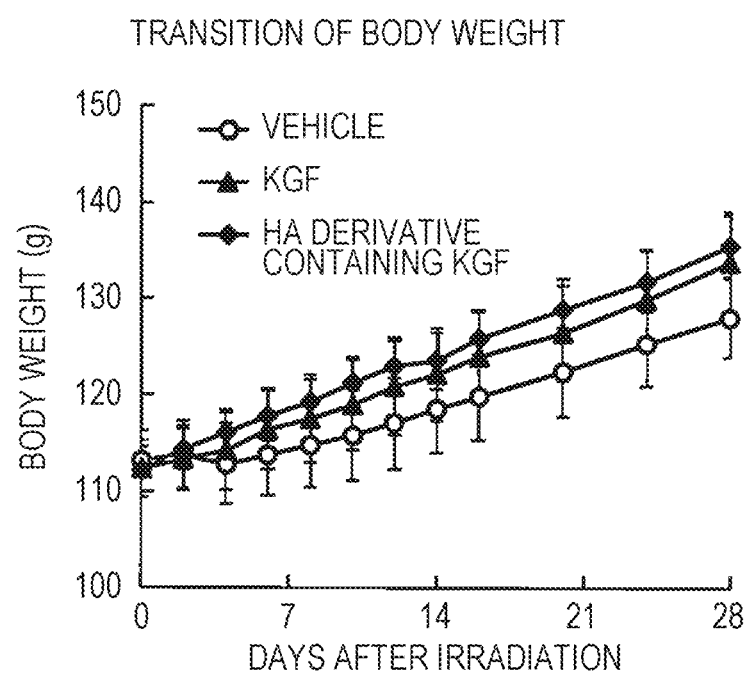

FIG. 17-1 is a graph illustrating stomatitis score in topical administration of a HA derivative containing KGF in hamster models with radiation-induced stomatitis (Mean±SE, n=6).

FIG. 17-2 is a graph illustrating stomatitis score AUC in topical administration of a HA derivative containing KGF in hamster models with radiation-induced stomatitis (Mean+SE, n=6, p: Dunnett-test and t-test).

Figures 1, 3:
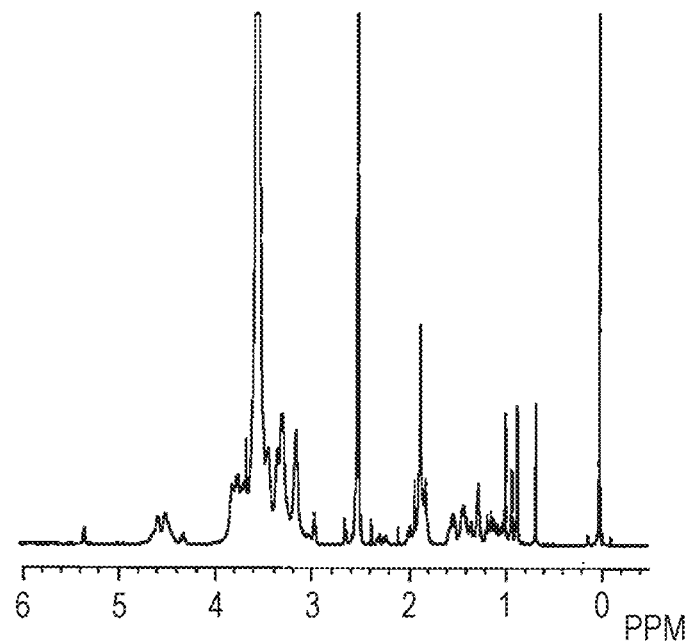
Figures 2, 3:
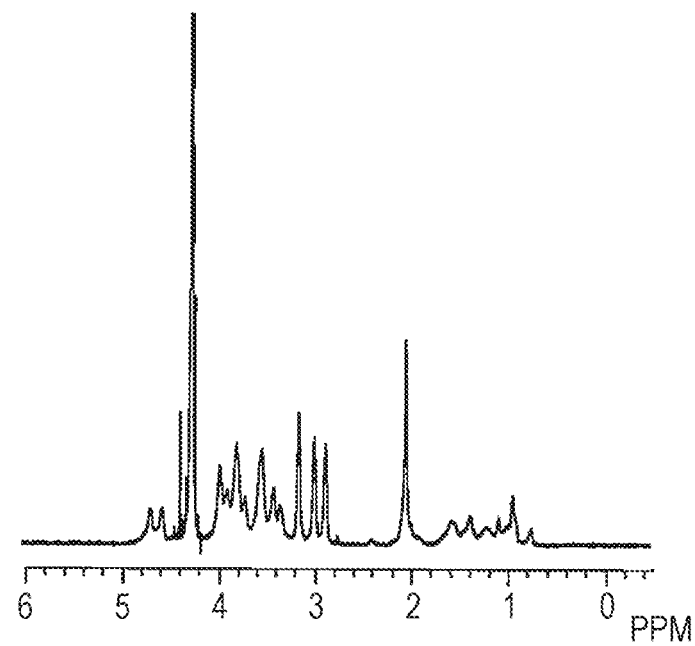

FIG. 17-3 is a graph illustrating transition in body weight by topical administration of a HA derivative containing KGF in hamster models with radiation-induced stomatitis (Mean±SE, n=6).

Figure 18:
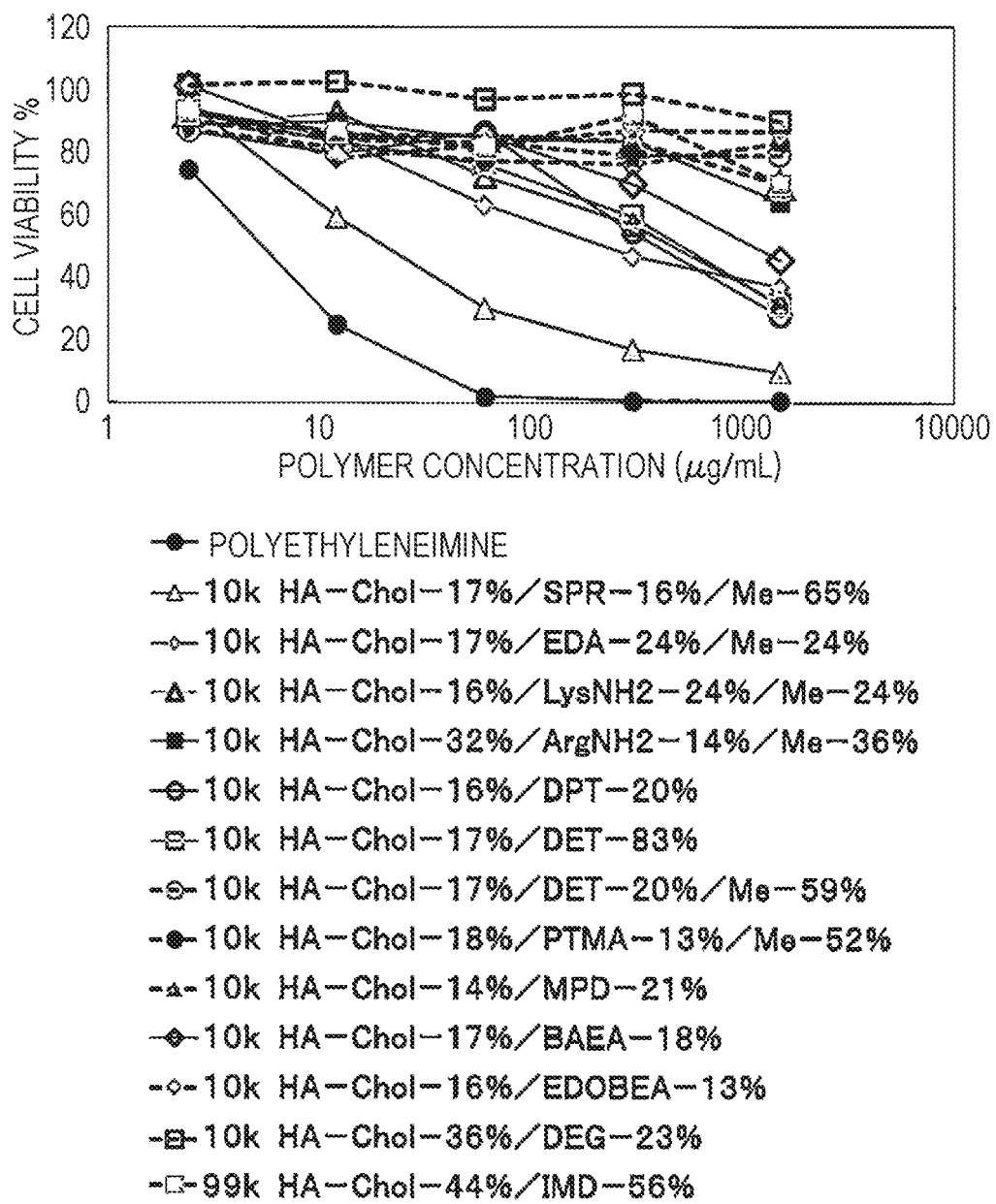

FIG. 18 is a graph illustrating effects of HA derivatives obtained in Examples 2 and 4 on cell proliferation as cell viabilities.

DESCRIPTION OF EMBODIMENTS

The present invention is described more specifically.

Hyaluronic acid derivatives of the present invention include one or more disaccharide units (which are also repeating units) represented by the formula (Ia) into which a group $X^1$ having a cationic site is introduced and one or more disaccharide units represented by the formula (Ib) into which a group $X^2$ having a hydrophobic site is introduced.

In one embodiment of the present invention, the hyaluronic acid derivatives further include, in addition to the disaccharide units represented by the formulas (Ia) and (Ib), disaccharide units represented by the formula (II), disaccharide units represented by the formula (III) into which a group $X^5$ is introduced or the disaccharide units represented by the formulas (II) and (III).

In one embodiment of the present invention, the hyaluronic acid derivatives are substantially consisted of repeating units represented by (1) the above formulas (Ia) and (Ib), (2) the above formulas (Ia), (Ib), and (II), (3) the above formulas (Ia), (Ib), and (III), or (4) the above formulas (Ia), (Ib), (II), and (III). In the hyaluronic acid derivatives, for example, 65% or more, preferably 80% or more, and more preferably 90% or more of the repeating units of disaccharide of D-glucuronic acid and N-acetylglucosamine included in the derivatives are repeating units of the formula (Ia), (Ib), (II), or (III). In one embodiment of the present invention, the hyaluronic acid derivatives are consisted of only the repeating units represented by (1) the above formulas (Ia) and (Ib), (2) the above formulas (Ia), (Ib), and (II), (3) the above formulas (Ia), (Ib), and (III), or (4) the above formulas (Ia), (Ib), (II), and (III).

The proportion of particular disaccharide units in the repeating units of disaccharide present in the hyaluronic acid derivative of the present invention means the proportion of the particular disaccharide units in all disaccharide units included in a certain amount of the hyaluronic acid derivatives of the present invention, which is a polysaccharide having disaccharide units as its repeating units.

In the formulas (Ia) and (Ib) representing disaccharide units included in the hyaluronic acid derivatives of the present invention, $R^{1x}$, $R^{2x}$, $R^{3x}$, and $R^{4x}$ and $R^{1y}$, $R^{2y}$, $R^{3y}$, and $R^{4y}$ are preferably all hydrogen atoms. $R^{5x}$ and $R^{5y}$ are preferably a hydrogen atom or ($C_{1-6}$ alkyl)carbonyl, more preferably a hydrogen atom or acetyl, and even more preferably acetyl. In the formulas (II) and (III) representing disaccharide units included in the hyaluronic acid derivatives of the present invention, $R^{1a}$, $R^{2a}$, $R^{3a}$, and $R^{4a}$ and $R^{1b}$, $R^{2b}$, $R^{3b}$, and $R^{4b}$ are preferably all hydrogen atoms. $R^{5a}$ and $R^{5b}$ are preferably a hydrogen atom or ($C_{1-6}$ alkyl)carbonyl, more preferably a hydrogen atom or acetyl, and even more preferably both acetyl.

When $X^1$ in the formula (Ia) representing disaccharide units, $X^2$ in the formula (Ib) representing disaccharide units, and/or $X^5$ in the formula (III) representing disaccharide units included in the hyaluronic acid derivatives of the present invention has/have an asymmetric center, optical isomers and mixtures thereof are also included in the present invention.

Specific examples of the cationic group $X^1$ in the formula (Ia) representing disaccharide units included in the hyaluronic acid derivatives of the present invention preferably include groups represented by the following formulas:

[Chem. 27]
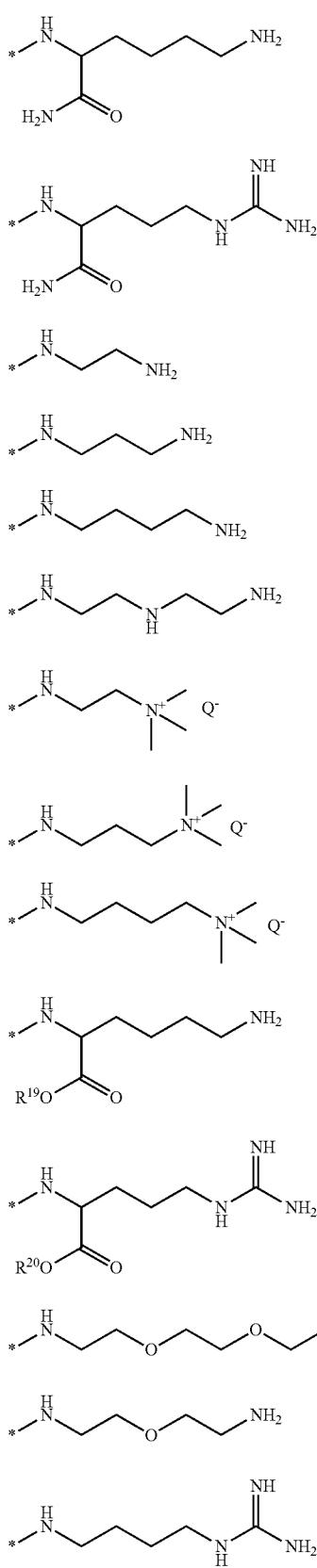
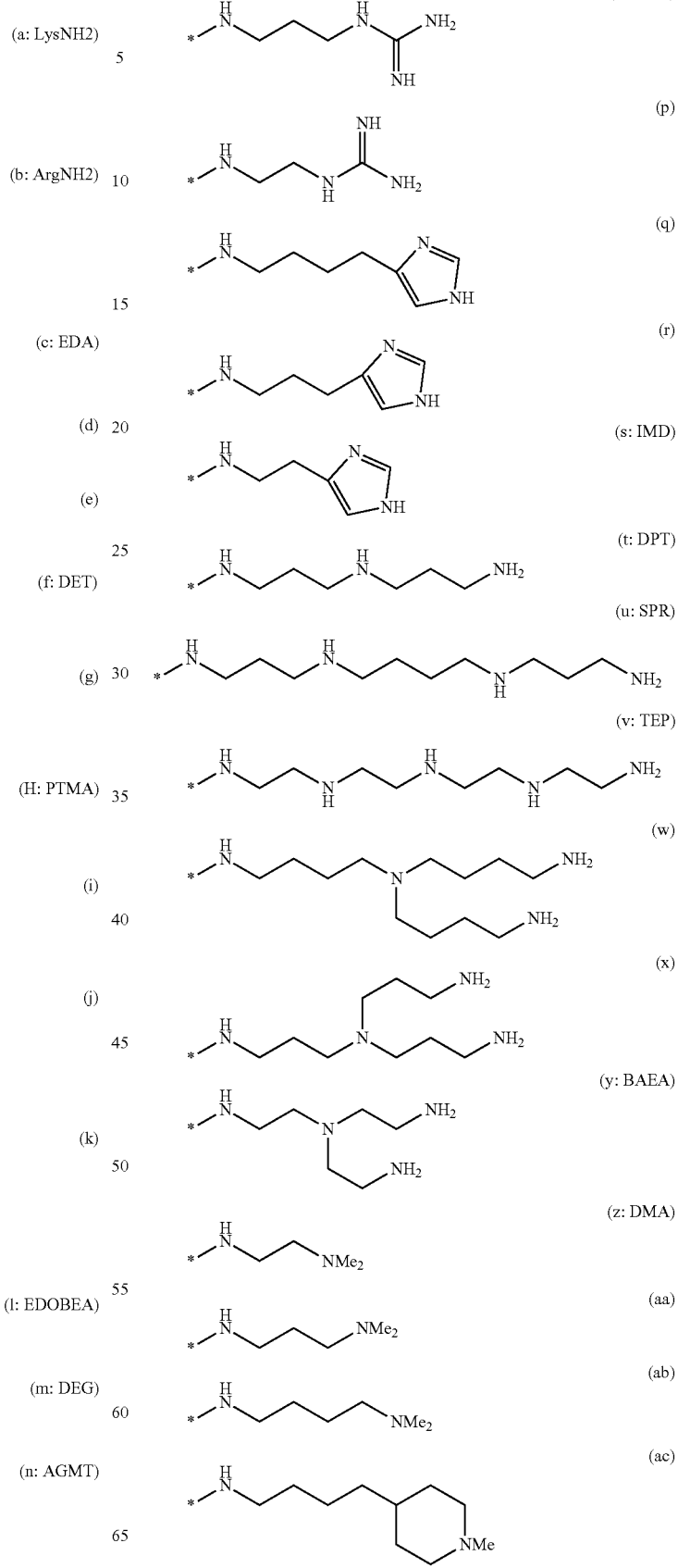

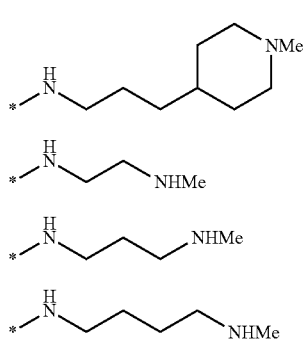

(ad)

(ae)

(af)

(ag)

in which "*" represents the attached position.

Specific examples of $X^1$ include, more preferably, groups represented by the formulas (a), (b), (c), (d), (e), (f), (g), (h), (i), (l), (m), (n), (o), (p), (q), (r), (s), (t), (u), (w), (x), (y), (z), (aa), (ab), (ac), (ad), and (ah) and more preferably groups represented by the formulas (a), (b), (c), (f), (h), (l), (m), (n), (s), (t), (u), (y), (z), and (ah). These $X^1$ are preferable from the viewpoint of the application of pharmaceutical compositions for transmucosal administration. Examples of $X^1$ that are more preferable from the above viewpoint include the groups represented by the formulas (a), (b), (c), (f), (h), (l), (u), (z), and (ah). The percent incorporation of $X^1$ that is more preferable from the above viewpoint is, for example, 3 to 95% and more preferably 6 to 84%. For example, when $X^1$ is the group represented by the formula (a), the percent incorporation of $X^1$ is preferably 10 to 50% and more preferably 19 to 45%. When $X^1$ is the group represented by the formula (b), the percent incorporation of $X^1$ is preferably 15 to 90% and more preferably 28 to 74%. When $X^1$ is the group represented by the formula (c), (d), or (e), the percent incorporation of $X^1$ is preferably 13 to 75% and more preferably 25 to 63%. When $X^1$ is the group represented by the formula (f), the percent incorporation of $X^1$ is preferably 10 to 90% and more preferably 22 to 84%. When $X^1$ is the group represented by the formula (g), (h), or (i), the percent incorporation of $X^1$ is preferably 3 to 60% and more preferably 6 to 46%. When $X^1$ is the group represented by the formula (l), the percent incorporation of $X^1$ is preferably 15 to 80%, more preferably 20 to 70%, more preferably 45 to 65%, and more preferably 52 to 54%. When $X^1$ is the group represented by the formula (m), the percent incorporation of $X^1$ is preferably 15 to 80%, more preferably 20 to 70%, more preferably 35 to 67%, more preferably 45 to 57%, and more preferably 50 to 52%. When $X^1$ is the group represented by the formula (n), (o), or (p), the percent incorporation of $X^1$ is preferably 15 to 80%, more preferably 20 to 70%, more preferably 46 to 90%, more preferably 56 to 80%, and more preferably 66 to 70%. When $X^1$ is the group represented by the formula (q), (r), or (s), the percent incorporation of $X^1$ is preferably 15 to 85%, more preferably 20 to 85%, more preferably 45 to 85%, and more preferably 67 to 71%. When $X^1$ is the group represented by the formula (t), the percent incorporation of $X^1$ is preferably 15 to 85%, more preferably 20 to 85%, more preferably 38 to 82%, more preferably 48 to 72%, and more preferably 58 to 62%. When $X^1$ is the group represented by the formula (u), the percent incorporation of $X^1$ is preferably 5 to 80%, more preferably 8 to 70%, more preferably 10 to 43%, and more preferably 15 to 27%. When $X^1$ is the group represented by the formula (w), (x), or (y), the percent incorporation of $X^1$ is preferably 15 to 80%, more preferably 20 to 70%, more preferably 30 to 70%, and more preferably 40 to 63%. When $X^1$ is the group represented by the formula (z), (aa), or (ab), the percent incorporation of $X^1$ is preferably 15 to 95%, more preferably 20 to 95%, more preferably 50 to 95%, more preferably 60 to 90%, and more preferably 74 to 78%. When $X^1$ is the group represented by the formula (ac), (ad), or (ah), the percent incorporation of $X^1$ is preferably 15 to 80%, more preferably 20 to 70%, more preferably 30 to 70%, more preferably 39 to 64%, and more preferably 49 to 54%.

Preferable examples of $X^1$ in terms of the hyaluronic acid derivatives suitable for the application of eye drops include groups represented by the formulas (a), (b), (c), (d), (e), (f), (g), (h), (i), (l), (m), (n), (o), (p), (q), (r), (s), (t), (u), (z), (aa), (ab), (ac), (ad) and (ah), more preferably groups represented by the formulas (a), (b), (c), (d), (e), (f), (g), (h), (i), (l), (m), (n), (q), (r), (s), (t), (u), (z), (ac), (ad), and (ah), more preferably groups represented by the formulas (a), (b), (c), (f), (h), (l), (m), (n), (s), (u), (z), and (ah), more preferably groups represented by the formulas (a), (b), (c), (h), (s), (u), and (ah), and more preferably groups represented by the formulas (a), (b), (c), (h), (s), and (ah).

A preferable example of $X^1$ for producing hyaluronic acid derivatives suitable for buccal administration including treatment of stomatitis is the group represented by the formula (b).

Specific examples of the group $X^5$ in the formula (III) representing disaccharide units included in the hyaluronic acid derivatives of the present invention preferably include groups represented by the following formulas:

[Chem. 28]

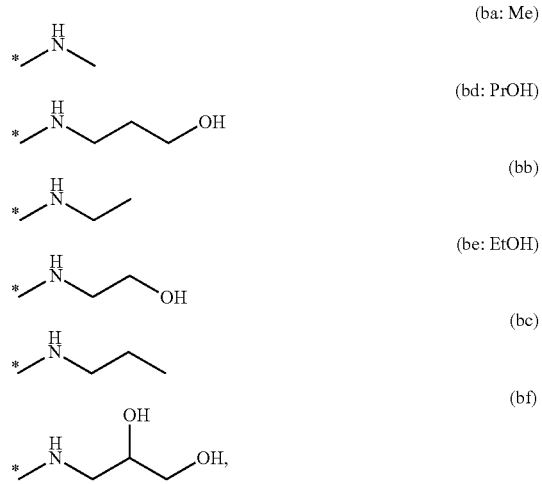

(ba: Me)

(bd: PrOH)

(bb)

(be: EtOH)

(bc)

(bf)

and more preferably groups represented by the formulas (ba), (bb), (bc), (bd), and (bf). Further, groups represented by the formulas (ba), (bb), (bc), (bd), and (be) are other more preferable groups.

The hyaluronic acid derivatives suitable for the application of eye drops may or may not include the disaccharide unit represented by the formula (III). If any, it is preferable that the repeating units represented by the formula (III) in which the groups $X^5$ are those represented by the formula (ba), (bd), and (be) are included and it is more preferable that the repeating units represented by the formula (III) in which the groups $X^5$ are those represented by i) the formulas (ba) and (be) or ii) the formulas (ba) and (bd) are included.

In the hyaluronic acid derivatives suitable for the application of eye drops, it is preferable that the disaccharide unit(s) represented by the formula (III) is/are included. It is more preferable that the repeating units represented by the formula (III) in which the group(s) $X^5$ is/are group(s) represented by the formula(s) (ba), (be) are included. The percent incorporation of $X^5$ is preferably 5 to 70%, and more preferably 7 to 63%.

From the viewpoint of the application of pharmaceutical compositions for transmucosal administration, it is preferable that the repeating unit represented by the formula (III) is not included or the repeating unit(s) represented by the formula (III) in which the group $X^5$ is the group represented by the formula (ba) is/are included. When a hyaluronic acid derivative of the present invention does not include the repeating unit represented by the formula (III), the percent incorporation of $X^1$ having a cationic site is preferably 10 to 90%, and more preferably 19 to 84%. When a hyaluronic acid derivative of the present invention includes the repeating unit(s) represented by the formula (III), the percent incorporation of $X^1$ is preferably 4 to 60%, and more preferably 6 to 46%. Further, a combination of the percent incorporation of $X^1$ and the percent incorporation of $X^5$ (the percent incorporation of $X^1$: the percent incorporation of $X^5$) is preferably (4 to 60%:2 to 80%), more preferably (6 to 46%:4 to 67%). The upper limit of the sum of the percent incorporations of $X^1$ and $X^5$ is 99%. The requirement for the lower limit is 6% or higher.

"$C_{1-20}$ alkyl" used herein refers to a linear or branched alkyl group having 1 to 20 carbon atoms. For example, the term includes "$C_{1-4}$ alkyl" such as methyl, ethyl, n-propyl, i-propyl, n-butyl, s-butyl, i-butyl, t-butyl, as well as, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl. $C_{1-20}$ alkyl includes "$C_{1-12}$ alkyl" having 1 to 12 carbon atoms, "$C_{1-10}$ alkyl" having 1 to 10 carbon atoms and "$C_{1-6}$ alkyl" having 1 to 6 carbon atoms. Likewise, "$C_{8-50}$ alkyl" refers to a linear or branched alkyl group having 8 to 50 carbon atoms.

"$C_{8-50}$ alkenyl" used herein refers to a linear or branched alkenyl group having 8 to 50 carbon atoms and having one or more carbon-carbon double bonds. "$C_{8-50}$ alkynyl" used herein refers to a linear or branched alkynyl group having 8 to 50 carbon atoms and having one or more carbon-carbon triple bonds. Among $C_{8-50}$ alkyl, $C_{8-50}$ alkenyl, and $C_{8-50}$ alkynyl, $C_{8-50}$ alkyl is preferable. Further, the number of carbon atoms is preferably 10 to 30, and more preferably 10 to 20. Specific examples include a lauryl group, a myristyl group, a cetyl group, and a stearyl group.

"($C_{1-6}$ alkyl)carbonyl" used herein refers to an alkylcarbonyl group in which the alkyl moiety is $C_{1-6}$ alkyl. For example, the term includes acetyl, propionyl, n-propylcarbonyl, i-propylcarbonyl, n-butylcarbonyl, s-butylcarbonyl, i-butylcarbonyl, and t-butylcarbonyl.

"Heteroaryl" used herein refers to a group in an aromatic ring including one or more heteroatoms selected from a nitrogen atom, an oxygen atom, and a sulfur atom as the atoms constituting the ring and may be partially saturated. The ring may be a monocyclic ring or bicyclic heteroaryl condensed with a benzene ring or a monocyclic heteroaryl ring. The ring may be constituted of, for example, 5 to 10 atoms. Examples of the heteroaryl include, for example, furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl; and imidazolyl is preferred.

"5- to 10-membered heteroaryl having 1 to 4 nitrogen atoms" used herein refers to heteroaryl including 1 to 4 nitrogen atoms among the 5 to 10 atoms constituting the ring. Examples include pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, indolizinyl, and imidapyridyl; and imidazolyl is preferred.

"$C_{2-30}$ alkylene" used herein refers to a linear or branched, saturated divalent hydrocarbon group having 2 to 30 carbon atoms. For example, the term includes ethylene and propylene, as well as $C_{2-10}$ alkylene having 2 to 10 carbon atoms and "$C_{2-8}$ alkylene" having 2 to 8 carbon atoms.

"$C_{1-30}$ alkylene" used herein refers to a linear or branched, saturated divalent hydrocarbon group having 1 to 30 carbon atoms. For example, the term includes methylene, ethylene, and propylene, as well as $C_{2-30}$ alkylene having 2 to 30 carbon atoms.

"$C_{1-5}$ alkylene" used herein refers to a linear or branched, saturated divalent hydrocarbon group having 1 to 5 carbon atoms. For example, the term includes ethylene (ethane-1,2-diyl, ethane-1,1-diyl), propylene (propane-1,1-diyl, propane-1,2-diyl, propane-1,3-diyl), butane-1,4-diyl and penetane-1,5-diyl.

"Amino $C_{2-20}$ alkyl" used herein refers to linear or branched alkyl having 2 to 20 carbon atoms and having amino as a substituent. For example, amino may be located on a carbon atom at an end of the alkyl. Amino $C_{2-20}$ alkyl includes "amino $C_{2-12}$ alkyl" having 2 to 12 carbon atoms.

"Hydroxy $C_{2-20}$ alkyl" used herein refers to a linear or branched alkyl group having 2 to 20 carbon atoms and having hydroxy as a substituent. For example, hydroxy may be located on a carbon atom at an end of the alkyl. Hydroxy $C_{2-20}$ alkyl includes "hydroxy $C_{2-12}$ alkyl" having 2 to 12 carbon atoms.

"Steryl group" used herein is not limited to any particular group as long as it is a group having a steroid backbone. Specific examples of steroid include cholesterol, dehydrocholesterol, coprostenol, coprosterol, cholestanol, campestanol, ergostanol, stigmastanol, coprostanol, stigmasterol, sitosterol, lanosterol, ergosterol, simiarenol, bile acids (cholanic acid, lithocholic acid, hyodeoxycholic acid, chenodeoxycholic acid, ursodeoxycholic acid, deoxycholic acid, apocholic acid, cholic acid, dehydrocholic acid, glycocholic acid, taurocholic acid), testosterone, estradiol, progesterone, cortisol, cortisone, aldosterone, corticosterone, and deoxycorticosterone. Examples of the steryl group include cholesteryl, stigmasteryl, lanosteryl, ergosteryl, cholanoyl, and choloyl groups. Preferred examples include a group represented by the following formula:

[Chem. 29]

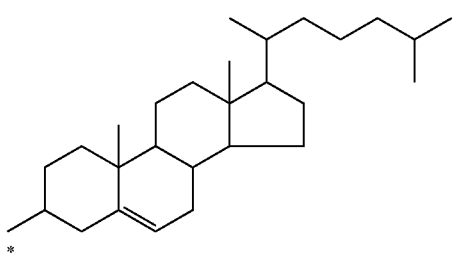
(ck)

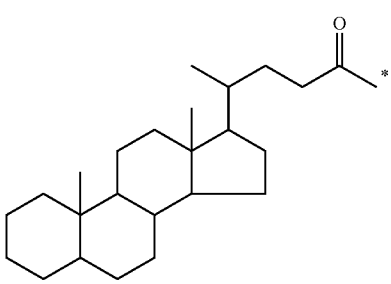
(cl: CA)

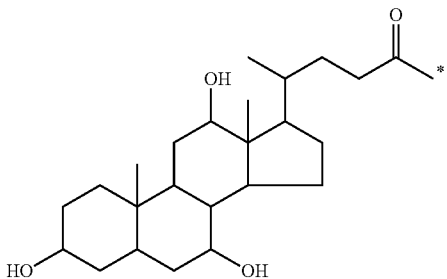
(cm)

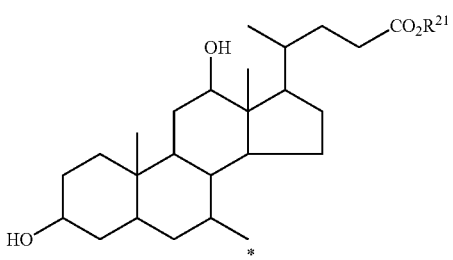
(cn)

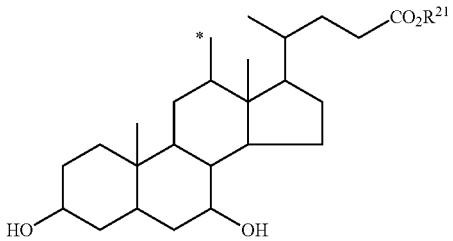
(co)

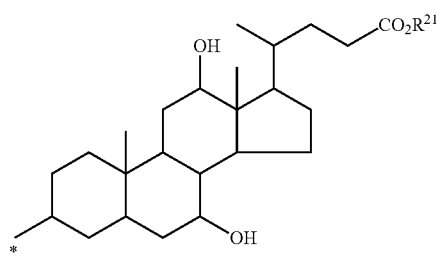
(cp)

in which $R^{21}$ independently represents a hydrogen atom or $C_{1-6}$ alkyl, and "*" represents the attached position. More preferred examples include groups represented by the formulas (ck), (cl) and (cm). Yet more preferred examples include cholesteryl groups (in particular, the cholest-5-en-3β-yl group represented by the following formula) and cholanoyl groups (in particular, the 5β-cholan-24-oyl group represented by the following formula):

[Chem. 30]

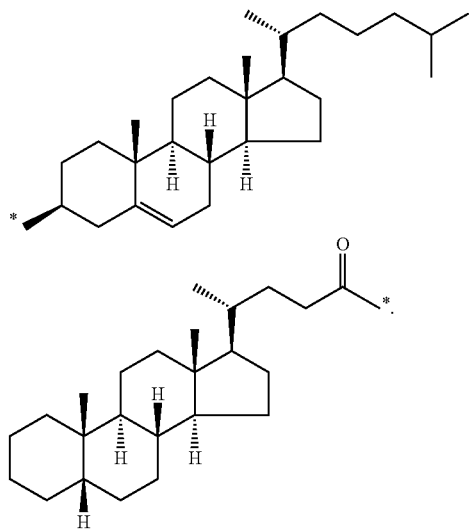

"$C_{2-8}$ alkenylene" used herein refers to a linear or branched, divalent hydrocarbon group having 2 to 8 carbon atoms and having one or more double bonds. For example, the term includes —CH=CH—, —C(CH$_3$)=CH—, 2-butene-1,4-diyl, hepta-2,4-diene-1,6-diyl, and octa-2,4,6-triene-1,8-diyl. When geometrical isomers exist, the term includes each of the isomers and mixtures thereof.

$Q^+$ is not particularly limited as long as it is a counter cation forming a salt with carboxy in water. When $Q^+$ is divalent or more, it forms a salt with a plurality of carboxy depending on the valency. Examples of the counter cation include metal ions such as a lithium ion, a sodium ion, a rubidium ion, a cesium ion, a magnesium ion, and a calcium ion as well as ammonium ions represented by formula $N^+R^jR^kR^lR^m$, in which $R^j$, $R^k$, $R^l$, and $R^m$ are each independently selected from a hydrogen atom and $C_{1-6}$ alkyl. Preferable examples include a sodium ion, a potassium ion, and tetraalkylammonium ions (for example, tetra-n-butylammonium ion). Preferably, $R^j$, $R^k$, $R^l$, and $R^m$ are all the same group selected from $C_{1-6}$ alkyl, and preferably n-butyl.

Q⁻ may be any counter anion that forms a salt with an ammonium salt. Examples of the counter anion include halogen ions such as a fluoride ion, a chlorine ion, a bromine ion, an iodine ion, and a hydroxy ion.

The hyaluronic acid derivatives of the present invention can be used as a drug carrier, and the drug carrier is preferably biodegradable. Further, the hyaluronic acid derivatives of the present invention have an increased mucosal permeability and the mucosal permeability of a drug can be increased by forming a complex with the drug.

Here, the increase of mucosal permeability means that after transmucosal administration to mammals, particularly mice, rats, rabbits, pigs and/or humans, the drug permeates a mucosal layer and the degree of reach to the epithelial layer or further internal tissue increases. "The degree of reach to the epithelial layer or further internal tissue" can be evaluated by, for example, examining the presence degree of a fluorescent-labeled hyaluronic acid derivative of the present invention or a fluorescent-labeled drug in the epithelial layer and internal tissue with a microscope. In the case of oral administrations, it can also be evaluated by measuring the concentration of a drug or a hyaluronic acid derivative of the present invention in blood. In vitro evaluations, some other methods may also be used such as a method of evaluating the degree of permeation through multilayered cells producing mucosa such as cornea and a method of overlaying mucosal components on cells that do not produce mucosa and evaluating the degree of permeation of a hyaluronic acid derivative of the present invention or a drug through the mucosal components.

In the present invention, the "transmucosal administration" includes application of eye drops on the conjunctiva or cornea, nasal inhalation through a mucous membrane covering the nasal cavity, pulmonary inhalation via a mucous membrane of the alveoli, inhalation to the tracheal mucosa and bronchial mucosa, buccal administration and sublingual administration through a mucous membrane in the oral cavity, vaginal administration via a mucous membrane in the vagina, oral administration or rectal administration via gastrointestinal mucosa of the stomach, duodenum, small intestine, and large intestine including the colon and rectum, and middle ear administration to the middle ear mucosa. Preferable administrations are application of eye drops, nasal inhalation, pulmonary inhalation, tracheal or bronchial inhalation, buccal administration, sublingual administration, and oral administration. More preferable administrations are application of eye drops, nasal inhalation, pulmonary inhalation, tracheal or bronchial inhalation, buccal administration, and sublingual administration.

According to another aspect of the present invention, there are provided the hyaluronic acid derivatives defined herein, in which the proportion of the repeating units represented by the formula (Ia) having the group $X^1$ (—NR$^7$—CHR$^8$—(CH$_2$)$_{n1}$-A$^1$-B$^1$ in which R$^7$, R$^8$, n1, A$^1$, and B$^1$ are as having already been defined in this specification) having a cationic site in the repeating units of disaccharide present therein (the percent incorporation of group $X^1$) is, for example, 1 to 75%.

According to further aspect of the present invention, there are provided the hyaluronic acid derivatives defined herein, in which the proportion of the repeating units represented by the formula (Ib) having the group $X^2$ (that is $X^2$ is —O—Z$^3$, —O—Z$^1$—Z$^2$, or —NR$^6$—Z$^1$—Z$^2$ in which Z$^3$, Z$^1$, Z$^2$, and R$^6$ are as having already been defined in this specification) having a hydrophobic site in the repeating units of disaccharide present therein (the percent incorporation of group $X^2$ having a hydrophobic site) is, for example, 3 to 55%.

According to further aspect of the present invention, there are provided the hyaluronic acid derivatives defined herein, in which the proportion of the repeating units represented by the formula (Ib) having the group $X^2$ (that is $X^2$ is —O—Z$^3$, —O—Z$^1$—Z$^2$, —O—Z$^0$—Z$^2$, —NR$^6$—Z$^1$—Z$^2$ or —NR$^{31}$—CHR$^{32}$—(CH$_2$)$_{n11}$-A$^3$-B$^2$ in which Z$^3$, Z$^1$, Z$^2$, Z$^0$, R$^6$, R$^{31}$, R$^{32}$, n11, A$^3$, and B$^2$ are as having already been defined in this specification) having a hydrophobic site in the repeating units of disaccharide present therein (the percent incorporation of group $X^2$ having a hydrophobic site) is, for example, 3 to 55%.

According to further aspect of the present invention, there are provided the hyaluronic acid derivatives defined herein, in which the sum of the percent incorporation of $X^1$ and the proportion of the repeating units represented by the formula (Ib) having the group $X^2$ being —NR$^{31}$—CHR$^{32}$—(CH$_2$)$_{n11}$-A$^3$-B$^2$ (in which R$^{31}$, R$^{32}$, n11, A$^3$, and B$^2$ are as having already been defined in this specification) in the repeating units of disaccharide present therein is, for example, 30 to 100%. The percent incorporation of group $X^1$ having a cationic site is, for example, 1 to 90%, preferably 1 to 75%, and specifically 1, 2.5, 6, 7.4, 11, 17, 21, 28, 35, 44, 53, 61, 65, 70, 73, or 75%. Further, a preferable percent incorporation of group $X^1$ is 2 to 90%, and specifically 3, 6, 8, 10, 11, 12, 13, 14, 15, 16, 17, 18, 19, 20, 21, 22, 23, 25, 26, 28, 29, 30, 31, 32, 34, 35, 40, 41, 42, 43, 45, 46, 48, 49, 50, 51, 52, 54, 60, 63, 65, 66, 67, 68, 70, 71, 75, 76, 79 or 85%.

In the hyaluronic acids suitable for the application of eye drops, the percent incorporation of group $X^1$ is preferably 2 to 80%, more preferably 3 to 76%, still more preferably 13 to 67%, specifically 3, 11, 13, 17, 22, 24, 28, 31, 41, 43, 46, 51, 52, 67, 68, 75 or 76%, and preferably 13, 17, 24, 28, 31, 41, 43, 46, 51 or 67%.

In the hyaluronic acids suitable for buccal administration, a preferable percent incorporation of group $X^1$ is 5 to 50%, more preferably 10 to 30%, and specifically 16, 20, and 28%.

The percent incorporation of group $X^2$ having a hydrophobic site is, for example, 3 to 55%, and specifically 3, 8, 12, 16, 21, 25, 30, 34, 39, 43, 48, 51, or 55%. When the percent incorporation of $X^2$ has one of the above values, $X^2$ are preferably —O—Z$^3$, —O—Z$^1$—Z$^2$, and —NR$^6$—Z$^1$—Z$^2$. Further, when the $X^2$ are these groups, the sum the percent incorporation of $X^1$ and the percent incorporation of $X^2$ is 100% or less. For example, when the percent incorporation of $X^2$ is 55%, the percent incorporation of $X^1$ is 45% or less.

In the hyaluronic acids suitable for the application of eye drops and for buccal administration, $X^2$ is preferably —NR$^6$—Z$^1$—Z$^2$. The percent incorporation of $X^2$ is, for example, 8 to 50% and preferably 12 to 44% for the application of eye drops, and, for example, 5 to 40% and preferably 10 to 20% for buccal administration. Specific examples of the percent incorporation include 12, 15, 16, 17, 18, 26, 39, and 44%.

In —O—Z$^1$—Z$^2$ and —NR$^6$—Z$^1$—Z$^2$, when the atom in Z$^2$ bound to Z$^1$ is an oxygen atom or a nitrogen atom, Z$^1$ being C$_{1-30}$ alkylene is preferably C$_{2-30}$ alkylene. Likewise, in —O—Z$^0$—Z$^1$—Z$^2$ the atoms in Z$^0$ and Z$^2$ bound to Z$^1$ are each an oxygen atom or a nitrogen atom, Z$^1$ being C$_{1-30}$ alkylene is preferably C$_{2-30}$ alkylene. When Z$^1$ is the C$_1$ alkylene (i.e., —CH$_2$—), the carbon atom may be modified with a hydroxy or C$_{1-6}$ alkyl, or —CH$_2$— may be substituted with an amino acid residue. For example, —CH$_2$— may be substituted with a serine residue —CH(CH$_2$OH)—.

Specific examples of the group —NR$^b$—Z$^3$, which is an example of the group X$^2$, include a group represented by the following formula:

[Chem. 31]

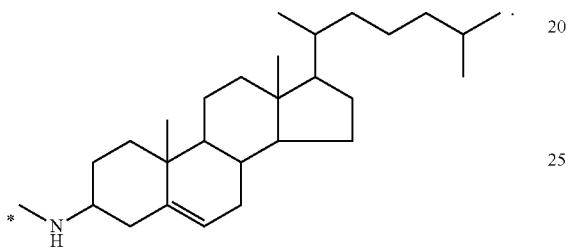

Examples of —NR$^6$—Z$^1$—Z$^2$, which is an example of the group X$^2$, include groups represented by the following formulas:

[Chem. 32]

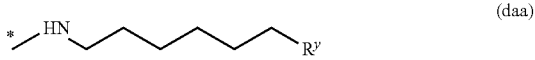

(daa)

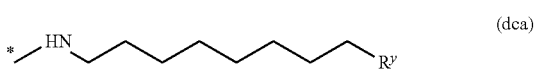

(dca)

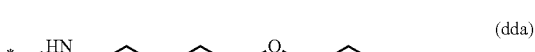

(dda)

(dba)

(dea)

in which R$^y$ is a group represented by the formulas (ca), (cb), (cc), (cd), (ce), (cf), and (cg) given below. Preferable examples of the group —NR$^6$—Z$^1$—Z$^2$ include groups represented by the formulas (daa), (dba), (dca), and (dda) in which each R$^y$ is (ca), and groups represented by the formulas (daa), (dba), and (dda) in which each R$^y$ is (cg). More preferable examples include a group represented by the following formula:

[Chem. 33]

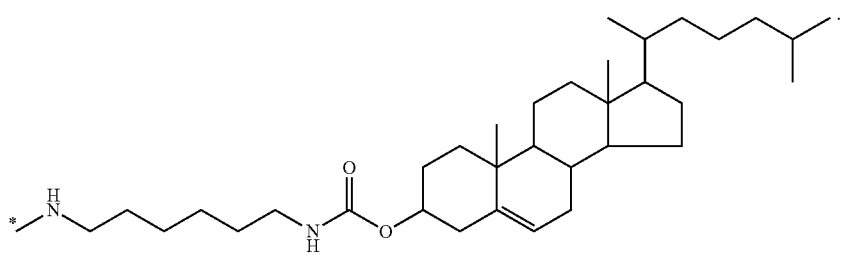

Examples of the groups —O—Z$^1$—Z$^2$, —O—Z$^0$—Z$^1$—Z$^2$, and —O—Z$^0$—Z$^2$, which are examples of the group X$^2$, include groups represented by the following formulas:
[Chem. 34]
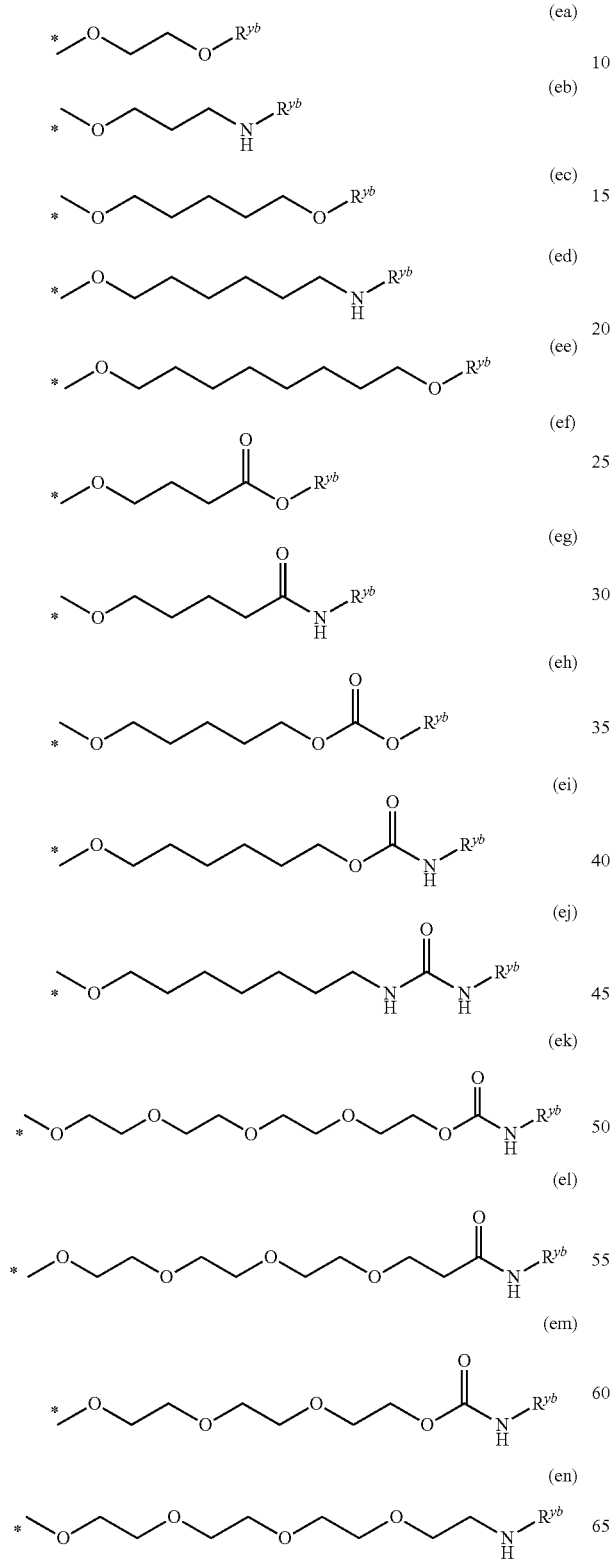
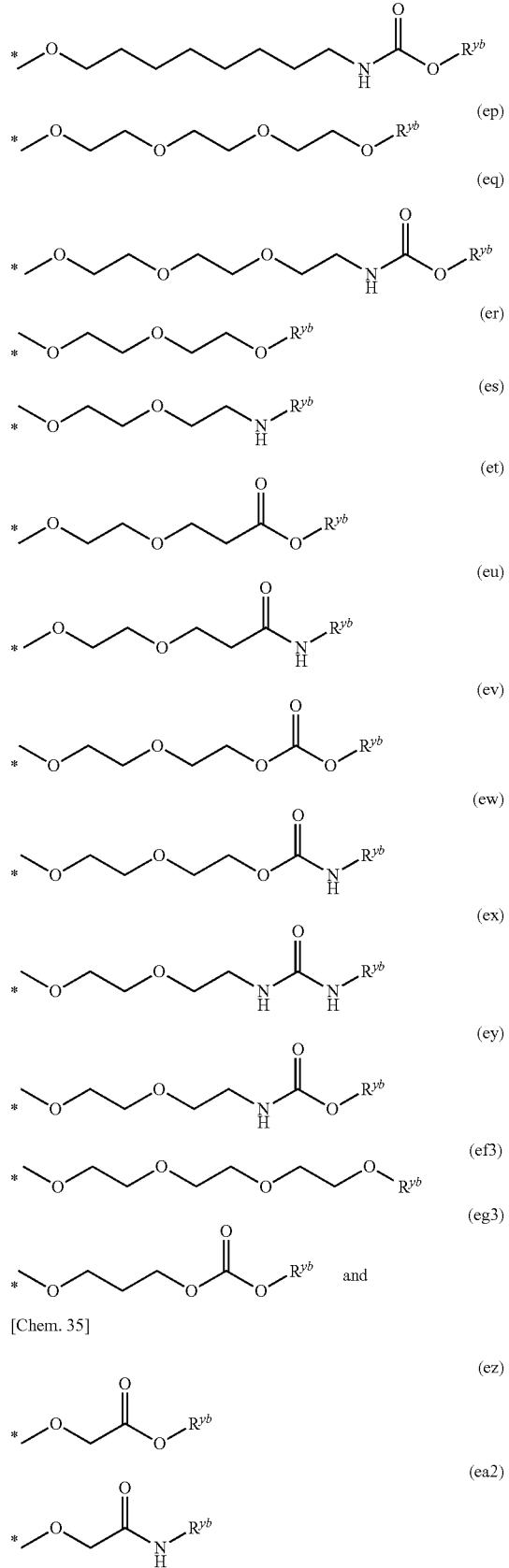
[Chem. 35]

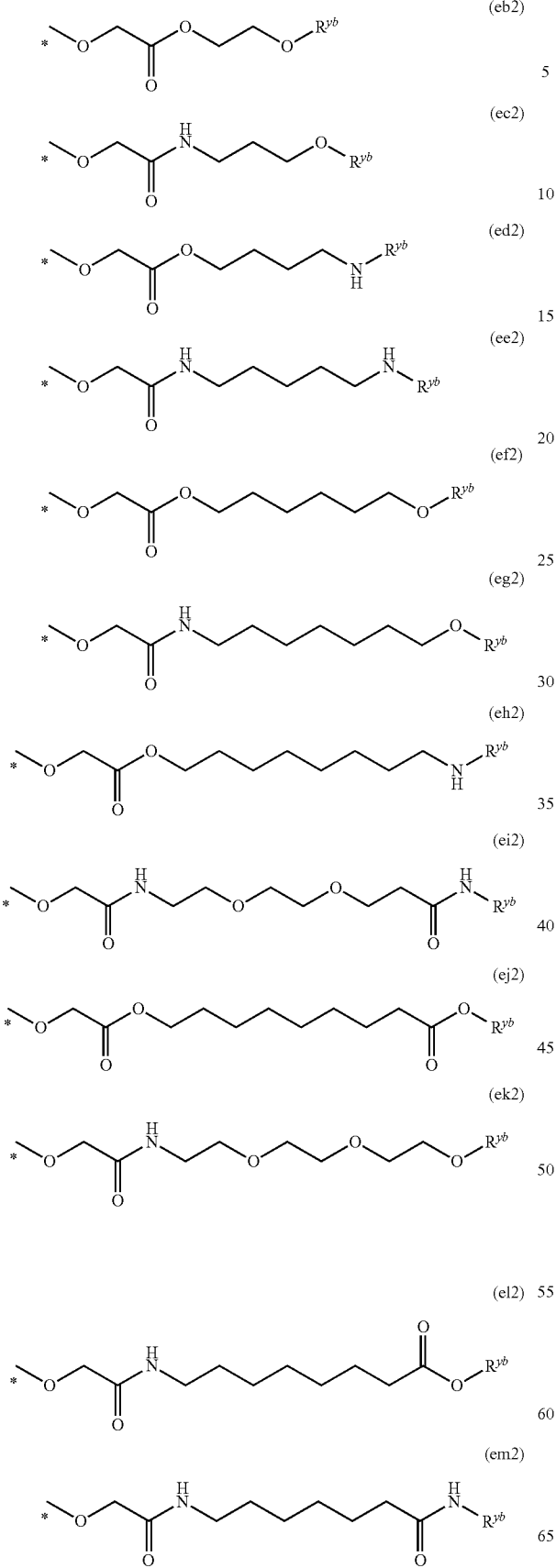
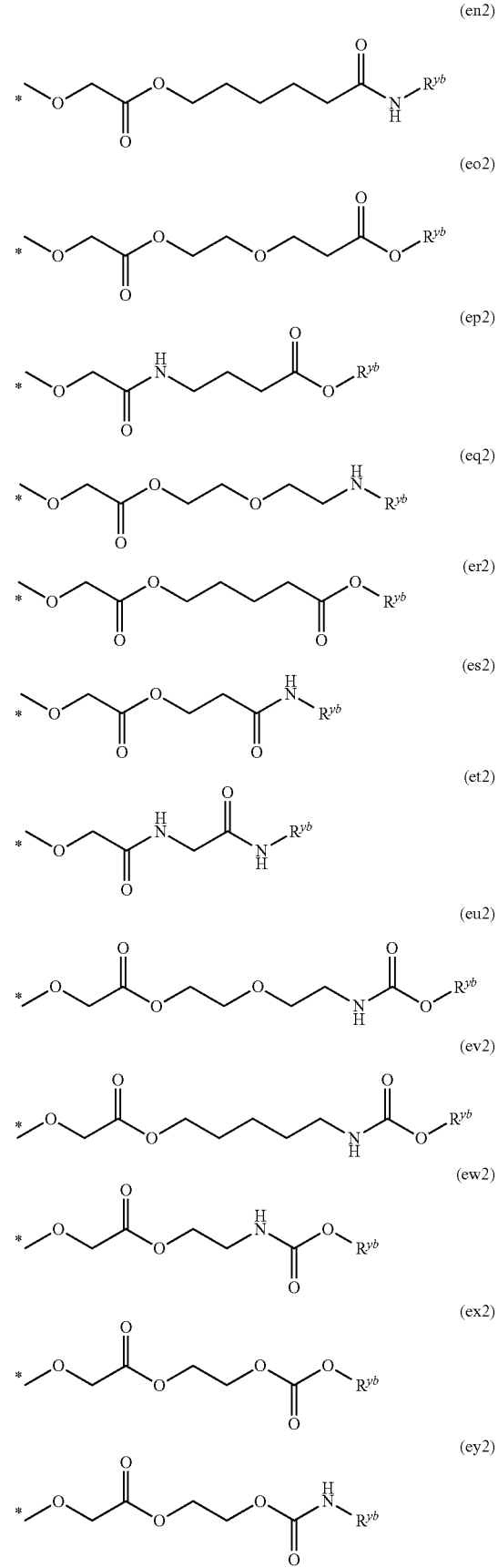

-continued

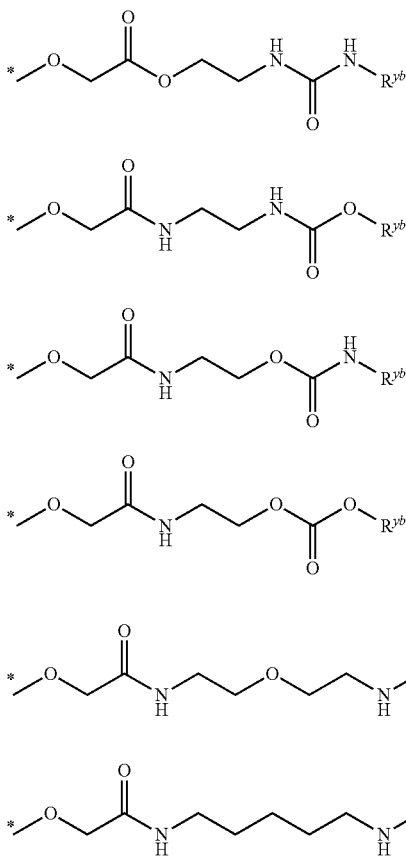

in which $R^{yb}$ is a group represented by the formulas (ck), (cl), and (cm) given below. —O—$Z^1$—$Z^2$, —O—$Z^0$—$Z^1$—$Z^2$, and —O—$Z^0$—$Z^2$ are preferably groups represented by the formulas (ec), (ee), (ep), (eq), (er), (ef3), (eg3), and (ez), and more preferably groups represented by the formulas (eq), (ef3), (eg3), and (ez). Further, in the groups represented by the formulas (ea), (eb), (ec), (ed), (ee), (en), (ep), (er), (es), (ef3), (eb2), (ec2), (ed2), (ee2), (ef2), (eg2), (eh2), (ek2), and (eq2), $R^{yb}$ is preferably (cl) and (cm), and in the groups represented by the formulas (ef), (eg), (eh), (ei), (ej), (ek), (el), (em), (eo), (eq), (et), (eu), (ev), (ew), (ex), (ey), (eg3), (ez), (ea2), (ei2), (ej2), (el2), (em2), (en2), (eo2), (ep2), (er2), (es2), (et2), (eu2), (ev2), (ew2), (ex2), (ey2), (ez2), (ea3), (eb3), (ec3), (ed3), and (ee3), $R^{yb}$ is preferably (ck). —O—$Z^1$—$Z^2$, —O—$Z^0$—$Z^1$—$Z^2$, and —O—$Z^0$—$Z^2$ are preferably groups represented by the formula (ef3) in which $R^{yb}$ is (cl) and (cm) and the groups represented by the formulas (eq), (eg3), and (ez) in which $R^{yb}$ is (ck), and more preferably groups represented by the formulas (eg3) and (ez) in which $R^{yb}$ is (ck).

When $X^2$ is —$NR^{31}$—$CHR^{32}$—$(CH_2)_{n11}$-$A^3$-$B^2$, the percent incorporation of $X^2$ is, for example, 3 to 55% and specifically 3, 4, 8, 12, 16, 18, 21, 23, 25, 30, 34, 39, 43, 47, 48, 51, or 55%.

When the group $X^2$ is —$NR^{31}$—$CHR^{32}$—$(CH_2)_{n11}$-$A^3$-$B^2$, the sum of the percent incorporation of group $X^1$ and the percent incorporation of group $X^2$ is, for example, 30 to 100% and specifically 30, 36, 41, 44, 49, 56, 61, 66, 70, 75, 79, 83, 88, 92, 96, or 100%.

Herein, the percent incorporation of group $X^2$ is, for example, 3, 8, 12, 16, 21, 25, 30, 34, 39, 43, 48, 51, or 55% and the percent incorporation of group $X^1$ is, for example, 15, 20, 25, 30, 35, 40, 45, 50, 55, 60, 72, 84, 95 or 97%.

When the group $X^2$ is —$NR^{31}$—$CHR^{32}$—$(CH_2)_{n11}$-$A^3$-$B^2$, it is preferable that $R^{32}$ is —$CONH_2$, $A^3$ is a single bond, $B^2$ is —NH—$X^4$, and $X^4$ is —$Z^3$, —$CO_2$—$Z^3$, and —CO—$(C_{2-6}$ alkylene)-COO—$Z^3$, and specific examples include groups represented by the following formulas:

[Chem. 36]

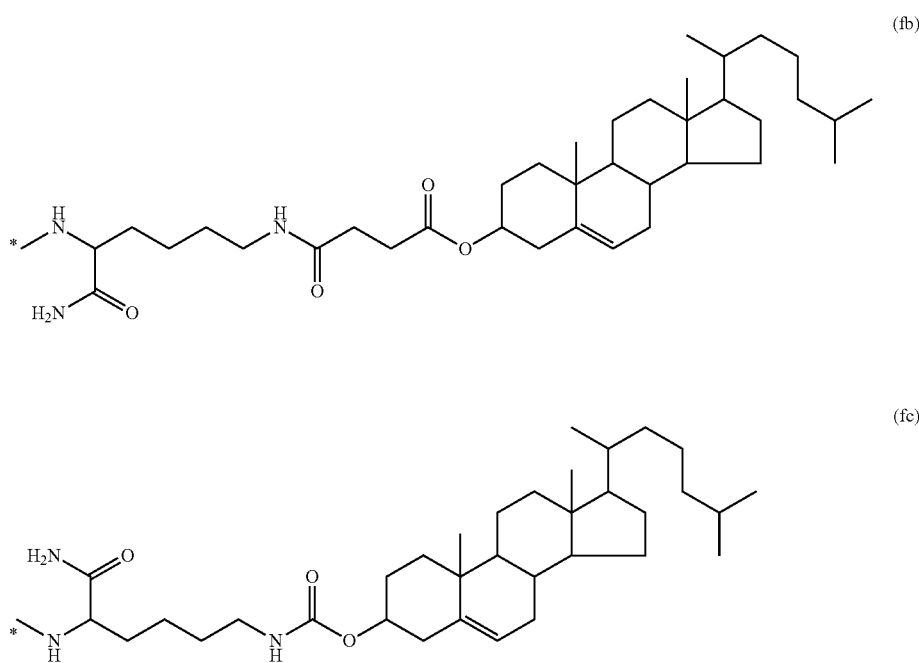

-continued

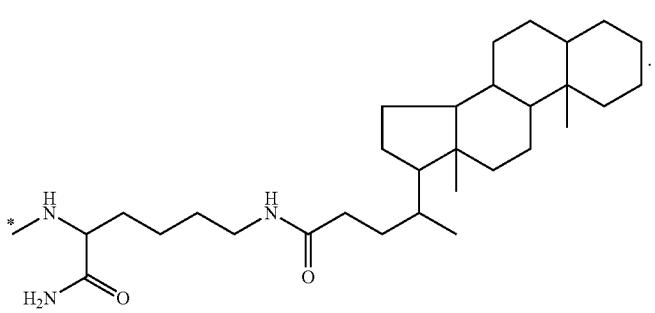

(fa)

When the group $X^2$ is $-NR^{31}-CHR^{32}-(CH_2)_{n11}-A^3-B^2$, more preferable combinations of the groups $X^1$ and $X^2$ are as follows: $X^1$ is the group represented by the formula (a) and $X^2$ is the groups represented by the formulas (fa), (fb), and (fc); and still more preferable combinations of $X^1$ and $X^2$ are as follows: $X^1$ is the group represented by the formula (a) and $X^2$ is the group represented by the formula (fa). The combinations of these groups are preferable for pharmaceutical compositions for transmucosal administration. A combination of the percent incorporations of $X^1$ and $X^2$ (the percent incorporation of $X^1$: the percent incorporation of $X^2$) is preferably (30 to 90%:2 to 70%) and more preferably (42 to 83%:3 to 50%).

According to further aspect of the present invention, there are provided the hyaluronic acid derivatives defined herein, the hyaluronic acid derivatives including repeating units of disaccharide represented by the formula (Ia) having the group $X^1$ and the formula (Ib) having the group $X^2$ as well as repeating units of disaccharide represented by the formula (II) having a group $X^a$ (hydroxy or $-O^-Q^+$ in which $Q^+$ represents a counter cation), or the formula (II) having the group $X^a$ and the formula (III) having the group $X^5$ ($-NR^{17}-R^{18}$ in which $R^{17}$ and $R^{18}$ are as having already been defined in this specification).

In the hyaluronic acid derivatives defined herein, the proportion of the repeating units represented by the formula (III) having the group $X^5$ in the repeating units of disaccharide present in the hyaluronic acid derivative (the percent incorporation of $X^5$) is, for example, 0 to 90%, preferably 0 and 1 to 90%, more preferably 0 and 4 to 62%.

Herein, the percent incorporation of $X^1$, the percent incorporation of $X^2$, or the percent incorporation of $X^5$ is calculated by the following equation:

$$\text{Percent incorporation of the introduced group (\%)} = \frac{\text{The number of repeating units of disaccharide into which the introduced group is introduced}}{\text{The number of repeating units of disaccharide being present}} \times 100 \quad [\text{Exp. 1}]$$

The "repeating units of disaccharide present in the derivative" include the repeating units of the formulas of (Ia), (Ib), (II), and (III). The percent incorporation can be controlled by reaction conditions such as a ratio of reagents and can be determined by, for example, NMR analysis.

Hyaluronic acid or salts thereof can be used as starting materials for producing hyaluronic acid derivatives of the present invention. Examples of the salts of hyaluronic acid include alkali metal salts such as sodium salts, potassium salts, and lithium salts, and tetraalkylammonium salts (for example, tetrabutylammonium (TBA) salts). For example, sodium salts frequently used as pharmaceutical products can be used by converting them into tetraalkylammonium salts such as tetrabutylammonium (TBA) salts. HA or pharmaceutically acceptable salts thereof can be produced by known methods, such as by methods including extraction of those derived from living organisms such as from cockscombs and porcine subcutaneous tissue or by fermentation. They are also commercially available (for example, from DENKI KAGAKU KOGYO KABUSHIKI KAISHA, Shiseido Co., Ltd., SEIKAGAKU CORPORATION, and R&D Systems, Inc.).

The weight-average molecular weight of hyaluronic acid (including salts thereof) consisted of only disaccharide units represented by the formula (II) used as a starting material is, for example, 1 kDa to 2,000 kDa. From the viewpoint of the mucosal permeability of drugs, it is preferably 3 kDa to 1000 Da, more preferably 5 kDa to 200 kDa, more preferably 5 kDa to 150 kDa, and more preferably 10 kDa to 100 kDa. To have a smaller particle size, a lower viscosity, or a higher solubility, the weight-average molecular weight is preferably 1 kDa to 500 kDa, more preferably 5 kDa to 200 kDa, and more preferably 5 kDa to 150 kDa. To have a higher viscosity or an increased retention under the skin or in the articular cavity, eyes, ears, nasal cavity, vagina, and mouth, the weight-average molecular weight is preferably 45 kDa to 2000 kDa, more preferably 50 kDa to 2000 kDa, more preferably 100 kDa to 1000 kDa, and more preferably 200 kDa to 1000 kDa. Specific examples of the weight-average molecular weight include, for example, 1 kDa, 3 kDa, 5 kDa, 8 kDa, 10 kDa, 25 kDa, 40 kDa, 45 kDa, 50 kDa, 65 kDa, 78 kDa, 89 kDa, 92 kDa, 99 kDa, 100 kDa, 112 kDa, 126 kDa, 134 kDa, 150 kDa, 168 kDa, 182 kDa, 200 kDa, 230 kDa, 271 kDa, 314 kDa, 379 kDa, 423 kDa, 468 kDa, 500 kDa, 651 kDa, 786 kDa, 824 kDa, 915 kDa, 1000 kDa, 1058 kDa, 1265 kDa, 1355 kDa, 1412 kDa, 1500 kDa, 1617 kDa, 1768 kDa, 1853 kDa, 1945 kDa, and 2000 kDa. "kDa" is an abbreviation for "kilodalton."

The weight-average molecular weight of the hyaluronic acid (including salts thereof) consisted of only disaccharide units represented by the formula (II) refers to a weight-average molecular weight calculated as the hyaluronic acid in which $R^{1a}$, $R^{2a}$, $R^{3a}$, and $R^{4a}$ are all hydrogen atoms, $R^{5a}$ is acetyl, and $X^a$ is $-O^-Na^+$ in the formula (II) with the backbone structure of the hyaluronic acid derivative of the present invention maintained. Accordingly, for example, when $X^a$ is $-O-$(tetra-n-butyl ammonium ion) in some or all disaccharide units in a starting material actually used and its weight-average molecular weight calculated as described above is within the aforementioned range of the weight-average molecular weight, they are included in preferable embodiments of the present invention.

In an aspect of the present invention, the non-derivatized hyaluronic acid having a backbone structure corresponding to that of the hyaluronic acid derivatives of the present invention has a weight-average molecular weight of 1 kDa to 2,000 kDa. Herein, the non-derivatized hyaluronic acid is hyaluronic acid consisted of only the repeating units represented by the formula (II) that has already been defined in which $R^{1a}$, $R^{2a}$, $R^{3a}$, and $R^{4a}$ are hydrogen atoms, $R^{5a}$ is acetyl, and $X^a$—$O^-Na^+$. From the viewpoint of the mucosal permeability of drugs, it is preferably 3 kDa to 1000 Da, more preferably 5 kDa to 200 kDa, more preferably 5 kDa to 150 kDa, and more preferably 10 kDa to 100 kDa. To have a smaller particle size, a lower viscosity, or a higher solubility, the weight-average molecular weight is preferably 1 kDa to 500 kDa, more preferably 5 kDa to 200 kDa, and more preferably 5 kDa to 150 kDa. To have a higher viscosity or an increased retention under the skin or in the articular cavity, eyes, ears, nasal cavity, vagina, and mouth, the weight-average molecular weight is preferably 45 kDa to 2000 kDa, more preferably 50 kDa to 2000 kDa, more preferably 100 kDa to 1000 kDa, and more preferably 200 kDa to 1000 kDa. Specific examples of the weight-average molecular weight include, for example, 1 kDa, 3 kDa, 5 kDa, 8 kDa, 10 kDa, 25 kDa, 40 kDa, 45 kDa, 50 kDa, 65 kDa, 78 kDa, 89 kDa, 92 kDa, 99 kDa, 100 kDa, 112 kDa, 126 kDa, 134 kDa, 150 kDa, 168 kDa, 182 kDa, 200 kDa, 230 kDa, 271 kDa, 314 kDa, 379 kDa, 423 kDa, 468 kDa, 500 kDa, 651 kDa, 786 kDa, 824 kDa, 915 kDa, 1000 kDa, 1058 kDa, 1265 kDa, 1355 kDa, 1412 kDa, 1500 kDa, 1617 kDa, 1768 kDa, 1853 kDa, 1945 kDa, and 2000 kDa.

The molecular weight of hyaluronic acid (including salts thereof) is calculated as a number average molecular weight or a weight-average molecular weight, since it is difficult to obtain hyaluronic acid as a single molecular species. In the present invention, the molecular weight is calculated as a weight-average molecular weight. The weight-average molecular weight can be measured by any of various known methods such as those measuring light scattering, osmotic pressure, or viscosity, as described in, for example, Seiichi Nakahama et al. "Essential Polymer Science" (KODANSHA LTD., ISBN 4-06-153310-X). The viscosity average molecular weight used herein can be measured by a method generally used in the art to which the present invention belongs, for example, by using an Ubbelohde viscometer. Accordingly, molecular weights of hyaluronic acid (including salts thereof) used as a starting material and the hyaluronic acid derivatives of the present invention are calculated as a weight-average molecular weight. When a commercially available hyaluronic acid (including salts thereof) whose molecular weight is specifically indicated is used, the indicated value may be used as the molecular weight of the hyaluronic acid.

The hyaluronic acid derivatives of the present invention may have any molecular weight, but when mucosal permeability is required, hyaluronic acids having a low viscosity and a low molecular weight are preferable; and when retention at a site of administration is required, hyaluronic acids having a high viscosity and a high molecular weight are preferable.

In the present invention, the group $X^1$ having a cationic site in the disaccharide unit represented by the formula (Ia) can be introduced by converting the carboxy in the glucuronic acid moiety to amide (step 1). For example, this can be achieved by converting hyaluronic acid (including salts or compounds thereof) as a starting material, preferably hyaluronic acid consisted of only disaccharide units represented by the formula (II) into a tetraalkylammonium salt (for example, a tetrabutylammonium (TBA) salt) by ion exchange; and reacting the salt of the hyaluronic acid with a compound represented by the formula $HNR^7$—$CHR^8$—$(CH_2)_{n1}$-$A^1$-$B^1$ (in which $R^7$, R, n1, $A^1$, and $B^1$ are as having already been defined in this specification) in the presence of a suitable condensation agent in a solvent.

In the present invention, the group $X^2$ having a hydrophobic site in the disaccharide unit represented by the formula (Ib) can be introduced by converting the carboxy of the glucuronic acid moiety to amide or ester (step 2).

The conversion to amide can be achieved by, for example, converting hyaluronic acid or its derivative as a starting material into a tetraalkylammonium salt (for example, a tetrabutylammonium (TBA) salt) by ion exchange; and reacting the salt of the hyaluronic acid with an amine into which a hydrophobic group represented by the formula $HNR^6$—$Z^1$—$Z^2$ (in which $R^6$, $Z^1$, and $Z^2$ are as having already been defined in this specification) is introduced or with an amine represented by the formula $HNR^b$—$Z^3$, $HNR^{31}$—$CHR^{32}$—$(CH_2)_{n11}$-$A^3$-$B^2$ or $HNR^aR^{5z}$ (in which $R^b$, $Z^3$, $R^{31}$, $R^{32}$, n11, $A^3$, $B^2$, $R^a$, and $R^{5z}$ are as having already been defined in this specification), in the presence of a suitable condensation agent in a solvent.

The conversion to ester can be achieved by, for example, converting hyaluronic acid or its derivative as a starting material into a tetraalkylammonium salt (for example, a tetrabutylammonium (TBA) salt) by ion exchange; and reacting, in a solvent, the salt of the hyaluronic acid with a halide into which a hydrophobic group represented by the formula Hal-$Z^3$, Hal-$R^a$, Hal-$Z^1$—$Z^2$, Hal-$Z^0$—$Z^1$—$Z^2$ or Hal-$Z^0$—$Z^2$ (in which $Z^3$, $R^a$, $Z^0$, $Z^1$, and $Z^2$ are as having already been defined in this specification, and Hal represents a halogen atom) is introduced (method 1) or by converting hyaluronic acid or its derivative as a starting material into a tetraalkylammonium salt (for example, a tetrabutylammonium (TBA) salt) when necessary, in the presence of a suitable condensation agent in a solvent; and reacting the salt of the hyaluronic acid with an alcohol into which a hydrophobic group represented by the formula HO—$Z^3$, HO—$R^a$, HO—$Z^1$—$Z^2$, HO—$Z^0$—$Z^1$—$Z^2$ or HO—$Z^0$—$Z^2$ (in which $Z^3$, $R^a$, $Z^0$, $Z^1$, and $Z^2$ are as having already been defined in this specification) is introduced (method 2).

In the present invention, the group $X^5$ in the disaccharide unit represented by the formula (III) can be introduced by converting the carboxy in the glucuronic acid moiety to amide (step 3). For example, this can be achieved by converting hyaluronic acid or its derivative as a starting material into a tetraalkylammonium salt (for example, a tetrabutylammonium (TBA) salt) by ion exchange; and reacting the salt of the hyaluronic acid with amine into which a group represented by the formula $HNR^{17}$—$R^{18}$ (in which $R^{17}$, and $R^{18}$ are as having already been defined in this specification) is introduced, in the presence of a suitable condensation agent in a solvent.

The group $X^1$ in the formula (Ia), the group $X^2$ in the formula (Ib), and the group $X^5$ in the formula (III) may be the same or different among a plurality of disaccharide units present in the hyaluronic acid derivative. For example, compounds represented by different formulas can be used to carry out the above reaction. Further, the group $X^a$ in the formula (II) may also be the same or different among a plurality of disaccharide units present in the hyaluronic acid derivative.

Condensation agents that can be used in the conversion reaction to amide described above include, but are not particularly limited, for example, 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP), 1-ethyl-3-(3-dimethylaminopropyl)carbodiimide (EDC), or N-hydroxysuccinimide (NHS).

Without particular limitation, DMT-MM is preferable in that the reaction proceeds efficiently in a mixed solvent of water and an organic solvent. In addition, the use of DMT-MM as a condensation agent allows highly selective formation of an amide bond between amino and carboxy while suppressing formation of an ester bond in a system with a large number of hydroxy. The use of the condensation agent prevents, for example, the reaction between a solvent alcohol and a carboxy in the hyaluronic acid moiety and intramolecular or intermolecular bonding between hydroxy and carboxy collocated on the hyaluronic acid moiety to form undesired crosslinking.

Examples of the solvent used in the conversion reaction to amide described above include water, dimethyl sulfoxide (DMSO), dimethylformamide (DMF), dimethylacetamide (DMAc), 1,3-dimethyl-2-imidazolidinone (DMI), sulfolane (SF), N-methylpyrrolidone (NMP), dioxane (for example, 1,4-dioxane), methanol, ethanol, propanol, butanol, acetonitrile, tetrahydrofuran (THF), dichloromethane, chloroform, hexane, diethyl ether, ethyl acetate and mixed solvents thereof. With respect to the solubility of starting materials, modifying reagents ed products and products and reactivity of condensation agents, DMSO alone or a water/DMSO mixed solvent is preferably used. Depending on the type of amino-carboxylic acid that is the modifying reagent, it may be used for a reaction as a methanol or dioxane solution.

Condensation agents used in the conversion reaction to ester described above include 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP) or 1-ethyl-3-(3-dimethylaminopropyl)carbodiimide (EDC) or N-hydroxysuccinimide (NHS), preferably, DMT-MM.

Examples of the solvent used in the conversion reaction to ester described above include water, DMSO, methanol, ethanol, propanol, butanol, acetonitrile, DMF, THF, dichloromethane, chloroform, hexane, diethyl ether, ethyl acetate and mixed solvents thereof.

The conversion reaction to amide can be achieved by, when the group $X^2$ is —$NR^6$—$Z^1$—$Z^2$, converting the hyaluronic acid or its derivative as a starting material into a tetraalkylammonium salt (for example, a tetrabutylammonium (TBA) salt) by ion exchange; reacting the salt of the hyaluronic acid with a spacer moiety in the presence of a suitable condensation agent in a solvent (in this step, protection and deprotection reactions may be conducted, if necessary); converting the carboxy (—COOH) or a salt thereof in the hyaluronic acid as a starting material or its derivative; and then reacting it with a suitable reagent.

Exemplary combinations of groups converted from the carboxy and reaction reagents are shown below.

—$CONR^6$—$Z^1$—$NR^bH$+Hal-$Z^3$,
—$CONR^6$—$Z^1$—$NR^bH$+Hal-$COOZ^3$,
—$CONR^6$—$Z^1$—$NR^bH$+HOCO—$Z^3$,
—$CONR^6$—$Z^1$—$NR^bH$+Hal-CO—$Z^3$,
—$CONR^6$—$Z^1$—COOH+HO—$Z^3$,
—$CONR^6$—$Z^1$—OH+Hal-COO—$Z^3$,
—$CONR^6$—$Z^1$—COOH+$NR^c$—$Z^3$,
—$CONR^6$—$Z^1$—OCO-Hal+$NR^c$—$Z^3$,
—$CONR^6$—$Z^1$—OCOOH+HO—$Z^3$,
—$CONR^6$—$Z^1$—OCOOH+Hal-$Z^3$,
—$CONR^6$—$Z^1$—OCO-Hal+HO—$Z^3$,
—$CONR^6$—$Z^1$—SH+Hal-$Z^3$,
—$CONR^6$—$Z^1$-Hal+HS-$Z^3$,
—$CONR^6$—$Z^1$—CO—$Z^a$-Hal+HS—$Z^3$,
—$CONR^6$—$Z^1$—CO—$Z^a$—SH+Hal-$Z^3$,
—$CONR^6$—$Z^1$—O—CO—CH=$CH_2$+HS—$Z^3$,
—$CONR^6$—$Z^1$—$NR^b$—CO—C($CH_3$)=$CH_2$+HS—$Z^3$,
and
—$CONR^6$—$Z^1$—SH+HS—R, in which $R^6$, $Z^1$, $R^b$, $R^c$, and $Z^3$ are as defined hereinabove, and Hal represents a halogen atom selected from a fluorine atom, a chlorine atom, a bromine atom and iodine.

Examples of the reaction pattern mode include dehydrohalogenation reactions, condensation reactions, dehydration reactions, nucleophilic addition reactions such as Michael addition, and oxidative disulfide-formation reaction, which are well-known reactions, and can be appropriately selected and carried out in preferable reaction conditions by a person skilled in the art. If a converted product or reaction reagent has carboxy, it can be converted into N-hydroxy succinic acid imide (hereinafter also referred to as "NHS") ester to be reacted.

Exemplary methods also include a method including reacting 2-aminoethyl-2-pyridyldisulfide with a carboxy in hyaluronic acid or its derivative as a starting material to prepare a hyaluronic acid derivative modified with a spacer having a mercapto modified with a leaving group at the terminus, and reacting this with thiocholesterol by a nucleophilic substitution reaction to form a disulfide bond.

Exemplary methods also include a method preparing a compound modified with a part of a spacer on a carboxy in hyaluronic acid or its derivative as a starting material and a compound modified with a part of the spacer on a steryl group and reacting these compounds. While some of specific examples are listed above, exemplary methods further include a method preparing a hyaluronic acid derivative modified with a spacer having mercapto at the terminus on a carboxy in hyaluronic acid or its derivative as a starting material and a steryl group modified with a spacer having mercapto at the terminus and reacting them oxidatively to form a disulfide bond. In this method, one mercapto may be reacted with 2-mercaptopyridine to form disulfide, and then it may be substituted with the other mercapto.

The conversion reaction to ester can be achieved by, when $X^2$ is —O—$Z^1$—$Z^2$, converting hyaluronic acid or its derivative as a starting material into a tetraalkylammonium salt (for example, a tetrabutylammonium (TBA) salt) by ion exchange; reacting the salt of the hyaluronic acid with a spacer moiety, in the presence of a suitable condensation agent in a solvent (in this step, protection and deprotection reactions may be conducted, if necessary); converting the carboxy (—COOH) of the hyaluronic acid or its derivative as a starting material; and then reacting it with a suitable reagent. Exemplary combinations of groups converted from the carboxys and reaction reagents are shown below.

—COO—$Z^1$—NR$^b$H+Hal-$Z^3$,
—COO—$Z^1$—NR$^b$H+Hal-COO—$Z^3$,
—COO—$Z^1$—NR$^b$H+HOCO—$Z^3$,
—COO—$Z^1$—NR$^b$H+Hal-CO—$Z^3$,
—COO—$Z^1$—NR$^b$—COOH+HNR$^c$—$Z^3$,
—COO—$Z^1$—NR$^b$—CONR$^c$H+Hal-$Z^3$,
—COO—$Z^1$—NR$^b$H+HOCO—NR$^c$—$Z^3$,
—COO—$Z^1$—NR$^b$H+Hal-CO—NR$^c$—$Z^3$,
—COO—$Z^1$—COOH+HO—$Z^3$,
—COO—$Z^1$—COOH+H$_2$NR$^c$—$Z^3$,
—COO—$Z^1$—OH+Hal-CO—NR$^c$—$Z^3$,
—COO—$Z^1$—OH+Hal-COO—$Z^3$,
—COO—$Z^1$—OCOOH+Hal-$Z^3$,
—COO—$Z^1$—OCO-Hal+HO—$Z^3$,
—COO—$Z^1$—SH+Hal-$Z^3$,
—COO—$Z^1$-Hal+HS—$Z^3$,
—COO—$Z^1$—CO—$Z^a$-Hal+HS—$Z^3$,
—COO—$Z^1$—CO—$Z^a$—SH+Hal-$Z^3$,
—COO—$Z^1$—O—CO—CH=CH$_2$+HS—$Z^3$,
—COO—$Z^1$—NR$^b$—CO—C(CH3)=CH$_2$+HS—$Z^3$, and
—COO—$Z^1$—SH+HS—$Z^3$,
in which $Z^1$, $Z^2$, $Z^3$, R$^b$, R$^c$, and $Z^a$ are as having already been defined in this specification, and Hal represents a halogen atom selected from a fluorine atom, a chlorine atom, a bromine atom and iodine.

Examples of the reaction pattern include dehydrohalogenation reactions, condensation reactions, dehydration reactions, nucleophilic addition reactions such as Michael addition, and oxidative disulfide-formation reaction, which are well-known reactions, and can be appropriately selected and carried out in preferable reaction conditions by a person skilled in the art. If a converted product or reaction reagent has carboxy, it can be converted into N-hydroxy succinic acid imide (hereinafter also referred to as "NHS") ester to be reacted.

Specific examples of a protecting group used in the reaction described above are described in, for example, T. W. Greene, P. G. M. Wuts, Protective Groups in Organic Synthesis, Third Edition, John Wiley & Sons, Inc., New York, 1999.

Examples of the protecting group for hydroxy include (C$_{1-6}$ alkyl)carbonyl, arylcarbonyl, heteroarylcarbonyl, (C$_{1-6}$ alkoxy)carbonyl, (C$_{1-6}$ alkoxy)C$_{1-6}$ alkyl, (C$_{1-6}$ alkyl)aminocarbonyl, di(C$_{1-6}$ alkyl)aminocarbonyl, aryl (C$_{1-6}$ alkyl), heteroaryl(C$_{1-6}$ alkyl), (aryl(C$_{1-6}$ alkyl))aminocarbonyl, C$_{1-6}$ alkyl, C$_{1-6}$ alkylsulfonyl, ((amino C$_{1-6}$ alkyl)carbonyloxy)-C$_{1-6}$ alkyl, unsaturated heterocycle carbonyloxy C$_{1-6}$ alkyl, aryldi (C$_{1-6}$ alkyl)silyl, and tri(C$_{1-6}$ alkyl)silyl. Preferable examples of the protecting group for hydroxy include acetyl.

Examples of the protecting group for —NH— or amino include (C$_{1-6}$ alkyl)carbonyl, aryl (C$_{1-6}$ alkyl)carbonyl, arylcarbonyl, heteroarylcarbonyl, (C$_{1-6}$ alkoxy)carbonyl, (C$_{1-6}$ alkyl)aminocarbonyl, di(C$_{1-6}$ alkyl)aminocarbonyl, aryl (C$_{1-6}$ alkyl), heteroaryl (C$_{1-6}$ alkyl), (aryl (C$_{1-6}$ alkyl))aminocarbonyl. Preferable examples of the protecting group for amino include acetyl, t-butoxycarbonyl, and 9-fluorenylmethoxycarbonyl. By protection, amino may form a saturated or unsaturated heterocyclic group such as a phthalic acid imide, a succinic acid imide, a glutaric acid imide, and 1-pyrrolyl.

Examples of the protecting group for mercapto include, C$_{1-6}$ alkylthio such as ethylthio and t-butylthio, substituted phenylthio such as 2-nitrophenylthio and 2-carboxy phenylthio, and heteroarylthio such as 2-pyridylthio. A preferable example is 2-pyridylthio.

Examples of the protecting group for the carboxy include methoxy, ethoxy, t-butoxy, allyloxy, phenoxy, benzyloxy, methylthio, and ethylthio. A preferable example is ethoxy.

The order of steps 1, 2, and 3 is not restricted. Further, the step 3 may or may not be included. For example, hyaluronic acid (including salts or compounds thereof) as a starting material, preferably hyaluronic acid consisted of only disaccharide units represented by the formula (IIb), may be converted by ion exchange into a tetraalkylammonium salt (for example, a tetrabutylammonium (TBA) salt), the salt of the hyaluronic acid may be reacted with an amine modified with a hydrophobic group represented by the formula HNR$^6$—$Z^1$—$Z^2$ (in which R$^6$, $Z^1$, and $Z^2$ are as having already been defined in this specification) in the presence of a suitable condensation agent in a solvent, and then the reaction product may be reacted with a compound represented by the formula HNR$^7$—CHR$^8$—(CH$_2$)$_{n1}$-A$^1$-B$^1$ (in which R$^7$, R$^8$, n1, A$^1$, and B$^1$ are as having already been defined in this specification), in the presence of a suitable condensation agent in a solvent.

Examples of the compound represented by the formula HNR$^7$—CHR$^8$—(CH$_2$)$_{n1}$-A$^1$-B$^1$ include compounds represented by the following formulas:

[Chem. 37]

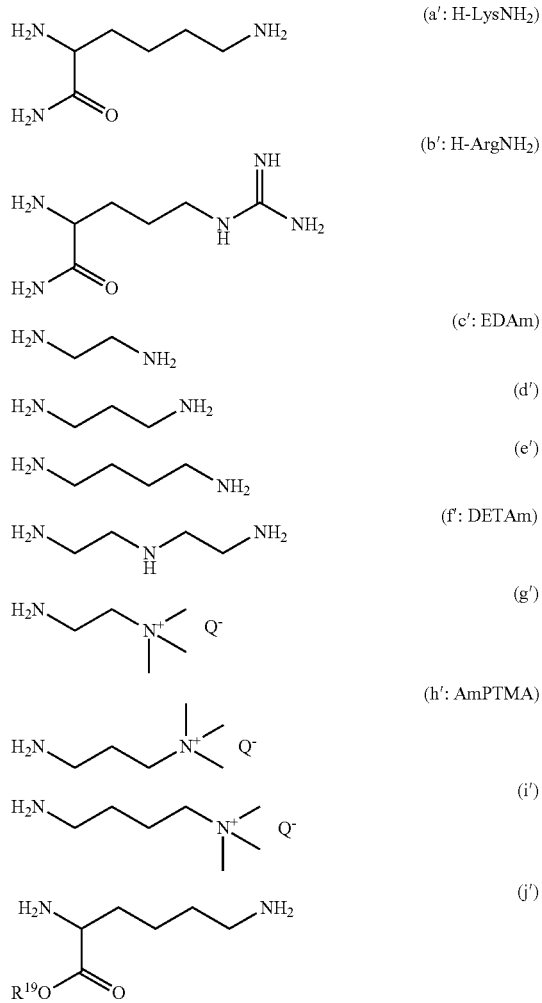

and preferable examples are compounds represented by the formulas (a'), (b'), (c'), (f'), (h'), (l'), (m'), (o'), (s'), (t'), (u'), (v'), (y'), (z'), (ae'), and (ah'); compounds represented by the formulas (a'), (b'), (c'), (d'), (f'), (h'), (j'), (k'), (l'), (m'), (n'), (o'), (p'), (s'), (t'), (u'), (v'), (y'), (z'), (ae'), and (ah'); compounds represented by the formulas (a'), (b'), (c'), (d'), (f'), (j'), (k'), (l'), (m'), (n'), (o'), (p'), (s'), (t'), (v'), (z'), (ae'), and (ah'); compounds represented by the formulas (a'), (b'), (c'), (d'), (f'), (j'), (k'), (l'), (m'), (n'), (o'), (p'), (s'), (t'), (z'), (ae'), and (ah'); compounds represented by the formulas (a'), (b'), (c'), (f'), (h'), (l'), (m'), (o'), (s'), (t'), (y'), (z'), (ae'), and (ah'); compounds represented by the formulas (a'), (b'), (c'), (f'), (h'), (l'), (m'), (o'), (s'), (t'), (u'), (y'), (z'), (ae'), and (ah'); compounds represented by the formulas (a'), (b'), (c'), (f'), (l'), (m'), (o'), (s'), (t'), (u'), (v'), (y'), (z'), (ae'), and (ah'); compounds represented by the formulas (a'), (b'), (c'), (f'), (h'), (l'), (m'), (o'), (s'), (t'), (u'), (v'), (z'), (ae'), and (ah'); compounds represented by the formulas (a'), (b'), (c'), (f'), (h'), (l'), (m'), (o'), (s'), (u'), (v'), (y'), (z'), (ae'), and (ah'); compounds represented by the formulas (a'), (b'), (c'), (f'), (h'), (l'), (m'), (o'), (u'), (v'), (y'), (z'), (ae'), and (ah'); compounds represented by the formulas (a'), (b'), (j'), (k'), (n'), (o'), and (p'); compounds represented by the formulas (c'), (d'), (l'), and (m'); compounds represented by the formulas (f'), (t'), (u'), and (v'); compounds represented by the formula (q'), (r'), (s'), (z'), (aa'), (ab'), (ac'), (ad'), (ae'), (af'), (ag'), and (ah'); compounds represented by the formulas (g'), (h'), and (i'); and compounds represented by the formulas (w'), (x'), and (y').

Most of the compounds represented by the formulas (b') and (k') are introduced into carboxy of hyaluronic acid or its derivative as starting materials as groups represented by the formulas (b) and (k), but some of them may be introduced as groups represented by the following formulas because amino of guanidino is bound to a carboxy of hyaluronic acid or its derivative as starting materials:

[Chem. 38]

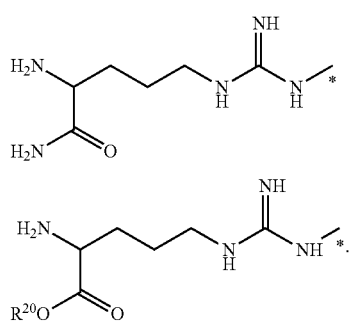

Hyaluronic acid derivatives including such repeating units are also included in the hyaluronic acid derivatives of the present invention as well as the hyaluronic acid derivatives substantially consisted of the repeating units of: (1) the above formulas (Ia) and (Ib), (2) the above formulas (Ia), (Ib), (II), (3) the above formulas (Ia), (Ib), and (III), or (4) the above formulas (Ia), (Ib), (II), and (III).

Examples of the compounds represented by the formula $HNR^6-Z^1-Z^2$ include compounds represented by the following formulas:

[Chem. 39]

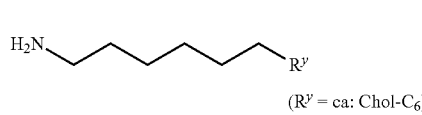
(da)
($R^y$ = ca: Chol-C$_6$)

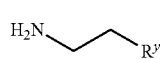
(db)

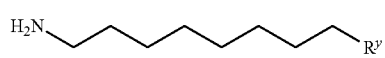
(dc)

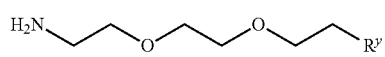
(dd)

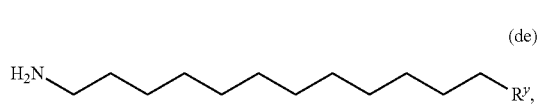
(de)

in which $R^y$ is groups represented by the following formulas:

[Chem. 40]

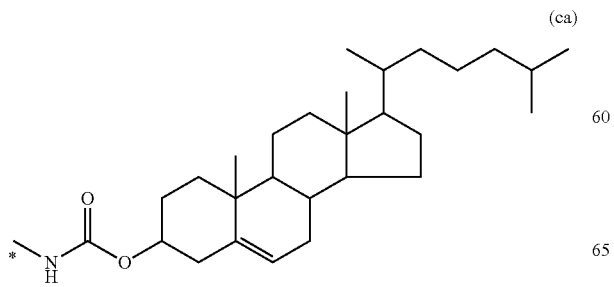
(ca)

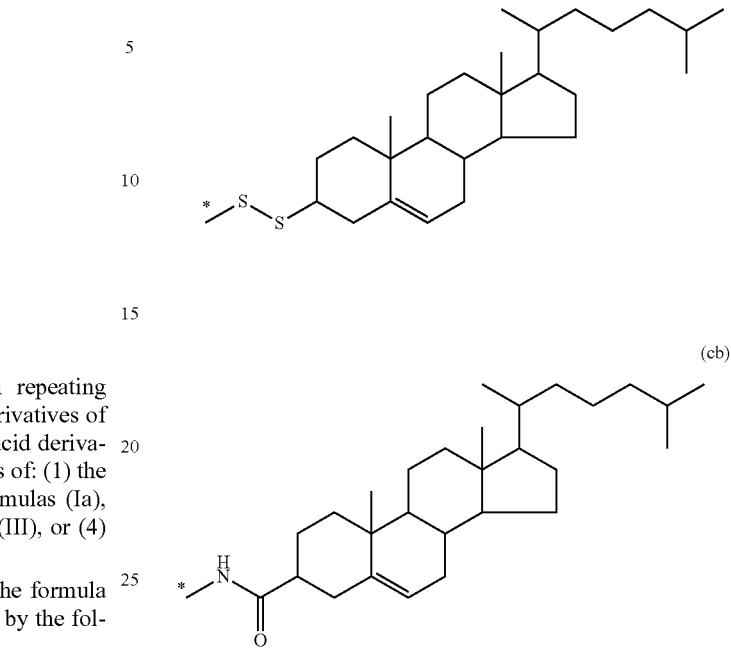
(ce)
(cb)
(cf)
(cc)

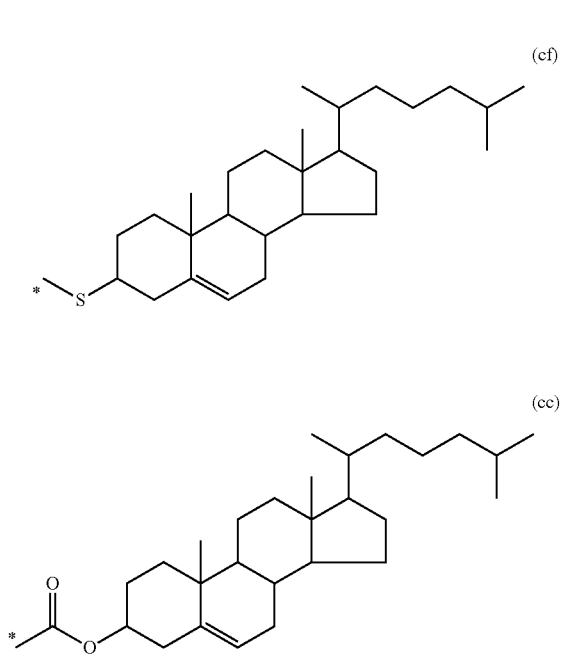

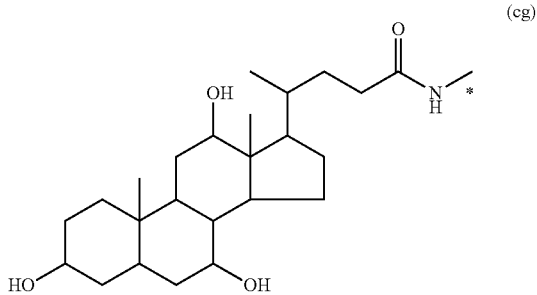
(cg)

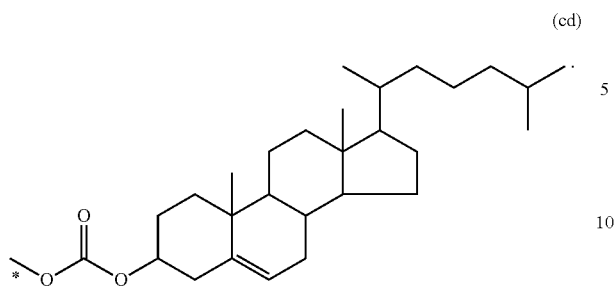
(cd)

Examples of the compound represented by the formula $HNR^6$—$Z^1$—$Z^2$ include, preferably, compounds represented by the formulas (da), (db), (dc), and (dd) in which each $R^y$ is (ca) and compounds represented by the formulas (da), (db), and (dd) in which each $R^y$ is (cg).

The compound represented by the formula $HNR^b$—$Z^3$ is, for example, preferably a compound represented by the following formula:

[Chem. 41]

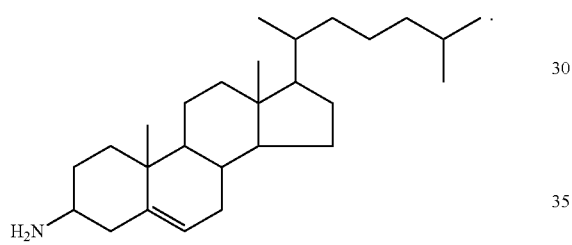

Examples of the compounds represented by the formula $HNR^{31}$—$CHR^{32}$—$(CH_2)_{n11}$-$A^3$-$B^2$ include compounds represented by the following formulas:

[Chem. 42]

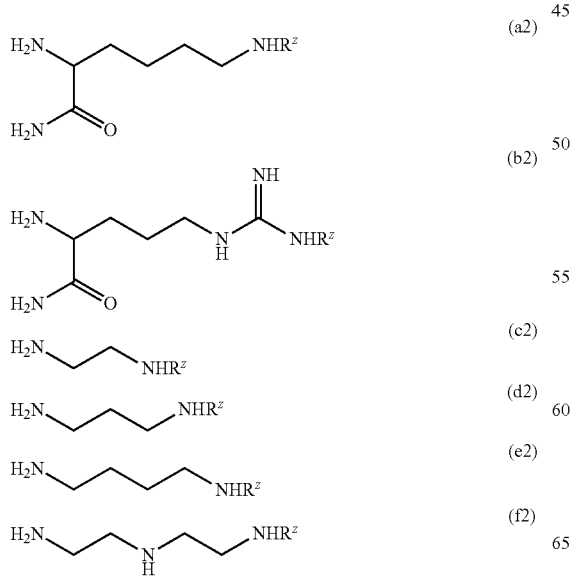

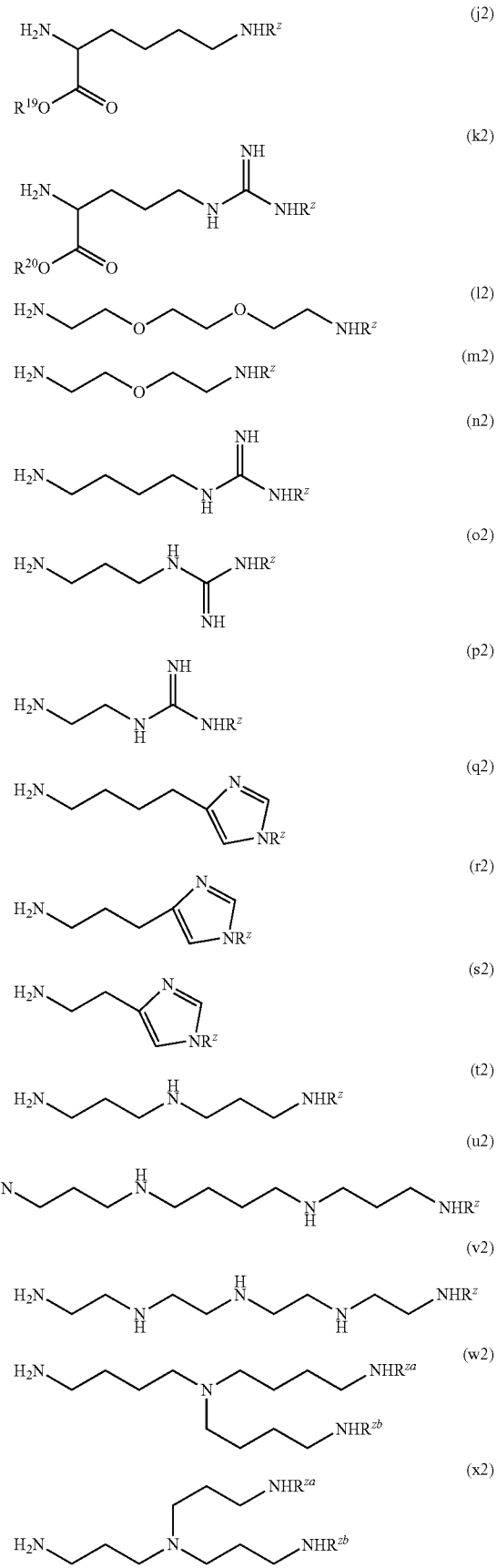

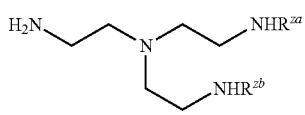 (y2)

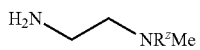 (ae2)

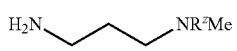 (af2)

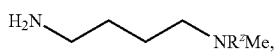 (ag2)

preferably compounds represented by the formulas (a2), (b2), (c2), (d2), (f2), (j2), (k2), (l2), (m2), (n2), (o2), (p2), (t2), (u2), (v2), (y2), and (ae), and more preferably compounds represented by the formulas (a2), (b2), (c2), (d2), (f2), (l2), (m2), (o2), (t2), (u2), (v2), (y2), and (ae), in which $R^z$ represents groups represented by the following formulas:

[Chem. 43]

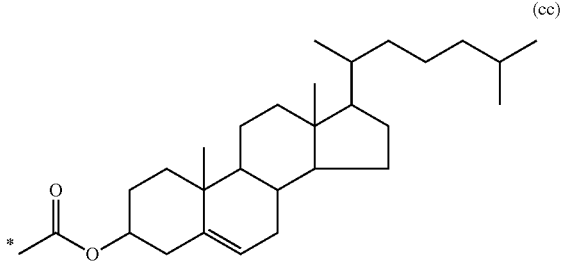 (cc)

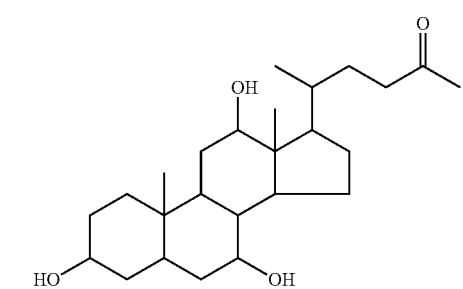 (ch)

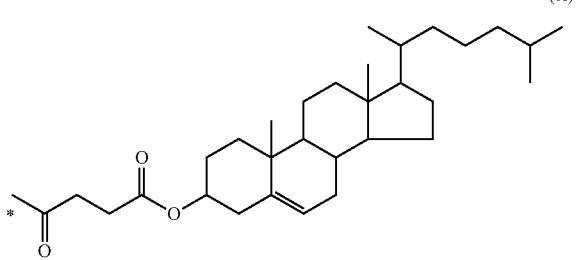 (ci)

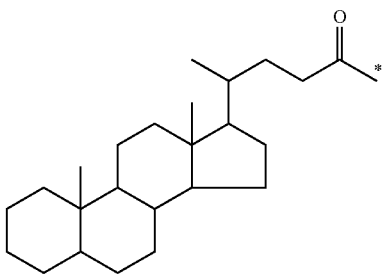 (cj)

or a group represented by (cc), (ci) or (ch). $R^{za}$ and $R^{zb}$ independently represent a hydrogen atom, a group represented by (cc), (ci), (ch) or (cj), or a hydrogen atom, a group represented by (cc), (ci) or (ch), provided that $R^{za}$ and $R^{zb}$ are not hydrogen atoms at the same time.

Examples of the compounds represented by the formula Hal-$Z^3$ include compounds represented by the following formulas:

[Chem. 44]

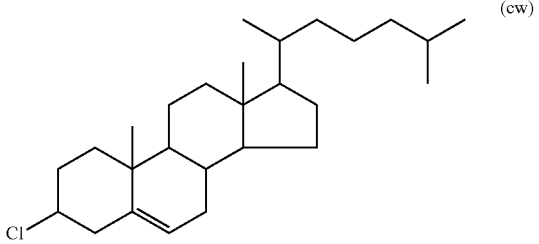 (cw)

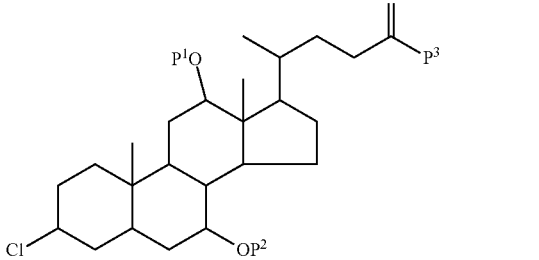 (cy)

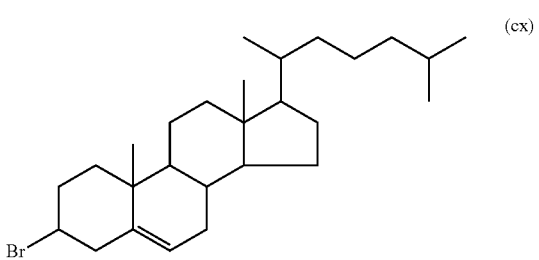 (cx)

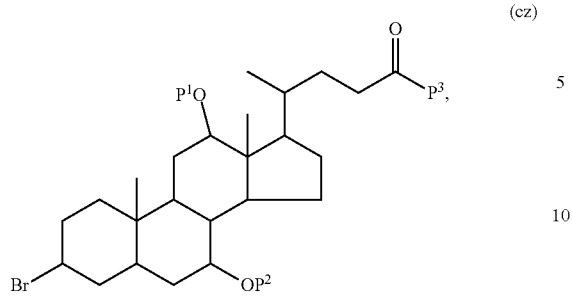

preferably a compound represented by the formula (cw). $P^1$ and $P^2$ independently represent a hydrogen atom or a protecting group for hydroxy, and $P^3$ represents a protecting group for hydroxy or carboxy.

Examples of the compound represented by the formula Hal-$Z^1$—$Z^2$ include compounds represented by the following formulas:

[Chem. 45]

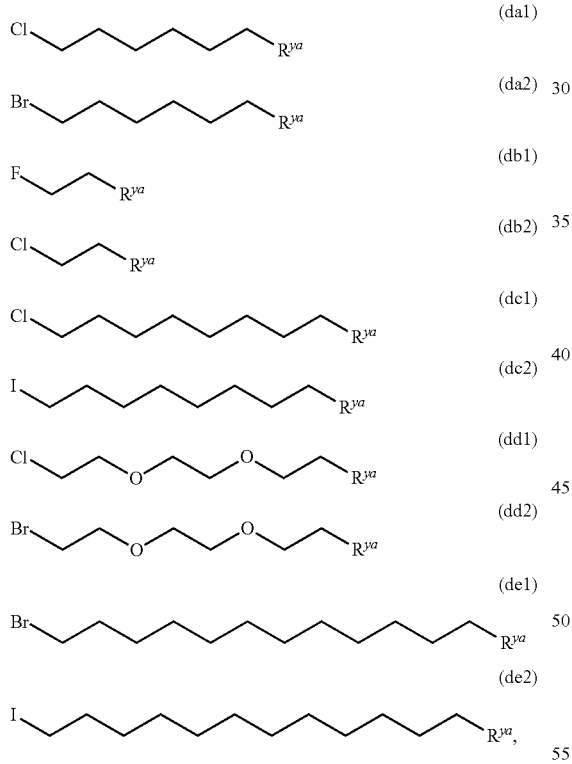

in which $R^{ya}$ is groups represented by the formula (ca), (cb), (cc), (cd), (cf), and (cg). The compound represented by the formula Hal-$Z^1$—$Z^2$ is, preferably, compounds represented by the formulas (da1), (da2), (db1), (db2), (dd1), and (dd2) in which each $R^{ya}$ is (ca) and compounds represented by the formulas (da1), (da2), (db1), (db2), (dd1), and (dd2) in which each $R^{ya}$ is (cg).

Further, examples of the compounds represented by the formulas Hal-$Z^1$—$Z^2$, Hal-$Z^0$—$Z^1$—$Z^2$, and Hal-$Z^0$—$Z^2$ include compounds represented by the following formulas:

[Chem. 46]

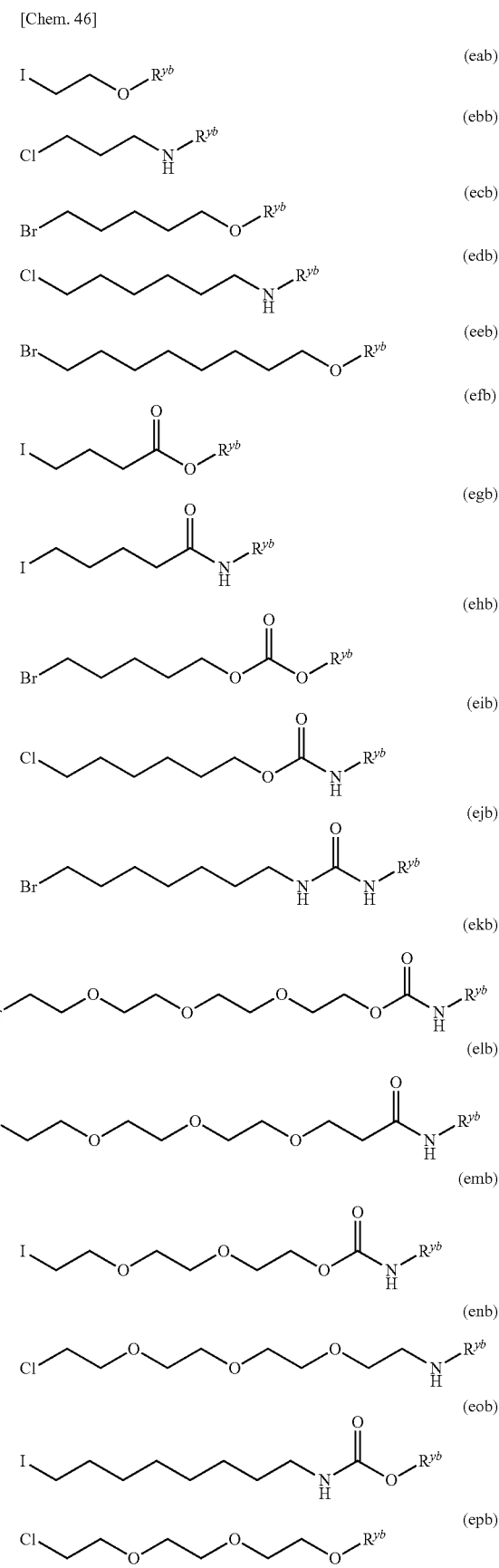

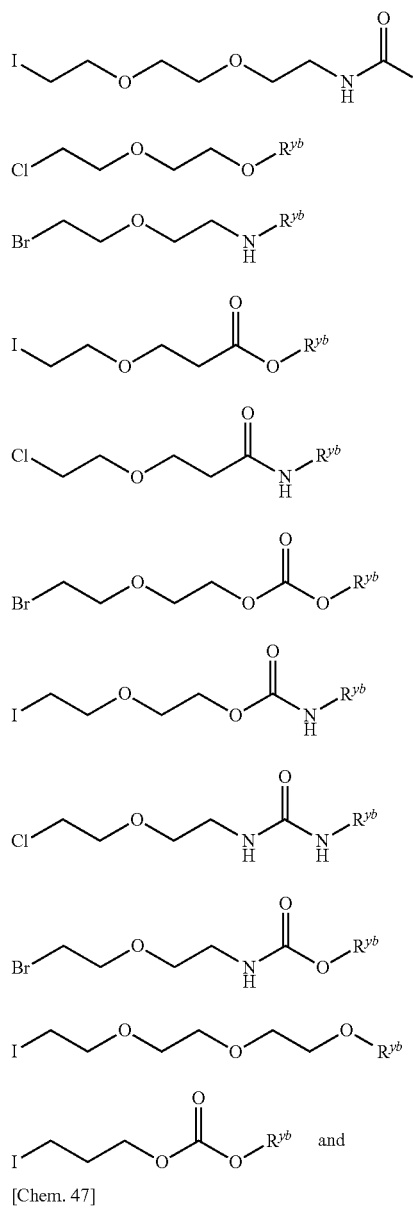

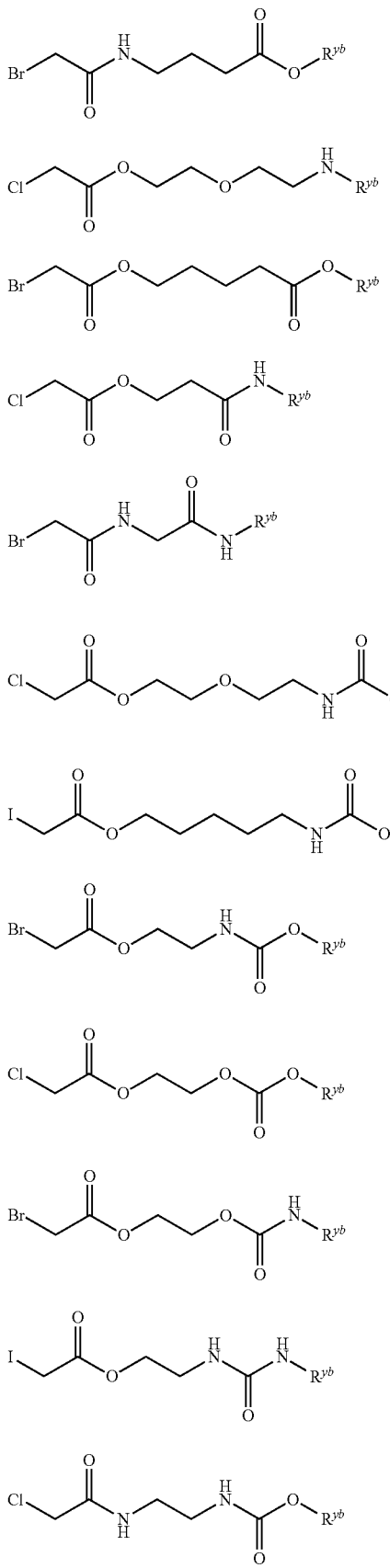

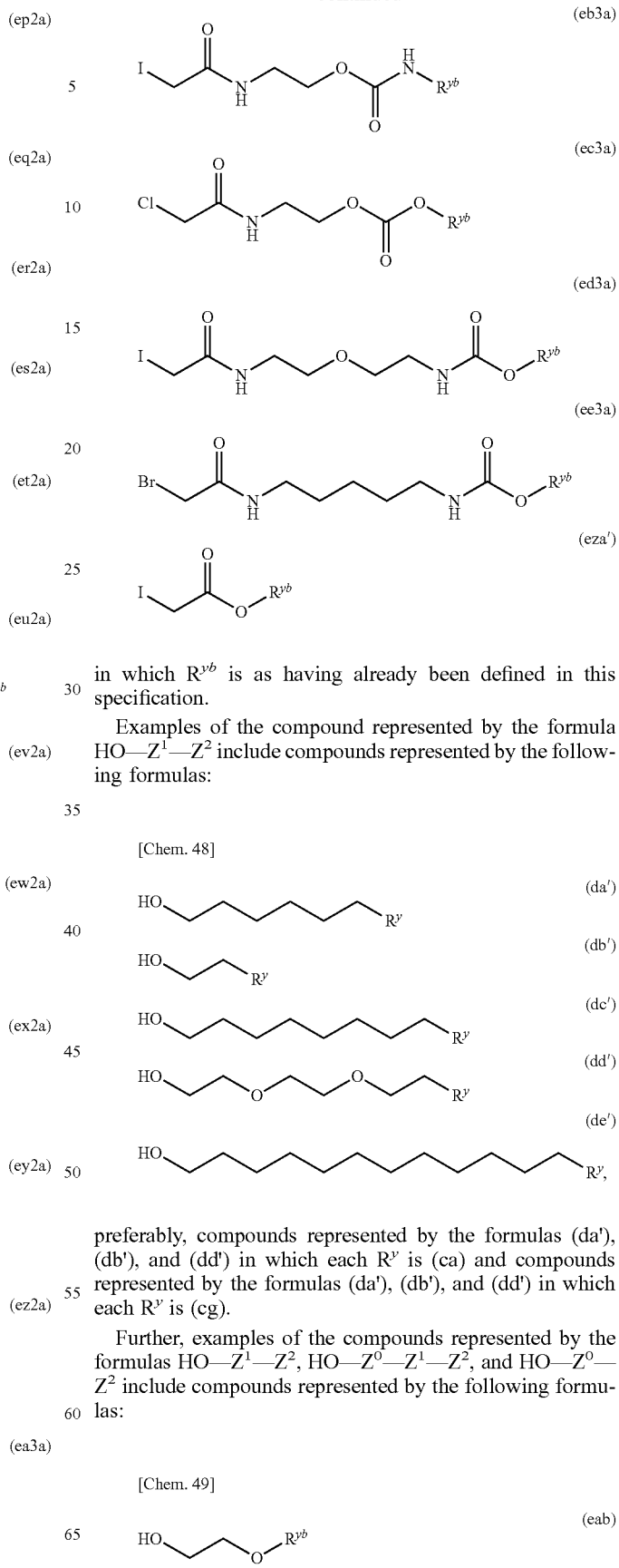

in which $R^{yb}$ is as having already been defined in this specification.

Examples of the compound represented by the formula HO—$Z^1$—$Z^2$ include compounds represented by the following formulas:

[Chem. 48]

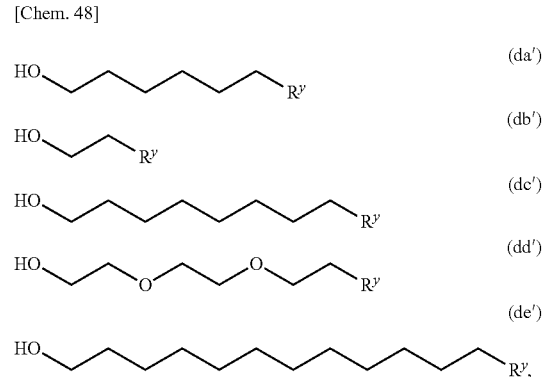

preferably, compounds represented by the formulas (da'), (db'), and (dd') in which each $R^y$ is (ca) and compounds represented by the formulas (da'), (db'), and (dd') in which each $R^y$ is (cg).

Further, examples of the compounds represented by the formulas HO—$Z^1$—$Z^2$, HO—$Z^0$—$Z^1$—$Z^2$, and HO—$Z^0$—$Z^2$ include compounds represented by the following formulas:

[Chem. 49]

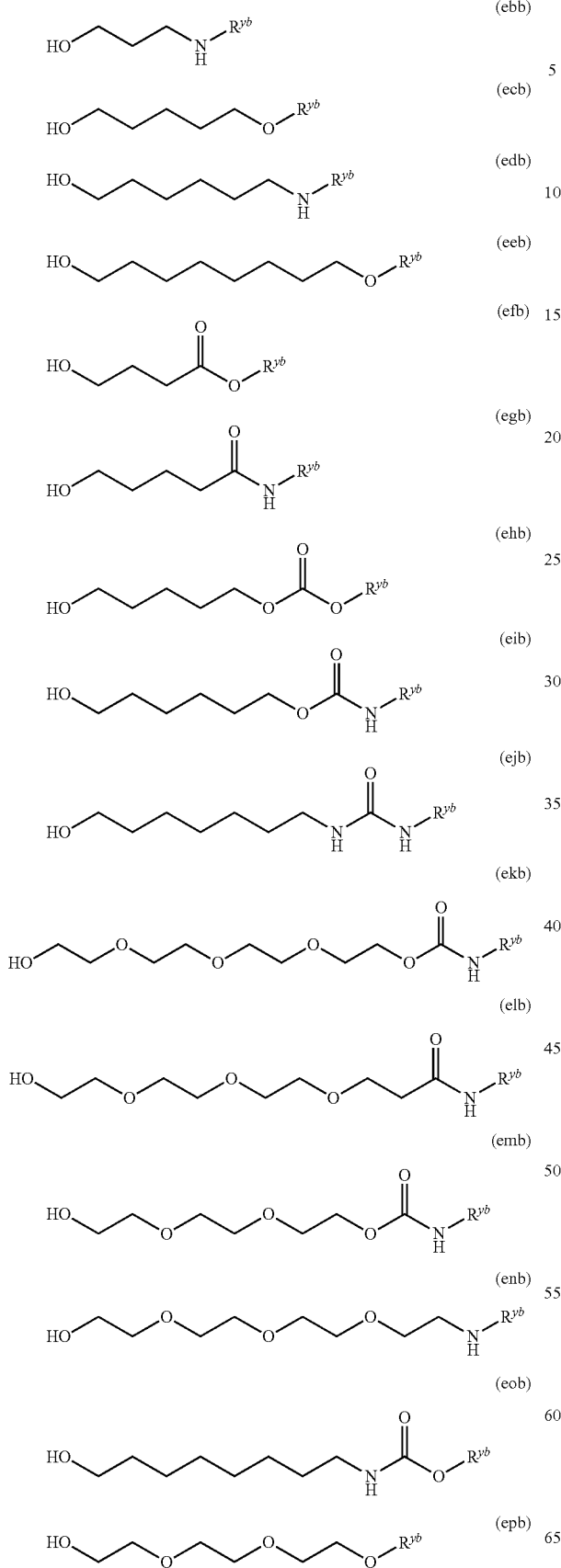
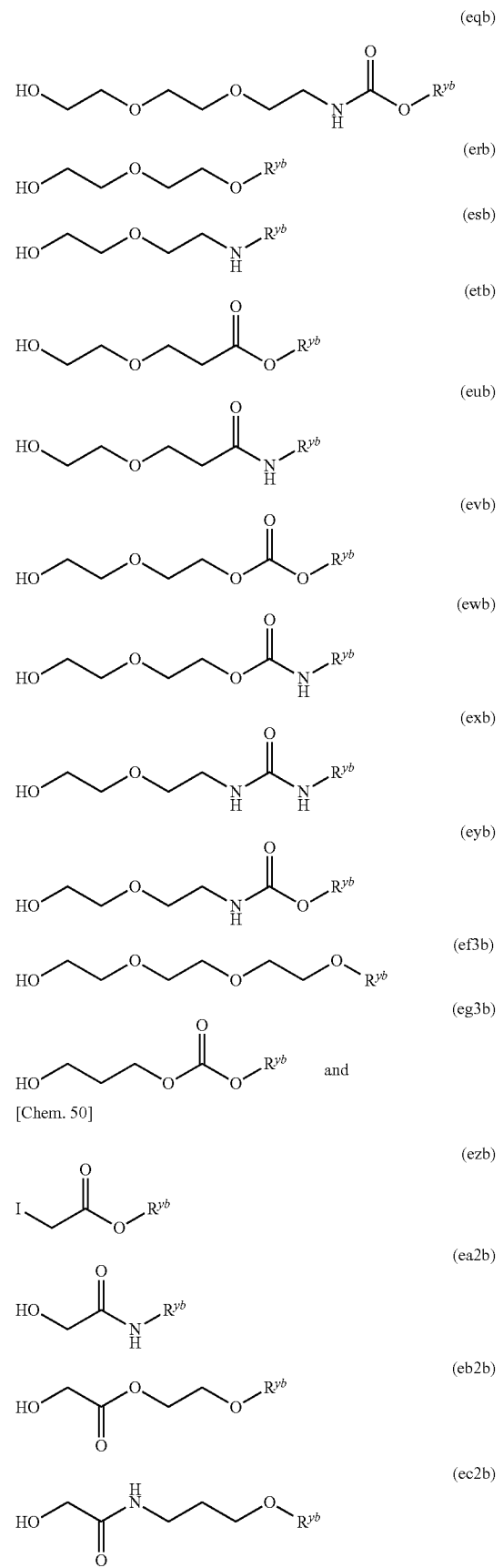

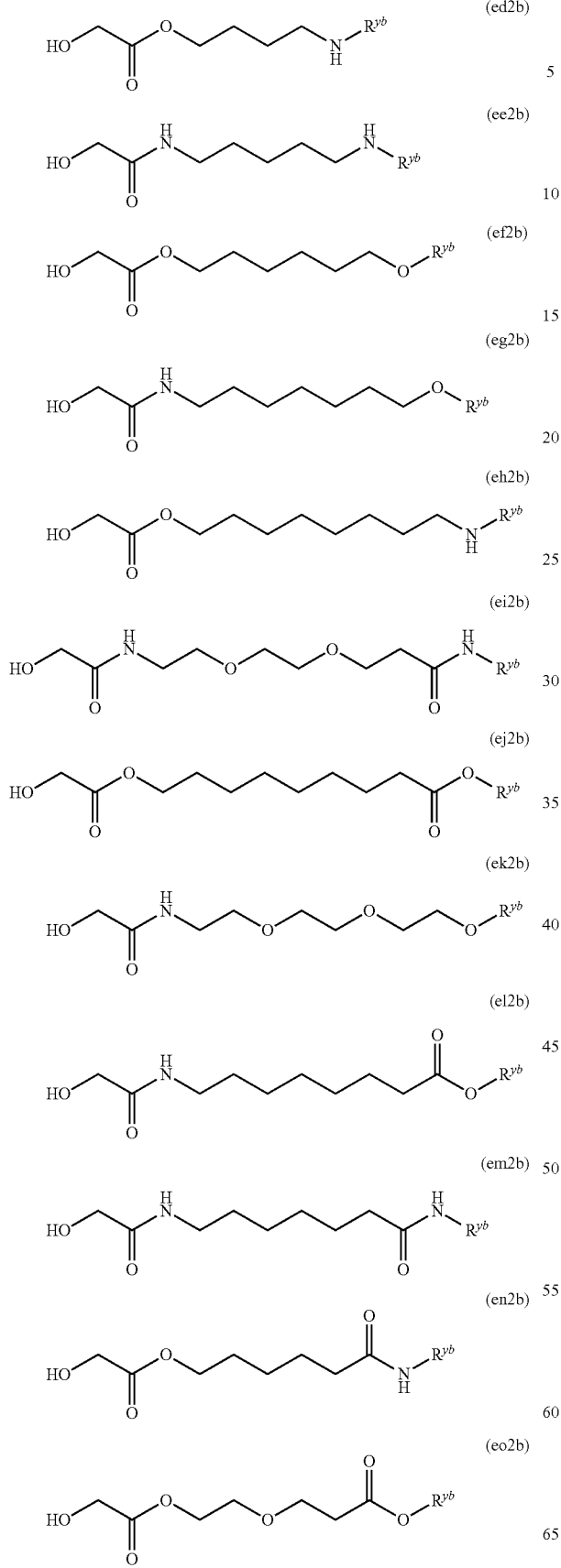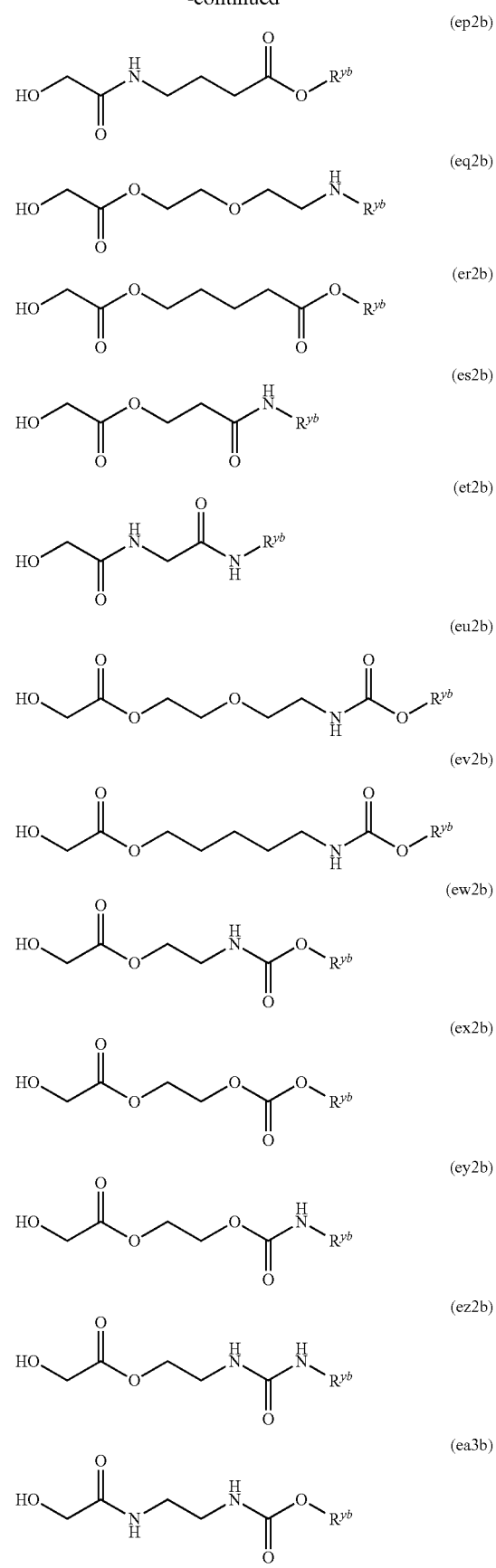

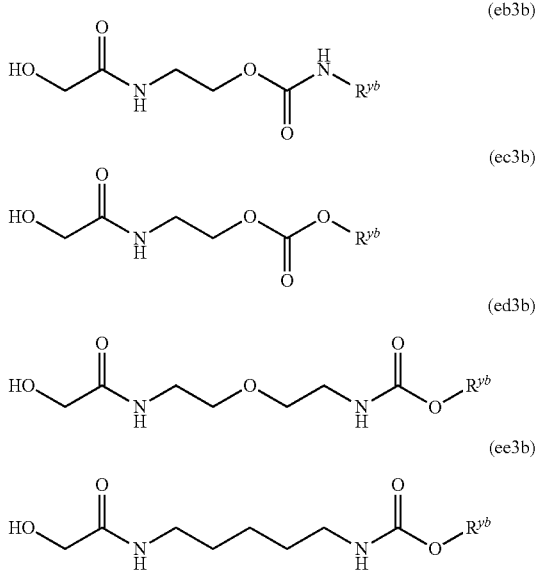

in which $R^{yb}$ is as having already been defined in this specification.

Examples of the compound represented by the formula $HNR^{17}-R^{18}$ include compounds represented by the following formulas:

[Chem. 51]

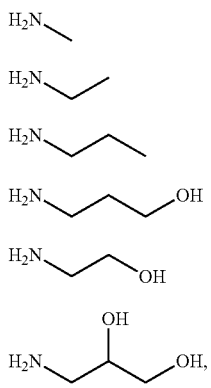

and preferably compounds represented by the formula (ba'), (bb'), (bc'), (bd'), and (bf').

When two or more different kinds of substituents are introduced into carboxy of hyaluronic acid, these substituents may be introduced simultaneously or sequentially.

According to further aspect of the present invention, there are provided the hyaluronic acid derivatives defined herein which can form fine particles by association in water. While not particularly limited, the hyaluronic acid derivatives have a property of forming nanoscale fine particles by self-association in water because of hydrophobic interactions of the introduced groups $-O-Z^3$, $-O-Z^1-Z^2$, $-NR^6-Z^1-Z^2$, and $-NR^{31}-CHR^{32}-(CH_2)_{n11}-A^3-B^2$, or $-O-Z^3$, $-O-Z^1-Z^2$, $-O-Z^0-Z^1-Z^2$, $-O-Z^0-Z^2$, $-NR^6-Z^1-Z^2$, and $-NR^{31}-CHR^{32}-(CH_2)_{n11}-A^3-B^2$. Nanoparticles formed by the hyaluronic acid derivatives of the present invention are one of very effective approaches for developing a desired drug delivery system, and can be used as capsules for delivering proteins, peptides, or low-molecular-weight compounds as active ingredients to a target site while retaining them in the hydrophobic domains formed. Further, drugs can be delivered to a target site by covalently binding a drug to the hyaluronic acid derivative of the present invention to form a conjugate.

Nanoscale fine particles can be administered transmucosally, subcutaneously, transdermally, and intravenously, and can be used as carriers for permeation through mucous membranes, permeation through tissue, controlled drug release of enclosed (complexed) drugs or for targeting, by which drugs are delivered selectively to target organs and cells. When used as carriers for targeting, targeting elements can be added for targeting to each organ and cell. Examples of the targeting element include target tissue specific peptides, antibodies, antibody fragments, aptamers, RGD peptides for cancer cells, folic acid, anisamide, transferrin, galactose for the liver, and tocopherol. To ensure drug retention in the blood, hyaluronic acid derivatives may be further crosslinked chemically.

Fine particles of the hyaluronic acid derivatives are formed by self-association in aqueous solution and can thus be formed by dissolving a solid hyaluronic acid derivative in water or an aqueous salt solution. Alternatively, fine particles can be formed by dissolving the hyaluronic acid derivative in another solvent (for example, DMSO), and then replacing the solvent with water or an aqueous salt solution. Ultrasonication can be performed to equalize the size of fine particles.

As the percent incorporation of the hydrophobic groups into the hyaluronic acid derivative increases, its solubility in water decreases. Therefore, to form fine particles that can be dispersed in aqueous solution, it is preferable to use the hyaluronic acid derivative prepared so that the percent incorporation of the hydrophobic groups is 80% or less, and preferably 60% or less.

Since the hyaluronic acid derivatives of the present invention have hydrophobic groups, the higher the ionic strength in a system is, the lower their solubilities become. Accordingly, by controlling the percent incorporation of hydrophobic groups, hyaluronic acid derivatives that dissolve at low salt concentrations or under salt-free conditions and agglomerate or precipitate at physiological salt concentrations can be prepared. They can be used as a matrix for subcutaneous and topical controlled release formulations. Further, hyaluronic acid derivatives modified with a hydrophobic group in such a degree that stable fine particles are formed at physiological salt concentrations can be used as drug carriers for systemic administrations.

Using the hyaluronic acid derivatives of the present invention, it is also possible to allow them to form complexes with additives such as PLGA and lipid, crystal particles of a drug, and amorphous particles and thereby to form new particles.

The hyaluronic acid derivatives of the present invention can be used as drug carriers for pharmaceutical compositions and can provide pharmaceutical compositions including the hyaluronic acid derivative of the present invention and a drug. It is also possible to provide pharmaceutical compositions including the hyaluronic acid derivative of the present invention itself as an active ingredient. The hyaluronic acid derivatives of the present invention included in these pharmaceutical compositions are those described in (1) to (11) and, when the pharmaceutical composition is used for transmucosal administration, the one described in (13). Since the hyaluronic acid derivatives of the present invention can spontaneously form complexes with a drug in aqueous solution, it is possible to allow the hyaluronic acid derivative to form a carrier-drug complex and thus support the drug by mixing the hyaluronic acid derivative and the drug in aqueous solution and incubating the mixture, without requiring any special operation. The dynamics of the complex formation mainly relies on hydrophobic interactions between hydrophobic groups of the hyaluronic acid derivative and a drug, but, when the drug is basic or acidic, electrostatic interactions with carboxylic acid or a cationic group of the hyaluronic acid derivative may contribute in some cases. At biological salt concentrations, electrostatic interactions become weak, and the hydrophobic interactions become stronger, so that it is considered that complexes are mainly formed by hydrophobic interactions.

If $Z^1$ is alkylene in the formula (Ib) above, as the longer the carbon chain of the alkylene, the higher the hydrophobicity of the group is, and the robuster fine particles can be formed by the higher hydrophobic interaction. In addition, longer alkylene produces larger intermolecular entanglement and thus the viscosity can be increased. Further, sizes of fine particles can be controlled by changing the length of alkylene.

If the linker (spacer) moiety in a hydrophobic group is ester or carbonate (for example, $X^2$ contains —COO—$Z^3$ or —O—COO—$Z^3$), the ester or carbonate decomposes in a living body and the hydrophobicity of the hyaluronic acid derivative is decreased. This increases the biodegradability and is preferable in terms of safety. In addition, tumor tissue is known to have decreased pH around the tissue. By having such a spacer, assemblies of the hyaluronic acid derivative of the present invention that supports a drug of interest can be broken down around the tumor and release the drug around the tumor.

Particularly, if the linker has a β-thiocarboxylate ester structure such as —O—CO—$CH_2$—$CH_2$—S—, decomposition is promoted by a slight decrease in pH (at pH 6 or so). Therefore, its response to pH change is more sensitive than usual ester. If it is intended to deliver a drug into cells, such a linker responds to pH decrease in endosomes, and is capable of releasing the drug only after the drug is incorporated in cells.

If a linker (spacer) moiety has a disulfide bond (for example, $X^2$ contains —S—S—$Z^3$), the linker decomposes under reducing conditions and assemblies of the hyaluronic acid derivative of the present invention are broken down due to the decrease in hydrophobicity of the hyaluronic acid derivative. Since cytoplasm is known to be a reducing environment, it is possible to allow the hyaluronic acid derivative to release a drug only in cytoplasm but not in the blood and tissue by enclosing the drug in the hyaluronic acid derivative with this linker and administering it.

Conditions during carrier-drug complex formation, such as a solvent, salt concentration, pH, temperature, time, and addition of denaturant, can be changed as appropriate dependent on the drug to be used. For example, depending on the salt concentration and pH during enclosure of the drug, the density of the hyaluronic acid derivatives changes and the ionization state of the drug is also varied. Examples of the denaturants to be used include urea, guanidine hydrochloride, and sodium dodecyl sulfate. If a denaturant is added, the excessive denaturant can be removed by washing with excessive water after the complex formation.

For example, without limitation, if a complex of the hyaluronic acid derivative of the present invention and a protein is formed, the amount of the protein contained in the complex can be increased by carrying out the complex formation in the vicinity of the isoelectric point, since this can suppress electrostatic repulsion of the hyaluronic acid derivative and the protein. In addition, by carrying out the complex formation step under conditions at pH equal to or lower than pKa (approximately 4.0) of carboxy in the hyaluronic acid derivative, the amount of the protein contained in the complex can be increased since the negative charge that the hyaluronic acid derivative has can be weakened and electrostatic repulsion can be suppressed, if the protein is negatively charged in the conditions. Furthermore, by carrying out the complex formation step, for example, at a salt concentration lower than those in a living body, the amount of the protein contained in the complex can be increased since the density of fine particles of the hyaluronic acid derivative formed in the aqueous solution decreases. In addition, by increasing the salt concentration in such a state, the density of the fine particles can be increased, and the protein can be enclosed robustly.

The complex formation of the hyaluronic acid derivative and the protein can be affected by the molecular weight of the protein. Generally, as the lower molecular weight the protein has, the higher the speed of transfer of the protein into the fine particles of the hyaluronic acid derivative is. In addition, the density of fine particles depending on the percent incorporation of the hydrophobic groups can affect the speed of the complex formation with the protein and the amount of the protein contained in the complex.

The complex formation of the hyaluronic acid derivative and a nucleic acid can also be affected by the molecular weight and hydrophobicity of the nucleic acid. In general, single-stranded nucleic acids forms complexes with the hyaluronic acid derivatives more easily than double-stranded nucleic acids. In addition, high-molecular-weight double-stranded nucleic acids such as plasmids form complexes with the hyaluronic acid derivatives more easily than low molecular double-stranded nucleic acids such as siRNA.

The drug release from the complex of the hyaluronic acid derivative and the drug in the living body is promoted by substitution of the drug with components in the living body, in addition to the diffusion of the drug from the complex. The controlled release of the drug can be controlled by increasing or decreasing the density of the fine particles to control this diffusion and substitution.

The living body contains biological components such as plasma proteins and lipids. When a complex of the hyaluronic acid derivative and a drug is administered to a living body such as subcutaneous tissues or the blood, the drug may be released by substitution of the drug in the complex with these components in the living body. Albumin is expected to be a major protein in the body, which causes such substitution.

Exemplary methods for using the hyaluronic acid derivative of the present invention as a drug carrier include a method of allowing the derivative to spontaneously form a complex with a drug in aqueous solution described above, as well as a method of making a conjugate in which the drug is bound via a covalent bond with the hyaluronic acid derivative of the present invention. Accordingly, in another aspect of the present invention, there are provided hyaluronic acid derivative-drug conjugates, in which one or more of the drugs described above are bound to the hyaluronic acid derivative including the disaccharide units represented by the formula (Ia) and the disaccharide units represented by the formula (Ib). In one embodiment of this aspect, as the hyaluronic acid derivatives, those including one or more disaccharide units represented by (1) the formulas (Ia) and (Ib), (2) the formulas (Ia), (Ib), and (II), (3)

the formulas (Ia), (Ib), and (III), and (4) the formulas (Ia), (Ib), (II), and (III) can be used.

The hydroxys in the 4-position of the glucuronic acid and in the 1-position of the acetylglucosamine present at the ends of the backbone of the hyaluronic acid derivative of the present invention may be converted into different groups, and examples of such groups include $C_{1-6}$ alkoxy, formyloxy, and $C_{1-6}$ alkylcarbonyloxy.

To prepare a conjugate of the hyaluronic acid derivative of the present invention and a drug, a method used in the preparation of a conjugate of a known polymer and a drug can be used and, for example, the following reactions can be used:

a reaction of carboxy of the glucuronic acid moiety of the hyaluronic acid derivative with amino, hydroxy, iodo, or bromo in a drug or amino, hydroxy, bromo, or iodo introduced into a drug;

a reaction of hydroxy in the 6-position of the N-acetylglucosamine moiety of the hyaluronic acid derivative with carboxy in a drug or carboxy introduced into a drug;

a reaction of amino introduced into the hyaluronic acid derivative with carboxy in a drug or carboxy introduced into a drug;

a reaction of amino introduced into the hyaluronic acid derivative with a drug converted into a group such as isothiocyanate, isocyanate, acylazide, NHS ester, and epoxide by modification;

a reaction of amino in a drug or amino introduced into a drug with the hyaluronic acid derivative converted into a group such as isothiocyanate, isocyanate, acylazide, carbonyl, NHS ester, and epoxide by modification;

Schiff base formation and reductive amination of amino in the hyaluronic acid derivative and a drug (such as aldehyde and ketone) having carbonyl or a drug into which carbonyl is introduced;

Schiff base formation and reductive amination of amino in a drug or amino introduced into a drug and the hyaluronic acid derivative into which carbonyl is introduced by modification;

a reaction of mercapto introduced into the hyaluronic acid derivative with a drug which is a compound having an unsaturated bond (such as maleimide, acrylate ester, acrylamide, methacrylate ester, methacrylamide, an allyl compound, and vinylsulfone), a halide (such as chloroacetatester, bromoacetate ester, iodoacetate ester, chloroacetamide, bromoacetamide, and iodoacetamide), or thiol or a drug converted into such a compound by modification; and a reaction of mercapto introduced into a drug with the hyaluronic acid derivative converted into a compound which has an unsaturated bond (maleimide, acrylate ester, acrylamide, methacrylate ester, methacrylamide, an allyl compound, vinylsulfone), a halide (chloroacetate ester, bromoacetate ester, iodoacetate ester, chloroacetamide, bromoacetamide, iodoacetamide) or thiol by modification.

In addition, the linker (spacer), used to introduce the hydrophobic group described above into the hyaluronic acid derivative, and containing an ester or carbonate, β-thioester, disulfide, or a peptide that is cleaved at a specific site, can be used as a linker for the conjugation with a drug. These linkers are cleaved at a target site to release the drug, as described above.

Reagents used for modifying the hyaluronic acid derivative or the drug for the preparation of conjugates are not particularly limited, as long as they cause no undesired reaction in the preparation of the conjugates. The compounds are those that are available as a reagent or that can be synthesized in reference to a method known to the public through publication.

Specifically, by synthesizing the hyaluronic acid derivative of the present invention and reacting the derivative with a drug having amino or a drug into which amino is introduced using a condensation agent such as DMT-MM, a conjugate can be prepared by amide bond formation. In this reaction, the drug and an introduced group such as a hydrophobic group or a cationic group may be introduced at the same time. In addition, such compound may be added after or before the drug. In addition, the drug may be reacted after synthesis and purification of the hyaluronic acid derivative of the present invention, or the introduced group such as a hydrophobic group or a cationic group may be introduced after synthesis and purification of the hyaluronic acid derivative into which the drug is introduced.

In addition, a drug may be conjugated to the hyaluronic acid derivative via an ester bond by synthesizing hyaluronic acid derivative of the present invention, and reacting a drug having hydroxy or a drug into which hydroxy is introduced using a condensation agent such as DMT-MM, 1,3-dichlorohexyl carbodiimide (DCC). In this reaction, the drug may be introduced with the introduced group such as a hydrophobic group or a cationic group at the same time. In addition, such compound may be added after or before the drug. However, it is desirable to conjugate the drug after the introduction of the introduced group such as a hydrophobic group or a cationic group to avoid hydrolysis of esters and amides. The above method can be carried out in reference to a report (Bioconjugate Vol. 19, 1319-1325, 2008) that paclitaxel was introduced into hyaluronic acid by ester.

In addition, a drug can be conjugated by synthesizing the hyaluronic acid derivative of the present invention, reacting a drug which is a bromide or an iodide or a drug converted into a bromide or an iodide by modification, and converting carboxy in the hyaluronic acid derivative to ester. It is desirable to conjugate the drug after the introduction of the introduced group such as a hydrophobic group or a cationic group to avoid hydrolysis of esters and amides.

A drug may be conjugated to the hyaluronic acid derivative via an ester bond by synthesizing the hyaluronic acid derivative of the present invention, converting a drug having carboxy or a drug into which carboxy is introduced into NHS ester, and reacting the carboxy with hydroxy in the 6-position in the N-acetylglucosamine moiety. In this reaction, the drug may be added after introducing the introduced group such as a hydrophobic group or a cationic group into the hyaluronic acid, or the drug may be added before the introduction. In addition, the drug may be reacted after synthesis and purification of the hyaluronic acid derivative of the present invention or the introduced group such as a hydrophobic group or a cationic group may be introduced after synthesis and purification of the hyaluronic acid derivative into which a drug is introduced. To avoid hydrolysis of an ester bond or an amide bond, it is desirable to conjugate the drug after the introduction of the introduced group such as a hydrophobic group or a cationic group. The above method can be carried out in reference to a report (International Publication No. 2009/074678) that camptothecin was introduced into hyaluronic acid by ester.

In one embodiment, amino can be introduced by dehydration reaction of carboxy of the glucuronic acid moiety and diamine such as ethylenediamine after synthesis of the hyaluronic acid derivative of the present invention. Some of the compounds represented by the formula $HNR^7-CHR^8-(CH_2)_{n1}-A^1-B^1$ for introducing a cationic group may be used as diamine such as ethylenediamine or some of diamine such as ethylenediamine for conjugating a drug may be used as the compounds represented by the formula $HNR^7$—$CHR^8$—$(CH_2)_{n1}$-$A^1$-$B^1$. Furthermore, the hyaluronic acid derivative into which iodoacetyl was introduced can be synthesized by reacting N-succinimidyl iodoacetate (PIERCE) or N-succinimidyl [4-iodoacetyl] aminobenzoate (PIERCE) with amino. A drug having mercapto can be conjugated to this hyaluronic acid derivative. This method is particularly effective for high-molecular-weight drugs, such as proteins, peptides, and nucleic acids, which have many reactive groups such as amino, since the conjugation can be mercapto selectively. In this reaction, the introduction of the drug may be before or after the introduction of an introduced group such as a hydrophobic group or a cationic group into hyaluronic acid.

The hyaluronic acid derivative of the present invention is synthesized and a part of carboxys in the glucuronic acid moiety of the hyaluronic acid derivative is reacted with 2-aminoethyl 2-pyridyl disulfide hydrochloride. To this hyaluronic acid derivative, a drug having mercapto and a drug into which mercapto is introduced can be introduced by disulfide bond exchange reaction, i.e. a substitution reaction.

In this reaction, the length of a linker between the drug and the hyaluronic acid derivative can be adjusted to keep the bioactivity of the conjugate effective. In addition, a peptide linker cut with an enzyme at a specific site in the living body can be introduced. For example, this can be done in reference to a report (International Publication No. 2005/095464) that methotrexate was introduced into HA via a linker containing a peptide and a report (International Publication No. 2002/090209) that doxorubicin was introduced via a linker containing HPMA (N-(2-hydroxypropyl)methacrylamide) and a peptide, or the like.

In addition, there are many reports on ADC (Antibody Drug Conjugate) in which a low-molecular-weight compound is conjugated to an antibody (International Publication No. 2009/026274; Expert Opinion. Vol. 15, p. 1087-1103, 2005; Bioconjugate Chem. Vol. 19, p. 1960-1963, 2008; Bioconjugate Chem. in press, Bernhard Stump et al., Antibody-Drug Conjugates: Linking Cytotoxic Payloads to Monoclonal Antibodies) and a conjugate of the hyaluronic acid derivative and a low-molecular-weight compound can be prepared in reference to these reports.

A pharmaceutical composition containing one or more drugs and the hyaluronic acid derivative of the present invention, a complex of the hyaluronic acid derivative of the present invention and one or more drugs, and a conjugate in which one or more drugs are bound with the hyaluronic acid derivative of the present invention may be in the form of nanoparticles, microparticles, a solution, a capsule, a tablet, fine grain, a patch, an emulsion, a suspension, a gel, micelles, an implant, powder, or a film. Powder can be produced by crushing a solid obtained by lyophilization or spray drying or produced from a material obtained by drying precipitate.

In the pharmaceutical compositions of the present invention, the drug may be enclosed in, adhered to, covered with, or mixed or blended with the hyaluronic acid derivative. Furthermore, when used for preventing or treating, for example, stomatitis, the hyaluronic acid derivative itself may be contained in the pharmaceutical composition of the present invention as a drug, with or without other drug(s).

The pharmaceutical compositions, complexes and conjugates of the present invention may be administered via an oral, parenteral, intranasal, intrapulmonary, trachea, bronchial, intravaginal, intrarectal, intraocular, eye drop, subconjunctival, sub-Tenon's capsule, intra-aural, subcutaneous, intravenous, intramuscular, intradermal, intraperitoneal, intraarticular, intracerebral or buccal route, but in either route it is preferable that they are administered via mucous membranes or through mucous membranes.

When the pharmaceutical compositions, complexes and conjugates of the present invention are particularly intended to increase the mucosal permeability, their sizes in a dissolved state are preferably 1 μm or less, preferably 500 nm or less, and preferably 300 nm, 200 nm, 100 nm, 50 nm or less.

When the pharmaceutical compositions, complexes and conjugates of the present invention are intended to increase mucoadhesion or sustained release properties, their sizes in a dissolved state is preferably 200 μm or less. From the viewpoint of mucoadhesion, it is preferable that the percent incorporation of cationic groups of the hyaluronic acid derivative used is higher.

When the pharmaceutical compositions, complexes and conjugates of the present invention are intended for the accumulation in specific tissues and organs by injection administration, their sizes are preferably 500 nm or less, more preferably 200 nm or less, and yet preferably 100 nm or less.

The pharmaceutical compositions, complexes and conjugates of the present invention are preferably 5 μm or less in size, particularly when they are intended to target to hyaluronic acid receptors including CD44.

Drugs forming a complex with the hyaluronic acid derivative of the present invention are not particularly limited as long as it can form a complex. In addition, drugs to be bound with the hyaluronic acid derivative of the present invention are not particularly limited, as long as a conjugate can be prepared. Examples of the drugs include protein and/or peptide, polysaccharide, nuclear acid, low-molecular-weight compounds, and preferable examples include protein and/or peptide, and low-molecular-weight compounds.

Examples of the low-molecular-weight compounds include, but not limited to, anticancer agents (such as, for example, alkylating agents, antimetabolites, alkaloids such as paclitaxel), immunosuppressive drugs such as cyclosporine, anti-inflammatory agents (such as steroid and non-steroid anti-inflammatory agents), antirheumatic agents, and antibiotics (such as beta-lactam antibiotics, aminoglycoside derivative antibiotics, macrolide derivative antibiotics, tetracycline antibiotics, new quinolone antibiotics, and sulfa drugs).

Examples of the proteins and the peptides include, but not limited to, erythropoietin (EPO), granulocyte-colony stimulating factor (G-CSF), Interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, diagram body, mini-body, and antibody fragments.

Examples of the nuclear acids include, but not limited to, DNA, RNA, antisense, decoy, ribozyme, small interfering RNA, RNA aptamer, and messenger RNA. Further, examples of the nucleic acids also include nucleic acid derivatives obtained by chemically treating the nucleic acids, such as phosphothioate, methoxymethyl analogues and LNA.

When the drugs are nucleic acids such as small interfering RNA, hyaluronic acid derivatives forming complexes with the drugs are preferably the hyaluronic acid derivatives described in (1) to (11). By allowing these hyaluronic acid derivatives to form complexes with nucleic acids such as small interfering RNA, it is possible to deliver the nucleic acids into target cells.

In the hyaluronic acid derivatives forming complexes with nucleic acids, preferable specific examples of the group $X^1$ having a cationic site include groups represented by the formulas (a), (b), (c), (f), (h), (l), (m), (s), (t), (u), (y), (z), and (ah), more preferably groups represented by the formulas (a), (b), (c), (f), (h), (l), (m), (s), (t), (y), (z), and (ah), more preferably groups represented by the formulas (a), (b), (c), (f), (h), (l), (m), and (s), more preferably groups represented by the formulas (a), (b), (c), (f), (l), (m), and (s), more preferably groups represented by the formulas (a), (b), (c), (l), (m), and (s), more preferably groups represented by the formulas (a), (b), (c), (l), and (m), and more preferably groups represented by the formulas (b), (c), and (m).

In the hyaluronic acid derivatives forming complexes with nucleic acids, the percent incorporation of $X^1$ is preferably 4 to 85%, and more preferably 6 to 78%. The percent incorporation of $X^2$ having a hydrophobic site is preferably 10 to 60%, and more preferably 14 to 48%.

In the hyaluronic acid derivatives forming complexes with nucleic acids, a combination of the percent incorporation of $X^1$ and the percent incorporation of $X^2$ (the percent incorporation of $X^1$: the percent incorporation of $X^2$) is, when $X^1$ is the group represented by the formula (b), preferably (5 to 85%:10 to 55%), more preferably (11 to 74%:17 to 47%). When $X^1$ is the group represented by the formula (c), it is preferably (10 to 45%:15 to 65%), and more preferably (19 to 31%:29 to 48%). When $X^1$ is the group represented by the formula (m), it is preferably (5 to 65%:10 to 50%), and more preferably (6 to 52%:14 to 17%). It should be noted that the upper limit of the sum of the percent incorporation of $X^1$ and the percent incorporation of $X^2$ is 100%. The lower limit is required to be 7% or higher.

The hyaluronic acid derivatives of the present invention, complexes of the hyaluronic acid derivative and a drug, or hyaluronic acid derivative-drug conjugates can be administered in an appropriate form depending on a desired route of administration, as pharmaceutical compositions including, for example, one or more of pharmaceutically acceptable diluents, wetting agents, emulsifiers, dispersants, adjuvants, preservatives, buffers, binders, stabilizers, surfactants, lipids, and matrices. The route of administration may be a parenteral route or an oral route.

The pharmaceutical compositions of the present invention can be administered by transmucosal or transdermal administration using devices such as spray, a dry powder inhaler, drip, iontophoresis, electroporation, and sonophoresis (ultrasound) as well as a method of transmucosal or transdermal administration using, for example, microcannula, microneedle, needle-free injection, and polishing. They can also be administered orally, vaginally or rectally using a pill or tablet. Administration using a syringe is also possible. Creams, ointments, and poultices are also possible.

According to the present invention, it is possible to allow the drugs to adhere to mucous membranes and permeate them into a target site which cannot be attained by conventional pharmaceutical compositions, it is possible to release the drug for a long period and/or it is possible to provide highly safe pharmaceutical compositions having appropriate biodegradability.

EXAMPLES

Preferable specific embodiments of the present invention will be described as Examples below.

The term "HA unit" used in the following description refers to a single repeating unit consisting of N-acetylglucosamine and glucuronic acid of hyaluronic acid (HA). The $^1$H-NMR spectra were measured using a spectrometer JNM-ECX 50011 produced by JEOL Ltd. Dialysis was conducted using dialysis membranes made of regenerated cellulose produced by Spectrum, Inc. (a Spectra/Por 4 dialysis membrane with a molecular weight cut-off of 12-14 kDa for sodium salts of hyaluronic acid having MW 50 kDa and 99 kDa as starting materials; and a Spectra/Por 3 dialysis membrane with a molecular weight cut-off of 3.5 kDa and a Spectra/Por 7 dialysis membrane with a molecular weight cut-off of 1 kDa or 2 kDa for sodium salt of hyaluronic acid having MW 10 kDa as a starting material).

Example 1Synthesis of cholesteryl (6-aminohexyl)carbamate hydrochloride and Preparation of TBA Salt of HA (Example 1-1) Preparation of cholesteryl (6-aminohexyl)carbamate hydrochloride Cholesteryl 6-aminohexylcarbamate (Chol-$C_6$) hydrochloride was synthesized according to the method described in WO2014/038641.

(Example 1-2) Preparation of TBA Salt of HA

Sodium salts of hyaluronic acid (HA-Na, available from Shiseido Company, Limited or CONTIPRO) having a molecular weight of 10 kDa, 50 kDa or 99 kDa were used to prepare TBA salts of HA according to the method described in WO2014/038641.

Example 2Synthesis of HA Derivatives (Example 2-1) Synthesis of a HA Derivative (HA-Chol/ArgNH$_2$) Modified with L-Arginine Amide (H-ArgNH$_2$) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and 4-(4,6-dimethoxy-1,3,5-triazin-2-yl)-4-methylmorpholinium chloride (DMT-MM) were added to the solutions at ratios per HA unit shown in Table 1 below and stirred at room temperature for 2 hours or more. Next, L-arginine amide hydrochloride (Watanabe Chemical Industries, Ltd.) and DMT-MM were added to the HA units at ratios shown in Table 1 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/ArgNH$_2$) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 1.

A representative $^1$H-NMR spectrum (of the product derived from HA of 99 kDa with the percent incorporation of cholesteryl of 17% and the percent incorporation of ArgNH$_2$ of 31%) using 0.02 N DCl DMSO-d$_6$/D$_2$O mixed solution (2N DCl D$_2$O:DMSO-d$_6$=1:99) as a measurement solvent is shown in FIG. 1. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 1). Since a peak around 1.7 to 2.0 ppm including the peak for acetyl of N-acetylglucosamine is overlapping with the peak for the cholesteryl group (5H) and the peak for the introduced ArgNH$_2$ (1H), a value calculated by subtracting ⅔ of the integrated value of the peak for methyl (—CH$_3$, 0.7 ppm; 3H) of the cholesteryl group and 1/1 of the integrated value of the peak for methine (—NH—CH(CONH$_2$)CH$_2$—, 4.2 ppm; 1H) of ArgNH$_2$ from the integrated value of the peak around 1.7 to 2.0 ppm (i.e., the integrated value (1.7 to 2.0 ppm) –the integrated value (0.7 ppm)×⅔–the integrated value (4.2 ppm)×1/1) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad [\text{Exp. 2}]$$

(1.7 – 2.0 ppm; value after correction)

Based on the integrated value of the peak for acetyl (—COCH$_3$, 1.7 to 2.0 ppm; 3H) of N-acetylglucosamine in HA and the integrated value of the peak for methine (—NH—CH(CONH$_2$)CH$_2$—, 4.2 ppm; 1H) of the introduced ArgNH$_2$, the percent incorporation of arginine amide (the percent incorporation of ArgNH$_2$) in the HA units was calculated according to the following equation (Table 1).

$$\text{Percent incorporation of ArgNH}_2 \text{ (\%)} = \frac{\text{Integrated value for methine in ArgNH}_2 \text{ (4.2 ppm)}}{\text{Integrated value for acetyl in } HA} \times \frac{3}{1} \times 100 \quad [\text{Exp. 3}]$$

(1.7 – 2.0 ppm; value after correction)

TABLE 1

Amount of reagent used in preparing HA-Chol/ArgNH$_2$ and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | State of solution |
|---|---|---|---|---|
| 10k HA-Chol-14%/ArgNH$_2$-28% | 10k | 100/16/19 14% | 100/5000/50 28% | O |
| 10k HA-Chol-14%/ArgNH$_2$-33% | 10k | 100/16/19 14% | 100/5000/50 33% | O |
| 10k HA-Chol-15%/ArgNH$_2$-53% | 10k | 100/16/19 15% | 100/5000/100 53% | O |
| 10k HA-Chol-15%/ArgNH$_2$-60% | 10k | 100/16/19 15% | 100/5000/150 60% | O |
| 10k HA-Chol-13%/ArgNH$_2$-71% | 10k | 100/16/19 13% | 100/5000/200 71% | O |
| 10k HA-Chol-31%/ArgNH$_2$-26% | 10k | 100/42/50 31% | 100/5000/50 26% | X |
| 10k HA-Chol-31%/ArgNH$_2$-36% | 10k | 100/42/50 31% | 100/5000/100 36% | X |
| 10k HA-Chol-31%/ArgNH$_2$-38% | 10k | 100/42/50 31% | 100/5000/150 38% | O |
| 10k HA-Chol-31%/ArgNH$_2$-41% | 10k | 100/42/50 31% | 100/5000/200 41% | O |
| 99k HA-Chol-16%/ArgNH$_2$-8% | 99k | 100/18/22 16% | 100/5006/13 8% | O |
| 99k HA-Chol-16%/ArgNH$_2$-15% | 99k | 100/18/22 16% | 100/5006/25 15% | O |
| 99k HA-Chol-17%/ArgNH$_2$-31% | 99k | 100/18/22 17% | 100/5006/50 31% | O |
| 99k HA-Chol-17%/ArgNH$_2$-45% | 99k | 100/18/22 17% | 100/5006/80 45% | O |
| 99k HA-Chol-17%/ArgNH$_2$-63% | 99k | 100/18/22 17% | 100/5006/130 63% | O |
| 99k HA-Chol-28%/ArgNH$_2$-14% | 99k | 100/40/44 28% | 100/4000/25 14% | O |
| 99k HA-Chol-28%/ArgNH$_2$-28% | 99k | 100/40/44 28% | 100/4000/50 28% | O |
| 99k HA-Chol-27%/ArgNH$_2$-37% | 99k | 100/40/44 27% | 100/4000/75 37% | O |
| 99k HA-Chol-25%/ArgNH$_2$-46% | 99k | 100/40/44 25% | 100/4000/100 46% | O |
| 99k HA-Chol-33%/ArgNH$_2$-19% | 99k | 100/40/46 33% | 100/4005/30 19% | O |

TABLE 1-continued

Amount of reagent used in preparing HA-Chol/ArgNH₂ and percent incorporation

| Abbreviation | MW (Da) | Molar ratio of added Chol-C₆ hydrochloride and DMT-MM (HA unit/Chol-C₆/DMT-MM) & percent incorporation of Chol | Molar ratio of added H-ArgNH₂ hydrochloride and DMT-MM (HA unit/H-ArgNH₂/DMT-MM) & percent incorporation of ArgNH₂ | State of solution |
|---|---|---|---|---|
| 99k HA-Chol-34%/ArgNH₂-34% | 99k | 100/40/46  34% | 100/4005/60  34% | X |
| 99k HA-Chol-34%/ArgNH₂-42% | 99k | 100/40/46  34% | 100/4005/90  42% | X |
| 99k HA-Chol-33%/ArgNH₂-48% | 99k | 100/40/46  33% | 100/4005/140  48% | ○ |
| 99k HA-Chol-33%/ArgNH₂-49% | 99k | 100/40/46  33% | 100/4005/200  49% | ○ |
| 99k HA-Chol-42%/ArgNH₂-17% | 99k | 100/50/63  42% | 100/4020/30  17% | ○ |
| 99k HA-Chol-42%/ArgNH₂-27% | 99k | 100/50/63  42% | 100/4020/60  27% | X |
| 99k HA-Chol-40%/ArgNH₂-34% | 99k | 100/50/63  40% | 100/4020/90  34% | X |
| 99k HA-Chol-42%/ArgNH₂-39% | 99k | 100/50/63  42% | 100/4020/140  39% | ○ |
| 99k HA-Chol-43%/ArgNH₂-41% | 99k | 100/50/63  43% | 100/4020/200  41% | ○ |

(Example 2-2) Synthesis of a HA Derivative (HA-Chol/EDA) Modified with ethylenediamine (EDAm) and cholesteryl (6-aminohexyl)carbamate Solutions of HA-TBAs synthesized from the sodium salts of hyaluronic acids (HA-Na; 10 kDa and 99 kDa) in Example 1-2 in anhydrous DMSO were prepared. Chol-C₆ hydrochloride prepared in Example 1-1 and DMT-MM were added to the solutions at ratios per HA unit shown in Table 2 below and stirred at room temperature for 2 hours or more. Next, mono-Fmoc ethylenediamine hydrochloride (Watanabe Chemical Industries, Ltd.) and DMT-MM were added to the HA units at ratios shown in Table 2 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/EDA) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 2.

A representative ¹H-NMR spectrum (of the product derived from HA of 99 kDa with the percent incorporation of cholesteryl of 17% and the percent incorporation of EDA of 37%) using 0.02 N DCl DMSO-d₆/D₂O mixed solution (2N DCl D₂O:DMSO-d₆=1:99) as a measurement solvent is shown in FIG. 2. Based on the integrated value of the peak for acetyl (—COCH₃, 1.7 to 2.0 ppm; 3H) of N-acetylglucosamine in HA and the integrated value of the peak for methyl (—CH₃, 0.7 ppm; 3H) of the introduced cholesteryl group, the percent incorporation of cholesteryl in the HA units was calculated according to the equation given below (Table 2). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—CH₃, 0.7 ppm; 3H) of the cholesteryl group from the integrated value of the peak around 1.7 to 2.0 ppm (i.e., the integrated value (1.7 to 2.0 ppm) –the integrated value (0.7 ppm)×5/3) was used as the integrated value for acetyl in HA for the calculation of the percent incorporation.

Percent incorporation of cholesteryl (%) = [Exp. 4]

$$\frac{\text{Integrated value for methyl in cholesteryl (0.7 ppm)}}{\text{Integrated value for acetyl in } HA} \times 100$$

(1.7 – 2.0 ppm; value after correction)

Based on the integrated value of the peak for acetyl (—COCH₃, 1.7 to 2.0 ppm; 3H) of N-acetylglucosamine in HA and the integrated value of the peak for methylene (—CH₂—, 3.0 ppm; 2H) of the introduced EDA, the percent incorporation of ethylenediamine (the percent incorporation of EDA) in the HA units was calculated according to the equation given below (Table 2). Since a peak around 3.0 ppm including the peak for methylene of EDA is overlapping with the peak for methylene (2H) of cholesteryl 6-aminohexyl, a value calculated by subtracting 2/3 of the integrated value of the peak for methyl (—CH₃, 0.7 ppm; 3H) of the cholesteryl group from the integrated value of the peak around 3.0 ppm (i.e., the integrated value (3.0 ppm) –the integrated value (0.7 ppm)×2/3) was used as the integrated value for methylene in EDA for the calculation of the percent incorporation.

Percent incorporation of EDA (%) = [Exp. 5]

$$\frac{\text{Integrated value for methylene in } EDA \text{ (3.0 ppm; value after correction)}}{\text{Integrated value for acetyl in } HA} \times \frac{3}{2} \times 100$$

(1.7 – 2.0 ppm; value after correction)

TABLE 2

Amount of reagent used in preparing HA-Chol/EDA and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added FmocEDAm hydrochloride and DMT-MM (HA unit/FmocEDAm/DMT-MM) & percent incorporation of EDA | State of solution |
|---|---|---|---|---|
| 10k HA-Chol-17%/EDA-40% | 10k | 100/16/19 17% | 100/42/200 40% | ○ |
| 10k HA-Chol-16%/EDA-44% | 10k | 100/16/19 16% | 100/52/200 44% | ○ |
| 10k HA-Chol-16%/EDA-56% | 10k | 100/16/19 16% | 100/62/200 56% | ○ |
| 10k HA-Chol-16%/EDA-53% | 10k | 100/16/19 16% | 100/72/200 53% | ○ |
| 10k HA-Chol-16%/EDA-55% | 10k | 100/16/19 16% | 100/82/200 55% | ○ |
| 10k HA-Chol-15%/EDA-57% | 10k | 100/16/19 15% | 100/92/200 57% | ○ |
| 10k HA-Chol-37%/EDA-24% | 10k | 100/42/50 37% | 100/30/200 24% | ○ |
| 10k HA-Chol-35%/EDA-26% | 10k | 100/42/50 35% | 100/40/200 26% | ○ |
| 10k HA-Chol-41%/EDA-29% | 10k | 100/42/50 41% | 100/50/200 29% | ○ |
| 10k HA-Chol-34%/EDA-38% | 10k | 100/42/50 34% | 100/90/200 38% | ○ |
| 10k HA-Chol-34%/EDA-18% | 10k | 100/40/47 34% | 100/25/33 18% | ○ |
| 10k HA-Chol-36%/EDA-36% | 10k | 100/40/47 36% | 100/50/65 36% | X |
| 10k HA-Chol-34%/EDA-40% | 10k | 100/40/47 34% | 100/75/98 40% | X |
| 10k HA-Chol-33%/EDA-46% | 10k | 100/40/47 33% | 100/125/163 46% | ○ |
| 10k HA-Chol-32%/EDA-49% | 10k | 100/40/47 32% | 100/200/260 49% | ○ |
| 10k HA-Chol-51%/EDA-14% | 10k | 100/60/70 51% | 100/25/32 14% | ○ |
| 10k HA-Chol-50%/EDA-23% | 10k | 100/60/70 50% | 100/50/65 23% | ○ |
| 10k HA-Chol-50%/EDA-27% | 10k | 100/60/70 50% | 100/75/98 27% | ○ |
| 10k HA-Chol-49%/EDA-32% | 10k | 100/60/70 49% | 100/125/163 32% | ○ |
| 10k HA-Chol-47%/EDA-36% | 10k | 100/60/70 47% | 100/200/260 36% | ○ |
| 99k HA-Chol-17%/EDA-17% | 99k | 100/18/21 17% | 100/25/33 17% | ○ |
| 99k HA-Chol-17%/EDA-37% | 99k | 100/18/21 17% | 100/50/65 37% | X |
| 99k HA-Chol-17%/EDA-53% | 99k | 100/18/21 17% | 100/80/104 53% | ○ |
| 99k HA-Chol-16%/EDA-65% | 99k | 100/18/21 16% | 100/130/169 65% | ○ |
| 99k HA-Chol-34%/EDA-19% | 99k | 100/40/47 34% | 100/25/33 19% | ○ |
| 99k HA-Chol-35%/EDA-32% | 99k | 100/40/47 35% | 100/50/65 32% | ○ |
| 99k HA-Chol-36%/EDA-49% | 99k | 100/40/47 36% | 100/75/98 49% | X |
| 99k HA-Chol-32%/EDA-52% | 99k | 100/40/47 32% | 100/125/163 52% | ○ |
| 99k HA-Chol-32%/EDA-54% | 99k | 100/40/47 32% | 100/200/260 54% | ○ |
| 99k HA-Chol-52%/EDA-13% | 99k | 100/60/70 52% | 100/25/32 13% | ○ |
| 99k HA-Chol-53%/EDA-22% | 99k | 100/60/70 53% | 100/50/65 22% | ○ |
| 99k HA-Chol-52%/EDA-37% | 99k | 100/60/70 52% | 100/75/98 37% | ○ |
| 99k HA-Chol-50%/EDA-44% | 99k | 100/60/70 50% | 100/125/162 44% | ○ |
| 99k HA-Chol-51%/EDA-44% | 99k | 100/60/70 51% | 100/200/260 44% | ○ |

(Example 2-3) Synthesis of a HA Derivative (HA-Chol/DET) Modified with diethylenetriamine (DETAm) and cholesteryl (6-aminohexyl)carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 3 below and stirred at room temperature for 2 hours or more. Next, diethylenetriamine (Tokyo Chemical Industry Co., Ltd.) and tripyrrolidinophosphonium hexafluorophosphate (PyBOP, Wako Pure Chemical Industries, Ltd.) were added to the HA units at ratios shown in Table 3 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/DET) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 3.

Representative $^1$H-NMR spectra (of the product derived from HA of 10 kDa with the percent incorporation of cholesteryl of 15% and the percent incorporation of DET of 69%) using 0.02 N DC1 DMSO-$d_6$/$D_2$O mixed solution (2N DC1 $D_2$O:DMSO-$d_6$=1:99) and $D_2$O as measurement solvents are shown in FIGS. 3-1 and 3-2, respectively. In the NMR spectrum using 0.02 N DC1 DMSO-$d_6$/$D_2$O mixed solution, based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 3). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm) –the integrated value (0.7 ppm)×5/3) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad \text{[Exp. 6]}$$

(1.7 – 2.0 ppm; value after correction)

In the NMR spectrum using $D_2$O, based on the integrated value of the peak for acetyl (—$COCH_3$, 1.7 to 2.0 ppm; 3H) of N-acetylglucosamine in HA and the integrated value of the peak for methylene (—$CH_2$—, 2.9 ppm; 2H) of the introduced DET, the percent incorporation of diethylenetriamine (the percent incorporation of DET) in the HA units was calculated according to the equation given below (Table 3).

$$\text{Percent incorporation of } DET \text{ (\%)} = \frac{\text{Integrated value for methylene in } DET \text{ (2.9 ppm)}}{\text{Integrated value for acetyl in } HA} \times \frac{3}{2} \times 100 \quad \text{[Exp. 7]}$$

(1.7 – 2.0 ppm; value after correction)

TABLE 3

Amount of reagent used in preparing HA-Chol/DET and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | State of solution |
|---|---|---|---|---|
| 10k HA-Chol-15%/DET-70% | 10k | 100/16/19 15% | 100/5000/200 70% | O |
| 10k HA-Chol-30%/DET | 10k | 100/36/43 30% | 100/5007/15 Percent incorporation could not be calculated | X |
| 10k HA-Chol-30%/DET | 10k | 100/36/43 30% | 100/5007/35 Percent incorporation could not be calculated | X |
| 10k HA-Chol-30%/DET | 10k | 100/36/43 30% | 100/5007/55 Percent incorporation could not be calculated | X |
| 10k HA-Chol-31%/DET | 10k | 100/36/43 31% | 100/5007/100 Percent incorporation could not be calculated | X |
| 10k HA-Chol-37%/DET | 10k | 100/50/58 37% | 100/5006/15 Percent incorporation could not be calculated | X |
| 10k HA-Chol-36%/DET | 10k | 100/50/58 36% | 100/5006/35 Percent incorporation could not be calculated | X |
| 10k HA-Chol-37%/DET | 10k | 100/50/58 37% | 100/5006/55 Percent incorporation could not be calculated | X |

TABLE 3-continued

Amount of reagent used in preparing HA-Chol/DET and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | State of solution |
|---|---|---|---|---|
| 10k HA-Chol-37%/DET | 10k | 100/50/58<br>37% | 100/5006/100<br>Percent incorporation could not be calculated | X |
| 99k HA-Chol-15%/DET | 99k | 100/18/21<br>15% | 100/5045/20<br>Percent incorporation could not be calculated | X |
| 99k HA-Chol-16%/DET | 99k | 100/18/21<br>16% | 100/5045/45<br>Percent incorporation could not be calculated | X |
| 99k HA-Chol-16%/DET | 99k | 100/18/21<br>16% | 100/5045/75<br>Percent incorporation could not be calculated | X |
| 99k HA-Chol-15%/DET | 99k | 100/18/21<br>15% | 100/5045/110<br>Percent incorporation could not be calculated | X |
| 99k HA-Chol-31%/DET | 99k | 100/36/43<br>31% | 100/5007/15<br>Percent incorporation could not be calculated | X |
| 99k HA-Chol-31%/DET | 99k | 100/36/43<br>31% | 100/5007/35<br>Percent incorporation could not be calculated | X |
| 99k HA-Chol-31%/DET | 99k | 100/36/43<br>31% | 100/5007/55<br>Percent incorporation could not be calculated | X |
| 99k HA-Chol-31%/DET | 99k | 100/36/43<br>31% | 100/5007/100<br>Percent incorporation could not be calculated | X |
| 99k HA-Chol-37%/DET | 99k | 100/50/57<br>37% | 100/5007/15<br>Percent incorporation could not be calculated | X |
| 99k HA-Chol-36%/DET | 99k | 100/50/57<br>36% | 100/5007/35<br>Percent incorporation could not be calculated | X |
| 99k HA-Chol-37%/DET | 99k | 100/50/57<br>37% | 100/5007/55<br>Percent incorporation could not be calculated | X |
| 99k HA-Chol-38%/DET | 99k | 100/50/57<br>38% | 100/5007/100<br>Percent incorporation could not be calculated | X |

It should be noted that the indication "percent incorporation could not be calculated" means that the sample did not have a sufficient solubility to the solvent and NMR analysis could not be performed.

(Example 2-4) Synthesis of a HA Derivative (HA-Chol/LysNH$_2$) Modified with L-Lysine Amide (H-LysNH$_2$) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 4 below and stirred at room temperature for 2 hours or more. Next, mono-Fmoc-L-lysine amide hydrochloride (Watanabe Chemical Industries, Ltd.) and DMT-MM were added to the HA units at ratios shown in Table 4 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/LysNH$_2$) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 4.

A representative $^1$H-NMR spectrum (of the product derived from HA of 99 kDa with the percent incorporation of cholesteryl of 16% and the percent incorporation of LysNH$_2$ of 36%) using 0.02 N DCl DMSO-d$_6$/D$_2$O mixed solution (2N DCl D$_2$O:DMSO-d$_6$=1:99) as a measurement solvent is shown in FIG. 4. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 4). Since a peak around 1.7 to 2.0 ppm including the peak for acetyl of N-acetylglucosamine is overlapping with the peak for the cholesteryl group (5H) and the peak for the introduced LysNH$_2$ (1H), a value calculated by subtracting ⅝ of the integrated value of the peak for methyl (—CH$_3$, 0.7 ppm; 3H) of the cholesteryl group and ½ of the integrated value of the peak for methylene (—CH$_2$—, 2.8 ppm; 2H) of LysNH$_2$ from the integrated value of the peak around 1.7 to 2.0 ppm (i.e., the integrated value (1.7 to 2.0 ppm) –the integrated value (0.7 ppm)×⅔– the integrated value (2.8 ppm)×½) was used as the integrated value for acetyl in HA for the calculation of the percent incorporation.

Percent incorporation of cholesteryl (%) = [Exp. 8]

$$\frac{\text{Integrated value for methyl in cholesteryl (0.7 ppm)}}{\text{Integrated value for acetyl in HA (1.7 – 2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 2.8 ppm; 2H) of the introduced LysNH$_2$, the percent incorporation of lysine amide (the percent incorporation of LysNH$_2$) in the HA units was calculated according to the following equation (Table 4).

Percent incorporation of LysNH$_2$(%) = [Exp. 9]

$$\frac{\text{Integrated value for methylene in LysNH}_2 \text{(2.8 ppm)}}{\text{Integrated value for acetyl in HA (1.7-2.0 ppm; value after correction)}} \times \frac{3}{2} \times 100$$

TABLE 4

Amount of reagent used in preparing HA-Chol/LysNH$_2$ and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added Fmoc—H-LysNH$_2$ and DMT-MM (HA unit/Fmoc—H-LysNH$_2$/DMT-MM) & percent incorporation of LysNH$_2$ | State of solution |
|---|---|---|---|---|
| 10k HA-Chol-16%/LysNH$_2$-17% | 10k | 100/18/21  16% | 100/20/29  17% | ○ |
| 10k HA-Chol-17%/LysNH$_2$-36% | 10k | 100/18/21  17% | 100/51/75  36% | ○ |
| 10k HA-Chol-17%/LysNH$_2$-51% | 10k | 100/18/21  17% | 100/103/149  51% | ○ |
| 10k HA-Chol-31%/LysNH$_2$-11% | 10k | 100/36/39  31% | 100/16/23  11% | ○ |
| 10k HA-Chol-31%/LysNH$_2$-25% | 10k | 100/36/39  31% | 100/39/57  25% | ○ |
| 10k HA-Chol-29%/LysNH$_2$-40% | 10k | 100/36/39  29% | 100/95/138  40% | ○ |
| 10k HA-Chol-40%/LysNH$_2$-9% | 10k | 100/50/57  40% | 100/16/23  9% | ○ |
| 10k HA-Chol-41%/LysNH$_2$-21% | 10k | 100/50/57  41% | 100/39/57  21% | ○ |
| 10k HA-Chol-40%/LysNH$_2$-34% | 10k | 100/50/57  40% | 100/95/138  34% | ○ |
| 99k HA-Chol-18%/LysNH$_2$-17% | 99k | 100/18/21  18% | 100/20/29  17% | ○ |
| 99k HA-Chol-16%/LysNH$_2$-36% | 99k | 100/18/21  16% | 100/51/75  36% | ○ |
| 99k HA-Chol-16%/LysNH$_2$-53% | 99k | 100/18/21  16% | 100/103/150  53% | ○ |
| 99k HA-Chol-31%/LysNH$_2$-13% | 99k | 100/36/40  31% | 100/16/23  13% | ○ |
| 99k HA-Chol-32%/LysNH$_2$-25% | 99k | 100/36/40  32% | 100/39/57  25% | ○ |
| 99k HA-Chol-33%/LysNH$_2$-42% | 99k | 100/36/40  33% | 100/95/138  42% | ○ |
| 99k HA-Chol-41%/LysNH$_2$-11% | 99k | 100/50/55  41% | 100/16/23  11% | ○ |
| 99k HA-Chol-44%/LysNH$_2$-25% | 99k | 100/50/55  44% | 100/39/57  25% | ○ |
| 99k HA-Chol-43%/LysNH$_2$-37% | 99k | 100/50/55  43% | 100/95/138  37% | ○ |

(Example 2-5) Synthesis of a HA Derivative (HA-Chol/ArgNH$_2$/Me) Modified with L-Arginine Amide (H-ArgNH$_2$), Methylamine (MeAm), and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to the solutions at ratios per HA unit shown in Table 5 below and stirred at room temperature for 2 hours or more. Next, methylamine hydrochloride (Tokyo Chemical Industry Co., Ltd.) and DMT-MM were added to each of the solutions at their ratios to the HA unit as shown in Table 5 below and stirred at room temperature for 2 hours or more. Next, L-arginine amide hydrochloride (Watanabe Chemical Industries, Ltd.) and DMT-MM were added to the HA units at ratios shown in Table 5 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/ArgNH$_2$/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 5.

A representative $^1$H-NMR spectrum (of the product derived from HA of 10 kDa with the percent incorporation of cholesteryl of 38%, the percent incorporation of ArgNH$_2$ of 22%, and the percent incorporation of Me of 17%) using 0.02 N DC1 DMSO-d$_6$/D$_2$O mixed solution (2N DC1 D$_2$O: DMSO-d$_6$=1:99) as a measurement solvent is shown in FIG. 5. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 5). Since a peak around 1.7 to 2.0 ppm including the peak for acetyl of N-acetylglucosamine is overlapping with the peak for the cholesteryl group (5H) and the peak for the introduced ArgNH$_2$ (1H), a value calculated by subtracting 5/3 of the integrated value of the peak for methyl (—CH$_3$, 0.7 ppm; 3H) of the cholesteryl group and 1/1 of the integrated value of the peak for methine (—NH—CH(CONH$_2$)CH$_2$—, 4.2 ppm; 1H) of ArgNH$_2$ from the integrated value of the peak around 1.7 to 2.0 ppm (i.e., the integrated value (1.7 to 2.0 ppm) –the integrated value (0.7 ppm)×5/3–the integrated value (4.2 ppm)×1/1) was used as the integrated value for acetyl in HA for the calculation of the percent incorporation.

Percent incorporation of cholesteryl(%) = [Exp. 10]

$$\frac{\text{Integrated value for methyl in cholesteryl}(0.7\ ppm)}{\text{Integrated value for acetyl in } HA} \times 100$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methine (—NH—CH(CONH$_2$)CH$_2$—, 4.2 ppm; 1H) of the introduced ArgNH$_2$, the percent incorporation of arginine amide (the percent incorporation of ArgNH$_2$) in the HA units was calculated according to the following equation (Table 5).

Percent incorporation of ArgNH$_2$(%) = [Exp. 11]

$$\frac{\text{Integrated value for methine in ArgNH}_2(4.2\ ppm)}{\text{Integrated value for acetyl in } HA} \times \frac{3}{1} \times 100$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for Me (—CH$_3$, 2.7 ppm; 3H), the percent incorporation of methylamine (the percent incorporation of Me) in the HA units was calculated according to the following equation (Table 5).

Percent incorporation of Me(%) = [Exp. 12]

$$\frac{\text{Integrated value for Me}(2.7\ ppm)}{\text{Integrated value for acetyl in } HA} \times 100$$

(1.7-2.0 ppm; value after correction)

TABLE 5

Amount of reagent used in preparing HA-Chol/ArgNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-19%/ArgNH$_2$-17%/Me-52% | 10k | 100/16/24 19% | 100/5000/300 17% | 100/64/192 52% | O |
| 10k HA-Chol-19%/ArgNH$_2$-19%/Me-43% | 10k | 100/16/24 19% | 100/5000/300 19% | 100/44/132 43% | O |
| 10k HA-Chol-32%/ArgNH$_2$-11%/Me-34% | 10k | 100/32/48 32% | 100/5000/300 11% | 100/48/144 34% | O |

TABLE 5-continued

Amount of reagent used in preparing HA-Chol/ArgNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-33%/ArgNH$_2$-18%/Me-25% | 10k | 100/32/48 33% | 100/5000/300 18% | 100/28/84 25% | ○ |
| 10k HA-Chol-42%/ArgNH$_2$-17%/Me-28% | 10k | 100/42/63 42% | 100/5000/300 17% | 100/38/114 28% | ○ |
| 10k HA-Chol-38%/ArgNH$_2$-22%/Me-17% | 10k | 100/42/63 38% | 100/5000/300 22% | 100/18/54 17% | ○ |
| 99k HA-Chol-27%/ArgNH$_2$-17%/Me-29% | 99k | 100/42/63 27% | 100/5000/300 17% | 100/38/114 29% | ○ |
| 99k HA-Chol-30%/ArgNH$_2$-29%/Me-16% | 99k | 100/42/63 28% | 100/5000/300 29% | 100/18/54 16% | ○ |

(Example 2-6) Synthesis of a HA Derivative (HA-Chol/EDA/Me) Modified with ethylenediamine (EDAm), methylamine (MeAm) and cholesteryl (6-aminohexyl)carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to the solutions at ratios per HA unit shown in Table 6 below and stirred at room temperature for 2 hours or more. Next, mono-Fmoc ethylenediamine hydrochloride (Watanabe Chemical Industries, Ltd.) and DMT-MM were added to the HA units at ratios shown in Table 6 below and stirred at room temperature for 2 hours or more. Next, methylamine hydrochloride (Tokyo Chemical Industry Co., Ltd.) and DMT-MM were added to each of the solutions at their ratios to the HA unit as shown in Table 6 below and the solutions were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/EDA/Me) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 6.

A representative $^1$H-NMR spectrum (of the product derived from HA of 10 kDa with the percent incorporation of cholesteryl of 33%, the percent incorporation of EDA of 30%, and the percent incorporation of Me of 10%) using 0.02 N DC1 DMSO-d$_6$/D$_2$O mixed solution (2N DC1 D$_2$O: DMSO-d$_6$=1:99) as a measurement solvent is shown in FIG. 6. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 6). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm) –the integrated value (0.7 ppm)×5/3) was used as the integrated value for acetyl in HA for the calculation of the percent incorporation.

Percent incorporation of cholesteryl(%) = [Exp. 13]
$$\frac{\text{Integrated value for methyl in cholesteryl}(0.7\ ppm)}{\text{Integrated value for acetyl in } HA} \times 100$$
(1.7–2.0 ppm; value after correction)

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) of the introduced EDA, the percent incorporation of ethylenediamine (the percent incorporation of EDA) in the HA units was calculated according to the equation given below (Table 6). Since a peak around 3.0 ppm including the peak for methylene of EDA is overlapping with the peak for methylene (2H) of cholesteryl 6-aminohexyl, a value calculated by subtracting 2/3 of the integrated value of the peak for methyl (—CH$_3$, 0.7 ppm; 3H) of the cholesteryl group from the integrated value of the peak around 3.0 ppm (i.e., the integrated value (3.0 ppm) –the integrated value (0.7 ppm)×2/3) was used as the integrated value for methylene in EDA for the calculation of the percent incorporation.

Percent incorporation of $EDA(\%) =$ [Exp. 14]

$$\frac{\text{Integrated value for methylene in } EDA(3.0 \text{ ppm; after correction})}{\text{Integrated value for acetyl in } HA} \times \frac{3}{2} \times 100$$

(1.7-2.0 ppm; value after correction)

Based on the integrated value of the peak for acetyl (—$COCH_3$, 2.0 ppm; 3H) of N-acetylglucosamine in HA and the integrated value of the peak for the introduced Me (—$CH_3$, 2.7 ppm; 3H), the percent incorporation of methylamine (the percent incorporation of Me) in the HA units was calculated according to the following equation (Table 6).

Percent incorporation of $Me(\%) =$ [Exp. 15]

$$\frac{\text{Integrated value for Me}(2.7 \text{ ppm})}{\text{Integrated value for acetyl in } HA} \times 100$$

(1.7-2.0 ppm; value after correction)

TABLE 6

Amount of reagent used in preparing HA-Chol/EDA/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added FmocEDAm hydrochloride and DMT-MM (HA unit/FmocEDAm/DMT-MM) & percent incorporation of EDA | Molar ratio of added methylamine hydrochloride and DMT-MM (HA unit/MeAm/DMT-MM) & percent incorporation of Me | State of solution |
|---|---|---|---|---|---|
| 10k HA-Chol-19%/EDA-18%/Me-35% | 10k | 100/16/24 19% | 100/22/66 18% | 100/186/300 35% | ○ |
| 10k HA-Chol-20%/EDA-34%/Me-19% | 10k | 100/16/24 20% | 100/44/132 34% | 100/120/300 19% | ○ |
| 10k HA-Chol-32%/EDA-17%/Me-24% | 10k | 100/32/48 32% | 100/22/66 17% | 100/138/300 24% | ○ |
| 10k HA-Chol-33%/EDA-30%/Me-10% | 10k | 100/32/48 33% | 100/44/132 30% | 100/72/300 10% | ○ |
| 10k HA-Chol-39%/EDA-15%/Me-19% | 10k | 100/42/63 39% | 100/22/66 15% | 100/108/300 19% | ○ |
| 10k HA-Chol-39%/EDA-26%/Me-7% | 10k | 100/42/63 39% | 100/44/132 26% | 100/42/300 7% | ○ |
| 99k HA-Chol-29%/EDA-19%/Me-25% | 99k | 100/32/48 29% | 100/22/66 19% | 100/138/300 25% | ○ |
| 99k HA-Chol-27%/EDA-33%/Me-14% | 99k | 100/32/48 27% | 100/44/132 33% | 100/72/300 14% | ○ |
| 99k HA-Chol-35%/EDA-17%/Me-21% | 99k | 100/42/63 35% | 100/22/66 17% | 100/108/300 21% | ○ |
| 99k HA-Chol-35%/EDA-27%/Me-8% | 99k | 100/42/63 35% | 100/44/132 27% | 100/42/300 8% | ○ |

(Example 2-7) Synthesis of a HA Derivative (HA-Chol/DET/Me) Modified with Diethylenetriamine (DETAm), Methylamine (MeAm) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 7 below and stirred at room temperature for 2 hours or more. Next, methylamine hydrochloride (Tokyo Chemical Industry Co., Ltd. and DMT-MM were added to each of the solutions at their ratios to the HA unit as shown in Table 7 below and the solutions were stirred at room temperature for 2 hours or more. Next, diethylenetriamine (Tokyo Chemical Industry Co., Ltd.) and tripyrrolidinophosphonium hexafluorophosphate (PyBOP, Wako Pure Chemical Industries, Ltd.) were added to the HA units at ratios shown in Table 7 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/DET/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 7.

Representative $^1$H-NMR spectra (of the product derived from HA of 10 kDa with the percent incorporation of cholesteryl of 17%, the percent incorporation of DET of 29%, and the percent incorporation of DET of 43%) using 0.02 N DCl DMSO-$d_6$/$D_2$O mixed solution (2N DCl $D_2$O: DMSO-$d_6$=1:99) and $D_2$O as measurement solvents are shown in FIGS. 7-1 and 7-2, respectively. In the NMR spectrum using 0.02 N DCl DMSO-$d_6$/$D_2$O mixed solution, based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 7). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm) –the integrated value (0.7 ppm)×5/3) was used as the integrated value for acetyl in HA for the calculation of the percent incorporation.

$$\text{Percent incorporation of cholesteryl}(\%) = \quad\quad [\text{Exp. 16}]$$

$$\frac{\text{Integrated value for methyl in cholesteryl}(0.7\ ppm)}{\text{Integrated value for acetyl in } HA} \times 100$$

(1.7-2.0 ppm; value after correction)

In the NMR spectrum using $D_2$O, based on the integrated value of the peak for acetyl (—$COCH_3$, 1.7 to 2.0 ppm; 3H) of N-acetylglucosamine in HA and the introduced DET, the percent incorporation of diethylenetriamine (the percent incorporation of DET) in the HA units was calculated according to the equation given below (Table 7).

$$\text{Percent incorporation of } DET(\%) = \quad\quad [\text{Exp. 17}]$$

$$\frac{\text{Integrated value for methylene in } DET(2.9\ ppm)}{\text{Integrated value for acetyl in } HA} \times \frac{3}{2} \times 100$$

(1.7-2.0 ppm; value after correction)

Based on the integrated value of the peak for acetyl (—$COCH_3$, 2.0 ppm; 3H) of N-acetylglucosamine in HA and the integrated value of the peak for Me (—$CH_3$, 2.8 ppm; 3H), the percent incorporation of methylamine (the percent incorporation of Me) in the HA units was calculated according to the following equation (Table 7). Since a peak around 2.8 ppm including the peak for Me is overlapping with the peak for methylene (2H) of the introduced DET, a value calculated by subtracting 1/1 of the integrated value of the peak for methylene (—$CH_2$—, 2.9 ppm; 2H) of DET (i.e., the integrated value (2.8 ppm) –the integrated value (2.9 ppm)×1/1) was used as the integrated value for Me for the calculation of the percent incorporation.

$$\text{Percent incorporation of Me}(\%) = \quad\quad [\text{Exp. 18}]$$

$$\frac{\text{Integrated value for Me}(2.8\ ppm;\ \text{value after correction})}{\text{Integrated value for acetyl in } HA} \times 100$$

(1.7-2.0 ppm; value after correction)

TABLE 7

Amount of reagent used in preparing HA-Chol/DET/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | Molar ratio of added methylamine hydrochloride and DMT-MM (HA unit/MeAm/DMT-MM) & percent incorporation of Me | State of solution |
|---|---|---|---|---|---|
| 10k HA-Chol-17%/DET-29%/Me-43% | 10k | 100/16/24 17% | 100/5000/300 29% | 100/64/192 43% | O |
| 10k HA-Chol-18%/DET-42%/Me-37% | 10k | 100/16/24 18% | 100/5000/300 42% | 100/44/132 37% | O |

TABLE 7-continued

Amount of reagent used in preparing HA-Chol/DET/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | Molar ratio of added methylamine hydrochloride and DMT-MM (HA unit/MeAm/DMT-MM) & percent incorporation of Me | State of solution |
|---|---|---|---|---|---|
| 10k HA-Chol-33%/DET-28%/Me-25% | 10k | 100/32/48 33% | 100/5000/300 28% | 100/48/144 25% | X |
| 10k HA-Chol-32%/DET-37%/Me-18% | 10k | 100/32/48 32% | 100/5000/300 37% | 100/28/84 18% | X |
| 10k HA-Chol-36%/DET/Me | 10k | 100/42/63 36% | 100/5000/300 Percent incorporation could not be calculated | 100/38/114 Percent incorporation could not be calculated | X |
| 10k HA-Chol-35%/DET/Me | 10k | 100/42/63 35% | 100/5000/300 Percent incorporation could not be calculated | 100/18/54 Percent incorporation could not be calculated | X |
| 99k HA-Chol-21%/DET/Me | 99k | 100/32/48 21% | 100/5000/300 Percent incorporation could not be calculated | 100/48/144 Percent incorporation could not be calculated | X |
| 99k HA-Chol-21%/DET/Me | 99k | 100/32/48 21% | 100/5000/300 Percent incorporation could not be calculated | 100/28/84 Percent incorporation could not be calculated | X |
| 99k HA-Chol-37%/DET/Me | 99k | 100/42/63 37% | 100/5000/300 Percent incorporation could not be calculated | 100/38/114 Percent incorporation could not be calculated | X |
| 99k HA-Chol-36%/DET/Me | 99k | 100/42/63 36% | 100/5000/300 Percent incorporation could not be calculated | 100/18/54 Percent incorporation could not be calculated | X |

It should be noted that the indication "percent incorporation could not be calculated" means that the sample did not have a sufficient solubility to the solvent and NMR analysis could not be performed.

(Example 2-8) Synthesis of a HA Derivative (HA-Chol/LysNH$_2$/Me) Modified with L-Lysine Amide (H-LysNH$_2$), Methylamine (MeAm), and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 8 below and stirred at room temperature for 2 hours or more. Next, mono-Fmoc-L-lysine amide hydrochloride (Watanabe Chemical Industries, Ltd.) and DMT-MM were added to the HA units at ratios shown in Table 8 below and stirred at room temperature for 2 hours or more. Next, methylamine hydrochloride (Tokyo Chemical Industry Co., Ltd.) and DMT-MM were added to each of the solutions at their ratios to the HA unit as shown in Table 8 below and the solutions were stirred at room temperature for 2 hours or more.

The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/LysNH$_2$/Me) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 8.

A representative $^1$H-NMR spectrum (of the product derived from HA of 10 kDa with the percent incorporation of cholesteryl of 37%, the percent incorporation of LysNH$_2$ of 22%, and the percent incorporation of Me of 11%) using 0.02 N DC1 DMSO-$d_6$/D$_2$O mixed solution (2N DC1 D$_2$O: DMSO-$d_6$=1:99) as a measurement solvent is shown in FIG. 8. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 8). Since a peak around 1.7 to 2.0 ppm including the peak for acetyl of N-acetylglucosamine is overlapping with the peak for the cholesteryl group (5H) and the peak for the introduced LysNH$_2$ (1H), a value calculated by subtracting ⅗ of the integrated value of the peak for methyl (—CH$_3$, 0.7 ppm; 3H) of the cholesteryl group and ½ of the integrated value of the peak for methylene (—CH$_2$—, 2.8 ppm; 2H) of LysNH$_2$ from the integrated value of the peak around 1.7 to 2.0 ppm (i.e., the integrated value (1.7 to 2.0 ppm)–the integrated value (0.7 ppm)×⅗–the integrated value (2.8 ppm)×½) was used as the integrated value for acetyl in HA for the calculation of the percent incorporation.

$$\text{Percent incorporation of cholesteryl}(\%) = \frac{\text{Integrated value for methyl in cholesteryl}(0.7\ ppm)}{\text{Integrated value for acetyl in } HA} \times 100 \quad [\text{Exp. 19}]$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methylene (—CH$_2$—, 2.8 ppm; 2H) of the introduced LysNH$_2$, the percent incorporation of lysine amide in the HA units (the percent incorporation of LysNH$_2$) was calculated according to the following equation (Table 8).

Percent incorporation of LysNH$_2$(%) =  [Exp. 20]

$$\frac{\text{Integrated value for methylene in LysNH}_2(2.8\ ppm)}{\text{Integrated value for acetyl in } HA} \times$$

(1.7-2.0 ppm; value after correction)

$$\frac{3}{2} \times 100$$

Based on the integrated value of the peak for acetyl (—COCH$_3$, 1.7 to 2.0 ppm; 3H) of N-acetylglucosamine in HA and the integrated value of the peak for the introduced Me (—CH$_3$, 2.7 ppm; 3H), the percent incorporation of methylamine (the percent incorporation of Me) in the HA units was calculated according to the following equation (Table 8).

Percent incorporation of Me(%) =  [Exp. 21]

$$\frac{\text{Integrated value for Me}(2.7\ ppm)}{\text{Integrated value for acetyl in } HA} \times 100$$

(1.7-2.0 ppm; value after correction)

TABLE 8

Amount of reagent used in HA-Chol/LysNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added Fmoc—H-LysNH$_2$ hydrochloride and DMT-MM (HA unit/Fmoc—H-LysNH$_2$/DMT-MM) & percent incorporation of LysNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-19%/LysNH$_2$-17%/Me-35% | 10k | 100/16/24  19% | 100/22/66  17% | 100/186/300  35% | ○ |
| 10k HA-Chol-19%/LysNH$_2$-29%/Me-17% | 10k | 100/16/24  19% | 100/44/132  29% | 100/120/300  17% | ○ |
| 10k HA-Chol-32%/LysNH$_2$-15%/Me-23% | 10k | 100/32/48  32% | 100/22/66  15% | 100/138/300  23% | ○ |
| 10k HA-Chol-33%/LysNH$_2$-25%/Me-15% | 10k | 100/32/48  33% | 100/44/132  25% | 100/72/300  15% | ○ |
| 10k HA-Chol-38%/LysNH$_2$-15%/Me-21% | 10k | 100/42/63  38% | 100/22/66  15% | 100/108/300  21% | ○ |
| 10k HA-Chol-36%/LysNH$_2$-21%/Me-8% | 10k | 100/42/63  36% | 100/44/132  21% | 100/42/300  8% | ○ |
| 99k HA-Chol-28%/LysNH$_2$-17%/Me-25% | 99k | 100/32/48  28% | 100/22/66  17% | 100/138/300  25% | ○ |
| 99k HA-Chol-26%/LysNH$_2$-28%/Me-14% | 99k | 100/32/48  26% | 100/44/132  28% | 100/72/300  14% | ○ |
| 99k HA-Chol-32%/LysNH$_2$-15%/Me-17% | 99k | 100/42/63  32% | 100/22/66  15% | 100/108/300  17% | ○ |
| 99k HA-Chol-34%/LysNH$_2$-28%/Me-7% | 99k | 100/42/63  34% | 100/44/132  28% | 100/42/300  7% | ○ |
| 10k HA-Chol-17%/LysNH$_2$-24%/Me-39% | 10k | 100/16/24  17% | 100/44/44  24% | 100/120/300  39% | ○ |
| 10k HA-Chol-16%/LysNH$_2$-29%/Me-27% | 10k | 100/16/24  16% | 100/44/88  29% | 100/120/300  27% | ○ |
| 10k HA-Chol-16%/LysNH$_2$-30%/Me-21% | 10k | 100/16/24  16% | 100/44/132  30% | 100/120/300  21% | ○ |
| 10k HA-Chol-36%/LysNH$_2$-19%/Me-15% | 10k | 100/42/63  36% | 100/44/44  19% | 100/42/300  15% | ○ |
| 10k HA-Chol-37%/LysNH$_2$-22%/Me-11% | 10k | 100/42/63  37% | 100/44/88  22% | 100/42/300  11% | ○ |
| 10k HA-Chol-36%/LysNH$_2$-20%/Me-11% | 10k | 100/42/63  36% | 100/44/132  20% | 100/42/300  11% | ○ |

(Example 2-9) Synthesis of a HA Derivative (HA-Chol/LysNH$_2$) Modified with L-Lysine Amide (H-LysNH$_2$), Methylamine (MeAm), and Cholesteryl (6-Aminohexyl)Carbamate The same process as described in Example 2-8 was performed except that mono-Fmoc-L-lysine amide hydrochloride, methylamine hydrochloride, and Chol-C$_6$ hydrochloride were added in this order to HA-TBA solutions in anhydrous DMSO, to obtain the desired product (HA-Chol/LysNH$_2$/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 9.

The percent incorporations of cholesteryl, LysNH$_2$, and Me were calculated in the same manner as Example 2-8 (Table 9).

TABLE 9

Amount of reagent used in preparing HA-Chol/LysNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added Fmoc—H-LysNH$_2$ hydrochloride and DMT-MM (HA unit/Fmoc—H-LysNH$_2$/DMT-MM) & percent incorporation of LysNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-7%/LysNH$_2$-16%/Me-52% | 10k | 100/48/53 7% | 100/22/24 16% | 100/62/68 52% | O |
| 10k HA-Chol-8%/LysNH$_2$-26%/Me-34% | 10k | 100/48/53 8% | 100/44/48 26% | 100/40/44 34% | O |
| 10k HA-Chol-26%/LysNH$_2$-16%/Me-33% | 10k | 100/126/139 26% | 100/22/24 16% | 100/36/40 33% | O |
| 10k HA-Chol-29%/LysNH$_2$-26%/Me-13% | 10k | 100/126/139 29% | 100/44/48 26% | 100/14/15 13% | O |
| 99k HA-Chol-26%/LysNH$_2$-18%/Me-33% | 99k | 100/126/139 26% | 100/22/24 18% | 100/36/40 33% | O |
| 99k HA-Chol-28%/LysNH$_2$-30%/Me-13% | 99k | 100/126/139 28% | 100/44/48 30% | 100/14/15 13% | O |

(Example 2-10) Synthesis of a HA Derivative (HA-Chol/SPR/Me) Modified with Spermine (H-SPR), Methylamine (MeAm), and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to each of the solutions at their ratios to the HA unit as shown in Table 10 below and the solutions were stirred at room temperature for 2 hours or more. Next, methylamine hydrochloride (Tokyo Chemical Industry Co., Ltd.) and DMT-MM were added to each of the solutions at their ratios to the HA unit as shown in Table 10 below and the solutions were stirred at room temperature for 2 hours or more. Next, spermine (Aldrich) and tripyrrolidinophosphonium hexafluorophosphate (PyBOP, Wako Pure Chemical Industries, Ltd.) were added to the HA units at ratios shown in Table 10 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/SPR/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 10.

A representative $^1$H-NMR spectrum (of the product derived from HA of 99 kDa with the percent incorporation of cholesteryl of 27%, the percent incorporation of SPR of 37%, and the percent incorporation of Me of 16%) using 0.02 N DC1 DMSO-d$_6$/D$_2$O mixed solution (2N DC1 D$_2$O:DMSO-d$_6$=1:99) as a measurement solvent is shown in FIG. 9. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 10). Since a peak around 1.7 to 2.0 ppm including the peak for acetyl of N-acetylglucosamine is overlapping with the peak for the cholesteryl group (5H) and the peak for the introduced SPR (6H), a value calculated by subtracting ⅝ of the integrated value of the peak for methyl (—CH$_3$, 0.7 ppm; 3H) of the cholesteryl group and 6/2 of the integrated value of the peak for methylene (—CH$_2$—, 2.1 ppm; 2H) of SPR from the integrated value of the peak around 1.7 to 2.0 ppm (i.e., the integrated value (1.7 to 2.0 ppm) –the integrated value (0.7 ppm)×⅝–the integrated value (2.1 ppm)×6/2) was used as the integrated value for acetyl in HA for the calculation of the percent incorporation.

Percent incorporation of cholesteryl(%) = [Exp. 22]

$$\frac{\text{Integrated value for methyl in cholesteryl}(0.7\ ppm)}{\text{Integrated value for acetyl in } HA} \times 100$$

(1.7-2.0 ppm; value after correction)

Based on the integrated value of the peak for acetyl (—COCH$_3$, 2.0 ppm; 3H) of N-acetylglucosamine in HA and the integrated value of the peak for methylene (—CH$_2$—, 2.1 ppm; 2H) of SPR, the percent incorporation of SPR (the percent incorporation of SPR) in the HA units was calculated according to the following equation (Table 10).

Percent incorporation of SPR(%) = [Exp. 23]

$$\frac{\text{Integrated value for methylene in } SPR}{\text{Integrated value for acetyl in } HA} \times \frac{3}{2} \times 100$$

(1.7-2.0 ppm; value after correction)

Based on the integrated value of the peak for acetyl (—COCH$_3$, 2.0 ppm; 3H) of N-acetylglucosamine in HA and the integrated value of the peak for methylene (—CH$_3$, 2.7 ppm; 3H) of Me, the percent incorporation of methylamine (the percent incorporation of Me) in the HA units was calculated according to the following equation (Table 10).

Percent incorporation of Me(%) = [Exp. 24]

$$\frac{\text{Integrated value for methyl in } Me(2.7\ ppm)}{\text{Integrated value for acetyl in } HA} \times 100$$

(1.7-2.0 ppm; value after correction)

TABLE 10

Amount of reagent used in preparing HA-Chol/SPR/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-SPR and PyBOP (HA unit/H-SPR/PyBOP) & percent incorporation of SPR | Molar ratio of added methylamine hydrochloride and DMT-MM (HA unit/MeAm/DMT-MM) & percent incorporation of Me | State of solution |
|---|---|---|---|---|---|
| 10k HA-Chol-14%/SPR-21%/Me-51% | 10k | 100/16/24 14% | 100/5000/300 21% | 100/74/222 51% | ○ |
| 10k HA-Chol-16%/SPR-29%/Me-52% | 10k | 100/16/24 16% | 100/5000/300 29% | 100/64/192 52% | ○ |
| 10k HA-Chol-14%/SPR-28%/Me-37% | 10k | 100/16/24 14% | 100/5000/300 28% | 100/44/132 37% | ○ |
| 10k HA-Chol-34%/SPR-27%/Me-28% | 10k | 100/42/63 34% | 100/5000/300 27% | 100/48/144 28% | ○ |
| 10k HA-Chol-31%/SPR-27%/Me-26% | 10k | 100/42/63 31% | 100/5000/300 27% | 100/38/114 26% | ○ |
| 10k HA-Chol-32%/SPR-33%/Me-16% | 10k | 100/42/63 32% | 100/5000/300 33% | 100/18/54 16% | ○ |
| 99k HA-Chol-29%/SPR-32%/Me-32% | 99k | 100/42/63 29% | 100/5000/300 32% | 100/48/144 32% | ○ |

TABLE 10-continued

Amount of reagent used in preparing HA-Chol/SPR/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added H-SPR and PyBOP (HA unit/H-SPR/PyBOP) & percent incorporation of SPR | Molar ratio of added methylamine hydrochloride and DMT-MM (HA unit/MeAm/DMT-MM) & percent incorporation of Me | State of solution |
|---|---|---|---|---|---|
| 99k HA-Chol-27%/SPR-34%/Me-28% | 99k | 100/42/63 27% | 100/5000/300 34% | 100/38/114 28% | ○ |
| 99k HA-Chol-27%/SPR-37%/Me-16% | 99k | 100/42/63 27% | 100/5000/300 37% | 100/18/54 16% | ○ |

(Example 2-11) Synthesis of a HA Derivative (HA-Chol/PTMA/Me) Modified with (3-Aminopropyl) Trimethylazanium (AmPTMA), Methylamine (MeAm), and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to each of the solutions at their ratios to the HA unit as shown in Table 11 below and the solutions were stirred at room temperature for 2 hours or more. Next, methylamine hydrochloride (Tokyo Chemical Industry Co., Ltd.) and DMT-MM were added to each of the solutions at their ratios to the HA unit as shown in Table 11 below and the solutions were stirred at room temperature for 2 hours or more. Next, (3-aminopropyl)trimethylazanium chloride (UkrOrgSyntez) and DMT-MM were added to the HA units at ratios shown in Table 11 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/PTMA/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 11.

Figure 10:
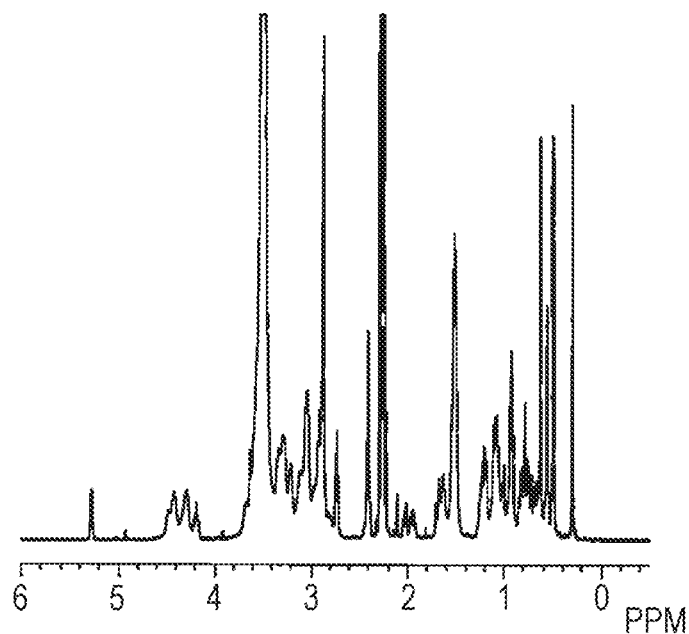
FIG. 10 represents an example of $^1$H-NMR spectrum of HA-Chol/PTMA/Me prepared in Example 2-11 in a DC1/DMSO/D$_2$O mixed solution (the percent incorporation of cholesteryl: 29%, the percent incorporation of PTMA: 29%, and the percent incorporation of Me: 31%).

A representative $^1$H-NMR spectrum (of the product derived from HA of 10 kDa with the percent incorporation of cholesteryl of 29%, the percent incorporation of PTMA of 29%, and the percent incorporation of Me of 31%) using 0.02 N DCl DMSO-$d_6$/$D_2$O mixed solution (2N DCl $D_2$O: DMSO-$d_6$=1:99) as a measurement solvent is shown in FIG. 10. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 11). Since a peak around 1.7 to 2.0 ppm including the peak for acetyl of N-acetylglucosamine is overlapping with the peak for the cholesteryl group (5H) and the peak for the introduced PTMA (2H), a value calculated by subtracting ⅔ of the integrated value of the peak for methyl (—$CH_3$, 0.7 ppm; 3H) of the cholesteryl group and ⅔ of the integrated value of the peak for methyl (—$N^+$—$(CH_3)_3$, 3.1 ppm; 9H) of PTMA from the integrated value of the peak around 1.7 to 2.0 ppm (i.e., the integrated value (1.7 to 2.0 ppm) –the integrated value (0.7 ppm)×⅔–the integrated value (3.1 ppm)×⅔) was used as the integrated value for acetyl in HA for the calculation of the percent incorporation.

Percent incorporation of cholesteryl(%) = [Exp. 25]

$$\frac{\text{Integrated value for methyl in cholesteryl}(0.7\ ppm)}{\text{Integrated value for acetyl in } HA} \times 100$$

(1.7-2.0 ppm; value after correction)

Based on the integrated value of the peak for acetyl (—$COCH_3$, 2.0 ppm; 3H) of N-acetylglucosamine in HA and the integrated value of the peak for methyl (—$N^+$—$(CH_3)_3$, 3.1 ppm; 9H) of the introduced PTMA, the percent incorporation of (3-aminopropyl)trimethylazanium (the percent incorporation of PTMA) in the HA units was calculated according to the following equation (Table 11).

Percent incorporation of PTMA(%) = [Exp. 26]

$$\frac{\text{Integrated value for methyl in } PTMA}{\text{Integrated value for acetyl in } HA} \times \frac{3}{9} \times 100$$

(1.7-2.0 ppm; value after correction)

Based on the integrated value of the peak for acetyl (—$COCH_3$, 2.0 ppm; 3H) of N-acetylglucosamine in HA and the integrated value of the peak for methyl (—$CH_3$, 2.7 ppm; 3H) of the introduced Me, the percent incorporation of methylamine (the percent incorporation of Me) in the HA units was calculated according to the following equation (Table 11).

Percent incorporation of Me(%) = [Exp. 27]

$$\frac{\text{Integrated value for methyl in Me}(2.7\ ppm)}{\text{Integrated value for acetyl in } HA} \times 100$$

(1.7-2.0 ppm; value after correction)

TABLE 11

Amount of reagent used in preparing HA-Chol/PTMA/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added AmPTMA chloride and DMT-MM (HA unit/AmPTMA/DMT-MM) & percent incorporation of PTMA | Molar ratio of added methylamine hydrochloride and DMT-MM (HA unit/MeAm/DMT-MM) & percent incorporation of Me | State of solution |
|---|---|---|---|---|---|
| 10k HA-Chol-15%/PTMA-26%/Me-46% | 10k | 100/16/19 15% | 100/300/300 26% | 100/64/77 46% | ○ |
| 10k HA-Chol-15%/PTMA-34%/Me-33% | 10k | 100/16/19 15% | 100/300/300 34% | 100/44/53 33% | ○ |
| 10k HA-Chol-29%/PTMA-29%/Me-31% | 10k | 100/32/38 29% | 100/300/300 29% | 100/48/58 31% | ○ |
| 10k HA-Chol-27%/PTMA-37%/Me-19% | 10k | 100/32/38 27% | 100/300/300 37% | 100/28/34 19% | ○ |
| 10k HA-Chol-35%/PTMA-32%/Me-23% | 10k | 100/42/50 35% | 100/300/300 32% | 100/38/46 23% | ○ |
| 10k HA-Chol-37%/PTMA-31%/Me-19% | 10k | 100/42/50 37% | 100/300/300 31% | 100/18/22 19% | ○ |
| 99k HA-Chol-20%/PTMA-27%/Me-33% | 99k | 100/32/38 20% | 100/300/300 27% | 100/48/58 33% | ○ |
| 99k HA-Chol-21%/PTMA-40%/Me-22% | 99k | 100/32/38 21% | 100/300/300 40% | 100/28/34 22% | ○ |
| 99k HA-Chol-28%/PTMA-29%/Me-24% | 99k | 100/42/50 28% | 100/300/300 29% | 100/38/46 24% | ○ |
| 99k HA-Chol-26%/PTMA-36%/Me-17% | 99k | 100/42/50 26% | 100/300/300 36% | 100/18/22 17% | ○ |

(Example 2-12) Synthesis of a HA Derivative (HA-Chol/ArgNH$_2$/Me) Modified with L-Arginine Amide (H-ArgNH$_2$), Methylamine (MeAm), and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to each of the solutions at their ratios to the HA unit as shown in Table 12 below and the solutions were stirred at room temperature for 2 hours or more. Next, L-arginine amide hydrochloride (Watanabe Chemical Industries, Ltd.) and DMT-MM were added to the HA units at ratios shown in Table 12 below and stirred at room temperature for 2 hours or more. The reaction solutions were transferred into a dialysis membrane and dialyzed against DMSO. Further, a TBA salt-equilibrated cation exchange resin prepared according to the method described in WO2014/038641 was added in 5 molar equivalent of ion exchange capacity of the resin defined as the number of moles of the HA unit. The mixture was stirred at room temperature for 30 minutes and centrifuged, and the supernatant was recovered. Next, methylamine hydrochloride (Tokyo Chemical Industry Co., Ltd.) and DMT-MM were added to each of the solutions at their ratios to the HA unit as shown in Table 12 below and the solutions were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/ArgNH$_2$/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 12.

The percent incorporations of cholesteryl, ArgNH$_2$, and Me were calculated in the same manner as Example 2-5 (Table 12).

TABLE 12

Amount of reagent used in preparing HA-Chol/ArgNH$_2$/Me and percent incorporation

| Asbbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-14%/ArgNH$_2$-47%/Me-13% | 10k | 100/16/24 14% | 100/5000/88 47% | 100/2000/300 13% | ○ |
| 10k HA-Chol-27%/ArgNH$_2$-31%/Me-13% | 10k | 100/42/63 27% | 100/5000/88 31% | 100/2000/300 13% | ○ |

It was revealed that HA-Chol/ArgNH$_2$/Me could be synthesized by adding cholesteryl (6-aminohexyl)carbamate, L-arginine amide, and methylamine in this order.

(Example 2-13) Synthesis of a HA Derivative (HA-Chol/ArgNH$_2$/Me)

Solutions f HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to each of the solutions at their ratios to the HA unit as shown in Table 13 below and the solutions were stirred at room temperature for 2 hours or more. Next, methylamine hydrochloride (Tokyo Chemical Industry Co., Ltd.) and DMT-MM were added to each of the solutions at their ratios to the HA unit as shown in Table 13 below and the solutions were stirred at room temperature for 2 hours or more. The reaction solutions were transferred into a dialysis membrane and dialyzed against DMSO. Further, a TBA salt-equilibrated cation exchange resin prepared according to the method described in WO2014/038641 was added in 5 molar equivalent of ion exchange capacity of the resin defined as the number of moles of the HA unit. The mixture was stirred at room temperature for 30 minutes and centrifuged, and the supernatant was recovered. Next, L-arginine amide hydrochloride (Watanabe Chemical Industries, Ltd.) and DMT-MM were added to the HA units at ratios shown in Table 13 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/ArgNH$_2$/Me) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 13.

The percent incorporations of cholesteryl, ArgNH$_2$, and Me were calculated in the same manner as Example 2-5 (Table 13).

TABLE 13

Amount of reagent used in preparing HA-Chol/ArgNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-30%/ArgNH$_2$-12%/Me-18% | 10k | 100/42/63 30% | 100/5000/300 12% | 100/2000/28 18% | ○ |

(Example 2-14) Synthesis of a HA Derivative (HA-Chol/ArgNH$_2$/PrOH) Modified with L-Arginine Amide (H-ArgNH$_2$), Propanolamine (PrOHAm), and Cholesteryl (6-Aminohexyl)Carbamate The same process as described in Example 2-13 was performed except that propanolamine hydrochloride was used in place of methylamine hydrochloride to obtain the desired product (HA-Chol/ArgNH$_2$/PrOH) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 14.

Figures 1, 11:
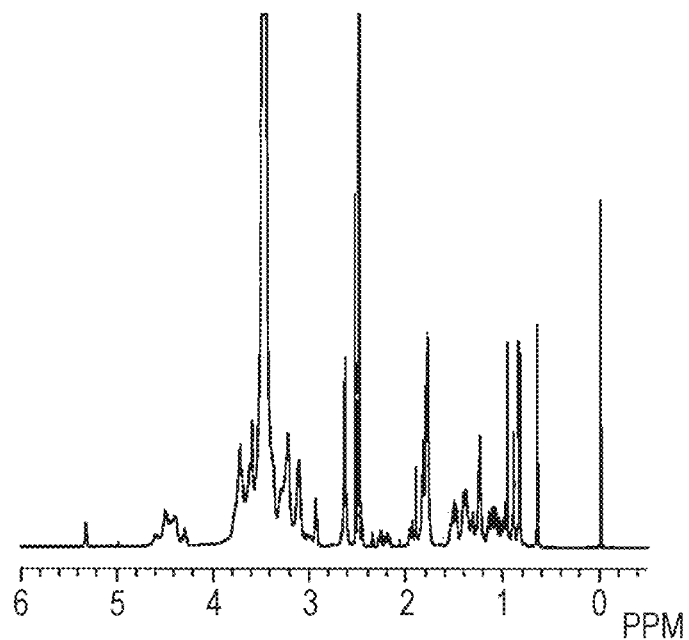
Figures 2, 11:
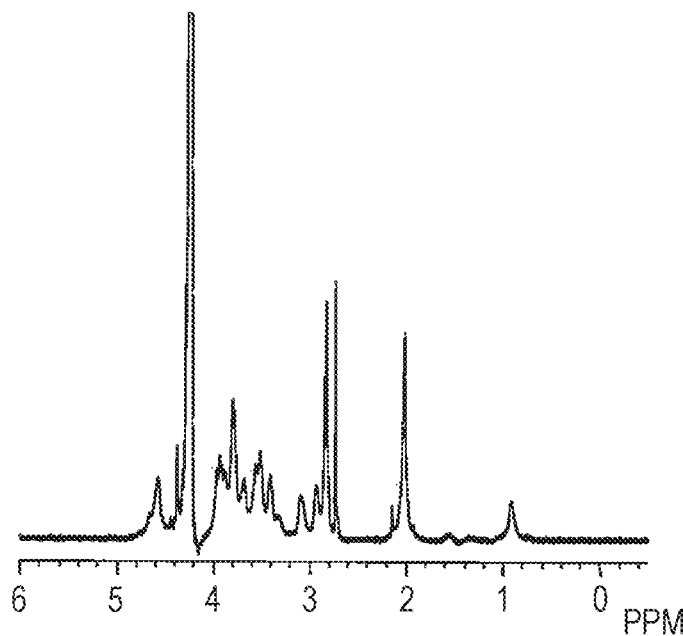

$^1$H-NMR spectra (of the product (intermediate) derived from HA of 10 kDa with the percent incorporation of cholesteryl of 31% and the percent incorporation of PrOH of 19%, and the product derived from HA of 10 kDa with the percent incorporation of cholesteryl of 31%, the percent incorporation of ArgNH$_2$ of 11%, and the percent incorporation of PrOH of 19%) using 0.02 N DCl DMSO-d$_6$/D$_2$O mixed solution (2N DCl D$_2$O:DMSO-d$_6$=1:99) as a measurement solvent are shown in FIGS. 11-1 and 11-2, respectively. In FIG. 11-2, based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 14). Since a peak around 1.7 to 2.0 ppm including the peak for acetyl of N-acetylglucosamine is overlapping with the peak for the cholesteryl group (5H) and the peak for the introduced ArgNH$_2$ (1H), a value calculated by subtracting ⅝ of the integrated value of the peak for methyl (—CH$_3$, 0.7 ppm; 3H) of the cholesteryl group and 1/1 of the integrated value of the peak for methine (—NH—CH(CONH$_2$)CH$_2$—, 4.2 ppm; 1H) of ArgNH$_2$ from the integrated value of the peak around 1.7 to 2.0 ppm (i.e., the integrated value (1.7 to 2.0 ppm)–the integrated value (0.7 ppm)×⅝–the integrated value (4.2 ppm)×1/1) was used as the integrated value for acetyl in HA for the calculation of the percent incorporation.

Percent incorporation of cholesteryl(%) = [Exp. 28]

$$\frac{\text{Integrated value for methyl in cholesteryl}(0.7\ ppm)}{\text{Integrated value for acetyl in } HA} \times 100$$

(1.7-2.0 ppm; value after correction)

Based on the integrated value of the peak for acetyl (—COCH$_3$, 2.0 ppm; 3H) of N-acetylglucosamine in HA and the integrated value of the peak for methine (—NH—CH(CONH$_2$)CH$_2$—, 4.2 ppm; 1H) of the introduced ArgNH$_2$, the percent incorporation of arginine amide in the HA units (the percent incorporation of ArgNH$_2$) was calculated according to the following equation (Table 14).

Percent incorporation of ArgNH$_2$(%) = [Exp. 29]

$$\frac{\text{Integrated value for methine in ArgNH}_2}{\text{Integrated value for acetyl in } HA} \times \frac{3}{1} \times 100$$

(1.7-2.0 ppm; value after correction)

In FIG. 11-1, based on the integrated value of the peak for acetyl (—COCH$_3$, 2.0 ppm; 3H) of N-acetylglucosamine in HA and the integrated value of the peak for methylene (—CH$_2$, 1.6 ppm; 2H) of the introduced PrOH, the percent incorporation of propanolamine (the percent incorporation of PrOH) in the HA units was calculated according to the equation given below (Table 14). Since a peak around 1.7 to 2.0 ppm including the peak for acetyl of N-acetylglucosamine is overlapping with the peak for the cholesteryl group (5H), a value calculated by subtracting ⅝ of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm) –the integrated value (0.7 ppm)×⅝) was used as the integrated value for acetyl in HA for the calculation of the percent incorporation.

Percent incorporation of PrOH(%) = [Exp. 30]

$$\frac{\text{Integrated value for methylene in PrOH}}{\text{Integrated value for acetyl in } HA} \times \frac{3}{2} \times 100$$

(1.7-2.0 ppm; value after correction)

TABLE 14

Amount of reagent used in preparing HA-Chol/ArgNH$_2$/PrOH and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added propanolamine hydrochloride and DMT-MM (HA unit/PrOHAm/DMT-MM) & percent incorporation of PrOH | State of solution |
|---|---|---|---|---|---|
| 10k HA-Chol-31%/ArgNH$_2$-11%/PrOH-19% | 10k | 100/42/63 31% | 100/5000/300 11% | 100/2000/28 19% | O |

(Example 2-15) Synthesis of a HA Derivative (HA-Chol/ArgNH$_2$) Modified with L-Arginine Amide (H-ArgNH$_2$) and Cholesteryl (6-Aminohexyl)Carbamate HA-Chol/ArgNH$_2$ for in vitro and in vivo studies was synthesized in the same manner as Example 2-1 (Table 15).

Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 15.

TABLE 15

Amount of reagent used in preparing HA-Chol/ArgNH$_2$ and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | State of solution |
|---|---|---|---|---|
| 10k HA-Chol-17%/ArgNH$_2$-34% | 10k | 100/16/24 17% | 100/4986/50 34% | O |
| 10k HA-Chol-18%/ArgNH$_2$-51% | 10k | 100/16/24 18% | 100/4986/63 51% | O |
| 10k HA-Chol-18%/ArgNH$_2$-64% | 10k | 100/16/24 18% | 100/4986/125 64% | O |
| 10k HA-Chol-17%/ArgNH$_2$-71% | 10k | 100/16/24 17% | 100/4986/310 71% | O |
| 10k HA-Chol-36%/ArgNH$_2$-23% | 10k | 100/32/48 36% | 100/4986/32 23% | O |
| 10k HA-Chol-35%/ArgNH$_2$-56% | 10k | 100/32/48 35% | 100/4986/302 56% | O |
| 10k HA-Chol-44%/ArgNH$_2$-42% | 10k | 100/42/63 44% | 100/4986/301 42% | O |
| 99k HA-Chol-15%/ArgNH$_2$-30% | 99k | 100/16/24 15% | 100/5597/34 30% | O |
| 99k HA-Chol-15%/ArgNH$_2$-74% | 99k | 100/16/24 15% | 100/5597/338 74% | O |
| 99k HA-Chol-31%/ArgNH$_2$-29% | 99k | 100/32/48 31% | 100/5000/35 29% | O |
| 99k HA-Chol-31%/ArgNH$_2$-57% | 99k | 100/32/48 31% | 100/5597/339 57% | O |
| 99k HA-Chol-42%/ArgNH$_2$-50% | 99k | 100/42/63 42% | 100/5597/338 50% | O |
| 10k HA-Chol-47%/ArgNH$_2$-24% | 10k | 100/50/58 47% | 100/4989/31 24% | O |
| 10k HA-Chol-45%/ArgNH$_2$-35% | 10k | 100/50/58 45% | 100/4989/300 35% | O |
| 99k HA-Chol-46%/ArgNH$_2$-30% | 99k | 100/53/60 46% | 100/4989/32 30% | O |
| 99k HA-Chol-44%/ArgNH$_2$-50% | 99k | 100/53/60 44% | 100/4989/301 50% | O |

(Example 2-16) Synthesis of a HA Derivative (HA-Chol/EDA) Modified with ethylenediamine (EDAm) and cholesteryl (6-aminohexyl)carbamate HA-Chol/EDA for in vitro and in vivo studies was synthesized in the same manner as Example 2-2 (Table 16). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 16.

TABLE 16

Amount of reagent used in preparing HA-Chol/EDA and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added FmocEDAm hydrochloride and DMT-MM (HA unit/FmocEDAm/DMT-MM) & percent incorporation of EDA | State of solution |
|---|---|---|---|---|
| 10k HA-Chol-17%/EDA-26% | 10k | 100/16/24 17% | 100/30/40 26% | O |

TABLE 16-continued

Amount of reagent used in preparing HA-Chol/EDA and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added FmocEDAm hydrochloride and DMT-MM (HA unit/FmocEDAm/DMT-MM) & percent incorporation of EDA | State of solution |
|---|---|---|---|---|
| 10k HA-Chol-18%/EDA-55% | 10k | 100/16/24 18% | 100/75/100 55% | ○ |
| 10k HA-Chol-17%/EDA-61% | 10k | 100/16/24 17% | 100/300/301 61% | ○ |
| 10k HA-Chol-34%/EDA-23% | 10k | 100/32/48 34% | 100/30/41 23% | ○ |
| 10k HA-Chol-33%/EDA-45% | 10k | 100/32/48 33% | 100/300/300 45% | ○ |
| 10k HA-Chol-45%/EDA-31% | 10k | 100/42/63 45% | 100/300/298 31% | ○ |
| 99k HA-Chol-14%/EDA-27% | 99k | 100/16/24 14% | 100/34/45 27% | ○ |
| 99k HA-Chol-14%/EDA-63% | 99k | 100/16/24 14% | 100/336/335 63% | ○ |
| 99k HA-Chol-29%/EDA-25% | 99k | 100/32/48 29% | 100/34/46 25% | ○ |
| 99k HA-Chol-29%/EDA-47% | 99k | 100/32/48 29% | 100/336/336 47% | ○ |
| 99k HA-Chol-44%/EDA-43% | 99k | 100/42/63 44% | 100/336/336 43% | ○ |
| 10k HA-Chol-47%/EDA-23% | 10k | 100/50/58 47% | 100/34/45 23% | ○ |
| 10k HA-Chol-44%/EDA-29% | 10k | 100/50/58 44% | 100/336/335 29% | ○ |
| 99k HA-Chol-48%/EDA-22% | 99k | 100/53/60 48% | 100/34/46 22% | ○ |
| 99k HA-Chol-43%/EDA-30% | 99k | 100/53/60 43% | 100/336/336 30% | ○ |

(Example 2-17) Synthesis of a HA Derivative (HA-Chol/DET) Modified with Diethylenetriamine (DETAm) and Cholesteryl (6-Aminohexyl)Carbamate HA-Chol/DET for in vitro and in vivo studies was synthesized in the same manner as Example 2-3 (Table 17). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 17.

TABLE 17

Amount of reagent used in preparing HA-Chol/DET and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | State of solution |
|---|---|---|---|---|
| 10k HA-Chol-17%/DET | 10k | 100/16/24 17% | 100/4999/24 Percent incorporation could not be calculated | ○ |
| 10k HA-Chol-17%/DET-76% | 10k | 100/16/24 17% | 100/4999/48 76% | ○ |
| 10k HA-Chol-17%/DET-84% | 10k | 100/16/24 17% | 100/4999/103 84% | ○ |
| 10k HA-Chol-17%/DET-78% | 10k | 100/16/24 17% | 100/4999/305 78% | ○ |
| 10k HA-Chol-17%/DET | 10k | 100/16/24 17% | 100/4999/25 Percent incorporation could not be calculated | ○ |
| 10k HA-Chol-17%/DET | 10k | 100/16/24 17% | 100/4999/50 Percent incorporation could not be calculated | ○ |
| 10k HA-Chol-17%/DET-76% | 10k | 100/16/24 17% | 100/4999/100 76% | ○ |
| 10k HA-Chol-17%/DET-75% | 10k | 100/16/24 16% | 100/4999/301 75% | ○ |

It should be noted that the indication "percent incorporation could not be calculated" means that the sample did not have a sufficient solubility to the solvent and NMR analysis could not be performed.

(Example 2-18) Synthesis of a HA Derivative (HA-Chol/LysNH$_2$) Modified with L-Lysine Amide (H-LysNH$_2$) and Cholesteryl (6-Aminohexyl)Carbamate HA-Chol/LysNH$_2$ for in vitro and in vivo studies was synthesized in the same manner as Example 2-4 (Table 18). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by 0 in Table 18.

TABLE 18

Amount of reagent used in preparing HA-Chol/LysNH$_2$ and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added Fmoc—H-LysNH$_2$ and DMT-MM (HA unit/Fmoc—H-LysNH$_2$/DMT-MM) & percent incorporation of LysNH$_2$ | State of solution |
| --- | --- | --- | --- | --- |
| 10k HA-Chol-16%/LysNH$_2$-23% | 10k | 100/16/24 16% | 100/25/40 23% | ○ |
| 10k HA-Chol-17%/LysNH$_2$-45% | 10k | 100/16/24 17% | 100/300/304 45% | ○ |
| 10k HA-Chol-33%/LysNH$_2$-19% | 10k | 100/32/48 33% | 100/25/40 19% | ○ |
| 10k HA-Chol-33%/LysNH$_2$-30% | 10k | 100/32/48 33% | 100/300/304 30% | ○ |

(Example 2-19) Synthesis of a HA Derivative (HA-Chol/ArgNH$_2$/Me) Modified with L-Arginine Amide (H-ArgNH$_2$), Methylamine (MeAm), and Cholesteryl (6-Aminohexyl)Carbamate HA-Chol/ArgNH$_2$/Me for in vitro and in vivo studies was synthesized in the same manner as Example 2-5 (Table 19). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 19.

TABLE 19

Amount of reagent used in preparing HA-Chol/ArgNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
| --- | --- | --- | --- | --- | --- |
| 10k HA-Chol-17%/ArgNH$_2$-11%/Me-51% | 10k | 100/16/24 17% | 100/5000/300 11% | 100/64/64 51% | ○ |
| 10k HA-Chol-17%/ArgNH$_2$-28%/Me-41% | 10k | 100/16/24 17% | 100/5000/300 28% | 100/44/44 41% | ○ |
| 10k HA-Chol-16%/ArgNH$_2$-44%/Me-23% | 10k | 100/16/24 16% | 100/5000/300 44% | 100/24/24 23% | ○ |

TABLE 19-continued

Amount of reagent used in preparing HA-Chol/ArgNH$_2$/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-32%/ArgNH$_2$-14%/Me-36% | 10k | 100/32/48 32% | 100/5000/300 14% | 100/48/48 36% | ○ |
| 10k HA-Chol-32%/ArgNH$_2$-30%/Me-24% | 10k | 100/32/48 32% | 100/5000/300 30% | 100/28/28 24% | ○ |
| 10k HA-Chol-39%/ArgNH$_2$-11%/Me-25% | 10k | 100/42/63 39% | 100/5000/300 11% | 100/38/38 25% | ○ |
| 10k HA-Chol-40%/ArgNH$_2$-26%/Me-14% | 10k | 100/42/63 40% | 100/5000/300 26% | 100/18/18 14% | ○ |
| 99k HA-Chol-27%/ArgNH$_2$-18%/Me-32% | 99k | 100/32/48 27% | 100/5000/300 18% | 100/48/48 32% | ○ |
| 99k HA-Chol-27%/ArgNH$_2$-32%/Me-21% | 99k | 100/32/48 27% | 100/5000/300 32% | 100/28/28 21% | ○ |

(Example 2-20) Synthesis of a HA Derivative (HA-Chol/EDA/Me) Modified with Ethylenediamine (EDAm), Methylamine (MeAm), and Cholesteryl (6-Aminohexyl)Carbamate HA-Chol/EDA/Me for in vitro and in vivo studies was synthesized in the same manner as Example 2-6 (Table 20).

Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 20.

TABLE 20

Amount of reagent used in preparing HA-Chol/EDA/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added FmocEDA hydrochloride and DMT-MM (HA unit/EDAm/DMT-MM) & percent incorporation of EDA | Molar ratio of added methylamine hydrochloride and DMT-MM (HA unit/MeAm/DMT-MM) & percent incorporation of Me | State of solution |
|---|---|---|---|---|---|
| 10k HA-Chol-17%/EDA-24%/Me-24% | 10k | 100/16/24 17% | 100/30/60 24% | 100/300/300 24% | ○ |
| 10k HA-Chol-16%/EDA-46%/Me-7% | 10k | 100/16/24 16% | 100/60/120 46% | 100/300/300 7% | ○ |
| 10k HA-Chol-32%/EDA-24%/Me-12% | 10k | 100/32/48 32% | 100/30/60 24% | 100/300/300 12% | ○ |
| 10k HA-Chol-32%/EDA-37%/Me-4% | 10k | 100/32/48 32% | 100/60/120 37% | 100/300/300 4% | ○ |
| 10k HA-Chol-39%/EDA-19%/Me-7% | 10k | 100/42/63 39% | 100/30/60 19% | 100/300/300 7% | ○ |
| 10k HA-Chol-37%/EDA-29%/Me-7% | 10k | 100/42/63 37% | 100/60/120 29% | 100/300/300 7% | ○ |
| 99k HA-Chol-26%/EDA-22%/Me-17% | 99k | 100/32/48 26% | 100/30/60 22% | 100/300/300 17% | ○ |
| 99k HA-Chol-25%/EDA-40%/Me-6% | 99k | 100/32/48 25% | 100/60/120 40% | 100/300/300 6% | ○ |

(Example 2-21) Synthesis of a HA Derivative (HA-Chol/DET/Me) Modified with Diethylenetriamine (DETAm), Methylamine (MeAm), and Cholesteryl (6-Aminohexyl)Carbamate HA-Chol/DET/Me for in vitro and in vivo studies was synthesized in the same manner as Example 2-7 (Table 21). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 21.

TABLE 21

Amount of reagent used in preparing HA-Chol/DET/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DETAm and PyBOP (HA unit/DETAm/PyBOP) & percent incorporation of DET | Molar ratio of added methylamine hydrochloride and DMT-MM (HA unit/MeAm/DMT-MM) & percent incorporation of Me | State of solution |
|---|---|---|---|---|---|
| 10k HA-Chol-17%/DET-20%/Me-59% | 10k | 100/16/24 17% | 100/5000/300 20% | 100/74/222 59% | O |
| 10k HA-Chol-17%/DET-22%/Me-55% | 10k | 100/16/24 17% | 100/5000/300 22% | 100/64/192 55% | O |
| 10k HA-Chol-17%/DET-25%/Me-46% | 10k | 100/16/24 17% | 100/5000/300 25% | 100/54/162 46% | O |
| 10k HA-Chol-17%/DET-35%/Me-38% | 10k | 100/16/24 17% | 100/5000/300 35% | 100/44/132 38% | O |

(Example 2-22) Synthesis of a HA Derivative (HA-Chol/LysNH$_2$/Me) Modified with L-lysine amide (H-LysNH$_2$), methylamine (MeAm) and cholesteryl (6-aminohexyl)carbamate HA-Chol/LysNH$_2$/Me for in vitro and in vivo studies was synthesized in the same manner as Example 2-8 (Table 22). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 22.

TABLE 22

Amount of reagent used in preparing HA-Chol/LysNH$_2$/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added Fmoc—H-LysNH$_2$ and DMT-MM (HA unit/Fmoc—H-LysNH$_2$/DMT-MM) & percent incorporation of LysNH$_2$ | Molar ratio of added methylamine hydrochloride and DMT-MM (HA unit/MeAm/DMT-MM) & percent incorporation of Me | State of solution |
|---|---|---|---|---|---|
| 10k HA-Chol-16%/LysNH$_2$-24%/Me-24% | 10k | 100/16/24 16% | 100/30/60 24% | 100/300/300 24% | O |
| 10k HA-Chol-16%/LysNH$_2$-41%/Me-8% | 10k | 100/16/24 16% | 100/60/120 41% | 100/300/300 8% | O |
| 10k HA-Chol-31%/LysNH$_2$-21%/Me-11% | 10k | 100/32/48 31% | 100/30/60 21% | 100/300/300 11% | O |
| 10k HA-Chol-31%/LysNH$_2$-31%/Me-5% | 10k | 100/32/48 31% | 100/60/120 31% | 100/300/300 5% | O |
| 10k HA-Chol-37%/LysNH$_2$-17%/Me-8% | 10k | 100/42/63 37% | 100/30/60 17% | 100/300/300 8% | O |

TABLE 22-continued

Amount of reagent used in preparing HA-Chol/LysNH₂/Me and percent incorporation

| Abbreviation | MW (Da) | Molar ratio of added Chol-C₆ hydrochloride and DMT-MM (HA unit/Chol-C₆/DMT-MM) & percent incorporation of Chol | Molar ratio of added Fmoc—H-LysNH₂ and DMT-MM (HA unit/Fmoc—H-LysNH₂/DMT-MM) & percent incorporation of LysNH₂ | Molar ratio of added methylamine hydrochloride and DMT-MM (HA unit/MeAm/DMT-MM) & percent incorporation of Me | State of solution |
|---|---|---|---|---|---|
| 10k HA-Chol-36%/LysNH₂-23%/Me-4% | 10k | 100/42/63  36% | 100/60/120  23% | 100/300/300  4% | ○ |
| 99k HA-Chol-24%/LysNH₂-20%/Me-16% | 99k | 100/32/48  24% | 100/30/60  20% | 100/300/300  16% | ○ |
| 99k HA-Chol-25%/LysNH₂-33%/Me-5% | 99k | 100/32/48  25% | 100/60/120  33% | 100/300/300  5% | ○ |

(Example 2-23) Synthesis of a HA Derivative (HA-Chol/SPR/Me) Modified with Spermine (H-SPR), Methylamine (MeAm), and Cholesteryl (6-Aminohexyl)Carbamate HA-Chol/SPR/Me for in vitro and in vivo studies was synthesized in the same manner as Example 2-10 (Table 23).

Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 23.

TABLE 23

Amount of reagent used in preparing HA-Chol/SPR/Me and percent incorporation

| Abbreviation | MW (Da) | Molar ratio of added Chol-C₆ hydrochloride and DMT-MM (HA unit/Chol-C₆/DMT-MM) & percent incorporation of Chol | Molar ratio of added H-SPR and PyBOP (HA unit/H-SPR/PyBOP) & percent incorporation of SPR | Molar ratio of added methylamine hydrochloride and DMT-MM (HA unit/MeAm/DMT-MM) & percent incorporation of Me | State of solution |
|---|---|---|---|---|---|
| 10k HA-Chol-16%/SPR-17%/Me-62% | 10k | 100/16/24  16% | 100/5000/300  17% | 100/82/98  62% | ○ |
| 10k HA-Chol-16%/SPR-17%/Me-61% | 10k | 100/16/24  16% | 100/5000/300  17% | 100/79/95  61% | ○ |
| 10k HA-Chol-16%/SPR-17%/Me-59% | 10k | 100/16/24  16% | 100/5000/300  17% | 100/74/89  59% | ○ |
| 10k HA-Chol-16%/SPR-21%/Me-56% | 10k | 100/16/24  16% | 100/5000/300  21% | 100/64/77  56% | ○ |
| 99k HA-Chol-26%/SPR-24%/Me-42% | 99k | 100/32/48  26% | 100/5000/300  24% | 100/66/79  42% | ○ |
| 99k HA-Chol-26%/SPR-24%/Me-40% | 99k | 100/32/48  26% | 100/5000/300  24% | 100/63/76  40% | ○ |
| 99k HA-Chol-27%/SPR-27%/Me-38% | 99k | 100/32/48  27% | 100/5000/300  27% | 100/58/70  38% | ○ |
| 99k HA-Chol-25%/SPR-26%/Me-33% | 99k | 100/32/48  25% | 100/5000/300  26% | 100/48/58  33% | ○ |
| 10k HA-Chol-17%/SPR-16%/Me-65% | 10k | 100/16/24  17% | 100/5000/7  16% | 100/82/98  65% | ○ |
| 10k HA-Chol-18%/SPR-15%/Me-67% | 10k | 100/16/24  18% | 100/5000/14  15% | 100/82/98  67% | ○ |

TABLE 23-continued

Amount of reagent used in preparing HA-Chol/SPR/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added H-SPR and PyBOP (HA unit/H-SPR/PyBOP) & percent incorporation of SPR | Molar ratio of added methylamine hydrochloride and DMT-MM (HA unit/MeAm/DMT-MM) & percent incorporation of Me | State of solution |
|---|---|---|---|---|---|
| 99k HA-Chol-27%/SPR-25%/Me-47% | 99k | 100/32/48 27% | 100/5000/7 25% | 100/66/79 47% | ○ |
| 99k HA-Chol-27%/SPR-26%/Me-47% | 99k | 100/32/48 27% | 100/5000/14 26% | 100/66/79 47% | ○ |

(Example 2-24) Synthesis of a HA Derivative (HA-Chol/PTMA/Me) Modified with (3-Aminopropyl) Trimethylazanium (AmPTMA), Methylamine (MeAm), and Cholesteryl (6-Aminohexyl)Carbamate HA-Chol/PTMA/Me for in vitro and in vivo studies was synthesized in the same manner as Example 2-11 (Table 24). Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 24.

TABLE 24

Amount of reagent used in preparing HA-Chol/PTMA/Me and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added AmPTMA chloride and DMT-MM (HA unit/AmPTMA/DMT-MM) & percent incorporation of PTMA | Molar ratio of added methylamine hydrochloride and DMT-MM (HA unit/MeAm/DMT-MM) & percent incorporation of Me | State of solution |
|---|---|---|---|---|---|
| 10k HA-Chol-17%/PTMA-3%/Me-63% | 10k | 100/16/24 17% | 100/300/300 3% | 100/79/95 63% | ○ |
| 10k HA-Chol-17%/PTMA-5%/Me-60% | 10k | 100/16/24 17% | 100/300/300 5% | 100/74/89 60% | ○ |
| 10k HA-Chol-17%/PTMA-7%/Me-55% | 10k | 100/16/24 17% | 100/300/300 7% | 100/64/77 55% | ○ |
| 99k HA-Chol-28%/PTMA-6%/Me-40% | 99k | 100/32/48 28% | 100/300/300 6% | 100/63/76 40% | ○ |
| 99k HA-Chol-26%/PTMA-7%/Me-40% | 99k | 100/32/48 26% | 100/300/300 7% | 100/58/70 40% | ○ |
| 99k HA-Chol-27%/PTMA-9%/Me-36% | 99k | 100/32/48 27% | 100/300/300 9% | 100/48/58 36% | ○ |
| 10k HA-Chol-18%/PTMA-6%/Me-62% | 10k | 100/16/24 18% | 100/300/300 6% | 100/64/77 62% | ○ |
| 10k HA-Chol-18%/PTMA-13%/Me-52% | 10k | 100/16/24 18% | 100/300/300 13% | 100/54/65 52% | ○ |

TABLE 24-continued

Amount of reagent used in preparing HA-Chol/PTMA/Me and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added AmPTMA chloride and DMT-MM (HA unit/AmPTMA/DMT-MM) & percent incorporation of PTMA | Molar ratio of added methylamine hydrochloride and DMT-MM (HA unit/MeAm/DMT-MM) & percent incorporation of Me | State of solution |
|---|---|---|---|---|---|
| 10k HA-Chol-18%/PTMA-31%/Me-35% | 10k | 100/16/24 18% | 100/300/300 31% | 100/35/42 35% | ○ |
| 99k HA-Chol-27%/PTMA-13%/Me-39% | 99k | 100/32/48 27% | 100/300/300 13% | 100/48/58 39% | ○ |
| 99k HA-Chol-27%/PTMA-21%/Me-31% | 99k | 100/32/48 27% | 100/300/300 21% | 100/38/46 31% | ○ |
| 99k HA-Chol-25%/PTMA-46%/Me-6% | 99k | 100/32/48 25% | 100/300/300 46% | 100/8/10 6% | ○ |

(Example 2-25) Synthesis of a HA Derivative (HA-Chol/ArgNH$_2$/EtOH) Modified with L-Arginine Amide (H-ArgNH$_2$), Ethanolamine (EtOHAm), and Cholesteryl (6-Aminohexyl)Carbamate The same process as described in Example 2-5 was performed except that ethanolamine hydrochloride was used in plate of methylamine hydrochloride to obtain the desired product (HA-Chol/ArgNH$_2$/EtOH) as a white solid. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 25.

Figure 12:
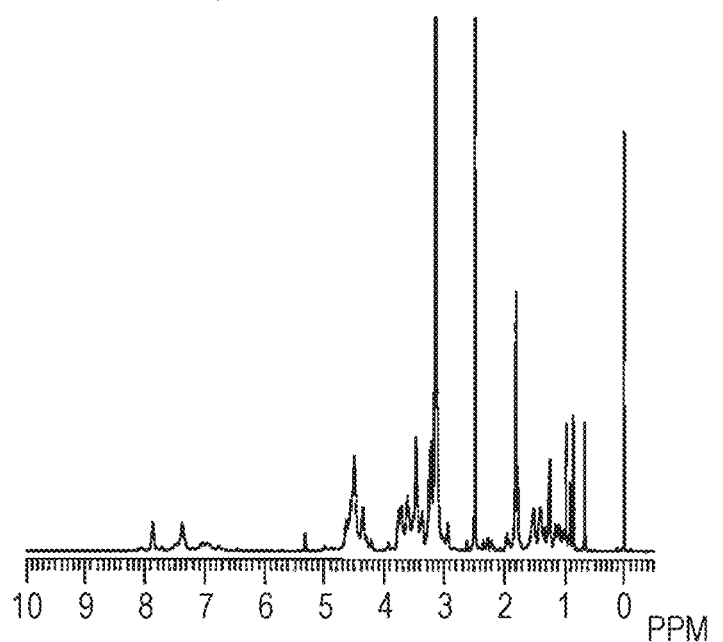
FIG. 12 represents an example of $^1$H-NMR spectrum of HA-Chol/ArgNH$_2$/EtOH prepared in Example 2-25 in DMSO (the percent incorporation of cholesteryl: 16%, the percent incorporation of ArgNH$_2$: 16%, and the percent incorporation of EtOH: 69%).

A $^1$H-NMR spectrum (of the product derived from HA of 10 kDa with the percent incorporation of cholesteryl of 16%, the percent incorporation of ArgNH$_2$ of 16%, and the percent incorporation of EtOH of 69%) using DMSO-d$_6$ as a measurement solvent is shown in FIG. 12. In FIG. 12, based on the integrated value of the peak for acetyl (—COCH$_3$, 1.7 to 2.0 ppm; 3H) of N-acetylglucosamine and the integrated value of the peak for methyl (—CH$_3$, 0.7 ppm; 3H) of the introduced cholesteryl group, the percent incorporation of cholesteryl in the HA units was calculated according to the equation given below (Table 25). Since a peak around 1.7 to 2.0 ppm including the peak for acetyl of N-acetylglucosamine is overlapping with the peak for the cholesteryl group (5H) and the peak for the introduced ArgNH$_2$ (1H), a value calculated by subtracting 5/3 of the integrated value of the peak for methyl (—CH$_3$, 0.7 ppm; 3H) of the cholesteryl group and 1/1 of the integrated value of the peak for methine (4.2 ppm; 1H) of ArgNH$_2$ from the integrated value of the peak around 1.7 to 2.0 ppm (i.e., the integrated value (1.7 to 2.0 ppm) −the integrated value (0.7 ppm)×5/3−the integrated value (4.2 ppm)×1/1) was used as the integrated value for acetyl in HA for the calculation of the percent incorporation.

Percent incorporation of cholesteryl(%) = [Exp. 31]

$$\frac{\text{Integrated value for methyl in cholesteryl}(0.7\ ppm)}{\text{Integrated value for acetyl in } HA} \times 100$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methine (—NH—CH(CONH$_2$)CH$_2$—, 4.2 ppm; 1H) of the introduced ArgNH$_2$, the percent incorporation of arginine amide in the HA units (the percent incorporation of ArgNH$_2$) was calculated according to the following equation (Table 25).

Percent incorporation of ArgNH$_2$(%) = [Exp. 32]

$$\frac{\text{Integrated value for methine in ArgNH}_2(4.2\ ppm)}{\text{Integrated value for acetyl in } HA} \times \frac{3}{1} \times 100$$

(1.7-2.0 ppm; value after correction)

In FIG. 12, based on the integrated value of the peak for amide (—NHCOCH$_3$, 7.4 ppm; 1H) of N-acetylglucosamine in HA and the integrated value of the peak for amide (—CONHCH$_2$—, 7.9 ppm; 1H) of the introduced EtOH, the percent incorporation of ethanolamine (the percent incorporation of EtOH) in the HA units was calculated according to the following equation (Table 25).

Percent incorporation of EtOH(%) = [Exp. 33]

$$\frac{\text{Integrated value for amide in EtOH}(7.9\ ppm)}{\text{Integrated value for amide in } HA(7.4\ ppm)} \times \frac{1}{1} \times 100$$

TABLE 25

Amount of reagent used in preparing HA-Chol/ArgNH$_2$/EtOH and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added ethanolamine hydrochloride and DMT-MM (HA unit/EtOHAm/DMT-MM) & percent incorporation of EtOH | State of solution |
|---|---|---|---|---|---|
| 10k HA-Chol-16%/ArgNH$_2$-18%/EtOH-66% | 10k | 100/16/18 16% | 100/1000/300 18% | 100/64/64 66% | ○ |
| 10k HA-Chol-16%/ArgNH$_2$-31%/EtOH-42% | 10k | 100/16/18 16% | 100/1000/300 31% | 100/44/444 2% | ○ |
| 10k HA-Chol-16%/ArgNH$_2$-16%/EtOH-69% | 10k | 100/16/18 16% | 100/1000/300 16% | 100/64/64 69% | ○ |
| 10k HA-Chol-15%/ArgNH$_2$-28%/EtOH-56% | 10k | 100/16/18 15% | 100/1000/300 28% | 100/64/64 56% | ○ |
| 10k HA-Chol-16%/ArgNH$_2$-21%/EtOH-59% | 10k | 100/16/18 16% | 100/1000/300 21% | 100/64/64 59% | ○ |

(Example 2-26) Synthesis of a Fluorescent-Labeled HA Derivative (HA-Chol/ArgNH$_2$/EtOH/FL) Modified with L-Arginine Amide (H-ArgNH$_2$), Ethanolamine (EtOHAm), and Cholesteryl (6-Aminohexyl)Carbamate The same process as described in Example 2-25 was performed except that, before the addition of chol-C$_6$ hydrochloride, 2 molar equivalent of 5-(aminomethyl)fluorescein (FL, Invitrogen) hydrochloride and 4 molar equivalent of DMT-MM were added to a HA unit 100 and stirred at room temperature for 2 hours to obtain the desired product (HA-Chol/ArgNH$_2$/EtOH/FL) as a yellow solid and the percent incorporation was calculated (Table 26). Water was added to the yellow solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 26.

TABLE 26

Amount of reagent used in preparing HA-Chol/ArgNH$_2$/EtOH/FL and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-ArgNH$_2$ hydrochloride and DMT-MM (HA unit/H-ArgNH$_2$/DMT-MM) & percent incorporation of ArgNH$_2$ | Molar ratio of added EtOH amine hydrochloride and DMT-MM (HA unit/EtOHAm/DMT-MM) & percent incorporation of EtOH | State of solution |
|---|---|---|---|---|---|
| 10k HA-Chol-10%/ArgNH$_2$-11%/EtOH-66%/FL | 10k | 100/8/9 10% | 100/1000/300 11% | 100/72/79 66% | ○ |
| 10k HA-Chol-17%/ArgNH$_2$-10%/EtOH-67%/FL | 10k | 100/16/18 17% | 100/1000/300 10% | 100/64/70 67% | ○ |

The samples with no precipitation observed are water-soluble and are useful because they can be easily formed into a complex with a drug by being mixed with the drug in water. It should be noted that the samples with precipitation observed can also have mucosal permeability and other functions in the form of compositions obtained by dissolving the sample in an organic solvent such as DMSO, then allowing it to form a complex with a drug, and replacing the organic solvent with an aqueous solution or with another solvent that can be administered.

Example 3Examination of Mucosal Permeability of HA Derivatives (Example 3-1) Assessment of Intraocular Migration of Eye Drops The 10k-HA-Chol-17%/ArgNH$_2$-10%/EtOH-67%/FL synthesized in Example 2-26 was dissolved in 10% sucrose solution to a concentration of 50 mg/mL, and 3 μL of the resulting solution was applied to both eyes of mice. Both eyeballs were taken out after 1 hour and frozen sections were prepared. The sections were observed for the distribution of the HA derivative by fluorescence detection with a confocal microscope. As a result, it was found that the HA derivative permeated through the mucosal layer of the corneal surface and present in the cornea. Further, it was also found that the HA derivative was present in the conjunctiva and the ciliary body. On the other hand, carboxyfluorescein was dissolved in 10% sucrose solution to a concentration of 0.0568 mg/mL, 3 μL of the resulting solution was applied to both eyes of mice, and an observation was performed as in the case of the 10k-HA-Chol-17%/ArgNH$_2$-10%/EtOH-67%/FL. As a result, fluorescence from carboxyfluorescein was not observed in any tissues of the eyes including the cornea, conjunctiva and ciliary body.

Example 4Synthesis of HA Derivatives 2

(Example 4-1-1) Synthesis of a HA Derivative (HA-Chol/EDOBEA) Modified with 2,2'-(Ethylenedioxy)Bis(Ethylamine) (EDOBEAm) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to the solutions at ratios per HA unit shown in Table 27 below and stirred at room temperature for 2 hours or more. Next, 2,2'-(ethylenedioxy)bis(ethylamine) (Sigma-Aldrich) and PyBOP were added to the HA units at ratios shown in Table 27 below and stirred at room temperature for 2 hours or more. At this time, portions of the solutions were removed, and the following steps were performed without the addition of 2,2'-(ethylenedioxy)bis(ethylamine) and PyBOP to obtain HA-Chol as comparison references during the calculation of percent incorporations. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/EDOBEA) as a white solid. The solution of the dialysate before lyophilization was passed through a filter having a pore diameter of 0.45 μm or 5 μm, and the samples which passed through the filter were denoted by O in Table 27. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 27. Hereinafter, in the observation of the state of the solution, the samples that passed through the filter are water-soluble and are useful because they can be easily formed into a complex with a drug by being mixed with the drug in water. Further, when ultrasonication was performed, the samples with no precipitation observed are water-soluble and are useful because they can be easily formed into a complex with a drug by being mixed with the drug in water. It should be noted that, even after the ultrasonication, the samples with precipitation observed can also have mucosal permeability and other functions in the form of compositions obtained by dissolving the sample in an organic solvent such as DMSO, then allowing it to form a complex with a drug, and replacing the organic solvent with an aqueous solution or with another solvent that can be administered.

A representative $^1$H-NMR spectrum (of the product derived from HA of 10 kDa with the percent incorporation of cholesteryl of 17% and the percent incorporation of EDOBEA of 52%) using 0.02 N DCl DMSO-d$_6$/D$_2$O mixed solution (2N DCl D$_2$O:DMSO-d$_6$=1:99) as a measurement solvent is shown in FIG. 13-1. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 27). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm) −the integrated value (0.7 ppm)×5/3) was used as the integrated value for acetyl in HA for the calculation of the percent incorporation.

$$\text{Percent incorporation of cholesteryl}(\%) = \frac{\text{Integrated value for methyl in cholesteryl}(0.7\ ppm)}{\text{Integrated value for acetyl in } HA} \times 100 \quad [\text{Exp. 34}]$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methylene (—CH$_2$—, 2.9 to 3.0 ppm; 2H) of the introduced EDOBEA, the percent incorporation of 2,2'-(ethylenedioxy)bis(ethylamine) (the percent incorporation of EDOBEA) in the HA units was calculated according to the following equation (Table 27). Since the peak for methylene of 2,2'-(ethylenedioxy)bis(ethylamine) is overlapping with the peak for HA, a value calculated by subtracting the integrated value of the peak around 2.9 to 3.0 ppm of HA-Chol obtained as a comparison reference was used as the integrated value for EDOBEA for the calculation of the percent incorporation.

Percent incorporation of $EDOBEA(\%) =$ [Exp. 35]

$$\frac{\text{Integrated value for methylene in } EDOBEA(2.9\text{-}3.0\ ppm; \text{value after correction})}{\text{Integrated value for acetyl in } HA\ (1.7\text{-}2.0\ ppm; \text{value after correction})} \times \frac{3}{2} \times 100$$

TABLE 27

Amount of reagent used in preparing HA-Chol/EDOBEA and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added EDOBEAm and PyBOP (HA unit/EDOBEAm/PyBOP) & percent incorporation of EDOBEA | State of solution |
|---|---|---|---|---|
| 10k HA-Chol-16%/EDOBEA-13% | 10k | 100/16/24 16% | 100/4000/26 13% | ○ |
| 10k HA-Chol-17%/EDOBEA-52% | 10k | 100/16/24 17% | 100/4000/301 52% | ○ |
| 10k HA-Chol-45%/EDOBEA-21% | 10k | 100/50/54 45% | 100/4001/26 21% | ○ |
| 10k HA-Chol-44%/EDOBEA-35% | 10k | 100/50/54 44% | 100/4001/297 35% | ○ |
| 99k HA-Chol-14%/EDOBEA-12% | 99k | 100/16/24 14% | 100/4000/26 12% | ○ |
| 99k HA-Chol-15%/EDOBEA-54% | 99k | 100/16/24 15% | 100/4000/301 54% | ○ |
| 99k HA-Chol-38%/EDOBEA-14% | 99k | 100/50/54 38% | 100/4001/25 14% | ○ |
| 99k HA-Chol-36%/EDOBEA-49% | 99k | 100/50/54 36% | 100/4001/299 49% | ○ |

(Example 4-1-2) Synthesis of a HA Derivative (HA-Chol/DEG) Modified with 2,2'-Oxybis(Ethylamine) (OBEA) and Cholesteryl (6-Aminohexyl) Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 28 below and stirred at room temperature for 2 hours or more. Next, 2,2'-oxybis(ethylamine) (Tokyo Chemical Industry Co., Ltd.) and PyBOP were added to the HA units at ratios shown in Table 28 below and stirred at room temperature for 2 hours or more. At this time, portions of the solutions were removed, and the following steps were performed without the addition of 2,2'-oxybis(ethylamine) and PyBOP to obtain HA-Chol as comparison references during the calculation of percent incorporations. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/DEG) as a white solid. The solution of the dialysate before lyophilization was passed through a filter having a pore diameter of 0.45 μm or 5 μm, and the samples which passed through the filter were denoted by ○ in Table 28. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by ○ in Table 28.

A representative $^1$H-NMR spectrum (of the product derived from HA of 10 kDa with the percent incorporation of cholesteryl of 17% and the percent incorporation of DEG of 51%) using 0.02 N DC1 DMSO-$d_6$/$D_2$O mixed solution (2N DC1 $D_2$O:DMSO-$d_6$=1:99) as a measurement solvent is shown in FIG. 13-2. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 28). Since a peak around 1.7 to 2.0 ppm including the peak for acetyl of N-acetylglucosamine is overlapping with the peak for the cholesteryl group (5H), a value calculated by subtracting ⅔ of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm)–the integrated value (0.7 ppm)×⅔) was used as the integrated value for acetyl in HA for the calculation of the percent incorporation.

Percent incorporation of cholesteryl(%) = [Exp. 36]

$$\frac{\text{Integrated value for methyl in cholesteryl}(0.7\ ppm)}{\text{Integrated value for acetyl in } HA\ (1.7\text{-}2.0\ ppm;\ \text{value after correction})} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 2.9 to 3.1 ppm; 2H) of the introduced 2,2'-oxybis (ethylamine), the percent incorporation of 2,2'-oxybis(ethylamine) (the percent incorporation of DEG) in the HA units was calculated according to the following equation (Table 28). Since the peak for methylene of DEG is overlapping with the peak for HA, a value calculated by subtracting the integrated value of the peak around 2.9 to 3.1 ppm of HA-Chol obtained as a comparison reference was used as the integrated value for DEG for the calculation of the percent incorporation.

$$\text{Percent incorporation of } DEG(\%) = \frac{\text{Integrated value for methylene in } DEG(3.0 \text{ ppm; value after correction})}{\text{Integrated value for acetyl in } HA (1.7\text{-}2.0 \text{ ppm; value after correction})} \times \frac{3}{2} \times 100 \quad [\text{Exp. 37}]$$

TABLE 28

Amount of reagent used in preparing HA-Chol/DEG and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added OBEA and PyBOP (HA unit/OBEA/PyBOP) & percent incorporation of DEG | State of solution |
|---|---|---|---|---|
| 10k HA-Chol-16%/DEG-8% | 10k | 100/16/24 16% | 100/4000/25 8% | ○ |
| 10k HA-Chol-17%/DEG-51% | 10k | 100/16/24 17% | 100/4000/300 51% | ○ |
| 10k HA-Chol-44%/DEG-10% | 10k | 100/50/54 44% | 100/4002/29 10% | ○ |
| 10k HA-Chol-49%/DEG-35% | 10k | 100/50/54 49% | 100/4002/303 35% | ○ |
| 99k HA-Chol-14%/DEG-6% | 99k | 100/16/24 14% | 100/4000/26 6% | ○ |
| 99k HA-Chol-15%/DEG-52% | 99k | 100/16/24 15% | 100/4000/298 52% | ○ |
| 99k HA-Chol-36%/DEG-23% | 99k | 100/50/54 36% | 100/4003/30 23% | ○ |
| 99k HA-Chol-35%/DEG-66% | 99k | 100/50/54 35% | 100/3782/296 66% | ○ |

(Example 4-1-3) Synthesis of a HA Derivative (HA-Chol/AGMT) Modified with Agmatine (H-AGMT) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 29 below and stirred at room temperature for 2 hours or more. Next, agmatine dihydrochloride (Ark Pharm Inc.) and DMT-MM were added to the HA units at ratios shown in Table 29 below and stirred at room temperature for 2 hours or more. At this time, portions of the solutions were removed, and the following steps were performed without the addition of agmatine di hydrochloride and DMT-MM to obtain HA-Chol as comparison references during the calculation of percent incorporations. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/AGMT) as a white solid. The solution of the dialysate before lyophilization was passed through a filter having a pore diameter of 0.45 μm or 5 μm, and the samples which passed through the filter were denoted by O in Table 29. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 29.

A representative $^1$H-NMR spectrum (of the product derived from HA of 10 kDa with the percent incorporation of cholesteryl of 17% and the percent incorporation of AGMT of 68%) using 0.02 N DC1 DMSO-$d_6$/$D_2$O mixed solution (2N DC1 $D_2$O:DMSO-$d_6$=1:99) as a measurement solvent is shown in FIG. 13-3. In the NMR spectrum using 0.02 N DC1 DMSO-$d_6$/$D_2$O mixed solution, based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 29). Since a peak around 1.7 to 2.0 ppm including the peak for acetyl of N-acetylglucosamine is overlapping with the peak for the cholesteryl group (5H), a value calculated by subtracting ⅔ of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm) −the integrated value (0.7 ppm)×⅔) was used as the integrated value for acetyl in HA for the calculation of the percent incorporation.

$$\text{Percent incorporation of cholesteryl}(\%) = \frac{\text{Integrated value for methyl in cholesteryl}(0.7\ ppm)}{\text{Integrated value for acetyl in } HA} \times 100$$

(1.7-2.0 ppm; value after correction) [Exp. 38]

Based on the integrated value of the peak for acetyl (—COCH$_3$, 1.7 to 2.0 ppm; 3H) of N-acetylglucosamine in HA and the integrated value of the peak for ethylene (—CH$_2$—CH$_2$—, 1.5 to 1.6 ppm; 4H) of the introduced AGMT, the percent incorporation of agmatine (the percent incorporation of AGMT) in the HA units was calculated according to the equation given below (Table 29). Since the peak for ethylene of AGMT is overlapping with the peak for Chol, a value calculated by subtracting the integrated value of the peak at 1.5 to 1.6 ppm of HA-Chol obtained as a comparison reference was used as the integrated value for AGMT for the calculation of the percent incorporation.

$$\text{Percent incorporation of } AGMT\,(\%) = \frac{\text{Integrated value for ethylene in } AGMT\ (1.5\text{-}1.6\ ppm;\ \text{value after correction})}{\text{Integrated value for acetyl in } HA\ (1.7\text{-}2.0\ ppm;\ \text{value after correction})} \times \frac{3}{4} \times 100$$

[Exp. 39]

TABLE 29

Amount of reagent used in preparing HA-Chol/AGMT and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added H-AGMT and DMT-MM (HA unit/H-AGMT/DMT-MM) & percent incorporation of AGMT | State of solution |
|---|---|---|---|---|
| 10k HA-Chol-17%/AGMT-32% | 10k | 100/16/24 17% | 100/3970/40 32% | X |
| 10k HA-Chol-17%/AGMT-68% | 10k | 100/16/24 17% | 100/4002/201 68% | ○ |
| 10k HA-Chol-45%/AGMT-22% | 10k | 100/50/59 45% | 100/2490/26 22% | ○ |
| 10k HA-Chol-43%/AGMT-45% | 10k | 100/50/59 43% | 100/2490/303 45% | ○ |
| 99k HA-Chol-17%/AGMT-34% | 99k | 100/16/24 17% | 100/4028/41 34% | X |
| 99k HA-Chol-14%/AGMT-70% | 99k | 100/16/24 14% | 100/4022/200 70% | ○ |
| 99k HA-Chol-38%/AGMT-31% | 99k | 100/50/60 38% | 100/2510/302 31% | ○ |

(Example 4-1-4) Synthesis of a HA Derivative (HA-Chol/IMD) Modified with Histamine (HIS) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 30 below and stirred at room temperature for 2 hours or more. Next, histamine (Nacalai Tesque Inc.) and PyBOP were added to the HA units at ratios shown in Table 30 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/IMD) as a white solid. The solution of the dialysate before lyophilization was passed through a filter having a pore diameter of 0.45 μm or 5 μm, and the samples which passed through the filter were denoted by O in Table 30. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 30.

A representative $^1$H-NMR spectrum (of the product derived from HA of 10 kDa with the percent incorporation of cholesteryl of 16% and the percent incorporation of IMD of 67%) using 0.02 N DC1 DMSO-$d_6$/$D_2O$ mixed solution (2N DC1 $D_2O$:DMSO-$d_6$=1:99) as a measurement solvent is shown in FIG. 13-4. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 30). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad [\text{Exp. 40}]$$

(1.7-2.0 ppm; value after correction)

Based on the integrated value of the peak for acetyl (—$COCH_3$, 1.7 to 2.0 ppm; 3H) of N-acetylglucosamine in HA and the integrated value of the peak for methine (—CH=, 8.9 to 9.0 ppm; 1H) of the introduced IMD, the percent incorporation of histamine (the percent incorporation of IMD) in the HA units was calculated according to the following equation (Table 30).

$$\text{Percent incorporation of } IMD \text{ (\%)} = \frac{\text{Integrated value for methine in } IMD \text{ (8.9-9.0 ppm)}}{\text{Integrated value for acetyl in } HA} \times \frac{3}{1} \times 100 \quad [\text{Exp. 41}]$$

(1.7-2.0 ppm; value after correction)

TABLE 30

Amount of reagent used in preparing HA-Chol/IMD and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added HIS and PyBOP (HA unit/HIS/PyBOP) & percent incorporation of IMD | State of solution |
|---|---|---|---|---|
| 10k HA-Chol-15%/IMD-16% | 10k | 100/16/24<br>15% | 100/27/51<br>16% | O |
| 10k HA-Chol-16%/IMD-67% | 10k | 100/16/24<br>16% | 100/492/299<br>67% | O |
| 10k HA-Chol-47%/IMD-12% | 10k | 100/50/54<br>47% | 100/25/51<br>12% | O |
| 10k HA-Chol-44%/IMD-42% | 10k | 100/50/54<br>44% | 100/489/299<br>42% | O |
| 99k HA-Chol-15%/IMD-17% | 99k | 100/16/24<br>15% | 100/26/49<br>17% | O |
| 99k HA-Chol-14%/IMD-71% | 99k | 100/16/24<br>14% | 100/506/304<br>71% | O |
| 99k HA-Chol-48%/IMD-13% | 99k | 100/50/54<br>48% | 100/25/50<br>13% | O |
| 99k HA-Chol-44%/IMD-56% | 99k | 100/50/54<br>44% | 100/490/299<br>56% | O |

(Example 4-1-5) Synthesis of a HA Derivative (HA-Chol/DPT) Modified with Bis(3-Aminopropyl) Amine (BAPA) and Cholesteryl (6-Aminohexyl) Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 31 below and stirred at room temperature for 2 hours or more. Next, bis(3-aminopropyl)amine (Wako Pure Chemical Industries, Ltd.) and PyBOP were added to each of the solutions at their ratios to the HA unit as shown in Table 31 below and the solutions were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/DPT) as a white solid. The solution of the dialysate before lyophilization was passed through a filter having a pore diameter of 0.45 μm or 5 μm, and the samples which passed through the filter were denoted by O in Table 31. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 31.

A representative $^1$H-NMR spectrum (of the product derived from HA of 10 kDa with the percent incorporation of cholesteryl of 15% and the percent incorporation of DPT of 60%) using 0.02 N DCl DMSO-$d_6$/$D_2$O mixed solution (2N DCl $D_2$O:DMSO-$d_6$=1:99) as a measurement solvent is shown in FIG. 13-5. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 31). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \qquad [\text{Exp. 42}]$$

(1.7-2.0 ppm; value after correction)

Based on the integrated value of the peak for acetyl (—$COCH_3$, 1.7 to 2.0 ppm; 3H) of N-acetylglucosamine in HA and the integrated value of the peak for methylene (—$CH_2$—, 2.0 to 2.1 ppm; 2H) of the introduced DPT, the percent incorporation of bis(3-aminopropyl)amine (the percent incorporation of DPT) in the HA units was calculated according to the equation given below (Table 31).

$$\text{Percent incorporation of } DPT \text{ (\%)} = \frac{\text{Integrated value for methylene in } DPT \text{ (2.0-2.1 ppm)}}{\text{Integrated value for acetyl in } HA} \times \frac{3}{2} \times 100 \qquad [\text{Exp. 43}]$$

(1.7-2.0 ppm; value after correction)

TABLE 31

Amount of reagent used in preparing HA-Chol/DPT and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added BAPA and PyBOP (HA unit/BAPA/PyBOP) & percent incorporation of DPT | State of solution |
|---|---|---|---|---|
| 10k HA-Chol-16%/DPT-20% | 10k | 100/16/24  16% | 100/4000/26  20% | O |
| 10k HA-Chol-16%/DPT-28% | 10k | 100/16/24  16% | 100/4003/40  28% | O |
| 10k HA-Chol-15%/DPT-60% | 10k | 100/16/24  15% | 100/4003/302  60% | O |
| 10k HA-Chol-44%/DPT-17% | 10k | 100/50/59  44% | 100/2501/26  17% | O |
| 10k HA-Chol-40%/DPT-45% | 10k | 100/50/59  40% | 100/2501/298  45% | O |
| 99k HA-Chol-14%/DPT-22% | 99k | 100/16/24  14% | 100/4000/25  22% | O |
| 99k HA-Chol-14%/DPT-30% | 99k | 100/16/24  14% | 100/3999/42  30% | O |
| 99k HA-Chol-15%/DPT-85% | 99k | 100/16/24  15% | 100/3999/296  85% | O |
| 99k HA-Chol-40%/DPT-32% | 99k | 100/50/60  40% | 100/2502/26  32% | O |

(Example 4-1-6) Synthesis of a HA Derivative (HA-Chol/BAEA) Modified with Tris(2-Aminoethyl)Amine (TAEA) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 32 below and stirred at room temperature for 2 hours or more. Next, tris(2-aminoethyl)amine (Wako Pure Chemical Industries, Ltd.) and PyBOP were added to the HA units at ratios shown in Table 32 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/BAEA) as a white solid. The solution of the dialysate before lyophilization was passed through a filter having a pore diameter of 0.45 μm or 5 μm, and the samples which passed through the filter were denoted by O in Table 32. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 32. The samples which did not pass through the filter and were not subjected to ultrasonication are denoted by (X) in Table 32.

A representative $^1$H-NMR spectrum (of the product derived from HA of 10 kDa with the percent incorporation of cholesteryl of 17% and the percent incorporation of BAEA of 63%) using 0.02 N DCl DMSO-$d_6$/$D_2$O mixed solution (2N DCl $D_2$O:DMSO-$d_6$=1:99) as a measurement solvent is shown in FIG. 13-6. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 32). Since a peak around 1.7 to 2.0 ppm including the peak for acetyl of N-acetylglucosamine is overlapping with the peak for the cholesteryl group (5H), a value calculated by subtracting ⅔ of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm) −the integrated value (0.7 ppm)×⅔) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad \text{[Exp. 44]}$$

(1.7-2.0 ppm; value after correction)

Based on the integrated value of the peak for acetyl (—$COCH_3$, 1.7 to 2.0 ppm; 3H) of N-acetylglucosamine in HA and the integrated value of the peak for methylene (—$CH_2$—, 2.7 ppm; 2H) of the introduced BAEA, the percent incorporation of tris(2-aminoethyl)amine (the percent incorporation of BAEA) in the HA units was calculated according to the following equation (Table 32).

$$\text{Percent incorporation of } BAEA \text{ (\%)} = \frac{\text{Integrated value for methylene in } BAEA \text{ (2.7 ppm)}}{\text{Integrated value for acetyl in } HA} \times \frac{3}{2} \times 100 \quad \text{[Exp. 45]}$$

(1.7-2.0 ppm; value after correction)

TABLE 32

Amount of reagent used in preparing HA-Chol/BAEA and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added TAEA and PyBOP (HA unit/TAEA/PyBOP) & percent incorporation of BAEA | State of solution |
|---|---|---|---|---|
| 10k HA-Chol-17%/BAEA-18% | 10k | 100/16/24 17% | 100/4000/26 18% | O |
| 10k HA-Chol-17%/BAEA-25% | 10k | 100/16/24 17% | 100/4000/51 25% | O |
| 10k HA-Chol-17%/BAEA-63% | 10k | 100/16/24 17% | 100/4000/299 63% | O |
| 10k HA-Chol-45%/BAEA-15% | 10k | 100/50/55 45% | 100/3997/25 15% | (X) |
| 10k HA-Chol-49%/BAEA-40% | 10k | 100/50/55 49% | 100/3997/301 40% | X |
| 99k HA-Chol-15%/BAEA-17% | 99k | 100/16/24 15% | 100/4000/25 17% | O |
| 99k HA-Chol-15%/BAEA-29% | 99k | 100/16/24 15% | 100/4003/50 29% | (X) |
| 99k HA-Chol-15%/BAEA-65% | 99k | 100/16/24 15% | 100/4003/295 65% | O |
| 99k HA-Chol-38%/BAEA-19% | 99k | 100/50/55 38% | 100/4003/25 19% | O |

(Example 4-1-7) Synthesis of a HA Derivative (HA-Chol/DMA) Modified with N,N-dimethylethylenediamine (DMEDA) and cholesteryl (6-aminohexyl)carbamate Solutions of HA-TBAs synthetized from the sodium salts of hyaluronic acids (HA-Na; 10 kDa and 99 kDa) in Example 1-2 in anhydrous DMSO were prepared. Chol-$C_6$ hydrochloride prepared in Example 1-1 and DMT-MM were added to the solutions at ratios per HA unit shown in Table 33 below and stirred at room temperature for 2 hours or more. Next, N,N-dimethylethylenediamine (Wako Pure Chemical Industries, Ltd.) and PyBOP were added to each of the solutions at their ratios to the HA unit as shown in Table 33 below and the solutions were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/DMA) as a white solid. The solution of the dialysate before lyophilization was passed through a filter having a pore diameter of 0.45 μm or 5 μm, and the samples which passed through the filter were denoted by O in Table 33. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 33.

A representative $^1$H-NMR spectrum (of the product derived from HA of 10 kDa with the percent incorporation of cholesteryl of 17% and the percent incorporation of DMA of 76%) using 0.02 N DC1 DMSO-$d_6$/$D_2O$ mixed solution (2N DC1 $D_2O$:DMSO-$d_6$=1:99) as a measurement solvent is shown in FIG. 13-7. In the NMR spectrum using 0.02 N DC1 DMSO-$d_6$/$D_2O$ mixed solution, based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) of the introduced cholesteryl group, the percent incorporation of cholesteryl in the HA units was calculated according to the equation given below (Table 33). Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—$CH_3$, 0.7 ppm; 3H) of the cholesteryl group from the integrated value of the peak around 1.7 to 2.0 ppm (i.e., the integrated value (1.7 to 2.0 ppm) −the integrated value (0.7 ppm)×5/3) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad \text{[Exp. 46]}$$

(1.7-2.0 ppm; value after correction)

Based on the integrated value of the peak for acetyl (—$COCH_3$, 1.7 to 2.0 ppm; 3H) of N-acetylglucosamine in HA and the integrated value of the peak for methyl ($CH_3$—, 2.8 ppm; 6H) of the introduced DMA, the percent incorporation of N,N-dimethylethylenediamine (the percent incorporation of DMA) in the HA units was calculated according to the following equation (Table 33).

$$\text{Percent incorporation of } DMA \text{ (\%)} = \frac{\text{Integrated value for methyl in } DMA \text{ (2.8 ppm)}}{\text{Integrated value for acetyl in } HA} \times \frac{3}{6} \times 100 \quad \text{[Exp. 47]}$$

(1.7-2.0 ppm; value after correction)

TABLE 33

Amount of reagent used in preparing HA-Chol/DMA and percent incorporation

| Abbreviation | MW (Da) | Molar ratio of added Chol-$C_6$ hydrochloride and DMT-MM (HA unit/Chol-$C_6$/DMT-MM) & percent incorporation of Chol | Molar ratio of added DMEDA and PyBOP (HA unit/DMEDA/PyBOP) & percent incorporation of DMA | State of solution |
|---|---|---|---|---|
| 10k HA-Chol-16%/DMA-25% | 10k | 100/16/24<br>16% | 100/30/41<br>25% | O |
| 10k HA-Chol-17%/DMA-76% | 10k | 100/16/24<br>17% | 100/500/298<br>76% | O |
| 10k HA-Chol-47%/DMA-20% | 10k | 100/50/55<br>47% | 100/30/30<br>20% | X |
| 10k HA-Chol-43%/DMA-52% | 10k | 100/50/55<br>43% | 100/500/297<br>52% | O |
| 99k HA-Chol-14%/DMA-29% | 99k | 100/16/24<br>14% | 100/30/40<br>29% | O |
| 99k HA-Chol-14%/DMA-79% | 99k | 100/16/24<br>14% | 100/500/304<br>79% | O |

(Example 4-1-8) Synthesis of a HA Derivative (HA-Chol/MPD) Modified with 2-(1-Methylpiperidin-4-Yl)Ethanamine (MPEA) and Cholesteryl (6-Aminohexyl)Carbamate Solutions of HA-TBAs synthetized from the sodium salts of hyaluronic acids (HA-Na; 10 kDa and 99 kDa) in Example 1-2 in anhydrous DMSO were prepared. Chol-C$_6$ hydrochloride prepared in Example 1-1 and DMT-MM were added to the solutions at ratios per HA unit shown in Table 34 below and stirred at room temperature for 2 hours or more. Next, 2-(1-methylpiperidin-4-yl)ethanamine (Ark Pharm Inc.) and PyBOP were added to the HA units at ratios shown in Table 34 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-Chol/MPD) as a white solid. The solution of the dialysate before lyophilization was passed through a filter having a pore diameter of 0.45 μm or m, and the samples which passed through the filter were denoted by O in Table 34. For the samples which did not pass through the filter, water was added to the lyophilized solids to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 34.

A representative $^1$H-NMR spectrum (of the product derived from HA of 10 kDa with the percent incorporation of cholesteryl of 12% and the percent incorporation of MPD of 51%) using 0.02 N DC1 DMSO-d$_6$/D$_2$O mixed solution (2N DC1 D$_2$O:DMSO-d$_6$=1:99) as a measurement solvent is shown in FIG. 13-8. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) of the introduced cholesteryl group, the percent incorporation of cholesteryl in the HA units was calculated according to the equation given below (Table 34). Since a peak around 1.7 to 2.0 ppm including the peak for acetyl of N-acetylglucosamine is overlapping with the peak for the cholesteryl group (5H), a value calculated by subtracting ⅝ of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm)–the integrated value (0.7 ppm)×⅝) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in } HA} \times 100 \quad [\text{Exp. 48}]$$

(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methyl (—CH$_3$, 2.70 to 2.75 ppm; 3H) of the introduced MPD, the percent incorporation of 2-(1-methylpiperidin-4-yl)ethanamine (the percent incorporation of MPD) in the HA units was calculated according to the equation given below (Table 34).

$$\text{Percent incorporation of } MPD \text{ (\%)} = \frac{\text{Integrated value for methyl in } MPD \text{ (2.70-2.75 ppm)}}{\text{Integrated value for acetyl in } HA} \times \frac{3}{3} \times 100 \quad [\text{Exp. 49}]$$

(1.7-2.0 ppm; value after correction)

TABLE 34

Amount of reagent used in preparing HA-Chol/MPD and percent incorporation

| Abbreviation | MW (Da) | Molar ratio of added Chol-C$_6$ hydrochloride and DMT-MM (HA unit/Chol-C$_6$/DMT-MM) & percent incorporation of Chol | Molar ratio of added MPEA and PyBOP (HA unit/MPEA/PyBOP) & percent incorporation of MPD | State of solution |
|---|---|---|---|---|
| 10k HA-Chol-14%/MPD-21% | 10k | 100/16/24<br>14% | 100/30/51<br>21% | ○ |
| 10k HA-Chol-12%/MPD-51% | 10k | 100/16/24<br>12% | 100/1999/298<br>51% | ○ |
| 10k HA-Chol-39%/MPD-11% | 10k | 100/50/59<br>39% | 100/25/49<br>11% | ○ |
| 10k HA-Chol-34%/MPD-45% | 10k | 100/50/59<br>34% | 100/1999/300<br>45% | ○ |
| 10k HA-Chol-36%/MPD-34% | 10k | 100/50/55<br>36% | 100/500/298<br>34% | ○ |
| 99k HA-Chol-13%/MPD-20% | 99k | 100/16/25<br>13% | 100/30/49<br>20% | ○ |
| 99k HA-Chol-9%/MPD-52% | 99k | 100/16/2<br>59% | 100/1998/301<br>52% | ○ |
| 99k HA-Chol-27%/MPD-50% | 99k | 100/50/60<br>27% | 100/1999/305<br>50% | ○ |
| 99k HA-Chol-33%/MPD-41% | 99k | 100/50/55<br>33% | 100/500/301<br>41% | ○ |

(Example 4-2) Synthesis of a HA Derivative (HA-LysNH$_2$/CA) Modified with L-Lysine Amide (H-LysNH$_2$) and 5β-Cholanic Acid Solutions of HA-TBAs synthetized from the sodium salts of hyaluronic acids (HA-Na; 10 kDa and 99 kDa) in Example 1-2 in anhydrous DMSO were prepared. Mono-Fmoc-L-lysine amide hydrochloride (Watanabe Chemical Industries, Ltd.) and DMT-MM were added to the HA units at ratios shown in Table 35 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired intermediate product (HA-LysNH$_2$) as a white solid. Here by the dialysis against 0.3M ammonium acetate/DMSO, the Fmoc-group was removed.

A $^1$H-NMR spectrum was measured using DMSO-d$_6$ as a measurement solvent. Based on the integrated value of the peak for acetyl (—COCH$_3$, 1.7 to 2.0 ppm; 3H) of N-acetyl-glucosamine in HA and the integrated value of the peak for methylene (—CH$_2$—, 2.8 ppm; 2H) or methylene and methine (—CH$_2$—CH$_2$—CH—, 1.2 to 1.7 ppm; 5H) of the introduced LysNH$_2$, the percent incorporation of lysine amide (the percent incorporation of LysNH$_2$) in the HA units was calculated according to the equation given below (Table 35).

TABLE 35

Amount of reagent used in preparing HA-LysNH$_2$ and percent incorporation

| Abbreviation | MW (Da) | Molar ratio of added Fmoc—H-LysNH$_2$ hydrochloride and DMT-MM (HA unit/Fmoc—H-LysNH$_2$/DMT-MM) & percent incorporation of LysNH$_2$ |
|---|---|---|
| 99k HA-LysNH$_2$-85% | 99k | 100/304/994 85% |
| 10k HA-LysNH$_2$-91% | 10k | 100/301/998 91% |
| 99k HA-LysNH$_2$-84% | 99k | 100/304/1002 84% |

Solutions of HA-LysNH$_2$ in anhydrous DMSO were prepared. 5β-cholanic acid and DMT-MM or PyBOP were added to the HA units at ratios shown in Table 36 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-LysNH$_2$/CA) as a white solid. The solution of the dialysate before lyophilization was passed through a filter having a pore diameter of 0.45 µm or 5 µm, and the samples which passed through the filter were denoted by O in Table 36. The samples whose filter permeability was not determined are denoted by "-" in Table 36.

A representative $^1$H-NMR spectrum (of the product derived from HA of 10 kDa with the percent incorporation of LysNH$_2$ of 91% and the percent incorporation of CA of 23%) using 0.02 N DC1 DMSO-d$_6$/D$_2$O mixed solution (2N DC1 D$_2$O:DMSO-d$_6$=1:99) as a measurement solvent is shown in FIG. 13-9. Based on the integrated value of the peak for methylene(—CH$_2$—, 2.8 ppm; 2H) of LysNH$_2$ and the integrated value of the peak for methyl (—CH$_3$, 0.7 ppm; 3H) of the introduced CA, the percent incorporation of CA in the HA units was calculated according to the equation given below (Table 36).

$$\text{Percent incorporation of } CA\ (\%) = \frac{\text{Integrated value for methyl in } CA\ (0.7\text{ ppm})}{\text{Integrated value for methylene in LysNH}_2\ (2.8\text{ ppm})} \times \frac{2}{3} \times \text{Percent incorporation of LysNH}_2\ (\%)$$

[Exp. 50]

TABLE 36

Reagent used and amount thereof in preparing HA-LysNH$_2$/CA and percent incorporation

| Abbreviation | MW (Da) | HA-LysNH$_2$ as a starting material & percent incorporation of LysNH$_2$ | Molar ratio of added 5β-cholanic acid and DMT-MM or PyBOP (HA unil/5β-cholanic acid/DMT-MM or PyBOP) & percent incorporation of CA | State of solution |
|---|---|---|---|---|
| 99k HA-LysNH$_2$-85%/CA-8% | 99k | 99k HA-LysNH$_2$-85% | 100/476/25(DMT-MM) 8% | — |
| 99k HA-LysNH$_2$-85%/CA-4% | 99k | 99k HA-LysNH$_2$-85% | 100/476/23(PyBOP) 4% | — |
| 10k HA-LysNH$_2$-91%/CA-23% | 10k | 10k HA-LysNH$_2$-91% | 100/502/296(DMT-MM) 23% | ◯ |
| 99k HA-LysNH$_2$-84%/CA-18% | 99k | 99k HA-LysNH$_2$-84% | 100/494/303(DMT-MM) 18% | ◯ |
| 10k HA-LysNH$_2$-91%/CA-47% | 10k | 10k HA-LysNH$_2$-91% | 100/1003/504(DMT-MM) 47% | ◯ |
| 99k HA-LysNH$_2$-84%/CA-30% | 99k | 99k HA-LysNH$_2$-84% | 100/987/498(DMT-MM) 30% | ◯ |

Example 5 Synthesis of HA Derivatives 3

(Example 5-1) Synthesis of I—C$_3$H$_6$—OCOO-Chol:10,13-dimethyl-17-(6-methylheptan-2-yl)-2,3,4,7,8,9,10,11,12,13,14,15,16,17-tetradecahydro-1H-cyclopenta[a]phenanthrene-3-yl (3-iodopropyl) carbonate

[Chem. 52]

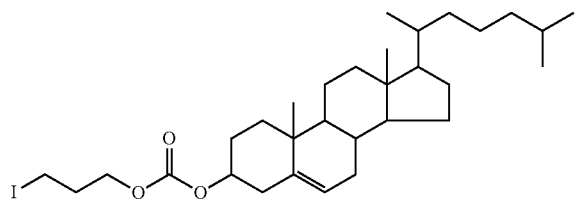

8,10,13-trimethyl-17-(6-methylheptan-2-yl)-2,3,4,7,8,9,10,11,12,13,14,15,16,17-tetradecahydro-1H-cyclopenta[a]phenanthrene-3-yl carbonochloridate (100 mg, 0.223 mmol), 3-iodo-1-propanol (0.173 mL, 1.781 mmol) and pyridine (0.022 mL, 0.267 mmol) were dissolved in toluene (1 mL) and stirred at room temperature for 24 hours. The reaction solution was purified by Pre-TLC (1-mm silica gel plate, eluent: hexane/EtOAc=10/1) to obtain 10,13-dimethyl-17-(6-methylheptan-2-yl)-2,3,4,7,8,9,10,11,12,13,14,15,16,17-tetradecahydro-1H-cyclopenta[a]phenanthrene-3-yl (3-iodopropyl)carbonate (128 mg, yields: 99%) as a white solid. ESI (positive mode) m/z 621.2775 [M+Na]$^+$.

(Example 5-2) Synthesis of HA-C$_3$H$_6$—OCOO-Chol/LysNH$_2$

Solutions of HA-TBAs in anhydrous DMSO synthesized from HA-Na (10 kDa) in Example 1-2 were prepared. Mono-Fmoc-L-lysine amide hydrochloride (Watanabe Chemical Industries, Ltd.) and DMT-MM were added to the HA units at ratios shown in Table 37 below and stirred at room temperature for 2 hours or more. The reaction solutions were dialyzed against DMSO. I—C$_3$H$_6$—OCOO-Chol prepared in Example 5-1 was added to the HA units at ratios shown in Table 37 below and stirred at room temperature for 1 hour or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-C$_3$H$_6$—OCOO-Chol/LysNH$_2$) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 37.

A representative $^1$H-NMR spectrum (of the product derived from HA of 10 kDa with the percent incorporation of cholesteryl of 20% and the percent incorporation of LysNH$_2$ of 29%) using 0.02 N DC1 DMSO-d$_6$/D$_2$O mixed solution (2N DC1 D$_2$O:DMSO-d$_6$=1:99) as a measurement solvent is shown in FIG. 14-1. The percent incorporations of cholesteryl and lysine amide were calculated in the same manner as Example 2-8 (Table 37).

TABLE 37

Reagent used and amount thereof in preparing HA-C$_3$H$_6$—OCOO-Chol/LysNH$_2$ and percent incorporation

| Abbreviation | MW (Da) | Molar ratio of added FmocLysNH$_2$ hydrochloride and DMT-MM (HA unit/LysNH$_2$/DMT-MM) & percent incorporation of LysNH$_2$ | Molar ratio of added I—C$_3$H$_6$—OCOO-Chol (HA unit/I—C$_3$H$_6$—OCOO-Chol) & percent incorporation of Chol | State of solution |
|---|---|---|---|---|
| 10k HA-C$_3$H$_6$—OCOO-Chol-29%/LysNH$_2$-26% | 10k | 100/50/75 26% | 100/120 29% | ◯ |

TABLE 37-continued

Reagent used and amount thereof in preparing HA-
$C_3H_6$—OCOO-Chol/LysNH$_2$ and percent incorporation

| Abbreviation | MW (Da) | Molar ratio of added FmocLysNH$_2$ hydrochloride and DMT-MM (HA unit/LysNH$_2$/DMT-MM) & percent incorporation of LysNH$_2$ | Molar ratio of added I—$C_3H_6$—OCOO-Chol (HA unit/I—$C_3H_6$—OCOO-Chol) & percent incorporation of Chol | State of solution |
|---|---|---|---|---|
| 10k HA-$C_3H_6$—OCOO-Chol-20%/LysNH$_2$-29% | 10k | 100/50/75 29% | 100/80 20% | ○ |

(Example 5-3) Synthesis of I—CH$_2$—COO-Chol: 10,13-dimethyl-17-(6-methylheptan-2-yl)-2,3,4,7,8,9,10,11,12,13,14,15,16,17-tetradecahydro-1H-cyclopenta[a]phenanthrene-3-yl 2-iodoacetate

[Chem. 53]

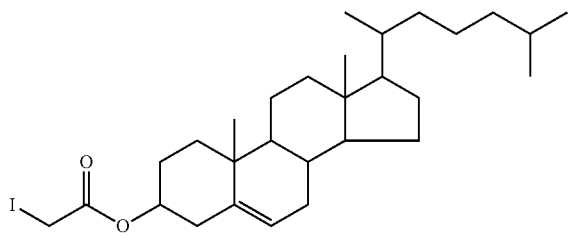

I—CH$_2$—COO-Chol:10,13-dimethyl-17-(6-methylheptan-2-yl)-2,3,4,7,8,9,10,11,12,13,14,15,16,17-tetradecahydro-1H-cyclopenta[a]phenanthrene-3-yl 2-iodoacetate was prepared using a known synthetic method (J. Med. Chem. 2014, 57(20), 8421-8444).

(Example 5-4) Synthesis of HA-CH$_2$—COO-Chol/LysNH$_2$

Solutions of HA-TBAs in anhydrous DMSO synthesized from HA-Na (10 kDa) in Example 1-2 were prepared. Mono-Fmoc-L-lysine amide hydrochloride (Watanabe Chemical Industries, Ltd.) and DMT-MM were added to the HA units at ratios shown in Table 38 below and stirred at room temperature for 2 hours or more. The reaction solutions were dialyzed against DMSO. I—CH$_2$—COO-Chol prepared in Example 5-3 was added to the HA units at ratios shown in Table 38 below and stirred at room temperature for 1 hour or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product (HA-CH$_2$—COO-Chol/LysNH$_2$) as a light yellow solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 38.

A representative $^1$H-NMR spectrum (of the product derived from HA of 10 kDa with the percent incorporation of cholesteryl of 13% and the percent incorporation of LysNH$_2$ of 70%) using 0.02 N DCl DMSO-d$_6$/D$_2$O mixed solution (2N DCl D$_2$O:DMSO-d$_6$=1:99) as a measurement solvent is shown in FIG. 14-2. The percent incorporations of cholesteryl and lysine amide were calculated in the same manner as Example 2-8 (Table 38).

TABLE 38

Reagent used and amount thereof in preparing HA-
CH$_2$—COO-Chol/LysNH$_2$ and percent incorporation

| Abbreviation | MW (Da) | Molar ratio of added Fmoc—H-LysNH$_2$ hydrochloride and DMT-MM (HA unit/Fmoc—H-LysNH$_2$/DMT-MM) & percent incorporation of LysNH$_2$ | Molar ratio of added I—CH$_2$—OCOO-Chol (HA unit/I—CH$_2$—OCOO-Chol) & percent incorporation of Chol | State of solution |
|---|---|---|---|---|
| 10k HA-CH$_2$—COO-Chol-9%/LysNH$_2$-31% | 10k | 100/50/75 31% | 100/100 9% | ○ |
| 10k HA-CH$_2$—COO-Chol-13%/LysNH$_2$-70% | 10k | 100/120/180 70% | 100/100 13% | ○ |

Example 6 Examination of Mucosal Permeability of HA Derivatives by Assessing Intraocular Migration of Sorafenib Administered as Eye Drops in Rabbits (Example 6-1) Preparation of a HA Derivative Containing Sorafenib The 10k-HA-Chol-15%/ArgNH$_2$-28%/EtOH-56% synthesized in Example 2-25 was dissolved in DMSO solution to a concentration of 50 mg/mL, and sorafenib was added thereto. The solution was transferred into a dialysis kit (Slide-A-Lyzer, molecular weight cut-off 2K) and dialyzed against ultrapure water and 10% sucrose solution. The concentration of sorafenib in the solution was measured by reversed-phase chromatography under the following conditions and adjusted to a final concentration of 1.0 mg/mL to obtain a solution to be administered. The size was measured using a Zetasizer ZS system (Malvern Panalytical) based on the dynamic light scattering (DLS) method and calculated to be 42.7 nm in diameter. Conditions of reversed-phase chromatography Column: PLRP-S 1000 Å (Agilent)
Column temperature: 40° C.
Mobile phase A: 0.1% TFA aqueous solution; Mobile phase B: 0.1% TFA acetonitrile solution
Flow rate: 2 mL/min
Detection: UV 254 nm
Injection volume: 50 µL (Comparative Example 6-1) Preparation of Sorafenib Microparticles By adding 200 µL of 25 mg/mL sorafenib in methanol dropwise to 12.5 mL of pure water, a stable dispersion was formed. 2 mL of 10% sucrose and 2 mL of 0.05% tween 80 were added thereto and the mixture was lyophilized. The lyophilized product was re-dispersed into 2 mL of ultrapure water. The concentration of sorafenib in the solution was measured by reversed-phase chromatography described in Example 6-1 and adjusted to a final concentration of 1.0 mg/mL to obtain a solution to be administered. The size was measured in the same manner as Example 6-1 and calculated to be 1549 nm in diameter.

(Comparative Example 6-2) Preparation of Sorafenib Nanoparticles

Mucus-penetrating particles (MPP) were prepared according to the International Publication No. WO2013/166436. Specifically, 200 mg of zirconia balls of 0.2 mm in diameter (NIKKATO CORPORATION, YTZ-0.2) were added to a glass tube and then 11 mg of sorafenib was added, followed by the addition of 200 µL of F127-containing solution (i.e., 5% F127, 0.9% NaCl, and 0.05% EDTA in 2.4% glycerol solution). A stir bar was put in the solution, which was stirred overnight at room temperature with a stirrer. The solution was passed through a 0.8-µm filter. The concentration of sorafenib in the solution was measured by reversed-phase chromatography described in Example 6-1 and adjusted to a final concentration of 1.0 mg/mL to obtain a solution to be administered. The size was measured in the same manner as Example 6-1 and calculated to be 271 nm in diameter.

(Example 6-2) Assessment of Intraocular Migration of Sorafenib Administered as Eye Drops in Rabbits (Both Eyes)

15- to 16-year-old New Zealand white SPF rabbits (KITAYAMA LABES CO., LTD.) were fixed to holders and the sorafenib-containing HA derivative prepared in Example 6-1, the sorafenib microparticles prepared in Comparative Example 6-1, the sorafenib nanoparticles (MPP) prepared in Comparative Example 6-2 were administered as a single eye drop on both eyes (50 µL/eye). The tests were performed on 3 rabbits per group (6 eyeballs). After the rabbits were subjected to euthanasia by dissecting abdominal aortas and veins under anesthesia by intravenous administration of a solution of pentobarbital sodium (Kyoritsu Pharmaceutical Co., Ltd.), eyeballs were removed. The palpebral conjunctiva was collected. Then, the eyeballs were frozen on dry ice and the cornea, ocular conjunctiva, iris and ciliary body, vitreous, retina, and choroid were collected.

Ocular tissue homogenates were produced using grinding beads, and the concentration of sorafenib in the tissue was measured by liquid chromatography-mass spectrometry (LC-MS) (Table 39).

TABLE 39

Concentration of sorafenib in ocular tissue (after administration as eye drops to both eyes)

| | Concentration of sorafenib ng/g at 1 hr. | | | |
|---|---|---|---|---|
| | Retina and choroid | Iris and ciliary body | Cornea | Palpebral conjunctiva |
| Sorafenib microparticles | 0.427 | 0.556 | 266 | 192 |
| Sorafenib nanoparticles (MPP) | 0.866 | 1.02 | 350 | 305 |
| Sorafenib-containing HA derivative | 6.23 | 5.7 | 5940 | 3190 |

It was found that the concentration of sorafenib was remarkably higher with the sorafenib-containing HA derivative than with the sorafenib microparticles and the sorafenib nanoparticles (MPP) in all ocular tissues. Based on the facts that sorafenib concentrations were high in the intraocular tissues such as the retina, choroid, iris, and ciliary body and that sorafenib concentrations were extremely high at the cornea, it was revealed that the HA derivative has a capacity of adhering to mucous membranes and allowing sorafenib to penetrate therethrough.

(Example 6-3) Assessment of Migration of Sorafenib Administered as Eye Drops to the Posterior Part of the Eye in Rabbits (Single Eyes Using a sorafenib-containing HA derivative prepared in the same manner as Example 6-1 as a solution to be administered, the assessment was performed in the same manner as Example 6-2 except that it was administered in a single eye drop on one of the eyes (50 µL/eye, 5 animals). The results are shown in Table 40.

TABLE 40

Concentration of sorafenib in ocular tissue (after administration as eye drops to one eye)

| | Concentration of sorafenib ng/g at 1 hr. | | | |
|---|---|---|---|---|
| | Retina and choroid | Iris and ciliary body | Cornea | Palpebral conjunctiva |
| Eye with no sorafenib | 1.59 | 1.02 | 0.763 | 2.91 |
| Eye with sorafenib | 4.86 | 3.7 | 2600 | 2520 |

It was found that the concentrations of the sorafenib in the intraocular tissues such as the retina, choroid, iris, and ciliary body were higher in the eyes that had received the sorafenib-containing HA derivative than in the eyes that had not received it. This indicated that the sorafenib migrated into the eyes via the surface thereof, not by the circulated blood (if the sorafenib had migrated into the eyes by the circulated blood, the concentrations of sorafenib would have been the same in the eyes with and without the administration of sorafenib).

(Example 6-4) Assessment of Intraocular Migration of Sorafenib Administered as Eye Drops in Rabbits (Comparison Among Various HA Derivatives Sorafenib-containing HA derivatives prepared in the same manner as Example 6-1 using various HA derivatives were used as solutions to be administered and experiments were performed in the same manner as Example 6-2.

TABLE 41

Concentration of sorafenib in ocular tissue (comparison among various HA derivatives)

| Sample | Concentration of sorafenib ng/g at 1 hr. | | |
|---|---|---|---|
| | Retina and choroid | Iris and ciliary body | Cornea |
| 99k HA-Chol-44%/EDA-43% | 4.52 | 3.50 | 1470 |
| 10k HA-Chol-16%/EDA-46%/Me-7% | 4.02 | 3.02 | 1010 |
| 10k HA-Chol-16%/LysNH$_2$-24%/Me-24% | 7.46 | 4.06 | 1780 |
| 10k HA-Chol-16%/LysNH$_2$-41%/Me-8% | 3.01 | 1.16 | 971 |
| 10k HA-Chol-17%/DET-75% | 1.89 | 2.47 | 566 |
| 10k HA-Chol-16%/SPR-17%/Me-59% | 15.7 | 4.22 | 1150 |
| 10k HA-Chol-18%/PTMA-31%/Me-35% | 4.57 | 2.69 | 1330 |
| 10k HA-Chol-17%/DMA-76% | 1.93 | 1.42 | 928 |
| 10k HA-Chol-17%/AGMT-68% | 2.15 | 2.75 | 941 |
| 10k HA-Chol-16%/IMD-67% | 5.54 | 3.04 | 2190 |
| 10k HA-Chol-39%/ArgNH$_2$-11%/Me-25% | 2.29 | 1.43 | 828 |
| 99k HA-Chol-26%/EDA-22%/Me-17% | 2.62 | 3.61 | 1510 |
| 10k HA-Chol-18%/PTMA-13%/Me-52% | 4.90 | 1.66 | 1320 |
| 10k HA-Chol-17%/EDOBEA-52% | 2.32 | 0.971 | 904 |
| 10k HA-Chol-12%/MPD-51% | 5.84 | 1.94 | 860 |
| 10k HA-Chol-17%/PTMA-3%/Me-63% | 2.42 | 1.35 | 991 |

It was found that all HA derivatives can deliver sorafenib to the intraocular tissues such as the retina, choroid, iris, and ciliary body.

Example 7 Assessment of Mucoadhesion and Permeability of HA Derivatives (Example 7-1) Preparation of HA Derivatives Containing Fluorescent-Labeled Insulin Insulin (derived from bovine spleen) (Sigma-Aldrich) was reacted with Alexa Fluor (registered trademark) 488 Carboxylic Acid, Succinimidyl Ester, mixed isomers (Thermo Fisher Scientific) in 100 mM carbonate buffer (pH 9), purified on a desalting column, and subjected to solvent substitution and concentration by ultrafiltration to prepare an aqueous solution of fluorescent-labeled insulin. Water was added to the HA derivatives obtained in Examples 2, 4, and 5 to a concentration of 2 mg/mL and were subjected to Ultrasonication (with an ultrasonicator E220X manufactured by Covaris Inc.), to which water, 100 mM phosphate buffer and the aqueous solution of fluorescent-labeled insulin were added to obtain solutions having a final composition of 1 mg/mL of HA derivative, 10 mM phosphate buffer (pH 7), and 50 μg/mL of fluorescent-labeled insulin. The solutions were gently mixed and left to stand at 37° C. overnight to prepare solutions of the HA derivatives containing fluorescent-labeled insulin.

(Comparative Example 7-1) Synthesis of a Chitosan Derivative (CS-Chol 100 mg of chitosan (Chitosan 5 manufactured by Wako Pure Chemical Industries, Ltd.; degree of deacetylation: 82% and degree of acetylation: 18%) was dissolved in 50 mM hydrochloric acid, to which a solution of 87.9 mg of cholesterol hydrogen succinate (Tokyo Chemical Industry Co., Ltd.) in DMF and a solution of 55.1 mg of DMT-MM (KOKUSAN CHEMICAL Co., Ltd.) in DMF were added and stirred overnight at room temperature. The reaction solution was dialyzed against DMF, 50 mM sodium nitrate in DMF, 0.15 M NaCl, and pure water in this order. The dialysate thus obtained was lyophilized to obtain the desired product (CS-Chol) as a white solid.

For NMR measurements, p-toluene sulfonate of CS-Chol was prepared according to a known preparation method (Chemistry Letters 2000, 29 (6), 596). According to a $^1$H-NMR spectrum using 0.02 N DCl DMSO-d$_6$/D$_2$O mixed solution (2N DCl D$_2$O:DMSO-d$_6$=1:99) as a measurement solvent, the percent incorporation of cholesteryl was calculated. Based on the integrated value of the peak for acetyl (—COCH$_3$, 1.7 to 2.0 ppm; 3H) of N-acetylglucosamine in chitosan and the integrated value of the peak for methyl (—CH$_3$, 0.7 ppm; 3H) of the introduced cholesteryl group, the percent incorporation of cholesteryl to acetyl was calculated. Further, using the percentage of acetyl groups of 18%, the percent incorporation of cholesteryl to chitosan monosaccharides was calculated according to the following equation. Since a peak around 1.7 to 2.0 ppm including the peak for acetyl of N-acetylglucosamine is overlapping with the peak for the cholesteryl group (5H), a value calculated by subtracting 5/3 of the integrated value of the peak for methyl (—CH$_3$, 0.7 ppm; 3H) of the cholesteryl group from the integrated value of the peak around 1.7 to 2.0 ppm (i.e., the integrated value (1.7 to 2.0 ppm) −the integrated value (0.7 ppm)×5/3) was used as the integrated value for acetyl in chitosan for the calculation of the percent incorporation.

$$\text{Percent incorporation of cholesteryl (\%)} = \frac{\text{Integrated value for methyl in cholesteryl (0.7 ppm)}}{\text{Integrated value for acetyl in chitosan}} \times 0.18 \times 100 \quad [\text{Exp. 51}]$$

(1.7-2.0 ppm; value after correction)

As a result, the percent incorporation of cholesterol per chitosan monosaccharide was calculated to be 10%. Since a HA unit is consisted of two monosaccharides, the percent incorporation of cholesterol per chitosan monosaccharide corresponds to 20% in the case of the percent incorporation per HA unit.

(Example 7-2) Assessment of Mucoadhesion and Permeability of HA Derivatives Containing Fluorescent-Labeled Insulin LabCyte CORNEA-MODEL (Japan Tissue Engineering Co., Ltd.) cultured in an assay medium for 1 hour or more according to the product instruction manual was used as a model of mucosa-producing corneal epithelial cells and the solution of HA derivative containing fluorescent-labeled insulin prepared in Example 7-1 was added. Only 10 mM phosphate buffer solution (pH 7) and fluorescent-labeled insulin were added for autofluorescence correction of tissue and for comparison, respectively. After being left to stand in a $CO_2$ incubator at 37° C. for 30 minutes, the added solution was discarded and the cells were rinsed three times with 10 mM phosphate buffer (pH 7). After being left to stand in the $CO_2$ incubator for about 16 hours, the cells were fixed with paraformaldehyde, and specimens were prepared on glass slides using an antifade agent containing DAPI as a mounting agent. The HA nanogels enclosing fluorescent-labeled insulin adhered to and permeated into a mucosa-producing corneal epithelial layer were observed with a confocal laser microscope. The quantity of fluorescent-labeled insulin permeated into the layer of mucosa-producing corneal epithelial cells was determined according to fluorescence intensities of z-stack images at three positions for each sample. Ratios of the fluorescent-labeled insulin contained in the HA derivatives permeated into the layer of mucosa-producing cornea epithelial cells and the fluorescent-labeled insulin that was not contained in the HA derivatives permeated into the layer of mucosa-producing cornea epithelial cells are shown in Table 42 as indexes of the mucoadhesion and permeabilities of the HA nanogels.

TABLE 42

Mucoadhesive property and permeability of HA derivative containing fluorescent-labeled insulin

| Abbreviation of HA derivatives prepared in Examples 2, 4, and 5 for preparing HA derivatives containing fluorescent-labeled insulin | Ratio of fluorescence intensity between fluorescent-labeled insulin contained in HA derivative permeated through layer of mucosa-producing corneal epithelial cells and fluorescent-labeled insulin not enclosed in HA derivative permeated through layer of mucosa-producing corneal epithelial cells |
|---|---|
| 10k HA-Chol-17%/ArgNH$_2$-28%/Me-41% | 6.1 |
| 10k HA-Chol-32%/ArgNH$_2$-30%/Me-24% | 5.1 |
| 99k HA-Chol-27%/ArgNH$_2$-32%/Me-21% | 14.5 |
| 10k HA-Chol-16%/ArgNH$_2$-44%/Me-23% | 13.5 |
| 10k HA-Chol-44%/ArgNH$_2$-42% | 3.5 |
| 99k HA-Chol-42%/ArgNH$_2$-50% | 27.6 |
| 99k HA-Chol-44%/ArgNH$_2$-50% | 10.2 |
| 10k HA-Chol-35%/ArgNH$_2$-56% | 68.1 |
| 99k HA-Chol-31%/ArgNH$_2$-57% | 32.1 |
| 10k HA-Chol-18%/ArgNH$_2$-64% | 120.9 |
| 10k HA-Chol-17%/ArgNH$_2$-71% | 69.6 |
| 99k HA-Chol-15%/ArgNH$_2$-74% | 56.3 |
| 10k HA-Chol-16%/LysNH$_2$-24%/Me-24% | 6.1 |
| 10k HA-Chol-31%/LysNH$_2$-31 %/Me-5% | 7.8 |
| 99k HA-Chol-25%/LysNH$_2$-33%/Me-5% | 12.0 |
| 10k HA-Chol-16%/LysNH$_2$-41%/Me-8% | 43.6 |
| 10k HA-Chol-33%/LysNH$_2$-19% | 2.5 |
| 10k HA-Chol-17%/LysNH$_2$-45% | 6.9 |
| 10k HA-Chol-32%/EDA-37%/Me-4% | 4.0 |
| 99k HA-Chol-25%/EDA-40%/Me-6% | 71.0 |
| 10k HA-Chol-16%/EDA-46%/Me-7% | 21.0 |
| 99k HA-Chol-29%/EDA-25% | 2.7 |
| 10k HA-Chol-44%/EDA-29% | 6.8 |
| 99k HA-Chol-43%/EDA-30% | 2.9 |
| 10k HA-Chol-45%/EDA-31% | 13.7 |
| 99k HA-Chol-44%/EDA-43% | 13.5 |
| 10k HA-Chol-33%/EDA-45% | 24.8 |
| 99k HA-Chol-29%/EDA-47% | 64.4 |
| 10k HA-Chol-18%/EDA-55% | 49.3 |
| 10k HA-Chol-17%/EDA-61% | 107.8 |
| 99k HA-Chol-14%/EDA-63% | 15.4 |
| 10k HA-Chol-17%/DET-22%/Me-55% | 3.7 |
| 10k HA-Chol-17%/DET-25%/Me-46% | 8.6 |
| 10k HA-Chol-17%/DET-35%/Me-38% | 4.2 |
| 10k HA-Chol-17%/DET-76% | 2.8 |
| 10k HA-Chol-17%/DET-76% | 61.4 |
| 10k HA-Chol-17%/DET-84% | 33.8 |
| 10k HA-Chol-18%/SPR-15%/Me-67% | 10.8 |
| 10k HA-Chol-17%/SPR-16%/Me-65% | 16.0 |
| 10k HA-Chol-16%/SPR-17%/Me-62% | 37.6 |

TABLE 42-continued

Mucoadhesive property and permeability of HA derivative containing fluorescent-labeled insulin

| Abbreviation of HA derivatives prepared in Examples 2, 4, and 5 for preparing HA derivatives containing fluorescent-labeled insulin | Ratio of fluorescence intensity between fluorescent-labeled insulin contained in HA derivative permeated through layer of mucosa-producing corneal epithelial cells and fluorescent-labeled insulin not enclosed in HA derivative permeated through layer of mucosa-producing corneal epithelial cells |
|---|---|
| 10k HA-Chol-16%/SPR-17%/Me-61% | 64.7 |
| 10k HA-Chol-16%/SPR-17%/Me-59% | 16.6 |
| 10k HA-Chol-16%/SPR-21%/Me-56% | 36.5 |
| 99k HA-Chol-26%/SPR-24%/Me-42% | 49.2 |
| 99k HA-Chol-26%/SPR-24%/Me-40% | 32.1 |
| 99k HA-Chol-25%/SPR-26%/Me-33% | 22.9 |
| 99k HA-Chol-27%/SPR-27%/Me-38% | 143.5 |
| 10k HA-Chol-18%/PTMA-6%/Me-62% | 9.8 |
| 99k HA-Chol-26%/PTMA-7%/Me-40% | 3.6 |
| 99k HA-Chol-27%/PTMA-9%/Me-36% | 3.9 |
| 10k HA-Chol-18%/PTMA-13%/Me-52% | 9.7 |
| 10k HA-Chol-18%/PTMA-31%/Me-35% | 32.0 |
| 99k HA-Chol-25%/PTMA-46%/Me-6% | 48.6 |
| 10k HA-Chol-17%/EDOBEA-52% | 110.3 |
| 99k HA-Chol-15%/EDOBEA-54% | 31.6 |
| 10k HA-Chol-17%/DEG-51% | 63.7 |
| 10k HA-Chol-17%/AGMT-68% | 26.3 |
| 10k HA-Chol-16%/IMD-67% | 13.9 |
| 99k HA-Chol-14%/IMD-71% | 9.0 |
| 10k HA-Chol-15%/DTP-60% | 23.6 |
| 10k HA-Chol-49%/BAEA-40% | 13.0 |
| 10k HA-Chol-17%/BAEA-63% | 10.8 |
| 10k HA-Chol-17%/DMA-76% | 43.6 |
| 10k HA-Chol-12%/MPD-51% | 42.0 |
| 99k HA-Chol-9%/MPD-52% | 20.4 |
| 10k HA-LysNH$_2$-91%/CA-23% | 78.9 |
| 99k HA-LysNH$_2$-84%/CA-18% | 65.3 |
| 10k HA-CH$_2$—COO-Chol-13%/LysNH$_2$-70% | 17.6 |
| CS-Chol | 0.4 |

It was revealed that the HA derivatives enhance the mucoadhesion and the permeabilities of the fluorescent-labeled insulin. On the other hand, when the fluorescent-labeled insulin was enclosed in a chitosan derivative (CS-Chol) obtained by introducing cholesteryl groups into chitosan which is a cationic polysaccharide, the mucoadhesion and the permeabilities were lower than those achieved with fluorescent-labeled insulin not enclosed.

Example 8 Preparation and Assessment of HA Derivatives Containing Nucleic Acid (Example 8-1) Preparation of HA Derivatives Containing Nucleic Acid ApoB (sense strand: 5'-GUCAUCACACUGAAUAC-CAAU-3' (SEQ ID No. 1, number of nucleotides: 21), antisense strand: 3'-CACAGUAGUGUGACUUAUG-GUUA-5' (SEQ ID No. 2, number of nucleotides: 23)) was used as siRNA. First, an aqueous solution of 0.5 mg/mL siRNA and 0.1-M Hepes buffer were mixed, to which 6 mg/mL aqueous solutions of the HA derivatives obtained in Examples 2 and 4 were added to an N/P ratio of 10 or 20 and was pipetted to prepare agents containing nucleic acid (the final concentration of siRNA was 800 nM and the final concentration of Hepes was 10 mM).

(Comparative Example 8-1) Preparation of DOPE/DOTAP Containing Nucleic Acid

DOPE (1,2-dioleoyl-sn-glycero-3-phosphoethanolamine; Tokyo Chemical Industry Co., Ltd.) and DOTAP (1,2-dioleoyl-3-trimethylammonium-propane; NOF CORPORATION) were dissolved in chloroform and mixed. The mixture was cast in a glass bottle with nitrogen gas. Ultrapure water was added for re-swelling and ultrasonication was performed to prepare a solution of DOPE (2.5 mg/mL)/DOTAP (2.5 mg/mL). ApoB described in Example 8-1 was used as siRNA and mixed with the solution of DOPE/DOTAP, and the mixture was pipetted to prepare a DOPE/DOTAP agent containing nucleic acid.

(Example 8-2) Assessment of Effects of HA Derivatives Containing Nucleic Acid to Suppress Gene Expression and Cytotoxicities Thereof (Example 8-2-1) Assessment of Suppression of Gene Expression In order to assess suppression effects of the HA derivatives containing nucleic acid obtained in Example 8-1 on gene expression, a transfection experiment was performed to HepG2 cells. The sucrose solutions containing the HA derivatives containing nucleic acid were added to a 96-well plate. HepG2 cells suspended in DMEM supplemented with 10% FBS was added to 1×10$^4$ cells/well and cultured for 24 hours. The final concentration of siRNA in transfection was 200 nM. Total RNA was extracted and purified according to the manual using a QIAGEN RNeasy 96 kit. By using the RNA-to-Ct 1 Step kit manufactured by Thermo Fisher Scientific, quantitative real-time PCR was performed on the target ApoB mRNA and GAPDH mRNA as the housekeeping gene using the following primers according to the instruction manual. For the quantitative real-time PCR, Rotor-Gene Q manufactured by QIAGEN was used. As to the expression level of ApoB after the correction by GAPDH, the relative expression levels of each treatment group when the ApoB expression level in the untreated group is defined as 1, are shown in Table 43.

The following commercially available ApoB and GAPDH primers were used for the experiment.

ApoB primer: Human apolipoprotein B (FAM/MGB probe) AssayID Hs01071205_m1, Thermo Fisher Scientific GAPDH primer: Human GAPD (GAPDH) Endogenous Control (VIC/MGB probe, primer limited), Thermo Fisher Scientific, product No. 4326317E (Example 8-2-2) Measurement of Cytotoxicity (CyQUANT In parallel with the transfection experiment of Example 8-2-1, effects of the HA derivatives containing nucleic acid on cell growth were evaluated using a CyQUANT Cell Proliferatino Assay kit (Thermo Fisher Scientific). In this method, cytotoxicity is evaluated based on the DNA content in cells. Sucrose solutions of the HA derivatives containing nucleic acid were put in 96-well plates. Then, HepG2 cells suspended in DMEM supplemented with 10% FBS were added at $1\times10^4$ cells/well and cultured for 24 hours. The HA derivatives containing nucleic acid were added at a final concentration of siRNA of 200 nM. The medium was discarded and the CyQUANT reagent was added according to the instruction manual, which was incubated at room temperature in a dark place for 30 minutes. A SPECTRA-MAX M2e plate reader (Molecular Devices Corporation) was used at Em/Ex=485/538 nm to measure fluorescence intensities. Relative intensities of the treatment groups expressed as a fraction of the fluorescence intensity of 1 in the untreated group are shown in Table 43.

(Example 8-2-3) Measurement of Cytotoxicities (WST)

In parallel with the transfection experiment of Example 8-2-1, effects of the HA derivatives containing nucleic acid on metabolic activities of cells were evaluated using a Cell Counting Kit-8 (WST-8, DOJINDO LABORATORIES). This method is for evaluating cytotoxicity based on metabolic activities of cells. Sucrose solutions of the HA derivatives containing nucleic acid were put in 96-well plates. Then, HepG2 cells suspended in DMEM supplemented with 10% FBS were added at $1\times10^4$ cells/well and cultured for 24 hours. The HA derivatives containing nucleic acid were added at a final concentration of siRNA of 200 nM. The medium was discarded and a medium containing the reagent of the Cell Counting Kit-8 was added according to the instruction manual, which was incubated at 37° C. A SPECTRAMAX M2e plate reader (Molecular Devices Corporation) was used to measure absorbances at 450 nm. Relative intensities of the treatment groups expressed as a fraction of the absorbance of 1 in the untreated group are shown in Table 43.

TABLE 43

Effect of suppressing gene expression and cytotoxicity of HA derivative containing nucleic acid

| HA derivative used | N/P | Efficiency of suppressing gene expression | Cytotoxicity (Cyquant) | Cytotoxicity (WST) |
|---|---|---|---|---|
| DOPE/DOTAP | 5 | Unmeasurable due to strong toxicity | 0.84 | 0.02 |
| DOPE/DOTAP | 10 | Unmeasurable due to strong toxicity | 0.84 | 0.01 |
| 10k HA-Chol-17%/ArgNH$_2$-11%/Me-51% | 20 | 0.45 | 0.82 | 1.33 |
| 10k HA-Chol-32%/ArgNH$_2$-14%/Me-36% | 20 | 0.58 | 0.72 | 1.36 |
| 99k HA-Chol-27%/ArgNH$_2$-18%/Me-32% | 20 | 0.43 | 0.81 | 0.84 |
| 10k HA-Chol-40%/ArgNH$_2$-26%/Me-14% | 20 | 0.59 | 0.70 | 1.01 |
| 10k HA-Chol-17%/ArgNH$_2$-28%/Me-41% | 20 | 0.40 | 0.51 | 0.89 |
| 10k HA-Chol-32%/ArgNH$_2$-30%/Me-24% | 20 | 0.64 | 0.52 | 1.17 |
| 99k HA-Chol-27%/ArgNH$_2$-32%/Me-21% | 20 | 0.42 | 0.61 | 0.61 |
| 10k HA-Chol-16%/ArgNH$_2$-44%/Me-23% | 20 | 0.47 | 0.54 | 1.36 |
| 10k HA-Chol-47%/ArgNH$_2$-24% | 20 | 0.55 | 0.92 | 2.12 |
| 99k HA-Chol-31%/ArgNH$_2$-29% | 20 | 0.34 | 0.90 | 1.5 |
| 99k HA-Chol-46%/ArgNH$_2$-30% | 20 | 0.46 | 0.87 | 2.05 |
| 10k HA-Chol-45%/ArgNH$_2$-35% | 20 | 0.68 | 1.12 | 1.11 |
| 10k HA-Chol-44%/ArgNH$_2$-42% | 20 | 0.69 | 0.73 | 1.07 |
| 99k HA-Chol-42%/ArgNH$_2$-50% | 20 | 0.81 | 0.67 | 0.89 |
| 99k HA-Chol-44%/ArgNH$_2$-50% | 20 | 0.74 | 0.69 | 0.97 |
| 10k HA-Chol-35%/ArgNH$_2$-56% | 20 | 0.63 | 0.80 | 1.21 |
| 99k HA-Chol-31%/ArgNH$_2$-57% | 10 | 0.63 | 0.72 | 1.43 |
| 10k HA-Chol-18%/ArgNH$_2$-64% | 20 | 0.42 | 0.76 | 1.21 |
| 10k HA-Chol-17%/ArgNH$_2$-71% | 20 | 0.45 | 0.73 | 1.01 |
| 99k HA-Chol-15%/ArgNH$_2$-74% | 10 | 0.57 | 0.82 | 0.87 |
| 10k HA-Chol-37%/LysNH$_2$-17%/Me-8% | 20 | 0.45 | 0.92 | 0.92 |
| 10k HA-Chol-31%/LysNH$_2$-21%/Me-11% | 20 | 0.40 | 0.69 | 0.85 |
| 10k HA-Chol-36%/LysNH$_2$-23%/Me-4% | 20 | 0.51 | 0.91 | 0.88 |

TABLE 43-continued

Effect of suppressing gene expression and cytotoxicity of HA derivative containing nucleic acid

| HA derivative used | N/P | Efficiency of suppressing gene expression | Cytotoxicity (Cyquant) | Cytotoxicity (WST) |
|---|---|---|---|---|
| 10k HA-Chol-33%/LysNH$_2$-19% | 20 | 0.27 | 1.02 | 1.69 |
| 10k HA-Chol-39%/EDA-19%/Me-7% | 20 | 0.63 | 0.80 | 0.73 |
| 10k HA-Chol-32%/EDA-24%/Me-12% | 10 | 0.47 | 0.87 | 1.03 |
| 10k HA-Chol-37%/EDA-29%/Me-7% | 10 | 0.55 | 0.96 | 0.92 |
| 10k HA-Chol-32%/EDA-37%/Me-4% | 10 | 0.41 | 0.82 | 0.84 |
| 99k HA-Chol-48%/EDA-22% | 20 | 0.48 | 0.77 | 1.49 |
| 10k HA-Chol-47%/EDA-23% | 20 | 0.53 | 0.74 | 1.30 |
| 10k HA-Chol-34%/EDA-23% | 20 | 0.38 | 0.88 | 1.91 |
| 10k HA-Chol-44%/EDA-29 | 10 | 0.64 | 0.66 | 1.07 |
| 99k HA-Chol-43%/EDA-30% | 10 | 0.30 | 0.69 | 0.93 |
| 10k HA-Chol-45%/EDA-31% | 10 | 0.51 | 0.62 | 0.89 |
| 99k HA-Chol-44%/EDA-43% | 10 | 0.27 | 0.66 | 1.07 |
| 10k HA-Chol-33%/EDA-45% | 10 | 0.30 | 0.65 | 0.94 |
| 99k HA-Chol-29%/EDA-47% | 20 | 0.34 | 0.60 | 0.69 |
| 10k HA-Chol-17%/DET-75% | 20 | 0.60 | 0.65 | 0.57 |
| 10k HA-Chol-17%/DET-78% | 20 | 0.63 | 0.67 | 0.52 |
| 10k HA-Chol-17%/DET-84% | 20 | 0.30 | 0.70 | 0.55 |
| 10k HA-Chol-18%/SPR-15%/Me-67% | 20 | 0.24 | 0.65 | 0.45 |
| 10k HA-Chol-17%/SPR-16%/Me-65% | 20 | 0.22 | 0.69 | 0.43 |
| 10k HA-Chol-16%/SPR-17%/Me-62% | 20 | 0.44 | 0.48 | 0.24 |
| 10k HA-Chol-16%/SPR-17%/Me-61% | 20 | 0.51 | 0.46 | 0.21 |
| 10k HA-Chol-16%/SPR-17%/Me-59% | 20 | 0.55 | 0.44 | 0.16 |
| 10k HA-Chol-16%/SPR-21%/Me-56% | 20 | 0.61 | 0.46 | 0.28 |
| 99k HA-Chol-26%/SPR-24%/Me-42% | 20 | 0.79 | 0.50 | 0.34 |
| 99k HA-Chol-26%/SPR-24%/Me-40% | 20 | 0.91 | 0.47 | 0.24 |
| 99k HA-Chol-27%/SPR-25%/Me-47% | 20 | 0.27 | 0.66 | 1.44 |
| 99k HA-Chol-27%/SPR-26%/Me-47% | 20 | 0.64 | 0.58 | 0.53 |
| 99k HA-Chol-27%/SPR-27%/Me-38% | 10 | 0.69 | 0.64 | 0.46 |
| 10k HA-Chol-17%/PTMA-3%/Me-63% | 10 | 0.36 | 1.01 | 0.62 |
| 10k HA-Chol-17%/PTMA-5%/Me-60% | 10 | 0.33 | 0.91 | 0.79 |
| 10k HA-Chol-16%/EDOBEA-13% | 10 | 0.33 | 1.02 | 1.00 |
| 10k HA-Chol-17%/EDOBEA-52% | 10 | 0.31 | 0.60 | 1.05 |
| 99k HA-Chol-14%/EDOBEA-12% | 10 | 0.37 | 1.08 | 1.13 |
| 99k HA-Chol-15%/EDOBEA-54% | 10 | 0.36 | 0.58 | 0.70 |
| 10k HA-Chol-16%/DEG-8% | 10 | 0.47 | 0.94 | 0.72 |
| 10k HA-Chol-17%/DEG-51% | 10 | 0.30 | 0.64 | 1.02 |
| 99k HA-Chol-14%/DEG-6% | 20 | 0.47 | 0.95 | 1.19 |
| 99k HA-Chol-15%/DEG-52% | 10 | 0.65 | 0.62 | 0.44 |
| 10k HA-Chol-17%/BAEA-18% | 20 | 0.42 | 0.72 | 1.35 |
| 99k HA-Chol-15%/BAEA-17% | 20 | 0.33 | 0.77 | 1.13 |
| 10k HA-Chol-17%/DMA-76% | 10 | 0.32 | 0.59 | 0.92 |
| 10k HA-Chol-14%/MPD-21% | 20 | 0.36 | 1.05 | 1.42 |
| 99k HA-Chol-13%/MPD-20% | 10 | 0.33 | 1.11 | 1.57 |
| 99k HA-Chol-9%/MPD-52% | 10 | 0.48 | 0.79 | 0.99 |

TABLE 43-continued

Effect of suppressing gene expression and cytotoxicity of HA derivative containing nucleic acid

| HA derivative used | N/P | Efficiency of suppressing gene expression | Cytotoxicity (Cyquant) | Cytotoxicity (WST) |
|---|---|---|---|---|
| 99k HA-Chol-9%/MPD-52% | 20 | 0.59 | 0.55 | 0.50 |
| 10k HA-Chol-16%/DPT-20% | 20 | 0.30 | 0.74 | 1.24 |
| 99k HA-Chol-14%/DPT-22% | 20 | 0.33 | 0.82 | 1.18 |
| 99k HA-Chol-14%/IMD-71% | 10 | 0.73 | 0.62 | 0.73 |

When the cells were treated with the HA derivatives containing nucleic acid, the expression of ApoB was obviously suppressed. In addition, in DOPE/DOTAP containing nucleic acid, strong toxicity was detected by the WST method and the efficiency of suppressing gene expression could not be measured. In contrast, such a strong toxicity was not detected in both CyQUANT and WST in the HA derivatives containing nucleic acid. It is obvious that siRNA alone does not have an effect of suppressing gene expression.

Example 9 Tests of HA Derivatives in Stomatitis Models

(Example 9-1) Preparation of an Agent of a HA Derivative Alone

The 10k-HA-Chol-16%/ArgNH$_2$-16%/EtOH-69% synthesized in Example 2-25 was dissolved in 10% sucrose in 10 mM phosphate buffer (pH 7.2) to 10 mg/mL to obtain an agent to be administered in a HA derivative group and stored at a temperature of 4° C. or lower. Further, 10% sucrose in 10 mM phosphate buffer (pH 7.2) was used as an agent in a vehicle group.

(Example 9-2) Evaluation of Effects of a HA Derivative Alone Using Hamster Models with 5-FU-Induced Stomatitis Fluorouracil (5-FU; Kyowa Hakko Kirin Co., Ltd.) was intraperitoneally administered to six-week-old hamsters (Slc: Syrian, SLC Japan, Inc.) at 70 mg/kg on Days 0 and 2. On Days 1 and 2, under isoflurane anesthesia, the inner oral mucosa of the left cheek pouch was tapped (scratched) with Wire Brush (FC 4571, MINITOR CO., LTD). On Day 2, 5-FU was administered after scratching.

On Day 3, the hamsters were assigned to the two groups: the vehicle group and the HA derivative group (n=10 per group) in such a manner that the stomatitis areas in these groups were not significantly different. A 30-µL of either the HA derivative or the vehicle was applied dropwise to the stomatitis site once a day from Day 3 to Day 7.

The stomatitis areas were calculated by measuring the major and minor axes of the stomatitis site with a vernier caliper. The major and minor axes were those obtained when the stomatitis site was enclosed in a rectangle at an angle such that the rectangle had the smallest area and the stomatitis area was calculated as the area of the rectangle. This measurement was performed under isoflurane anesthesia.

Microsoft Office Excel 2013 was used to calculate average values and standard deviations and create graphs. For the evaluation of healing properties, areas under the curve (AUC) for the stomatitis areas from Day 3 to Day 6 were compared in t-tests or Dunnett multiple comparison tests (JMP version 11.2.1, SAS Institute Inc.). The significance level was 5% on both sides.

Transitions of the stomatitis areas are shown in FIG. 15-1, and AUCs for the stomatitis areas are shown in FIG. 15-2. Based on these results, it was found that the HA derivative itself has an effect of promoting healing of stomatitis.

(Example 9-3) Preparation of an Agent of a HA Derivative Containing G-CSF

The 10k-HA-Chol-16%/ArgNH2-16%/EtOH-69% synthesized in Example 2-25 was dissolved in 10% sucrose in 10 mM phosphate buffer (pH 7.2) to 40 mg/mL. G-CSF solution (Chugai Pharmaceutical Co., Ltd.) was added to obtain 10% sucrose solution containing the HA derivative at a final concentration of 20 mg/mL and 0.1 mg/mL G-CSF in the 10 mM phosphate buffer (pH 7.2). This was used for administration as an agent of the HA derivative containing G-CSF.

Further, 10% sucrose in 10 mM phosphate buffer (pH 7.2) was used for administration as a vehicle agent while 10% sucrose in 10 mM phosphate buffer (pH 7.2) containing 0.1 mg/mL G-CSF was used for administration as the G-CSF an agent.

(Example 9-4) Assessment of the Agent of the HA Derivative Containing G-CSF Using Hamster Models with 5-FU-Induced Stomatitis Hamster models with 5-FU-induced stomatitis were made according to the method described in Example 9-2, and the agent of the HA derivative containing G-CSF, the vehicle agent, and the G-CSF agent prepared in Example 9-3 were administered.

Transitions of the stomatitis areas are shown in FIG. 16-1 and stomatitis area AUCs are shown in FIG. 16-2. Based on these results, it was found that the agent of the HA derivative containing G-CSF has an effect of promoting healing of stomatitis.

(Example 9-5) Preparation of an Agent of a HA Derivative Containing Keratinocyte Growth Factor (KGF)

The 10k-HA-Chol-15%/ArgNH$_2$-28%/EtOH-56% and 10k-HA-Chol-16%/ArgNH$_2$-21%/EtOH-59% synthesized in Example 2-25 were dissolved in 10% sucrose in 10 mM phosphate buffer (pH 7.2) to a concentration of 40 mg/mL.

A KGF solution (Kepivance, SOBI) was added to obtain, 10% sucrose solution containing 20 mg/mL (final concentration) of the HA derivative and 10% sucrose in 10 mM phosphate buffer (pH 7.2) containing 0.2 mg/mL KGF. This was used for administration as an agent of the HA derivative containing KGF.

Further, 10% sucrose in 10 mM phosphate buffer (pH 7.2) was used for administration as a vehicle agent while 10% sucrose in 10 mM phosphate buffer (pH 7.2) containing 0.2 mg/mL KGF was used for administration as the KGF agent.

(Example 9-6) Assessment of an Agent of a HA Derivative Containing KGF Using Hamster Models with Radiation-Induced Stomatitis Pentobarbital was administered at a dose of 60 mg/kg i.p. to 7-week-old hamsters (Slc: Syrian, SLC Japan, Inc.) for anesthesia, and a portion of the left cheek pouch taken from the oral cavity was irradiated with X rays under following conditions.
X-Ray Irradiation Conditions
  X-ray generator: MBR-1520R-4 (Hitachi Power Solutions Co., Ltd.)
  Voltage/current: 150 kV/20 mA
  Filter: 1-mm aluminum
  Distance from the source: 38 cm
  Dose rate: 50 Gy (4.5 Gy/min)
Administration
  50 µL of each agent for administration prepared in Example 9-5 was administered into the cheek pouch once a day from Day 0 (X-ray irradiation day) to Day 27. The agent was administered under anesthesia after scoring on scoring days and with no anesthesia on other days.
Scoring
  The left cheek pouch was taken under isoflurane anesthesia and scoring was performed according to the method of Sonis et al. (hereinafter, an Ulcer score). Scoring was performed on Days 6, 8, 10, 12, 14, 16, 17, 20, 24 and 28.
  Scoring criteria are described below.
  Ulcer Score
    0: Perfectly healthy cheek pouch. No erosion or vasodilatation found.
    1: Erythema, but no evidence of clear mucosal erosion.
    2: Severe erythema, vasodilatation, and superficial erosion.
    3: Ulceration at one or more places, but it did not exceed 25% of the cheek pouch surface area. Severe erythema and vasodilatation.
    4: Cumulative ulceration of about 50% of the cheek pouch surface area.
    5: Actual complete ulceration of cheek pouch mucosa. Loss of flexibility.
Method of Statistical Analysis
  Microsoft Office Excel 2013 was used to calculate average values and standard deviations and create graphs.
  The areas under the curve (AUC) for the stomatitis score from Day 6 to Day 28 were compared among the vehicle group, the KGF group and the KGF-containing HA derivative agent group in Dunnett's multiple comparison tests (JMP version 11.2.1, SAS Institute Inc.), and compared between the KGF-group and the KGF-containing HA derivative agent group in t-tests (JMP version 11.2.1, SAS Institute Inc.). The significance level of each test was 5% on both sides.
  Transitions of the stomatitis scores are shown in FIG. 17-1, the stomatitis score AUCs are shown in FIG. 17-2, and transitions of body weights are shown in FIG. 17-3.

Based on these results, it was found that the agent of the HA derivative containing KGF has an effect of promoting healing of stomatitis.

Example 10 Evaluation of Toxicity of HA Derivatives

Effects of the HA derivatives obtained in Examples 2 and 4 on cell growth were evaluated using a CyQUANT Cell Proliferatino Assay kit (Thermo Fisher Scientific). HepG2 cells were seeded in 96-well plates at $1.5 \times 10^4$ cells/well and cultured in DMEM supplemented with 10% FBS for 24 hours. Solutions of HA derivatives in a fresh medium were prepared to final concentrations of 1500, 300, 60, 12, and 2.4 µg/mL and replaced with the media in the plates. Twenty-four hours later, the medium was discarded and the CyQUANT reagent was added according to the instruction manual, which was incubated at room temperature in a dark place for 30 minutes. A SPECTRAMAX M2e plate reader (Molecular Devices Corporation) was used at Em/Ex=485/538 nm to measure fluorescence intensities. Relative intensities for the HA derivatives expressed as a fraction of the fluorescence intensity (100%) in the untreated group is shown in FIG. 18.

As a result, it was revealed that the HA derivatives have lower cytotoxicities than polyethyleneimine (Polysciences, Inc.; MW 10,000).

Example 11 Synthesis of HA Derivative 4

(Example 11-1) Synthesis of the HA Derivative ($HA-C_{18}/LysNH_2$) Modified with L-Lysine Amide ($H-LysNH_2$) and Octadecylamine Solutions of HA-TBAs in anhydrous DMSO synthesized from HA-Na (10 kDa) in Example 1-2 were prepared. Octadecylamine ($CH_3(CH_2)_{17}NH_2$, Sigma-Aldrich) and DMT-MM were added to the HA units at ratios shown in Table 44 below and stirred at room temperature for 30 minutes or more. Next, mono-Fmoc-L-lysine amide hydrochloride (Watanabe Chemical Industries, Ltd.) and DMT-MM were added to the HA units at ratios shown in Table 44 below and stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysate thus obtained was lyophilized to obtain the desired product ($HA-Cis/LysNH_2$) as a white solid. Here by the dialysis against 0.3M ammonium acetate/DMSO, the Fmoc-group was removed. Water was added to the white solid to a concentration of 2 mg/mL. Ultrasonication (with an ultrasonicator E220X manufactured by Covaris Inc.) was performed and the state of each solution was examined. Samples with precipitation observed were denoted by X and those with no precipitation observed were denoted by O in Table 44.

Based on an $^1$H-NMR spectrum using 0.02 N DCl DMSO-$d_6$/D$_2$O mixed solution (2N DCl D$_2$O:DMSO-$d_6$=1:99) as a measurement solvent, the percent incorporations of octadecyl and LysNH$_2$ were calculated. Based on the integrated value of the peak for acetyl (—COCH$_3$, 1.7 to 1.9 ppm; 3H) of N-acetylglucosamine in HA and the integrated value of the peak for methyl (—CH$_3$, 0.8 ppm; 3H) of the introduced octadecyl, the percent incorporation of octadecyl in the HA units was calculated according to the equation given below (Table 44).

Since a peak around 1.7 to 1.9 ppm including the peak for acetyl of N-acetylglucosamine is overlapping with the peak for the introduced $LysNH_2$ (1H), a value calculated by subtracting ½ of the integrated value of the peak for methylene($—CH_2—$, 2.8 ppm; 2H) of $LysNH_2$ from the integrated value of the peak around 1.7 to 1.9 ppm (i.e., the integrated value (1.7 to 1.9 ppm)–the integrated value (2.8 ppm)×½) was used as the integrated value for acetyl in HA for the calculation of the percent incorporation.

Based on the integrated value of the peak for acetyl ($—COCH_3$, 1.7 to 1.9 ppm; 3H) of N-acetylglucosamine in HA and the integrated value of the peak for methylene ($—CH_2—$, 2.8 ppm; 2H) of the introduced $LysNH_2$, the percent incorporation of lysine amide (the percent incorporation of $LysNH_2$) in the HA units was calculated according to the following equation (Table 44).

$$\text{Percent incorporation of octadecyl (\%)} = \frac{\text{Integrated value for methyl in octadecyl (0.8 ppm)}}{\text{Integrated value for acetyl in } HA} \times 100 \quad \text{[Exp. 52]}$$
(1.7-1.9 ppm; value after correction)

$$\text{Percent incorporation of LysNH}_2 \text{ (\%)} = \frac{\text{Integrated value for methylene in LysNH}_2 \text{ (2.8 ppm)}}{\text{Integrated value for acetyl in } HA} \times \frac{3}{2} \times 100 \quad \text{[Exp. 53]}$$
(1.7-1.9 ppm; value after correction)

TABLE 44

Amount of reagent used in preparing HA-$C_{18}$/$LysNH_2$ and percent incorporation

| Abbreviation | MW (Da) | Molar ratio of added octadecylamine and DMT-MM (HA unit/octadecylamine/DMT-MM) & percent incorporation of octadecyl | Molar ratio of added Fmoc—H-$LysNH_2$ and DMT-MM (HA unit/Fmoc—H-$LysNH_2$/DMT-MM) & percent incorporation of $LysNH_2$ | State of solution |
|---|---|---|---|---|
| 10k HA-$C_{18}$-19%/$LysNH_2$-34% | 10k | 100/16/18 19% | 100/50/75 34% | ○ |
| 10k HA-$C_{18}$-31%/$LysNH_2$-36% | 10k | 100/32/35 31% | 100/50/75 36% | ○ |
| 10k HA-$C_{18}$-48%/$LysNH_2$-34% | 10k | 100/48/53 48% | 100/50/75 34% | ○ |

The invention claimed is:
1. A hyaluronic acid derivative comprising:
   at least one repeating unit being represented by the formula (Ia):

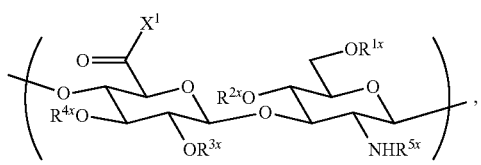

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;
$R^{5x}$ is selected from a hydrogen atom, formyl, and ($C_{1-6}$ alkyl)carbonyl;
$X^1$ represents —$NR^7$—$CHR^8$—$(CH_2)_{n1}$-$A^1$-$B^1$;
$R^7$ represents a hydrogen atom or $C_{1-6}$ alkyl;
$R^8$ is selected from a hydrogen atom, —$CONR^9R^{10}$, and —$CO_2R^{11}$;
$A^1$ is selected from a single bond, -($Y^1$—$CH_2$—$CH_2$)$_{n2}$—, and —($Y^2$—$CH_2$—$CH_2$—$(CH_2)_{na})_{n3}$-;
$B^1$ is selected from -$NR^{12}R^{13}$, —$N^+R^{12}R^{13}R^{14}Q^-$, —N(-$A^2$-$NR^{12}R^{13}$)$_2$, 5- to 10-membered heteroaryl having 1 to 4 nitrogen atoms, —$NHC(=NH)NH_2$, and a group:

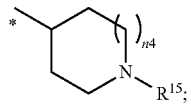

"*" represents the attached position;
$Y^1$ and $Y^2$ independently represent an oxygen atom or —$NR^{16}$—;
n1 represents an integer of 1 to 6, n2 and n3 independently represent an integer of 1 to 10, na represents an integer of 1 or 2, and n4 represents an integer of 0 to 3;
$A^2$ represents $C_{2-10}$ alkylene;
$R_9$, $R^{10}$, $R^{11}$, $R^{12}$, $R^{13}$, $R^{14}$, $R^{15}$, $R^{16a}$ independently represent a hydrogen atom or $C_{1-6}$ alkyl; and
$Q^-$ represents a counter anion;
with the proviso that when $R^8$ is a hydrogen atom and $B^1$ is —$NR^{12}R^{13}$, i) n1 is an integer of 1 to 3 and $A^1$ is a single bond, or ii) n1 is 1, $A^1$ is -($Y^1$—$CH_2$—$CH_2$)$_{n2}$—, and n2 is an integer of 1 to 3; and
at least one repeating unit being represented by the formula (Ib):

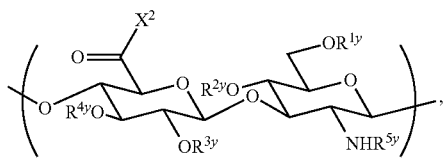

wherein
$R^{1y}$, $R^{2y}$, $R^{3y}$, and $R^{4y}$ are each independently selected from a hydrogen atom, $C_{1-6}$ alkyl, formyl, and ($C_{1-6}$ alkyl)carbonyl;

$R^{5y}$ is selected from a hydrogen atom, formyl, and ($C_{1-6}$ alkyl)carbonyl;
$X^2$ is —$NR^6$—$Z^1$-$Z^2$, —O—$Z^1$—$Z^2$ or —O-$Z^0$-$Z^2$; or
$X^2$ is —$NR^{31}$—$CHR^{32}$—$(CH_2)_{n11}$-$A^3$-$B^2$;
$R^6$ represents a hydrogen atom or $C_{1-6}$ alkyl;
$Z^0$ is selected from the following groups:

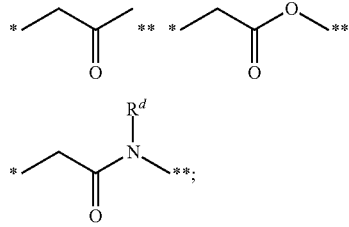

"*" represents the position attached to an oxygen atom and "**" represents the position attached to $Z^1$ or $Z^2$;
$Z^1$ is $C_{1-30}$ alkylene or —$(CH_2CH_2O)_m$-$CH_2CH_2$—, wherein one to five groups independently selected from —O—, —$NR^g$—, and —S—S— are optionally inserted into the alkylene, and m is an integer selected from 1 to 100;
$Z^2$ is selected from the following groups:
-$NR^b$—$Z^3$,
-$NR^b$—COO-$Z^3$,
-$NR^b$—CO—$Z^3$,
-$NR^b$—CO—$NR^c$-$Z^3$,
—COO-$Z^3$,
—CO—$NR^c$-$Z^3$,
—O—$Z^3$,
O—CO-$NR^c$-$Z^3$,
O—COO-$Z^3$,
—S—$Z^3$,
—CO-$Z^a$—S-$Z^3$,
—O—CO—$Z^b$—S—$Z^3$,
-$NR^b$—CO—$Z^b$—S—$Z^3$, and
—S—S—$Z^3$,
$R^b$ and $R^c$ are independently selected from a hydrogen atom, $C_{1-20}$ alkyl, amino $C_{2-20}$ alkyl, and hydroxy $C_{2-20}$ alkyl, wherein one to three groups independently selected from —O— and —$NR^f$— are optionally inserted into the alkyl moiety of the group;
$R^d$ independently represents a hydrogen atom or $C_{1-6}$ alkyl;
$R^f$ is independently selected from a hydrogen atom, $C_{1-12}$ alkyl, amino $C_{2-12}$ alkyl, and hydroxy $C_{2-12}$ alkyl, wherein one or two groups selected from —O— and —NH— are optionally inserted into the alkyl moiety of the group;
$R^g$ is independently selected from a hydrogen atom, $C_{1-20}$ alkyl, amino $C_{2-20}$ alkyl, and hydroxy $C_{2-20}$ alkyl, wherein one to three groups independently selected from —O— and —NH— are optionally inserted into the alkyl moiety of the group;

$Z^3$ is a steryl group represented by any one of the following formulas:

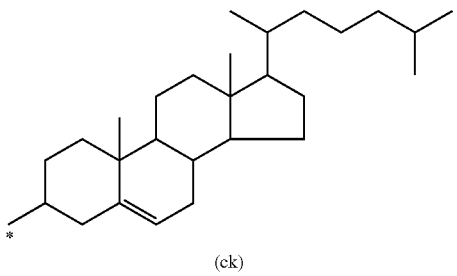
(ck)

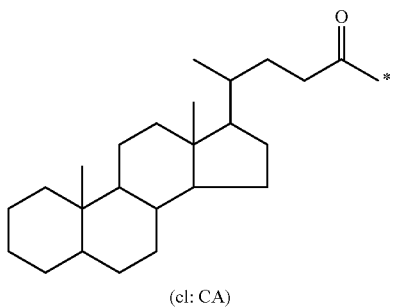
(cl: CA)

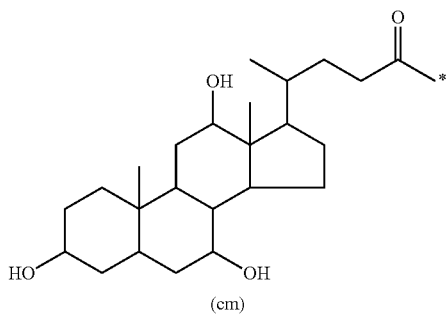
(cm)

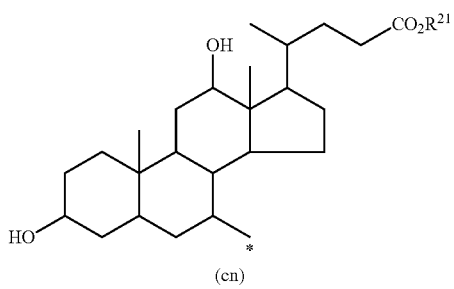
(cn)

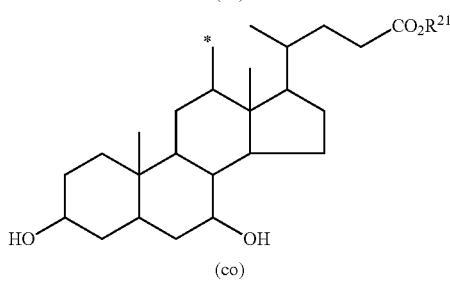
(co)

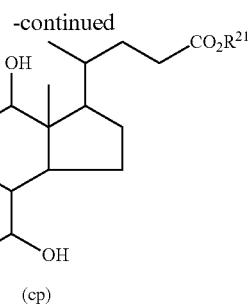
(cp)

wherein

"*" represents the attached position;

$R^{21}$ independently represents a hydrogen atom or $C_{1-6}$ alkyl;

$Z^a$ is $C_{1-5}$ alkylene;

$Z^b$ is $C_{2-8}$ alkylene or $C_{2-8}$ alkenylene;

$R^{31}$ represents a hydrogen atom or $C_{1-6}$ alkyl;

$R^{32}$ is selected from a hydrogen atom, —$CONR^{33}R^{34}$, and —$CO_2R^{35}$;

$A^3$ is selected from a single bond, -$(Y^3$—$CH_2$—$CH_2)_{n12}$—, and -$(Y^4$—$CH_2$—$CH_2$—$(CH_2)_{n14}$-;

$B^2$ is selected from —$NR^{36}$—$X^4$, —$N(-X^4)_2$, —$N(-A^4$-$NR^{36}R^{37})(-A^4$-$NR^{36}$—$X^4)$, —$N(-A^4$-$NR^{36}$—$X^4)_2$, and —$NHC(=NH)NH$—$X^4$;

$Y^3$ and $Y^4$ independently represent an oxygen atom or —$NR^{16a}$-;

n11 represents an integer of 1 to 6, n12 and n13 independently represent an integer of 1 to 10, and n14 represents an integer of 1 or 2;

$A^4$ represents $C_{2-10}$ alkylene;

$R^{33}$, $R^{34}$, $R^{35}$, $R^{36}$, and $R^{37}$ independently represent a hydrogen atom or $C_{1-6}$ alkyl; and $X^4$ is —$CO$—$Z^1$-$Z^2$ or —$Z^3$.

2. The hyaluronic acid derivative according to claim 1, further comprising at least one repeating unit being represented by the formula (II):

[Chem. 5]

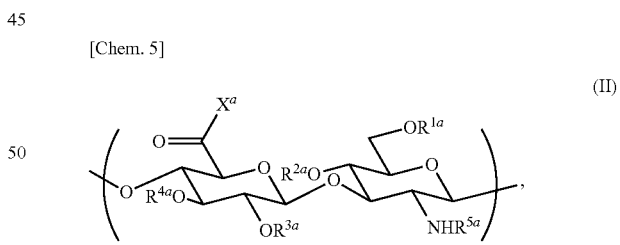
(II)

wherein $R^{1a}$, $R^{2a}$, $R^{3a}$, and $R^{4a}$ are each independently selected from a hydrogen atom, $C_{1-6}$ alkyl, formyl, and ($C_{1-6}$ alkyl)carbonyl;

$R^{5a}$ is selected from a hydrogen atom, formyl, and ($C_{1-6}$ alkyl)carbonyl; and $X^a$ is selected from hydroxy and -$O^-Q^+$, wherein $Q^+$ represents a counter cation.

3. The hyaluronic acid derivative according to claim 1, further comprising at least one repeating unit being represented by the formula (III):

[Chem. 6]

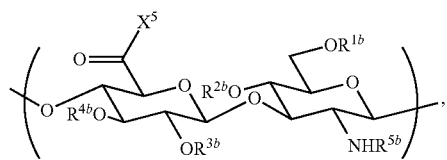   (III)

wherein $R^{1b}$, $R^{2b}$, $R^{3b}$, and $R^{4b}$ are each independently selected from a hydrogen atom, $C_{1-6}$ alkyl, formyl, and ($C_{1-6}$ alkyl)carbonyl;

$R^{5b}$ is selected from a hydrogen atom, formyl, and ($C_{1-6}$ alkyl)carbonyl;

$X^5$ represents $-NR^{17}-R^{18}$;

$R^{17}$ represents a hydrogen atom or $C_{1-6}$ alkyl; and $R^{18}$ represents $C_{1-10}$ alkyl optionally substituted with one or more hydroxy.

4. The hyaluronic acid derivative according to claim 1, wherein $X^1$ is independently selected from the following formulas:

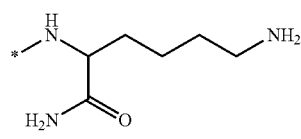   (a: LysNH$_2$)

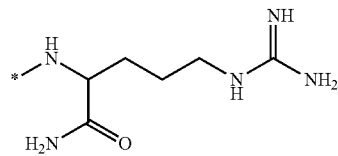   (b: ArgNH$_2$)

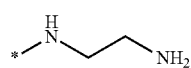   (c: EDA)

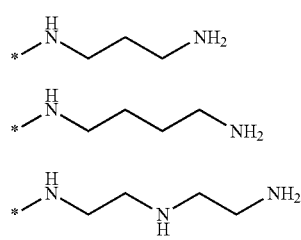   (d)

(e)

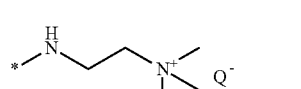   (f: DET)

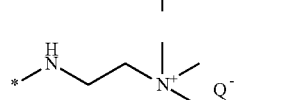   (g)

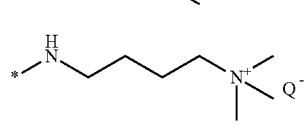   (h: PTMA)

   (i)

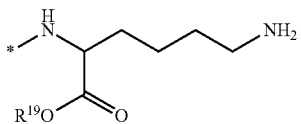   (j)

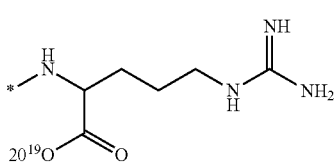   (k)

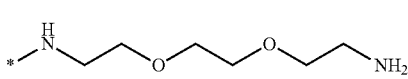   (l: EDOBEA)

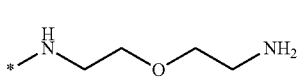   (m: DEG)

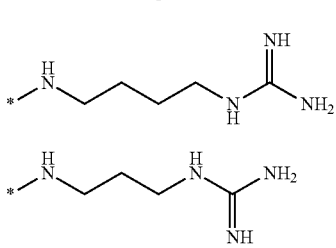   (n: AGMT)

(o: GND)

   (p)

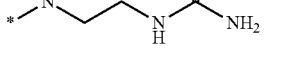   (q)

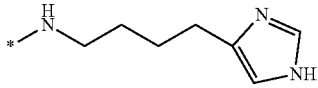   (r)

   (s: IMD)

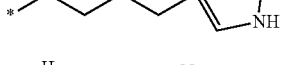   (t: DPT)

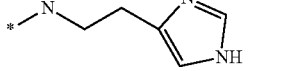   (u: SPR)

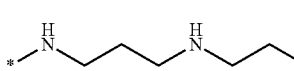   (v: TEP)

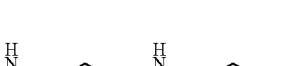   (w)

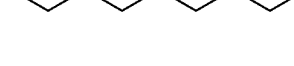

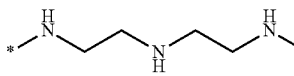   (x)

-continued

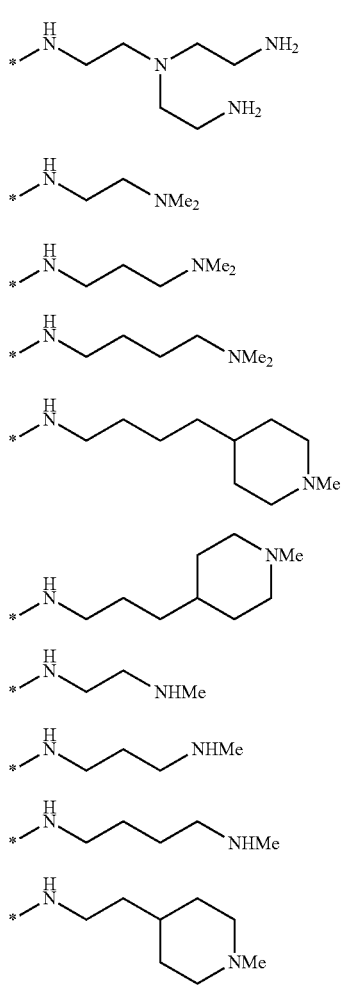

(y: BAEA)
(z: DMA)
(aa)
(ab)
(ac)
(ad)
(ae)
(af)
(ag)
(ah: MPD)

wherein
"*" represents the attached position;
$R^{19}$ and $R^{20}$ independently represent a hydrogen atom or $C_{1-6}$ alkyl, and $Q^-$ represents a counter anion.

5. The hyaluronic acid derivative according to claim 3, wherein $X^5$ is one or more groups represented by the formulas:

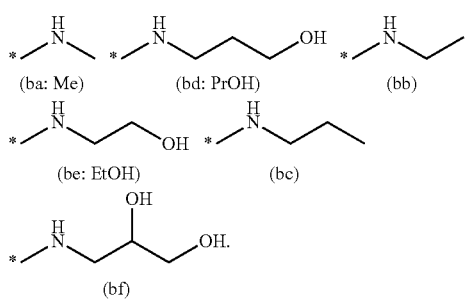

wherein "*" represents the attached position.

6. The hyaluronic acid derivative according to claim 1, wherein a proportion of the repeating units represented by the formula (Ib) wherein $X^2$ is —O-$z^7z^2$, —O-$z^0$-$z^2$, —NR$^6$-$z^1$-$Z^2$ or -NR$^{31}$-cHR$^{32}$—(CH$_2$)$_{n11}$-A$^3$-B$^2$ in repeating units of disaccharide present in the hyaluronic acid derivative is 3 to 55%.

7. The hyaluronic acid derivative according to claim 1, wherein a proportion of the repeating units represented by the formula (Ia) in repeating units of disaccharide present in the hyaluronic acid derivative is 1 to 75%.

8. The hyaluronic acid derivative according to claim 1, wherein a sum of a proportion of the repeating units represented by the formula (Ia) and a proportion of the repeating units represented by the formula (Ib) wherein $X^2$ is —NR$^{31}$—CHR$^{32}$—(CH$_2$)$_{n11}$-A$^3$-B$^2$ in repeating units of disaccharide present in the hyaluronic acid derivative is 30 to 100%.

9. The hyaluronic acid derivative according to claim 1, wherein
$R^8$ is selected from —CONR$^9$R$^{10}$ and —CO$_2$R$^{11}$; or
$B^1$ is selected from -N$^+$R$^{12}$R$^{13}$R$^{14}$Q$^-$, 5- to 10-membered heteroaryl having 1 to 4 nitrogen atoms, —NHC(=NH)NH$_2$, and a group:

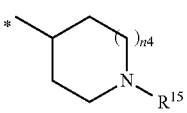

wherein "*" represents the attached position.

10. A pharmaceutical composition comprising the hyaluronic acid derivative according to claim 1.

11. A method of producing a pharmaceutical composition, the method comprising the step of complexing a drug and a hyaluronic acid derivative, the hyaluronic acid derivative comprising:
at least one repeating unit being represented by the formula (Ia):

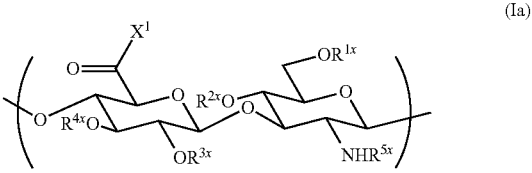

(Ia)

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;
$R^{5x}$ is selected from a hydrogen atom, formyl, and ($C_{1-6}$ alkyl)carbonyl;
$X^1$ represents —NR$^7$—CHR$^8$—(CH$_2$)$_{n1}$-A$^1$-B$^1$;
$R^7$ represents a hydrogen atom or $C_{1-6}$ alkyl;
$R^8$ is selected from a hydrogen atom, —CONR$^9$R$^{10}$, and —CO$_2$R$^{11}$;
$A^1$ is selected from a single bond, -(Y$^1$—CH$_2$—CH$_2$)$_{n2}$—, and -(Y$^2$—CH$_2$—CH$_2$—(CH$_2$)$_{na}$)$_{n3}$-;
$B^1$ is selected from -NR$^{12}$R$^{13}$, -N$^+$R$^{12}$R$^{13}$R$^{14}$Q$^-$, —N(-A$^2$-NR$^{12}$-R$^{13}$)$_2$5- to 10-membered heteroaryl having 1 to 4 nitrogen atoms, —NHC(=NH)NH$_2$, and a group:

[Chem. 12]

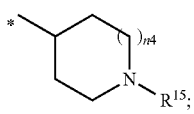

"*" represents the attached position;
Y$^1$ and Y$^2$ independently represent an oxygen atom or —NR$^{16}$—;
n1 represents an integer of 1 to 6, n2 and n3 independently represent an integer of 1 to 10, na represents an integer of 1 or 2, and n4 represents an integer of 0 to 3;
A$^2$ represents C$_{2-10}$ alkylene;
R$^9$, R$^{10}$, R$^{11}$, R$^{12}$, R$^{13}$, R$^{14}$, R$^{15}$, R$^{16}$, and R$^{16a}$ independently represent a hydrogen atom or C$_{1-6}$ alkyl; and
Q$^{31}$ represents a counter anion; and
at least one repeating unit being represented by the formula (Ib):

[Chem. 13]

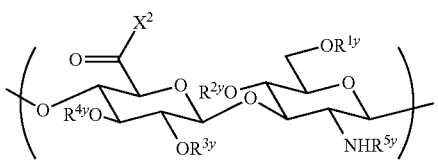

(Ib)

wherein
R$^{1y}$, R$^{2y}$, R$^{3y}$, and R$^{4y}$ are each independently selected from a hydrogen atom, C$_{1-6}$ alkyl, formyl, and (C$_{1-6}$ alkyl)carbonyl;
R$^{5y}$ is selected from a hydrogen atom, formyl, and (C$_{1-6}$ alkyl)carbonyl;
X$^2$ is —NR$^6$—Z$^1$-Z$^2$, —O—Z$^1$—Z$^2$ or —O-Z$^0$-Z$^2$; or
X$^2$ is —NR$^{31}$—CHR$^{32}$—(CH$_2$)$_{n11}$-A$^3$-B$^2$;
R$^6$ represents a hydrogen atom or C$_{1-6}$ alkyl;
Z$^0$ is selected from the following groups:

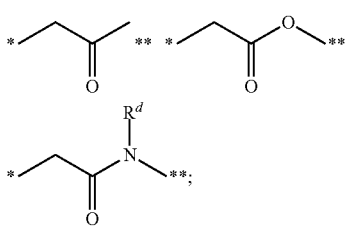

"*" represents the position attached to an oxygen atom and "**" represents the position attached to Z$^1$ or Z$^2$;
Z$^1$ is C$_{1-30}$ alkylene or —(CH$_2$CH$_2$O)$_m$-CH$_2$CH$_2$—, wherein one to five groups independently selected from —O—, —NR$^g$-, and —S—S— are optionally inserted into the alkylene, and m is an integer selected from 1 to 100;
Z$^2$ is selected from the following groups:
-NR$^b$—Z$^3$,
-NR$^b$—COO-Z$^3$,
-NR$^b$—CO—Z$^3$,
-NR$^b$—CO—NR$^c$-Z$^3$,
—COO-Z$^3$,
—CO—NR$^c$-Z$^3$,
—O—Z$^3$,
O—CO-NR$^c$-Z$^3$,
O—COO-Z$^3$,
—S—Z$^3$,
—CO-Z$^a$—S-Z$^3$,
—O—CO—Z$^b$—S—Z$^3$,
-NR$^b$—CO—Z$^b$—S—Z$^3$, and
S—S-Z$^3$;

R$^b$ and R$^c$ are independently selected from a hydrogen atom, C$_{1-20}$ alkyl, amino C$_{2-20}$ alkyl, and hydroxy C$_{2-20}$ alkyl, wherein one to three groups independently selected from —O— and —NR$^f$- are optionally inserted into the alkyl moiety of the group;

R$^d$ independently represents a hydrogen atom or C$_{1-6}$ alkyl;

R$^f$ is independently selected from a hydrogen atom, C$_{1-12}$ alkyl, amino C$_{2-12}$ alkyl, and hydroxy C$_{2-12}$ alkyl, wherein one or two groups selected from —O— and —NH— are optionally inserted into the alkyl moiety of the group;

R$^g$ is independently selected from a hydrogen atom, C$_{1-20}$ alkyl, amino C$_{2-20}$ alkyl, and hydroxy C$_{2-20}$ alkyl, wherein one to three groups independently selected from —O— and —NH— are optionally inserted into the alkyl moiety of the group;

Z$^3$ is a steryl group represented by any one of the following formulas:

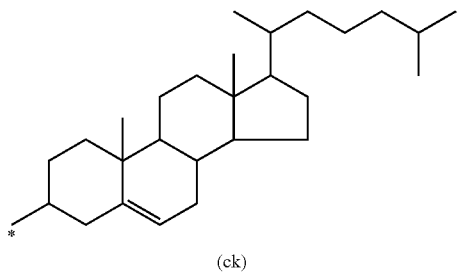

(ck)

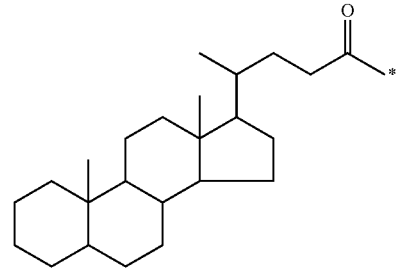

(cl: CA)

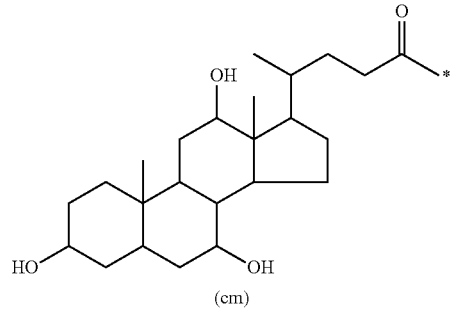

(cm)

189

-continued (cn)

(co)

(cp)

wherein
"*" represents the attached position;
$R^{21}$ independently represents a hydrogen atom or $C_{1-6}$ alkyl;
$Z^a$ is $C_{1-5}$ alkylene;
$Z^b$ is $C_{2-8}$ alkylene or $C_{2-8}$ alkenylene;
$R^{31}$ represents a hydrogen atom or $C_{1-6}$ alkyl;
$R^{32}$ is selected from a hydrogen atom, —CONR$^{33}$R$^{34}$, and —CO$_2$R$^{35}$;
$A^3$ is selected from a single bond, -(Y$^3$—CH$_2$—CH$_2$)$_{n12}$—, and -(Y$^4$—CH$_2$—CH$_2$—(CH$_2$)$_{n14}$)$_{n13}$-;
$B^2$ is selected from —NR$^{36}$—X$^4$, —N(-X$^4$)$_2$, —N(-A$^4$-NR$^{36}$R$^{37}$)(-A$^4$-NR$^{36}$—X$^4$), —N(-A$^4$-NR$^{36}$—X$^4$)$_2$, and —NHC(=NH)NH—X$^4$;
$Y^3$ and $Y^4$ independently represent an oxygen atom or —NR$^{16a}$-;
n11 represents an integer of 1 to 6, n12 and n13 independently represent an integer of 1 to 10, and n14 represents an integer of 1 or 2;
$A^4$ represents $C_{2-10}$ alkylene;
$R^{33}$, $R^{34}$, $R^{35}$, $R^{36}$, and $R^{37}$ independently represent a hydrogen atom or $C_{1-6}$ alkyl; and
$X^4$ is —CO—Z$^1$-Z$^2$ or -Z$^3$.

12. The method according to claim 11, wherein the hyaluronic acid derivative is a hyaluronic acid derivative comprising:

at least one repeating unit being represented by the formula (Ia):

(Ia)

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;
$R^{5x}$ is selected from a hydrogen atom, formyl, and ($C_{1-6}$ alkyl)carbonyl;
$X^1$ represents —NR$^7$—CHR$^8$—(CH$_2$)$_{n1}$-A$^1$-B$^1$;
$R^7$ represents a hydrogen atom or $C_{1-6}$ alkyl;
$R^8$ is selected from a hydrogen atom, —CONR$^9$R$^{10}$, and —CO$_2$R$^{11}$;
$A^1$ is selected from a single bond, -(Y$^1$—CH$_2$—CH$_2$)$_{n2}$—, and -(Y$^2$—CH$_2$—CH$_2$—(CH$_2$)$_{na}$)$_{n3}$-;
$B^1$ is selected from -NR$^{12}$R$^{13}$, -N$^+$R$_{12}$R$^{13}$R$^{14}$Q-, —N(-A$^2$-NR$^{12}$R$^{13}$)$_2$, 5- to 10-membered heteroaryl having 1 to 4 nitrogen atoms, —NHC(=NH)NH$_2$, and a group:

wherein "*" represents the attached position;
$Y^1$ and $Y^2$ independently represent an oxygen atom or —NR$^{16}$—;
n1 represents an integer of 1 to 6, n2 and n3 independently represent an integer of 1 to 10, na represents an integer of 1 or 2, and n4 represents an integer of 0 to 3;
$A^2$ represents $C_{2-10}$ alkylene;
$R^9$, $R^{10}$, $R^{11}$, $R^{12}$, $R^{13}$, $R^{14}$, $R^{15}$, $R^{16}$, and $R^{16a}$ independently represent a hydrogen atom or $C_{1-6}$ alkyl; and
$Q^-$ represents a counter anion;
with the proviso that when $R^8$ is a hydrogen atom and $B^1$ is —NR$^{12}$R$^{13}$, i) n1 is an integer of 1 to 3 and $A^1$ is a single bond, or ii) n1 is 1, $A^1$ is -(Y$^1$—CH$_2$—CH$_2$)$_{n2}$—, and n2 is an integer of 1 to 3; and
at least one repeating unit being represented by the formula (Ib):

(Ib)

wherein
$R^{1y}$, $R^{2y}$, $R^{3y}$, and $R^{4y}$ are each independently selected from a hydrogen atom, $C_{1-6}$ alkyl, formyl, and ($C_{1-6}$ alkyl)carbonyl;
$R^{5y}$ is selected from a hydrogen atom, formyl, and ($C_{1-6}$ alkyl)carbonyl;

$X^2$ is selected from $-O-Z^1-Z^2$, $-O-Z^0-Z^2$, $-NR^6-Z^1-Z^2$, and $-NR^{31}-CHR^{32}-(CH_2)_{n11}-A^3-B^2$;

$R^6$ represents a hydrogen atom or $C_{1-6}$ alkyl;

$Z^0$ is selected from the following groups:

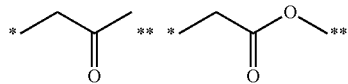

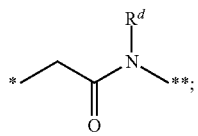

"*" represents the position attached to an oxygen atom and "**" represents the position attached to $Z^1$ or $Z^2$;

$Z^1$ is $C_{1-30}$ alkylene or $-(CH_2CH_2O)_m-CH_2CH_2-$, wherein one to five groups independently selected from $-O-$, $-NR^g-$, and $-S-S-$ are optionally inserted into the alkylene, and m is an integer selected from 1 to 100;

$Z^2$ is selected from the following groups:

$-NR^b-Z^3$,
$-NR^b-COO-Z^3$,
$-NR^b-CO-Z^3$,
$-NR^b-CO-NR^c-Z^3$,
$-COO-Z^3$,
$-CO-NR^c-Z^3$,
$-O-Z^3$,
$O-CO-NR^c-Z^3$,
$O-COO-Z^3$,
$-S-Z^3$,
$-CO-Z^a-S-Z^3$,
$-O-CO-Z^b-S-Z^3$,
$-NR^b-CO-Z^b-S-Z^3$, and
$-S-S-Z^3$, $R^b$ and $R^c$ are independently selected from a hydrogen atom, $C_{1-20}$ alkyl, amino $C_{2-20}$ alkyl, and hydroxy $C_{2-20}$ alkyl, wherein one to three groups independently selected from $-O-$ and $-NR^f-$ are optionally inserted into the alkyl moiety of the group;

$R^d$ independently represents a hydrogen atom or $C_{1-6}$ alkyl;

$R^f$ is independently selected from a hydrogen atom, $C_{1-12}$ alkyl, amino $C_{2-12}$ alkyl, and hydroxy $C_{2-12}$ alkyl, wherein one or two groups selected from $-O-$ and $-NH-$ are optionally inserted into the alkyl moiety of the group;

$R^g$ is independently selected from a hydrogen atom, $C_{1-20}$ alkyl, amino $C_{2-20}$ alkyl, and hydroxy $C_{2-20}$ alkyl, wherein one to three groups independently selected from $-O-$ and $-NH-$ are optionally inserted into the alkyl moiety of the group;

$Z^3$ is a steryl group represented by any one of the following formulas:

(ck)

(cl: CA)

(cm)

(cn)

(co)

-continued

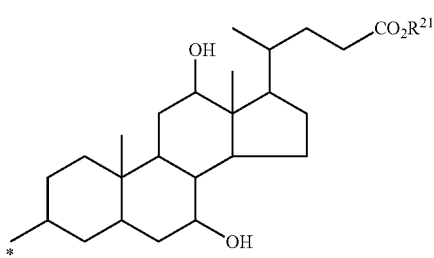

(cp)

wherein
- "*" represents the attached position;
- $R^{21}$ independently represents a hydrogen atom or $C_{1-6}$ alkyl;
- $Z^a$ is $C_{1-5}$ alkylene;
- $Z^b$ is $C_{2-8}$ alkylene or $C_{2-8}$ alkenylene;
- $R^{31}$ represents a hydrogen atom or $C_{1-6}$ alkyl;
- $R^{32}$ is selected from a hydrogen atom, $-CONR^{33}R^{34}$, and $-CO_2R^{35}$;
- $A^3$ is selected from a single bond, $-(Y^3-CH_2-CH_2)_{n12}-$, and $-(Y^4-CH_2-CH_2-(CH_2)_{n14})_{n13}-$;
- $B^2$ is selected from $-NR^{36}-X^4$, $-N(-X^4)_2$, $-N(-A^4-NR^{36}R^{37})(-A^4-NR^{36}-X^4)$, $-N(-A^4-NR^{36}-X^4)_2$, and $-NHC(=NH)NH-X^4$;
- $Y^3$ and $Y^4$ independently represent an oxygen atom or $-NR^{16a}-$;
- n11 represents an integer of 1 to 6, n12 and n13 independently represent an integer of 1 to 10, and n14 represents an integer of 1 or 2;
- $A^4$ represents $C_{2-10}$ alkylene;
- $R^{33}$, $R^{34}$, $R^{35}$, $R^{36}$, and $R^{37}$ independently represent a hydrogen atom or $C_{1-6}$ alkyl; and
- $X^4$ is $-CO-Z^1-Z^2$ or $-Z^3$.

13. A pharmaceutical composition for transmucosal administration comprising:
a drug; and
the hyaluronic acid derivative according to claim 1.

* * * * *

UNITED STATES PATENT AND TRADEMARK OFFICE
CERTIFICATE OF CORRECTION

PATENT NO. : 11,389,539 B2
APPLICATION NO. : 16/099770
DATED : July 19, 2022
INVENTOR(S) : Takashi Nakai et al.

It is certified that error appears in the above-identified patent and that said Letters Patent is hereby corrected as shown below:

In the Claims

At Claim 1, Column 179, Line 45, delete "R₉," and insert --$R^9$,--.

At Claim 1, Column 182, Line 46, delete "[Chem. 5]".

At Claim 3, Column 183, Line 1, delete "[Chem. 6]".

At Claim 4, Column 183, Line 60, delete " 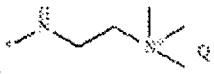 (h:PTMA)" and insert -- 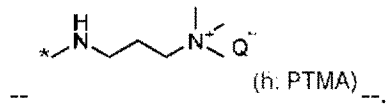 --.

At Claim 6, Column 185, Lines 67, delete "-O-$z^1$-$z^2$, -O-$z^0$-$z^2$, -$NR^6$-" and insert -- -O-$Z^1$-$Z^2$, -O-$Z^0$-$Z^2$, -$NR^6$- --.

At Claim 6, Column 186, Line 1, delete "$z^1$-$Z^2$ or –$NR^{31}$-c$HR^{32}$-$(CH_2)_{n11}$-$A^3$-$B^2$" and insert --$Z^1Z^2$ or –$NR^{31}$-$CHR^{32}$-$(CH_2)_{n11}$-$A^3$-$B^2$--.

At Claim 11, Column 186, Line 66, delete "$A^2$-$NR^{12}R^{13})_2 5$-" and insert --$A^2$-$NR^{12}R^{13})_2$, 5- --.

At Claim 11, Column 187, Line 1, delete "[Chem. 12]".

At Claim 11, Column 187, Line 18, delete "$Q^{31}$" and insert --$Q^-$--.

At Claim 11, Column 187, Line 22, delete "[Chem. 13]".

At Claim 11, Column 188, Line 2, delete "O-CO-$NR^c$-$Z^3$," and insert -- -O-CO-$NR^c$-$Z^3$,--.

Signed and Sealed this
Twenty-second Day of November, 2022

*Katherine Kelly Vidal*

Katherine Kelly Vidal
*Director of the United States Patent and Trademark Office*

CERTIFICATE OF CORRECTION (continued)
U.S. Pat. No. 11,389,539 B2

At Claim 11, Column 188, Line 3, delete "O-COO-$Z^3$," and insert -- -O-COO-$Z^3$,--.

At Claim 11, Column 188, Line 10, delete "S-S-$Z^3$;" and insert -- -S-S-$Z^3$;--.

At Claim 12, Column 190, Line 26, delete "-$N^+R_{12}R^{13}R^{14}Q^-$," and insert -- -$N^+R^{12}R^{13}R^{14}Q^-$,--.

At Claim 12, Column 191, Line 40, delete "O-CO-$NR^c$-$Z^3$," and insert -- -O-CO-$NR^c$-$Z^3$,--.

At Claim 12, Column 191, Line 40, delete "O-COO-$Z^3$," and insert -- -O-COO-$Z^3$,--.